(12) United States Patent
Labadie et al.

(10) Patent No.: US 12,233,052 B2
(45) Date of Patent: *Feb. 25, 2025

(54) TETRAHYDRO-PYRIDO[3,4-B]INDOLE ESTROGEN RECEPTOR MODULATORS AND USES THEREOF

(71) Applicant: Genentech, Inc., South San Francisco, CA (US)

(72) Inventors: Sharada Labadie, Sunnyvale, CA (US); Jun Liang, Los Altos, CA (US); Daniel Fred Ortwine, San Ramon, CA (US); Xiaojing Wang, Belmont, CA (US); Jason Zbieg, Montara, CA (US); Birong Zhang, Union City, CA (US); Simon Charles Goodacre, Harlow (GB); Nicholas Charles Ray, Great Dunnow (GB); Jun Li, San Bruno, CA (US)

(73) Assignee: Genentech, Inc., South San Francisco, CA (US)

( * ) Notice: Subject to any disclaimer, the term of this patent is extended or adjusted under 35 U.S.C. 154(b) by 888 days.

This patent is subject to a terminal disclaimer.

(21) Appl. No.: 17/185,319

(22) Filed: Feb. 25, 2021

(65) Prior Publication Data

US 2021/0236473 A1  Aug. 5, 2021
US 2023/0045776 A9  Feb. 9, 2023

Related U.S. Application Data

(63) Continuation of application No. 15/955,539, filed on Apr. 17, 2018, now Pat. No. 10,966,963, which is a
(Continued)

(51) Int. Cl.
| | |
|---|---|
| *A61K 31/437* | (2006.01) |
| *A61K 31/138* | (2006.01) |
| *A61K 31/4545* | (2006.01) |
| *A61K 31/497* | (2006.01) |
| *A61K 31/506* | (2006.01) |
| *A61K 31/565* | (2006.01) |
| *A61K 45/06* | (2006.01) |
| *C07D 471/04* | (2006.01) |
| *A61P 5/30* | (2006.01) |
| *A61P 35/00* | (2006.01) |
| *A61P 43/00* | (2006.01) |

(52) U.S. Cl.
CPC .......... *A61K 31/437* (2013.01); *A61K 31/138* (2013.01); *A61K 31/4545* (2013.01); *A61K 31/497* (2013.01); *A61K 31/506* (2013.01); *A61K 31/565* (2013.01); *A61K 45/06* (2013.01); *C07D 471/04* (2013.01)

(58) Field of Classification Search
CPC ................ A61K 31/437; A61K 31/138; A61K 31/4545; A61K 31/497; A61K 31/506; A61K 31/565; A61K 45/06; A61K 2300/00; C07D 471/04; A61P 5/30; A61P 35/00; A61P 43/00
See application file for complete search history.

(56) References Cited

U.S. PATENT DOCUMENTS

| | | |
|---|---|---|
| 5,206,377 A | 4/1993 | McAfee |
| 5,635,528 A | 6/1997 | Audia et al. |

(Continued)

FOREIGN PATENT DOCUMENTS

| | | |
|---|---|---|
| CA | 2485909 A1 | 12/2003 |
| CN | 102408425 | 4/2012 |

(Continued)

OTHER PUBLICATIONS

Bo, L., et al., "Studies on antiestrogen compounds and their structure-activity relationships" Chinese J Pharm Res 37(1):16-20 (Feb. 28, 2010).
Bentrem, D. et al., "Molecular Mechanism of Action at Estrogen Receptor a of a New Clinically Relevant Antiestrogen (GW7604) Related to Tamoxifen" Endocrinology 142(2):838-846 (Feb. 1, 2001).
Blizzard, T., et al., "Estrogen receptor ligands, Part 14: Application of novel antagonist side chains to existing platforms" Bioorg Med Chem Lett 15(23):5124-5128 (Dec. 1, 2005).
(Continued)

*Primary Examiner* — Bruck Kifle
*Assistant Examiner* — Kevin S Martin
(74) *Attorney, Agent, or Firm* — Genentech, Inc.

(57) ABSTRACT

Described herein are tetrahydro-pyrido[3,4-b]indol-1-yl compounds with estrogen receptor modulation activity or function having the Formula I structure:

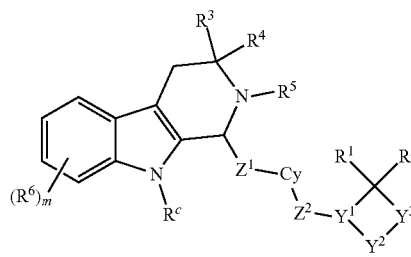

and stereoisomers, tautomers, or pharmaceutically acceptable salts thereof, and with the substituents and structural features described herein. Also described are pharmaceutical compositions and medicaments that include the Formula I compounds, as well as methods of using such estrogen receptor modulators, alone and in combination with other therapeutic agents, for treating diseases or conditions that are mediated or dependent upon estrogen receptors.

32 Claims, No Drawings

Related U.S. Application Data continuation of application No. 14/972,326, filed on Dec. 17, 2015, now Pat. No. 9,980,947.

(60) Provisional application No. 62/142,077, filed on Apr. 2, 2015, provisional application No. 62/110,998, filed on Feb. 2, 2015, provisional application No. 62/093,929, filed on Dec. 18, 2014.

(56) References Cited

U.S. PATENT DOCUMENTS

| | | |
|---|---|---|
| 5,861,425 A | 1/1999 | Audia et al. |
| 6,951,961 B2 | 10/2005 | Protopopova et al. |
| 8,053,442 B2 | 11/2011 | Ang et al. |
| 8,133,992 B2 | 3/2012 | Martin et al. |
| 8,703,810 B2 | 4/2014 | Kahraman et al. |
| 8,853,423 B2 | 10/2014 | Govek. et al. |
| 9,139,821 B2 | 9/2015 | Nazor et al. |
| 9,187,460 B2 | 11/2015 | Smith et al. |
| 9,193,714 B2 | 11/2015 | Smith et al. |
| 9,388,395 B2 | 7/2016 | Nazor et al. |
| 9,598,712 B2 | 3/2017 | Crowe et al. |
| 9,708,588 B2 | 7/2017 | Nazor et al. |
| 9,980,947 B2 * | 5/2018 | Labadie .................. A61K 45/06 |
| 10,966,963 B2 | 4/2021 | Labadie et al. |
| 2005/0282849 A1 | 12/2005 | Moon et al. |
| 2007/0254878 A1 | 11/2007 | Cao et al. |
| 2008/0064683 A1 | 3/2008 | Cao et al. |
| 2010/0249153 A1 | 9/2010 | Tandon et al. |
| 2013/0116232 A1 | 5/2013 | Kahraman et al. |
| 2013/0137746 A1 | 5/2013 | Govek et al. |
| 2014/0364427 A1 | 12/2014 | Smith et al. |
| 2016/0090377 A1 | 3/2016 | Govek et al. |
| 2016/0090378 A1 | 3/2016 | Kahraman et al. |
| 2016/0175284 A1 | 6/2016 | Labadie et al. |
| 2016/0175289 A1 | 6/2016 | Labadie et al. |

FOREIGN PATENT DOCUMENTS

| | | | |
|---|---|---|---|
| CN | 102480957 | | 5/2012 |
| CN | 103313989 A | | 9/2013 |
| EP | 2682119 A1 | | 1/2014 |
| GB | 2122617 A1 | | 1/1984 |
| JP | 2012-528192 A | | 12/2012 |
| KR | 102012-0073287 | | 7/2012 |
| WO | 2002/062339 A1 | | 8/2002 |
| WO | 2002/064590 A2 | | 8/2002 |
| WO | 2003/099821 A1 | | 12/2003 |
| WO | 2004/089470 A1 | | 10/2004 |
| WO | 2005/034857 A2 | | 4/2005 |
| WO | 2005/089764 A1 | | 9/2005 |
| WO | 2006/015035 A1 | | 2/2006 |
| WO | 2007/002051 A1 | | 1/2007 |
| WO | 2008/127714 A1 | | 10/2008 |
| WO | 2008/127715 A1 | | 10/2008 |
| WO | 2010/015815 A2 | | 2/2010 |
| WO | 2010/015816 A2 | | 2/2010 |
| WO | 2010/029313 A1 | | 3/2010 |
| WO | 2010/049678 A2 | | 5/2010 |
| WO | 2010/075282 A1 | | 7/2010 |
| WO | 2010/075286 A1 | | 7/2010 |
| WO | 2010/107485 A1 | | 9/2010 |
| WO | 2010/138652 A1 | | 12/2010 |
| WO | 2010/138659 A1 | | 12/2010 |
| WO | 2010/138685 A1 | | 12/2010 |
| WO | 2010/138695 A1 | | 12/2010 |
| WO | 2010/138706 A1 | | 12/2010 |
| WO | 2010/138758 A1 | | 12/2010 |
| WO | 2015/082990 A1 | | 6/2011 |
| WO | 2011/150162 A1 | | 12/2011 |
| WO | 2011/156518 A1 | | 12/2011 |
| WO | 2011/159769 A2 | | 12/2011 |
| WO | 2012/082997 A1 | | 6/2012 |
| WO | 2012/084711 A1 | | 6/2012 |
| WO | 2013/090829 A1 | | 6/2013 |
| WO | 2013/090836 A1 | | 6/2013 |
| WO | 2014/083529 A1 | | 6/2014 |
| WO | 2014/205136 A1 | | 12/2014 |
| WO | 2014/205138 A1 | | 12/2014 |
| WO | WO-2014191726 A1 * | 12/2014 | ........... A61K 31/437 |
| WO | 2015/066019 A1 | | 5/2015 |
| WO | 2015/136016 A2 | | 9/2015 |
| WO | 2015/136017 A1 | | 9/2015 |
| WO | 2015/197861 A1 | | 12/2015 |
| WO | 2016/097071 A1 | | 6/2016 |
| WO | 2016/097072 A1 | | 6/2016 |
| WO | 2016/097073 A1 | | 6/2016 |
| WO | 2017/059139 A1 | | 4/2017 |
| WO | 2017/136688 A1 | | 8/2017 |

OTHER PUBLICATIONS

CAS Registry Database, 404925-92-4, Creation Date Apr. 10, 2002.
CAS Registry Database, 404930-10-5,Creation Date Apr. 10, 2002.
Dardes, R., et al., "Effects of a New Clinically Relevant Antiestrogen (GW5638) Related to Tamoxifen on Breast and Endometrial Cancer Growth in vivo" Clin Cancer Res 8(6):1995-2001 (Jun. 1, 2002).
"International Search Report—PCT/EP2015/080119":pp. 1-8 (Mar. 7, 1996).
Komm, B., et al., "An Overview of Current and Emerging SERMs" J Steroid Biochem Mol Biol 143:207-222 (Mar. 22, 2014).
Lumachi, L., et al., "Treatment of Estrogen Receptor-Positive Breast Cancer" Curr Med Chem 20(5):596-604 (Jan. 1, 2013).
Mueller, M., et al., "Regulation of vascular endothelial growth factor (VEGF) gene transcription by estrogen receptors a and b" PNAS 97(20):10972-10977 (Sep. 26, 2000).
Willson, T., et al., "3-[4-(1,2-Diphenylbut-l-enyl) phenyl]acrylic Acid: A Non-Steroidal Estrogen with Functional Selectivity for Bone Over Uterus in Rats" J Med Chem 37(11):1550-1552 (May 27, 1994).
Zhang, C., et al., "Facile Formation of Cyclic Aminals through a Brønsted Acid-Promoted Redox Process" J Org Chem 74(1):419-422 (Jan. 2, 2009).

* cited by examiner

TETRAHYDRO-PYRIDO[3,4-B]INDOLE ESTROGEN RECEPTOR MODULATORS AND USES THEREOF

CROSS REFERENCE TO RELATED APPLICATIONS

This non-provisional application filed under 37 CFR § 1.53(b), claims the benefit under 35 USC § 119(e) of U.S. Provisional Application Ser. No. 62/093,929 filed on 18 Dec. 2014, U.S. Provisional Application Ser. No. 62/110,998 filed on 2 Feb. 2015, and U.S. Provisional Application Ser. No. 62/142,077 filed on 2 Apr. 2015, which are incorporated by reference in their entirety.

FIELD OF THE INVENTION

Described herein are compounds, including pharmaceutically acceptable salts, solvates, metabolites, prodrugs thereof, pharmaceutical compositions comprising such compounds, and methods of using such compounds to treat, prevent or diagnose diseases or conditions that are estrogen sensitive, estrogen receptor dependent or estrogen receptor mediated in combination with other therapeutic agents.

BACKGROUND OF THE INVENTION

The estrogen receptor ("ER") is a ligand-activated transcriptional regulatory protein that mediates induction of a variety of biological effects through its interaction with endogenous estrogens. Endogenous estrogens include 17β (beta)-estradiol and estrones. ER has been found to have two isoforms, ER-α (alpha) and ER-β (beta). Estrogens and estrogen receptors are implicated in a number of diseases or conditions, such as breast cancer, lung cancer, ovarian cancer, colon cancer, prostate cancer, endometrial cancer, uterine cancer, as well as others diseases or conditions. There is a need for new ER-α targeting agents that have activity in the setting of metastatic disease and acquired resistance.

SUMMARY OF THE INVENTION

The invention relates generally to tetrahydro-pyrido[3,4-b]indol-1-yl compounds with estrogen receptor modulation activity or function having the Formula I structure:

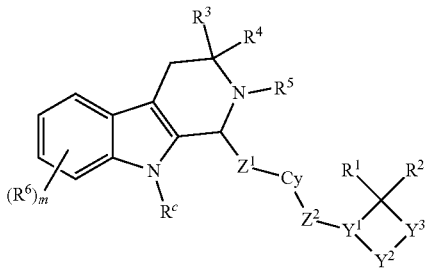

I and stereoisomers, tautomers, or pharmaceutically acceptable salts thereof, and with the substituents and structural features described herein.

An aspect of the invention is a pharmaceutical composition of a Formula I compound and a pharmaceutically acceptable carrier, glidant, diluent, or excipient.

An aspect of the invention is a process for making a Formula I compound or a pharmaceutical composition comprising a Formula I compound.

An aspect of the invention is a method of treating an ER-related disease or disorder in a patient comprising administering a therapeutically effective amount of the pharmaceutical composition to a patient with an ER-related disease or disorder.

An aspect of the invention is a kit for treating a condition mediated by an estrogen receptor, comprising:
a) a pharmaceutical composition comprising a Formula I compound; and
b) instructions for use.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this Application is based on IUPAC systematic nomenclature, unless indicated otherwise.

Definitions

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkyldiyl" as used herein refers to a saturated linear or branched-chain divalent hydrocarbon radical of about one to twelve carbon atoms ($C_1$-$C_{12}$), wherein the alkyldiyl radical may be optionally substituted independently with one or more substituents described below. In another embodiment, an alkyldiyl radical is one to eight carbon atoms ($C_1$-$C_8$), or one to six carbon atoms ($C_1$-$C_6$). Examples of alkyldiyl groups include, but are not limited to, methylene (—$CH_2$—), ethylene (—$CH_2CH_2$—), propylene (—$CH_2CH_2CH_2$—), and the like. An alkyldiyl group may also be referred to as an "alkylene" group.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—$CH=CH_2$), allyl (—$CH_2CH=CH_2$), and the like.

The terms "alkenylene" or "alkenyldiyl" refer to a linear or branched-chain divalent hydrocarbon radical of two to eight carbon atoms ($C_2$-$C_8$) with at least one site of unsaturation, i.e., a carbon-carbon, $sp^2$ double bond, wherein the alkenylene radical may be optionally substituted independently with one or more substituents described herein, and includes radicals having "cis" and "trans" orientations, or alternatively, "E" and "Z" orientations. Examples include, but are not limited to, ethylenylene or vinylene (—$CH=CH$—), allyl (—$CH_2CH=CH$—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" or "alkynyldiyl" refer to a linear or branched divalent hydrocarbon radical of two to eight carbon atoms ($C_2$-$C_8$) with at least one site of unsaturation, i.e., a carbon-carbon, sp triple bond, wherein the alkynylene radical may be optionally substituted independently with one or more substituents described herein. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Spiro carbocyclyl moieties are also included within the scope of this definition. Examples of spiro carbocyclyl moieties include [2.2]pentanyl, [2.3]hexanyl, and [2.4]heptanyl. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

The term "carbocyclyldiyl" refers to a divalent non-aromatic, saturated or partially unsaturated ring having 3 to 12 carbon atoms ($C_1$-$C_{12}$) as a monocyclic ring or 7 to 12 carbon atoms as a bicyclic ring.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

The terms "arylene" or "aryldiyl" mean a divalent aromatic hydrocarbon radical of 6-20 carbon atoms ($C_6$-$C_{20}$) derived by the removal of two hydrogen atom from a two carbon atoms of a parent aromatic ring system. Some aryldiyl groups are represented in the exemplary structures as "Ar". Aryldiyl includes bicyclic radicals comprising an aromatic ring fused to a saturated, partially unsaturated ring, or aromatic carbocyclic ring. Typical aryldiyl groups include, but are not limited to, radicals derived from benzene (phenyldiyl), substituted benzenes, naphthalene, anthracene, biphenylene, indenylene, indanylene, 1,2-dihydronaphthalene, 1,2,3,4-tetrahydronaphthyl, and the like. Aryldiyl groups are also referred to as "arylene", and are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro heterocyclyl moieties are also included within the scope of this definition. Examples of spiro heterocyclyl moieties include azaspiro[2.5]octanyl and azaspiro[2.4]heptanyl. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heterocyclyldiyl" refers to a divalent, saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents as described.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The term "heteroaryldiyl" refers to a divalent aromatic radical of 5-, 6-, or 7-membered rings, and includes fused ring systems (at least one of which is aromatic) of 5-20 atoms, containing one or more heteroatoms independently selected from nitrogen, oxygen, and sulfur.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to therapeutic treatment, wherein the object is to slow down (lessen) an undesired physiological change or disorder, such as the development or spread of arthritis or cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those with the condition or disorder.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

"Hematological malignancies" (British spelling "Haematological" malignancies) are the types of cancer that affect blood, bone marrow, and lymph nodes. As the three are intimately connected through the immune system, a disease affecting one of the three will often affect the others as well: although lymphoma is a disease of the lymph nodes, it often spreads to the bone marrow, affecting the blood. Hematological malignancies are malignant neoplasms ("cancer"), and they are generally treated by specialists in hematology and/or oncology. In some centers "Hematology/oncology" is a single subspecialty of internal medicine while in others they are considered separate divisions (there are also surgical and radiation oncologists). Not all hematological disorders are malignant ("cancerous"); these other blood conditions may also be managed by a hematologist. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin. Leukemias include Acute lymphoblastic leukemia (ALL), Acute myelogenous leukemia (AML), Chronic lymphocytic leukemia (CLL), Chronic myelogenous leukemia (CML), Acute monocytic leukemia (AMOL) and small lymphocytic lymphoma (SLL). Lymphomas include Hodgkin's lymphomas (all four subtypes) and Non-Hodgkin's lymphomas (NHL, all subtypes).

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: ibrutinib (IMBRUVICA™, APCI-32765, Pharmacyclics Inc./Janssen Biotech Inc.; CAS Reg. No. 936563-96-1, U.S. Pat. No. 7,514,444), idelalisib (ZYDELIG®, CAL-101, GS 1101, GS-1101, Gilead Sciences Inc.; CAS Reg. No. 1146702-54-6), erlotinib (TARCEVA®, Genentech/OSI Pharm.), docetaxel (TAXOTERE®, Sanofi-Aventis), 5-FU (fluorouracil, 5-fluorouracil, CAS Reg. No. 51-21-8), gemcitabine (GEMZAR®, Lilly), PD-0325901 (CAS No. 391210-10-9, Pfizer), cisplatin (Platinol®, (SP-4-2)-diamminedichloroplatinum(II), cis-diamine, dichloroplatinum (II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®, CAS No. 23214-92-8), Akti-1/2, HPPD, and rapamycin.

Chemotherapeutic agents include inhibitors of B-cell receptor targets such as BTK, Bcl-2 and JAK inhibitors.

More examples of chemotherapeutic agents include; oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, 11), vandetanib (rINN, ZD6474, ZACTIMA®, AstraZeneca), chlorambucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gammaII, calicheamicin omegaI1 (Angew Chem. Inti. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are; (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxy tamoxifen, trioxifene, keoxifene, LY117018, onapristone, and FARESTON® (toremifine citrate) and selective estrogen receptor modulators (SERDs) such as fulvestrant (FASLODEX®, Astra Zeneca); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozde, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors, such as cobimetinib (WO 2007/044515); (v) lipid kinase inhibitors, such as taselisib (GDC-0032, Genentech Inc.); (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rTL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (PERJETA™, 2C4, Genentech), trastuzumab (HERCEPTIN®, Genentech), trastuzumab emtansine (KADCYLA®, Genentech Inc.), and tositumomab (BEXXAR, Corixia).

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a Formula I compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral centers). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, and depicted in Table 1 structures for illustrative purposes, while stereochemistry is definitively established, such as from x-ray crystallographic data.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, aryl-aliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid "mesylate", ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins A "solvate" refers to an association or complex of one or more solvent molecules and a compound of the invention. Examples of solvents that form solvates include, but are not limited to, water, isopropanol, ethanol, methanol, DMSO, ethylacetate (EtOAc), acetic acid (AcOH), and ethanolamine.

The term "$EC_{50}$" is the half maximal effective concentration" and denotes the plasma concentration of a particular compound required for obtaining 50% of the maximum of a particular effect in vivo.

The term "Ki" is the inhibition constant and denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "$IC_{50}$" is the half maximal inhibitory concentration and denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed, and can be converted to an absolute inhibition constant (Ki) using the Cheng-Prusoff equation (Biochem. Pharmacol. (1973) 22:3099). Other percent inhibition parameters, such as $IC_{70}$, $IC_{90}$, etc., may be calculated.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 3 IP, 32P, 35S, 36O, and 125I. Various isotopically labeled compounds of the present invention, for example those into which radioactive isotopes such as 3H, 13C, and 14C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labeled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

Estrogen Receptor

Estrogen receptor alpha (ER-α; NR3A1) and estrogen receptor beta (ER-β; NR3A2) are steroid hormone receptors, which are members of the large nuclear receptor superfamily. Nuclear receptors share a common modular structure, which minimally includes a DNA binding domain (DBD) and a ligand binding domain (LBD). Steroid hormone receptors are soluble, intracellular proteins that act as ligand-regulated transcription factors. Vertebrates contain five closely related steroid hormone receptors (estrogen receptor, androgen receptor, progesterone receptor, glucocorticoid receptor, mineralcorticoid receptor), which regulate a wide spectrum of reproductive, metabolic and developmental activities. The activities of ER are controlled by the binding of endogenous estrogens, including 17 β-estradiol and estrones.

The ER-α (alpha) gene is located on 6q25.1 and encodes a 595 AA protein. The ER-β gene resides on chromosome 14q23.3 and produces a 530 AA protein. However, due to alternative splicing and translation start sites, each of these genes can give rise to multiple isoforms. In addition to the DNA binding domain (called C domain) and ligand binding domain (E domain) these receptors contain an N-terminal (A/B) domain, a hinge (D) domain that links the C and E domains, and a C-terminal extension (F domain) (Gronemeyer and Laudet; Protein Profile 2: 1173-1308, 1995). While the C and E domains of ER-α and ER-β are quite conserved (95% and 55% amino acid identity, respectively), conservation of the A/B, D and F domains is poor (below 30% amino acid identity). Both receptors are involved in the regulation and development of the female reproductive tract but also play various roles in the central nervous system, cardiovascular systems and bone metabolism.

The ligand binding pocket of steroid hormone receptors is deeply buried within the ligand binding domain. Upon binding, the ligand becomes part of the hydrophobic core of this domain. Consequently most steroid hormone receptors are instable in the absence of hormone and require assistance from chaperones, such as Hsp90, in order to maintain hormone-binding competency. The interaction with Hsp90 also controls nuclear translocation of these receptors. Ligand-binding stabilizes the receptor and initiates sequential conformational changes that release the chaperones, alter the interactions between the various receptor domains and remodel protein interaction surfaces that allow these receptors to translocate into the nucleus, bind DNA and engage in interactions with chromatin remodeling complexes and the transcriptional machinery. Although ER can interact with Hsp90, this interaction is not required for hormone binding and, dependent on the cellular context, apo-ER can be both cytoplasmic and nuclear. Biophysical studies indicated that DNA binding rather than ligand binding contributes to the stability of the receptor (Greenfield et al., Biochemistry 40: 6646-6652, 2001).

ER can interact with DNA either directly by binding to a specific DNA sequence motif called estrogen response element (ERE) (classical pathway), or indirectly via protein-protein interactions (nonclassical pathway) (Welboren et al., Endocrine-Related Cancer 16: 1073-1089, 2009). In the nonclassical pathway, ER has been shown to tether to other transcription factors including SP-1, AP-1 and NF-κB. These interactions appear to play critical roles in the ability of ER to regulate cell proliferation and differentiation.

Both types of ER DNA interactions can result in gene activation or repression dependent on the transcriptional coregulators that are recruited by the respective ER-ERE complex (Klinge, Steroid 65: 227-251, 2000). The recruitment of coregulators is primarily mediated by two protein interaction surfaces, the AF2 and AF1. AF2 is located in the ER E-domain and its conformation is directly regulated by the ligand (Brzozowski et al., (1997) Nature 389: 753-758,). Full agonists appear to promote the recruitment of co-activators, whereas weak agonists and antagonists facilitate the binding of co-repressors. The regulation of protein with the AF1 is less well understood but can be controlled by serine phosphorylation (Ward and Weigel, (2009) Biofactors 35: 528-536). One of the involved phosphorylation sites (SI 18) appears to control the transcriptional activity of ER in the presence of antagonists such as tamoxifen, which plays an important role in the treatment of breast cancer. While full agonists appear to arrest ER in certain conformation, weak agonists tend to maintain ER in equilibrium between different conformations, allowing cell-dependent differences in co-regulator repertoires to modulate the activity of ER in a cell-dependent manner (Tamrazi et al., Mol. Endocrinol. 17: 2593-2602, 2003). Interactions of ER with DNA are dynamic and include, but are not limited to, the degradation of ER by the proteasome (Reid et al., Mol Cell 11: 695-707, 2003). The degradation of ER with ligands provides an attractive treatment strategy for diseases or conditions that are estrogen-sensitive and/or resistant to available anti-hormonal treatments. ER signaling is crucial for the development and maintenance of female reproductive organs including breasts, ovulation and thickening of the endometrium. GR signaling also has a role in bone mass, lipid metabolism, cancers, etc. About 70% of breast cancers express ER-D (ER-D positive) and are dependent on estrogens for growth and survival. Other cancers also are thought to be dependent on ER-α signaling for growth and survival, such as for example ovarian and endometrial cancers. The ER-α antagonist tamoxifen has been used to treat early and advanced ER-α positive breast cancer in both pre- and post-menopausal women. Fulvestrant (FASLODEX®, AstraZeneca) a steroid-based ER antagonist is used to treat breast cancer in women which have progressed despite therapy with tamoxifen (Howell A. (2006) Endocr Relat Cancer; 13:689-706; U.S. Pat. Nos. 6,774,122; 7,456,160; 8,329,680; 8,466,139). Steroidal and non-steroidal aromatase inhibitors are also used to treat cancers in humans. In some embodiments, the steroidal and non-steroidal aromatase inhibitors block the production of estrogen from androstenedione and testosterone in post-menopausal women, thereby blocking ER dependent growth in the cancers. In addition to these anti-hormonal agents, progressive ER positive breast cancer is treated in some cases with a variety of other chemotherapeutics, such as for example, the anthracylines, platins, taxanes. In some cases, ER positive breast cancers that harbor genetic amplification of the ERB-B/HER2 tyrosine kinase receptor are treated with the monoclonal antibody trastuzumab (Herceptin®, Genentech Inc.) or the small molecule pan-ERB-B inhibitor lapatinib (TYKERB®, GlaxoSmith Kline Corp.). Despite this battery of anti-hormonal, chemotherapeutic and small-molecule and antibody-based targeted therapies, many women with ER-α positive breast develop progressive metastatic disease and are in need of new therapies. Importantly, the majority of ER positive tumors that progress on existing anti-hormonal, as well as and other therapies, are thought to remain dependent on ER-α for growth and survival. Thus, there is a need for new ER-α targeting agents that have activity in the setting of metastatic disease and acquired resistance. In one aspect, described herein are compounds that are selective estrogen receptor modulators (SERMs). In specific embodiments, the SERMs described herein are selective estrogen receptor degraders (SERDs). In some embodiments, in cell-based assays the compounds described herein result in a reduction in steady state ER-α levels (i.e. ER degradation) and are useful in the treatment of estrogen sensitive diseases or conditions and/or diseases or conditions that have developed resistant to anti-hormonal therapies.

Most breast cancer patients are treated with agents that either block estrogen synthesis (e.g., aromatase inhibitors; AIs) or antagonize the effects of estradiol via competitive ER binding (e.g., tamoxifen) (Puhalla S, et al Mol Oncol 2012; 6(2):222-236). Despite the well documented therapeutic utility of these agents in various stages of disease, many ER+ breast cancers recur and patients eventually succumb. Recently, next generation whole genome and targeted sequencing has identified ESR1 (estrogen receptor alpha gene) mutations in up to 20% of tumors from patients with advanced breast cancer who have progressed on endocrine therapies, largely aromatase inhibitors (Li S, et al. Cell Rep (2013); 4(6): 1116-1130; Merenbakh-Lamin K, et al. Cancer Res (2013); 73(23): 6856-6864; Robinson D R, et al. Nat Genet (2013); 45(12): 1446-1451; Toy W, et al. Nat Genet (2013); 45(12): 1439-1445; Jeselsohn R, et al. Clin Cancer Res (2014); 20: 1757-1767). These ligand-binding domain (LBD) mutations confer high basal activity of the apo-receptor rendering them ligand-independent and thus active in the setting of low estradiol. There is a need for therapies that target ER signaling with robust activity in the setting of progressive disease post AT or tamoxifen treatment including the subset of patients harboring ESR1 mutant tumors.

In some embodiments, Formula I compounds disclosed herein are used in methods for treating a hormone resistant-estrogen receptor (ER) positive breast cancer in a patient characterized as having a mutation in the ESR1 gene, comprising administering a therapeutically-effective amount of a Formula I compound. In some embodiments, the mutation in the ESR1 gene results in an ER polypeptide having an amino acid substitution at a position selected from among amino acids positions 6, 118, 269, 311, 341, 350, 380, 392, 394, 433, 463, 503, 534, 535, 536, 537, 538 and 555 of SEQ ID NO:2. In some embodiments, the mutation results in an ER polypeptide having an amino acid substitution selected from among H6Y, S118P, R269C, T311M, S341L, A350E, E380Q, V392I, R394H, S433P, S463P, R503W, V534E, P535H, L536R, L536P, L536Q, Y537N, Y537C, Y537S, D538G, and R555C. In some embodiments, the patient has two or more mutations in the ESR1 gene.

Given the central role of ER-α in breast cancer development and progression, compounds disclosed herein are useful in the treatment of breast cancer, either alone or in combination with other agents that can modulate other critical pathways in breast cancer, including but not limited to those that target IGF1R, EGFR, CDK 4/6, erB-B2 and 3, the PI3K/AKT/mTOR axis, HSP90, PARP or histone deacetylases.

Given the central role of ER-α in breast cancer development and progression, Formula I compounds disclosed herein are useful in the treatment of breast cancer, either alone or in combination with other agent used to treat breast cancer, including but not limited to aromatase inhibitors, anthracyclines, platins, nitrogen mustard alkylating agents, taxanes. Illustrative agent used to treat breast cancer, include, but are not limited to, PI3K inhibitors such as taselisib (GDC-0032, Genentech Inc.), paclitaxel, anastrozole, exemestane, cyclophosphamide, epirubicin, fulvestrant, letrozole (FEMARA®, Novartis, Corp.), gemcitabine, trastuzumab, pegfilgrastim, filgrastim, tamoxifen, docetaxel, toremifene, vinorelbine, capecitabine (XELODA®, Roche), ixabepilone, as well as others described herein.

ER-related diseases or conditions include ER-α dysfunction is associated with cancer (bone cancer, breast cancer, lung cancer, colorectal cancer, endometrial cancer, prostate cancer, ovarian and uterine cancer), central nervous system (CNS) defects (alcoholism, migraine), cardiovascular system defects (aortic aneurysm, susceptibility to myocardial infarction, aortic valve sclerosis, cardiovascular disease, coronary artery disease, hypertension), hematological system defects (deep vein thrombosis), immune and inflammation diseases (Graves' Disease, arthritis, multiple sclerosis, cirrhosis), susceptibility to infection (hepatitis B, chronic liver disease), metabolic defects (bone density, cholestasis, hypospadias, obesity, osteoarthritis, osteopenia, osteoporosis), neurological defects (Alzheimer's disease, Parkinson's disease, migraine, vertigo), psychiatric defects (anorexia nervosa, attention deficit hyperactivity disorder (ADHD), dementia, major depressive disorder, psychosis) and reproductive defects (age of menarche, endometriosis, infertility).

In some embodiments, compounds disclosed herein are used in the treatment of an estrogen receptor dependent or estrogen receptor mediated disease or condition in mammal.

In some embodiments, compounds disclosed herein are used to treat cancer in a mammal. In some embodiments, the cancer is breast cancer, ovarian cancer, endometrial cancer, prostate cancer, or uterine cancer. In some embodiments, the cancer is breast cancer, lung cancer, ovarian cancer, endometrial cancer, prostate cancer, or uterine cancer. In some embodiments, the cancer is breast cancer. In some embodiments, the cancer is a hormone dependent cancer. In some embodiments, the cancer is an estrogen receptor dependent cancer. In some embodiments, the cancer is an estrogen-sensitive cancer. In some embodiments, the cancer is resistant to anti-hormonal treatment. In some embodiments, the cancer is an estrogen-sensitive cancer or an estrogen receptor dependent cancer that is resistant to anti-hormonal treatment. In some embodiments, the cancer is a hormone-sensitive cancer or a hormone receptor dependent cancer that is resistant to anti-hormonal treatment. In some embodiments, anti-hormonal treatment includes treatment with at least one agent selected from tamoxifen, fulvestrant, steroidal aromatase inhibitors, and non-steroidal aromatase inhibitors.

In some embodiments, compounds disclosed herein are used to treat hormone receptor positive metastatic breast cancer in a postmenopausal woman with disease progression following anti-estrogen therapy.

In some embodiments, compounds disclosed herein are used to treat a hormonal dependent benign or malignant disease of the breast or reproductive tract in a mammal. In some embodiments, the benign or malignant disease is breast cancer.

In some embodiments, the compound used in any of the methods described herein is an estrogen receptor degrader; is an estrogen receptor antagonist; has minimal or negligible estrogen receptor agonist activity; or combinations thereof.

In some embodiments, methods of treatment with compounds described herein include a treatment regimen that includes administering radiation therapy to the mammal.

In some embodiments, methods of treatment with compounds described herein include administering the compound prior to or following surgery.

In some embodiments, methods of treatment with compounds described herein include administering to the mammal at least one additional anti-cancer agent.

In some embodiments, compounds disclosed herein are used to treat cancer in a mammal, wherein the mammal is chemotherapy-naïve.

In some embodiments, compounds disclosed herein are used in the treatment of cancer in a mammal. In some embodiments, compounds disclosed herein are used to treat cancer in a mammal, wherein the mammal is being treated for cancer with at least one anti-cancer agent. In one embodiment, the cancer is a hormone refractory cancer.

In some embodiments, compounds disclosed herein are used in the treatment or prevention of diseases or conditions of the uterus in a mammal. In some embodiments, the disease or condition of the uterus is leiomyoma, uterine leiomyoma, endometrial hyperplasia, or endometriosis. In some embodiments, the disease or condition of the uterus is a cancerous disease or condition of the uterus. In some other embodiments, the disease or condition of the uterus is a non-cancerous disease or condition of the uterus.

In some embodiments, compounds disclosed herein are used in the treatment of endometriosis in a mammal.

In some embodiments, compounds disclosed herein are used in the treatment of leiomyoma in a mammal. In some embodiments, the leiomyoma is a uterine leiomyoma, esophageal leiomyoma, cutaneous leiomyoma, or small bowel leiomyoma. In some embodiments, compounds disclosed herein are used in the treatment of fibroids in a mammal. In some embodiments, compounds disclosed herein are used in the treatment of uterine fibroids in a mammal.

Tetrahydro-pyrido[3,4-b]indol-1-yl Compounds

The present invention provides tetrahydro-pyrido[3,4-b]indol-1-yl compounds of Formula I, including Formulas Ia-If, and pharmaceutical formulations thereof, which are potentially useful in the treatment of diseases, conditions and/or disorders modulated by Estrogen Receptor alpha (ERa).

Formula I compounds have the structure:

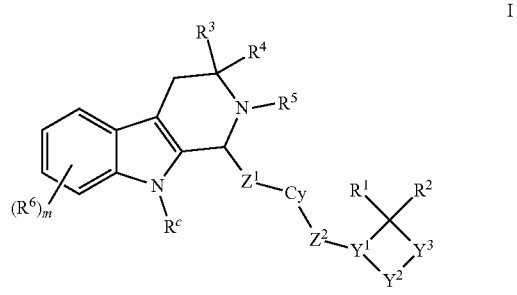

and stereoisomers, tautomers, or pharmaceutically acceptable salts thereof, wherein:

$Y^1$ is $CR^b$ or N;
$Y^2$ is —($CH_2$)—, —($CH_2CH_2$)— or $NR^a$;
$Y^3$ is $NR^a$ or $C(R^b)_2$;
where one of $Y^1$, $Y^2$ and $Y^3$ is N or $NR^a$;
$R^a$ is selected from H, $C_1$-$C_6$ alkyl, $C_2$-$C_8$ alkenyl, propargyl, $C_3$-$C_6$ cycloalkyl, and $C_3$-$C_6$ heterocyclyl, optionally substituted with one or more groups independently selected from F, Cl, Br, I, CN, OH, $OCH_3$, and $SO_2CH_3$;
$R^b$ is independently selected from H, —O($C_1$-$C_3$ alkyl), $C_1$-$C_6$ alkyl, $C_2$-$C_8$ alkenyl, propargyl, —($C_1$-$C_6$ alkyldiyl)-($C_3$-$C_6$ cycloalkyl), $C_3$-$C_6$ cycloalkyl, and $C_3$-$C_6$ heterocyclyl, optionally substituted with one or more groups independently selected from F, Cl, Br, I, CN, —$CH_2F$, —$CHF_2$, —$CF_3$, —$CH_2CF_3$, —$CH_2CHF_2$, —$CH_2CH_2F$, OH, $OCH_3$, and $SO_2CH_3$;
$R^c$ is selected from H, $C_1$-$C_6$ alkyl, allyl, propargyl, optionally substituted with one or more groups independently selected from F, Cl, Br, I, CN, OH, $OCH_3$, and $SO_2CH_3$;
$Z^1$ is selected from $CR^aR^b$, C(O), and a bond;
Cy is selected from $C_6$-$C_{20}$ aryldiyl, $C_3$-$C_{12}$ carbocyclyldiyl, $C_2$-$C_{20}$ heterocyclyldiyl, and $C_1$-$C_{20}$ heteroaryldiyl;
$Z^2$ is selected from O, S, $NR^a$, $C_1$-$C_6$ alkyldiyl, $C_1$-$C_6$ fluoroalkyldiyl, O—($C_1$-$C_6$ alkyldiyl), O—($C_1$-$C_6$ fluoroalkyldiyl), C(O), and a bond;
$R^1$, $R^2$, $R^3$ and $R^4$ are independently selected from H, F, Cl, Br, I, —CN, —$CH_3$, —$CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CH_2NH_2$, —$CH_2NHSO_2CH_3$, —$CH_2NHCH_3$, —$CH_2N(CH_3)_2$, —$CF_3$, —$CH_2CF_3$, —$CH_2CHF_2$, —$CH(CH_3)CN$, —$C(CH_3)_2CN$, —$CH_2CN$, —$CO_2H$, —$COCH_3$, —$CO_2CH_3$, —$CO_2C(CH_3)_3$, —$COCH(OH)CH_3$, —$CONH_2$, —$CONHCH_3$, —$CONHCH_2CH_3$, —$CONHCH(CH_3)_2$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, —$S(O)_3H$, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino;

R⁵ is selected from H, $C_1$-$C_9$ alkyl, $C_3$-$C_9$ cycloalkyl, $C_3$-$C_9$ heterocycle, $C_6$-$C_9$ aryl, $C_6$-$C_9$ heteroaryl, —($C_1$-$C_6$ alkyldiyl)-($C_3$-$C_9$ cycloalkyl), —($C_1$-$C_6$ alkyldiyl)-($C_3$-$C_9$ heterocycle), C(O)$R^b$, C(O)N$R^a$, SO₂$R^a$, and SO₂N$R^a$, optionally substituted with one or more of halogen, CN, O$R^a$, N($R^a$)₂, $C_1$-$C_9$ alkyl, $C_3$-$C_9$ cycloalkyl, $C_3$-$C_9$ heterocycle, $C_6$-$C_9$ aryl, $C_6$-$C_9$ heteroaryl, C(O)$R^b$, C(O)N$R^a$, SO₂$R^a$, and SO₂N$R^a$;

R⁶ is selected from F, Cl, Br, I, —CN, —CH₃, —CH₂CH₃, —CH(CH₃)₂, —CH₂CH(CH₃)₂, —CH₂OH, —CH₂OCH₃, —CH₂CH₂OH, —C(CH₃)₂OH, —CH(OH)CH(CH₃)₂, —C(CH₃)₂CH₂OH, —CH₂CH₂SO₂CH₃, —CH₂OP(O)(OH)₂, —CH₂F, —CHF₂, —CH₂NH₂, —CH₂NHSO₂CH₃, —CH₂NHCH₃, —CH₂N(CH₃)₂, —CF₃, —CH₂CF₃, —CH₂CHF₂, —CH(CH₃)CN, —C(CH₃)₂CN, —CH₂CN, —CO₂H, —COCH₃, —CO₂CH₃, —CO₂C(CH₃)₃, —COCH(OH)CH₃, —CONH₂, —CONHCH₃, —CONHCH₂CH₃, —CONHCH(CH₃)₂, —CON(CH₃)₂, —C(CH₃)₂CONH₂, —NH₂, —NHCH₃, —N(CH₃)₂, —NHCOCH₃, —N(CH₃)COCH₃, —NHS(O)₂CH₃, —N(CH₃)C(CH₃)₂CONH₂, —N(CH₃)CH₂CH₂S(O)₂CH₃, —NO₂, =O, —OH, —OCH₃, —OCH₂CH₃, —OCH₂CH₂OCH₃, —OCH₂CH₂OH, —OCH₂CH₂N(CH₃)₂, —OP(O)(OH)₂, —S(O)₂N(CH₃)₂, —SCH₃, —S(O)₂CH₃, —S(O)₃H, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino; and m is selected from 0, 1, 2, 3, and 4;

where alkyldiyl, fluoroalkyldiyl, aryldiyl, carbocyclyldiyl, heterocyclyldiyl, and heteroaryldiyl are optionally substituted with one or more groups independently selected from F, Cl, Br, I, —CN, —CH₃, —CH₂CH₃, —CH(CH₃)₂, —CH₂CH(CH₃)₂, —CH₂OH, —CH₂OCH₃, —CH₂CH₂OH, —C(CH₃)₂OH, —CH(OH)CH(CH₃)₂, —C(CH₃)₂CH₂OH, —CH₂CH₂SO₂CH₃, —CH₂OP(O)(OH)₂, —CH₂F, —CHF₂, —CF₃, —CH₂CF₃, —CH₂CHF₂, —CH₂CH₂F, —CH(CH₃)CN, —C(CH₃)₂CN, —CH₂CN, —CH₂NH₂, —CH₂NHSO₂CH₃, —CH₂NHCH₃, —CH₂N(CH₃)₂, —CO₂H, —COCH₃, —CO₂CH₃, —CO₂C(CH₃)₃, —COCH(OH)CH₃, —CONH₂, —CONHCH₃, —CON(CH₃)₂, —C(CH₃)₂CONH₂, —NH₂, —NHCH₃, —N(CH₃)₂, —NHCOCH₃, —N(CH₃)COCH₃, —NHS(O)₂CH₃, —N(CH₃)C(CH₃)₂CONH₂, —N(CH₃)CH₂CH₂S(O)₂CH₃, —NO₂, =O, —OH, —OCH₃, —OCH₂CH₃, —OCH₂CH₂OCH₃, —OCH₂CH₂OH, —OCH₂CH₂N(CH₃)₂, —OP(O)(OH)₂, —S(O)₂N(CH₃)₂, —SCH₃, —S(O)₂CH₃, —S(O)₃H, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino.

Formula Ia-k compounds have the structures:

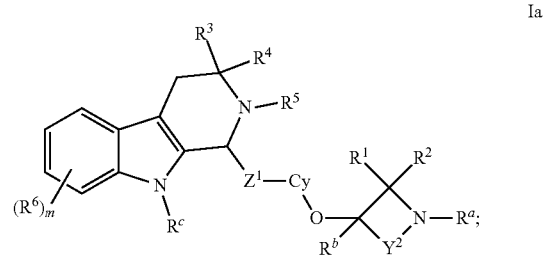

Ia

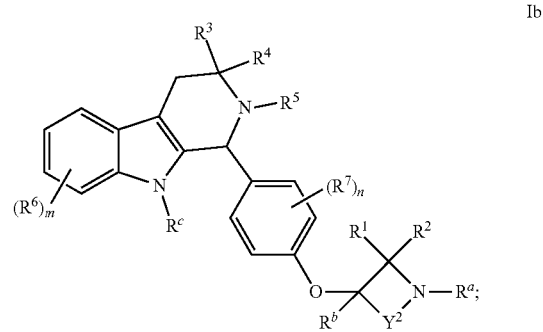

Ib wherein R⁷ is F, Cl, Br, I, —CN, —CH₃, —CH₂CH₃, —CH(CH₃)₂, —CH₂CH(CH₃)₂, —CH₂OH, —CH₂OCH₃, —CH₂CH₂OH, —C(CH₃)₂OH, —CH(OH)CH(CH₃)₂, —C(CH₃)₂CH₂OH, —CH₂CH₂SO₂CH₃, —CH₂OP(O)(OH)₂, —CH₂F, —CHF₂, —CH₂NH₂, —CH₂NHSO₂CH₃, —CH₂NHCH₃, —CH₂N(CH₃)₂, —CF₃, —CH₂CF₃, —CH₂CHF₂, —CH(CH₃)CN, —C(CH₃)₂CN, —CH₂CN, —CO₂H, —COCH₃, —CO₂CH₃, —CO₂C(CH₃)₃, —COCH(OH)CH₃, —CONH₂, —CONHCH₃, —CONHCH₂CH₃, —CONHCH(CH₃)₂, —CON(CH₃)₂, —C(CH₃)₂CONH₂, —NH₂, —NHCH₃, —N(CH₃)₂, —NHCOCH₃, —N(CH₃)COCH₃, —NHS(O)₂CH₃, —N(CH₃)C(CH₃)₂CONH₂, —N(CH₃)CH₂CH₂S(O)₂CH₃, —NO₂, =O, —OH, —OCH₃, —OCH₂CH₃, —OCH₂CH₂OCH₃, —OCH₂CH₂OH, —OCH₂CH₂N(CH₃)₂, —OP(O)(OH)₂, —S(O)₂N(CH₃)₂, —SCH₃, —S(O)₂CH₃, —S(O)₃H, cyclopropyl, cyclopropylamide, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morphdinomethyl, morpholino-methanone, and morpholino; and n is selected from 0, 1, 2, 3, and 4;

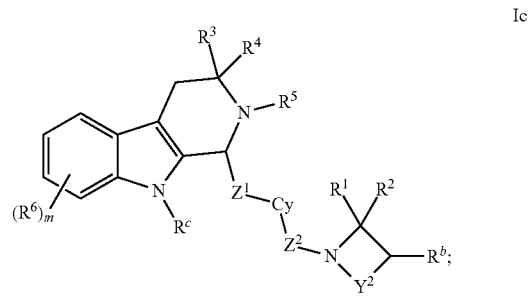

Ic

Id
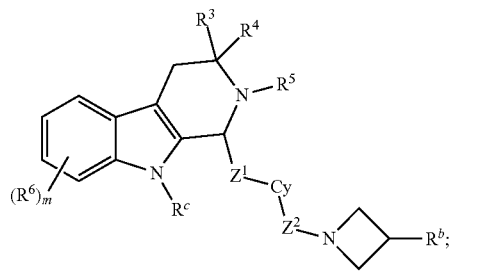

Ie
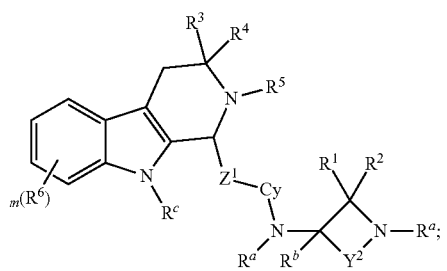

wherein R[8] is H or —CH₃;

If

Ig

Ih
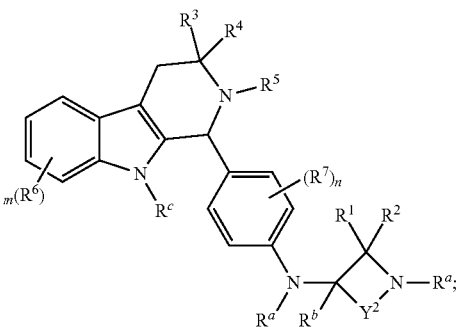

Ii
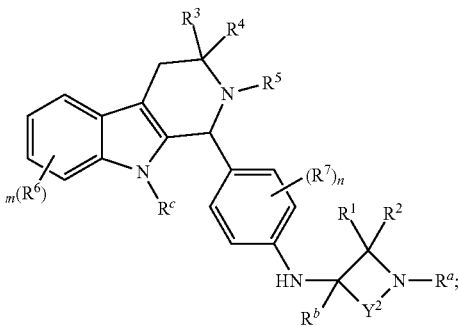

Ij

Ik
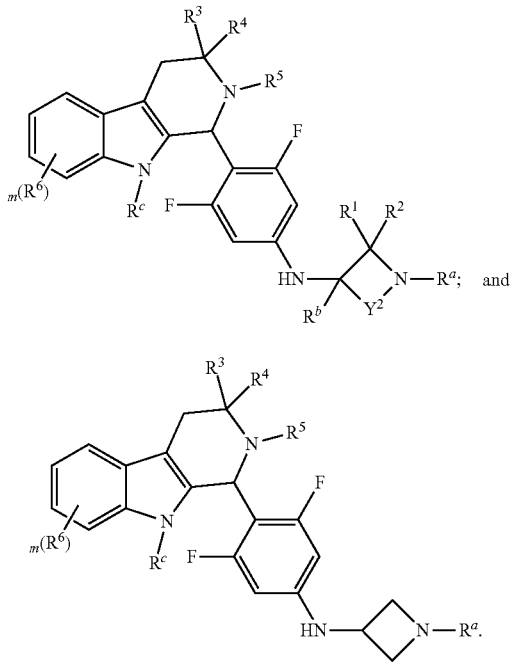

Exemplary embodiments of Formula I compounds include wherein $Y^1$ is $CR^b$ and $Y^3$ is $NR^a$.

Exemplary embodiments of Formula I compounds include wherein $Y^1$ is N and $Y^3$ is $C(R^b)_2$.

Exemplary embodiments of Formula I compounds include wherein $Y^2$ is —(CH₂)—.

Exemplary embodiments of Formula I compounds include wherein $Y^2$ is —(CH₂CH₂)—.

Exemplary embodiments of Formula I compounds include wherein $R^c$ is H.

Exemplary embodiments of Formula I compounds include wherein Cy is $C_6$-$C_{20}$ aryldiyl, $C_6$-$C_{20}$ aryldiyl is phenyldiyl, and phenyldiyl is substituted with one or more F.

Exemplary embodiments of Formula I compounds include wherein $R^1$ and $R^2$ are H.

Exemplary embodiments of Formula I compounds include wherein $R^3$ is H, and $R^4$ is —$CH_3$.

Exemplary embodiments of Formula I compounds include wherein $R^5$ is $C_1$-$C_6$ fluoroalkyl.

Exemplary embodiments of Formula I compounds include wherein m is 0.

The present invention also provides tetrahydro-pyrido[3,4-b]indol-1-yl compounds of Formula XI, including Formula XIa, and pharmaceutical formulations thereof, which are potentially useful in the treatment of diseases, conditions and/or disorders modulated by Estrogen Receptor alpha (ERa).

In some embodiments, a compound of the invention has the following structure of Formula (XI):

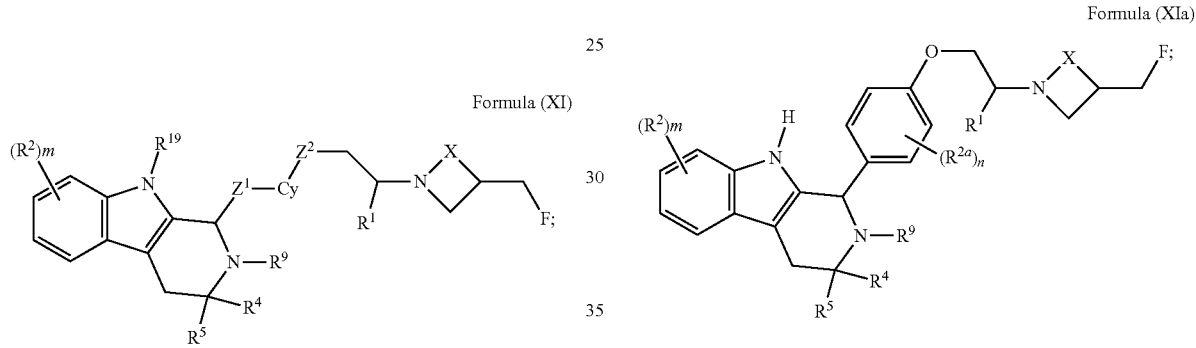

Formula (XI)

Formula (XIa)

wherein:
$Z^1$ and $Z^2$ are independently selected from —O—, —($CH_2$)—, —C(O)—, or a bond;
Cy is $C_6$-$C_{20}$ aryl, $C_3$-$C_{12}$ carbocyclyl, $C_2$-$C_{20}$ heterocyclyl, or $C_1$-$C_{20}$ heteroaryl;
X is —($CH_2$)— or —($CH_2CH_2$)—;
$R^1$ is selected from H, F, Cl, —CN, —$CH_2OH$, —CH($CH_3$)OH, —C($CH_3$)$_2$OH, —CH($CF_3$)OH, —$CH_2F$, —$CHF_2$, —$CH_2CHF_2$, —$CF_3$, —$CH_3$, —C(O)$NH_2$, —C(O)$NHCH_3$, and —C(O)N($CH_3$)$_2$;
each $R^2$ is independently selected from halogen, —CN, —$OR^{10}$, —$NR^{13}R^{14}$, $C_1$-$C_6$ alkyl, $C_3$-$C_8$ carbocyclyl, —$C_1$-$C_6$ alkyl-OH, $C_3$-$C_8$ carbocyclyl-OH, —$OC_2$—$C_6$ alkyl-OH, $C_1$-$C_6$ fluoroalkyl, $C_3$-$C_8$ fluorocarbocyclyl, —C(=O)$OR^{12}$, —NHC(=O)$R^{11}$, —C(=O)$NHR^{12}$, —$SO_2R^{11}$, —$NHSO_2R^{11}$, and —$SO_2NHR^{12}$;
$R^4$ and $R^5$ are each independently selected from $C_1$-$C_6$ alkyl, $C_3$-$C_8$ carbocyclyl, —$C_1$-$C_6$ alkyl-OH, $C_3$-$C_8$ carbocyclyl-OH, $C_1$-$C_6$ fluoroalkyl, $C_3$-$C_8$ fluorocarbocyclyl, —C(=O)$OR^{12}$;
$R^9$ is independently selected from $C_1$-$C_6$ alkyl, $C_3$-$C_8$ carbocyclyl, —$C_1$-$C_6$ alkyl-OH, $C_3$-$C_8$ carbocyclyl-OH, $C_1$-$C_6$ fluoroalkyl, $C_3$-$C_8$ fluorocarbocyclyl, $C_2$-$C_9$ heterocyclyl, $C_6$-$C_{10}$ aryl, and $C_1$-$C_{10}$ heteroaryl;
$R^{19}$ is independently selected from H, $C_1$-$C_6$ alkyl, $C_3$-$C_8$ carbocyclyl, —$C_1$-$C_6$ alkyl-OH, $C_3$-$C_8$ carbocyclyl-OH, $C_1$-$C_6$ fluoroalkyl, $C_3$-$C_8$ fluorocarbocyclyl, —C(=O)$OR^{12}$, —C(=O)$NHR^{12}$, —$SO_2R^{11}$, —$NHSO_2R^{11}$, —$SO_2NHR^{12}$, $C_6$-$C_{10}$ aryl, and $C_1$-$C_{10}$ heteroaryl;
each $R^{10}$ is independently selected from H, $C_1$-$C_4$ alkyl, and $C_1$-$C_4$ fluoroalkyl;
each $R^{11}$ is independently selected from $C_1$-$C_4$ alkyl and $C_1$-$C_4$ fluoroalkyl;
each $R^{12}$ is independently selected from H, $C_1$-$C_4$ alkyl, and $C_1$-$C_4$ fluoroalkyl;
each $R^{13}$ and each $R^{14}$ are independently selected from H and $C_1$-$C_4$ alkyl; and
m is 0, 1, 2 or 3;
or a pharmaceutically acceptable salt, solvate or prodrug thereof.

In some embodiments, the compound of Formula (XI) has the structure of Formula (XIa):

wherein $R^{2a}$ is independently H or F, n is 0, 1 or 2, and $R^4$ and $R^5$ are independently H or methyl.

In some embodiments is a compound of Formula (XI) wherein $Z^1$ is a bond. In some embodiments is a compound of Formula (XI) wherein $Z^1$ is —O—. In some embodiments is a compound of Formula (XI) wherein $Z^1$ is —($CH_2$)—. In some embodiments is a compound of Formula (XI) wherein $Z^1$ is —C(O)—. In some embodiments is a compound of Formula (XI) wherein $Z^2$ is a bond. In some embodiments is a compound of Formula (XI) wherein $Z^2$ is —O—. In some embodiments is a compound of Formula (XI) wherein $Z^2$ is —($CH_2$). In some embodiments is a compound of Formula (XI) wherein $Z^2$ is —C(O)—. In some embodiments is a compound of Formula (XI) wherein Cy is $C_6$-$C_{20}$ aryl. In some embodiments is a compound of Formula (XI) wherein Cy is phenyl. In some embodiments is a compound of Formula (XI) wherein Cy is $C_3$-$C_{12}$ carbocyclyl. In some embodiments is a compound of Formula (XI) wherein Cy is cyclohexyl. In some embodiments is a compound of Formula (XI) wherein Cy is $C_2$-$C_{20}$ heterocyclyl. In some embodiments is a compound of Formula (XI) wherein Cy is pyrazinyl. In some embodiments is a compound of Formula (XT) wherein Cy is piperidinyl. In some embodiments is a compound of Formula (XI) wherein Cy is $C_1$-$C_{20}$heteroaryl. In some embodiments is a compound of Formula (XI) wherein Cy is thiazolyl. In some embodiments is a compound of Formula (XI) wherein Cy is oxazolyl. In some embodiments is a compound of Formula (XI) wherein Cy is pyridyl. In some embodiments is a compound of Formula (XI) wherein $R^1$ is H. In some embodiments is a compound of Formula (XI) wherein $R^1$ is —$CH_3$. In some embodiments is a compound of Formula (XI) wherein X is —($CH_2$)—. In some embodiments is a compound of Formula (XI) wherein X is —($CH_2$)— and $R^1$ is H. In some embodiments is a compound of Formula (XI) wherein X is —($CH_2CH_2$)—. In some embodiments is a compound of Formula (XI) wherein X is —($CH_2CH_2$)— and $R^1$ is H. In some embodiments is a compound of Formula (XI) wherein X is —($CH_2CH_2$)— and $R^1$ is —$CH_3$.

In some embodiments is a compound of Formula (XI) wherein $Z^1$ is a bond, $Z^2$ is —O—, Cy is phenyl, X is —($CH_2$)—, and $R^1$ is H. In some embodiments is a compound of Formula (XI) wherein $Z^1$ is a bond, $Z^2$ is —O—, Cy is phenyl, X is —($CH_2CH_2$)—, and $R^1$ is H. In some embodiments is a compound of Formula (XI) wherein $Z^1$ is a bond, $Z^2$ is —O—, Cy is phenyl, X is —($CH_2CH_2$)—, and $R^1$ is —$CH_3$.

Biological Evaluation

The relative efficacies of Formula I compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". Determination of $IC_{50}$ values can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Cell proliferation, cytotoxicity, and cell viability of the Formula I compounds can be measure by the CellTiter-Glo® Luminescent Cell Viability Assay (Promega Corp.). The CellTiter-Glo® Luminescent Cell Viability Assay is a homogeneous method of determining the number of viable cells in culture based on quantitation of the ATP present, an indicator of metabolically active cells. The CellTiter-Glo® Assay is designed for use with multiwell formats, making it ideal for automated high-throughput screening (HTS), cell proliferation and cytotoxicity assays. The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

All of the exemplary Formula I compounds in Tables 1 and 2 were made and characterized by LCMS $[M+H]^+$ (liquid chromatography mass spectroscopy) with detection of parent ion. All of the exemplary Formula I compounds in Tables 1 and 2 were tested for binding to ERa (Estrogen Receptor alpha) and biological activity according to the assays, protocols, and procedures of Examples 901-907. ER-alpha MCF7 HCS $S_{inf}$ (%) values in Table 1 were measured by the Breast Cancer Cell ERa High Content Fluorescence Imaging Degradation Assay of Example 901. ER-alpha MCF7 HCS $EC_{50}$ (μM) values in Tables 1 and 2 were measured by the in vitro cell proliferation assays described in Examples 902 and 903. The rat uterine wet weight assays of Examples 906 and 907 allow rapid determination of compound antagonist activity in an ER responsive tissue (immature rat uterus) while competing against the native ER ligand estradiol, i.e. antagonist mode (Ashby, J.; et al (1997) Regulatory toxicology and pharmacology: RTP, 25 (3):226-31). Exemplary Formula I compounds in Tables 1 and 2 have the following structures, corresponding names (ChemBioDraw, Version 12.0.2, CambridgeSoft Corp., Cambridge Mass.), and biological activity. Where more than one name is associated with a Formula I compound or intermediate, the chemical structure shall define the compound.

TABLE 1

| No. | Structure | Name | ER-alpha MCF7 HCS $EC_{50}$ (μM) | ER-alpha MCF7 HCS $S_{inf}$ (%) |
|---|---|---|---|---|
| 101 | 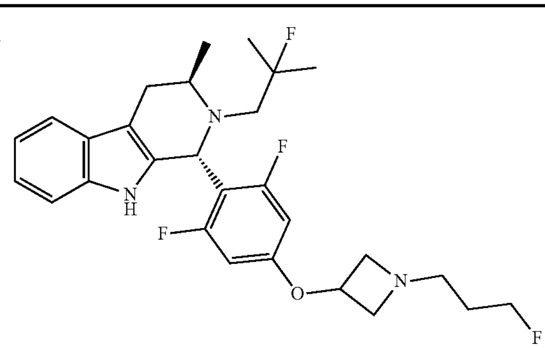 | (1R,3R)-1-(2,6-difluoro-4-((1-(3-fluoropropyl)azetidin-3-yl)oxy)phenyl)-2-(2-fluoro-2-methylpropyl)-3-methyl-2,3,4,9-tetrahydro-1H-pyrido[3,4-b]indole | 0.000049 | −100 |

TABLE 1-continued

| No. | Structure | Name | ER-alpha MCF7 HCS EC$_{50}$ (μM) | ER-alpha MCF7 HCS S$_{inf}$ (%) |
|---|---|---|---|---|
| 102 | 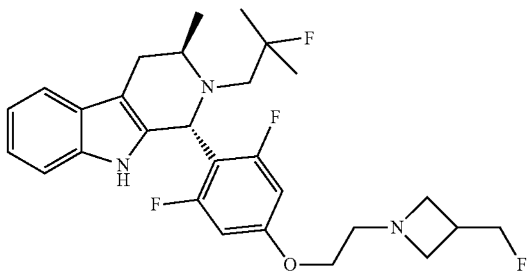 [SMILES: C[C@@H]1Cc2c([nH]c3ccccc23)[C@@H](c2c(F)cc(OCCN3CC(CF)C3)cc2F)N1CC(C)(C)F] | (1R,3R)-1-(2,6-difluoro-4-(2-(3-(fluoromethyl)azetidin-1-yl)ethoxy)phenyl)-2-(2-fluoro-2-methylpropyl)-3-methyl-2,3,4,9-tetrahydro-1H-pyrido[3,4-b]indole | 0.000014 | −98.9% |
| 103 | 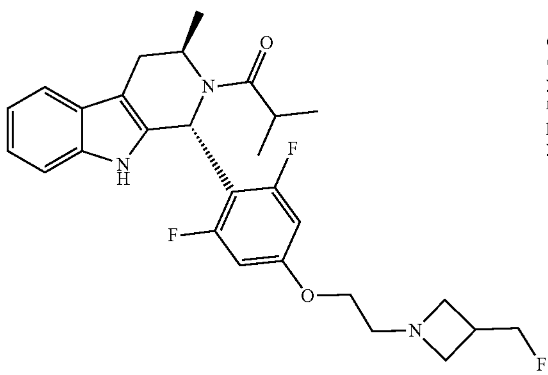 [SMILES: CC(C)C(=O)N1[C@H](c2c(F)cc(OCCN3CC(CF)C3)cc2F)c2[nH]c3ccccc3c2C[C@H]1C] | 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-methylpropan-1-one | 0.00011 | −91.8% |
| 104 | 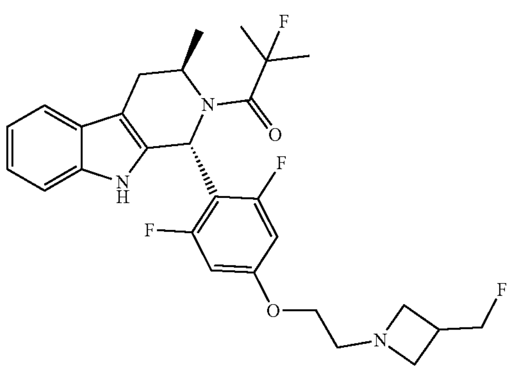 [SMILES: C[C@@H]1Cc2c([nH]c3ccccc23)[C@@H](c2c(F)cc(OCCN3CC(CF)C3)cc2F)N1C(=O)C(C)(C)F] | 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-fluoro-2-methylpropan-1-one | 0.000043 | −95.4% |
| 105 | 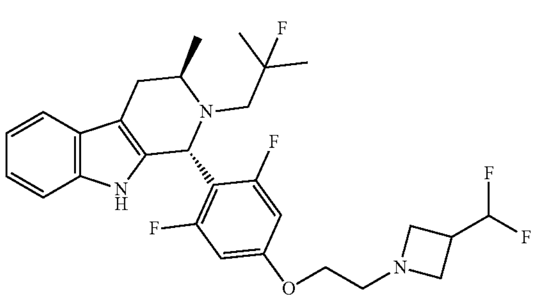 [SMILES: C[C@@H]1Cc2c([nH]c3ccccc23)[C@@H](c2c(F)cc(OCCN3CC(C(F)F)C3)cc2F)N1CC(C)(C)F] | (1R,3R)-1-(4-(2-(3-(difluoromethyl)azetidin-1-yl)ethoxy)-2,6-difluorophenyl)-2-(2-fluoro-2-methylpropyl)-3-methyl-2,3,4,9-tetrahydro-1H-pyrido[3,4-b]indole | 0.000027 | −94% |

TABLE 1-continued

| No. | Structure | Name | ER-alpha MCF7 HCS EC$_{50}$ (μM) | ER-alpha MCF7 HCS S$_{inf}$ (%) |
|---|---|---|---|---|
| 106 | 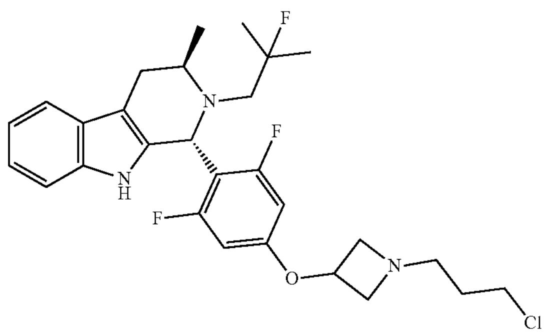 [SMILES: C[C@@H]1Cc2c([nH]c3ccccc23)[C@@H](c2c(F)cc(OC3CN(CCCCl)C3)cc2F)N1CC(C)(C)F] | (1R,3R)-1-(4-((1-(3-chloropropyl)azetidin-3-yl)oxy)-2,6-difluorophenyl)-2-(2-fluoro-2-methylpropyl)-3-methyl-2,3,4,9-tetrahydro-1H-pyrido[3,4-b]indole | 0.000142 | −90.4% |
| 107 | 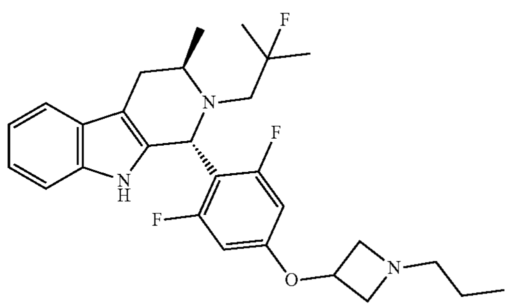 [SMILES: CCCN1CC(Oc2cc(F)c([C@@H]3c4[nH]c5ccccc5c4C[C@@H](C)N3CC(C)(C)F)c(F)c2)C1] | (1R,3R)-1-(2,6-difluoro-4-((1-propylazetidin-3-yl)oxy)phenyl)-2-(2-fluoro-2-methylpropyl)-3-methyl-2,3,4,9-tetrahydro-1H-pyrido[3,4-b]indole | 0.000024 | −97.6% |
| 108 | 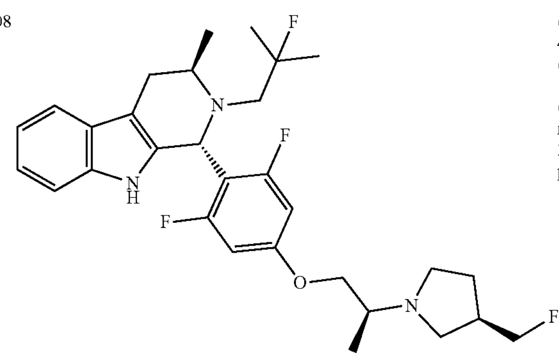 | (1R,3R)-1-(2,6-difluoro-4-((S)-2-((R)-3-(fluoromethyl)pyrrolidin-1-yl)propoxy)phenyl)-2-(2-fluoro-2-methylpropyl)-3-methyl-2,3,4,9-tetrahydro-1H-pyrido[3,4-b]indole | 0.00011 | −79.3% |
| 109 | 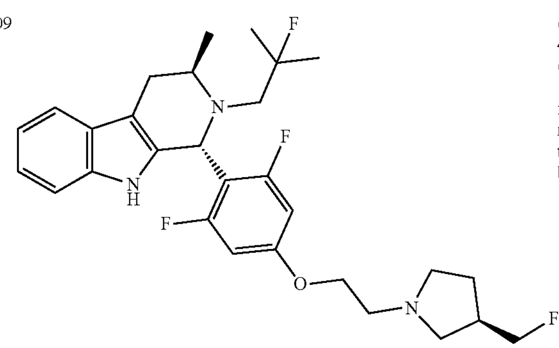 | (1R,3R)-1-(2,6-difluoro-4-(2-((R)-3-(fluoromethyl)pyrrolidin-1-yl)ethoxy)phenyl)-2-(2-fluoro-2-methylpropyl)-3-methyl-2,3,4,9-tetrahydro-1H-pyrido[3,4-b]indole | 0.000050 | −86.5% |

TABLE 1-continued

| No. | Structure | Name | ER-alpha MCF7 HCS EC$_{50}$ (μM) | ER-alpha MCF7 HCS S$_{inf}$ (%) |
|---|---|---|---|---|
| 110 | | | | |
| 111 | 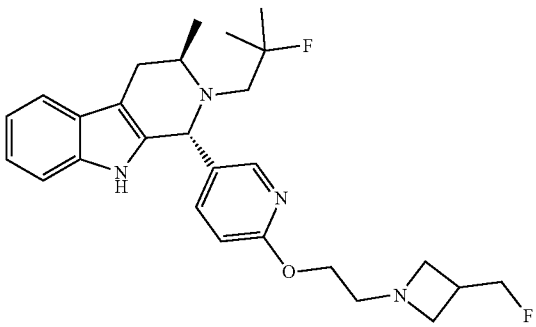 [SMILES: C[C@@H]1Cc2c([nH]c3ccccc23)[C@@H](c2ccc(OCCN3CC(CF)C3)nc2)N1CC(C)(C)F] | (1R,3R)-2-(2-fluoro-2-methylpropyl)-1-(6-(2-(3-(fluoromethyl)azetidin-1-yl)ethoxy)pyridin-3-yl)-3-methyl-2,3,4,9-tetrahydro-1H-pyrido[3,4-b]indole | 0.000898 | −96.8 |
| 112 | 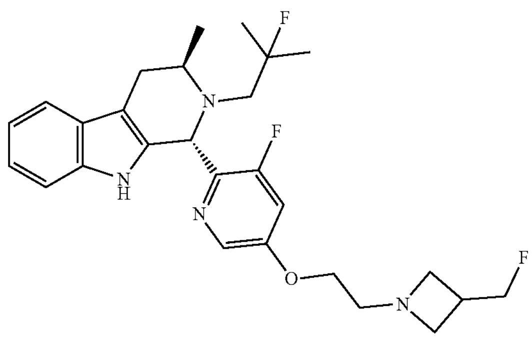 [SMILES: C[C@@H]1Cc2c([nH]c3ccccc23)[C@@H](c2ncc(OCCN3CC(CF)C3)cc2F)N1CC(C)(C)F] | (1S,3R)-2-(2-fluoro-2-methylpropyl)-1-(3-fluoro-5-(2-(3-(fluoromethyl)azetidin-1-yl)ethoxy)pyridin-2-yl)-3-methyl-2,3,4,9-tetrahydro-1H-pyrido[3,4-b]indole | 0.000092 | −93.9 |
| 113 | 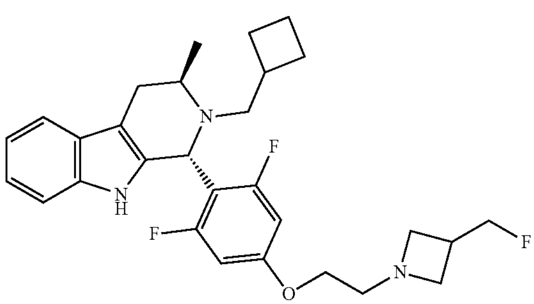 [SMILES: C[C@@H]1Cc2c([nH]c3ccccc23)[C@@H](c2c(F)cc(OCCN3CC(CF)C3)cc2F)N1CC1CCC1] | (1R,3R)-2-(cyclobutylmethyl)-1-(2,6-difluoro-4-(2-(3-(fluoromethyl)azetidin-1-yl)ethoxy)phenyl)-3-methyl-2,3,4,9-tetrahydro-1H-pyrido[3,4-b]indole | 0.00618 | −94.8 |
| 114 | 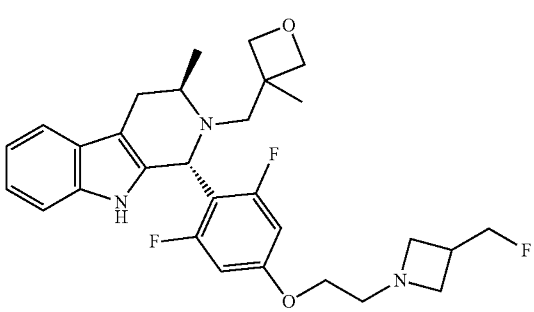 [SMILES: C[C@@H]1Cc2c([nH]c3ccccc23)[C@@H](c2c(F)cc(OCCN3CC(CF)C3)cc2F)N1CC1(C)COC1] | (1R,3R)-1-(2,6-difluoro-4-(2-(3-(fluoromethyl)azetidin-1-yl)ethoxy)phenyl)-3-methyl-2-((3-methyloxetan-3-yl)methyl)-2,3,4,9-tetrahydro-1H-pyrido[3,4-b]indole | 0.000715 | −97.8 |

TABLE 1-continued

| No. | Structure | Name | ER-alpha MCF7 HCS EC$_{50}$ (μM) | ER-alpha MCF7 HCS S$_{inf}$ (%) |
|---|---|---|---|---|
| 115 | 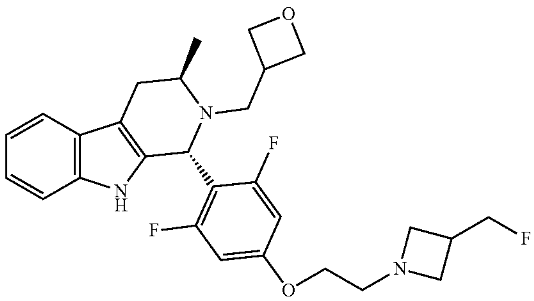 [SMILES: C[C@@H]1Cc2c([nH]c3ccccc23)[C@@H](c2c(F)cc(OCCN3CC(CF)C3)cc2F)N1CC1COC1] | (1R,3R)-1-(2,6-difluoro-4-(2-(3-(fluoromethyl)azetidin-1-yl)ethoxy)phenyl)-3-methyl-2-(oxetan-3-ylmethyl)-2,3,4,9-tetrahydro-1H-pyrido[3,4-b]indole | 0.0231 | −95.5 |
| 116 | 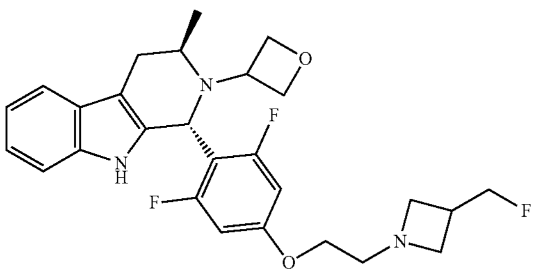 [SMILES: C[C@@H]1Cc2c([nH]c3ccccc23)[C@@H](c2c(F)cc(OCCN3CC(CF)C3)cc2F)N1C1COC1] | (1R,3R)-1-(2,6-difluoro-4-(2-(3-(fluoromethyl)azetidin-1-yl)ethoxy)phenyl)-3-methyl-2-(oxetan-3-yl)-2,3,4,9-tetrahydro-1H-pyrido[3,4-b]indole | 0.0414 | −85 |
| 117 | 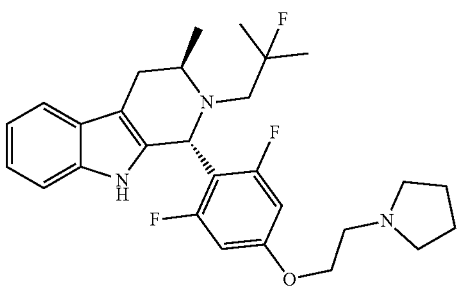 [SMILES: C[C@@H]1Cc2c([nH]c3ccccc23)[C@@H](c2c(F)cc(OCCN3CCCC3)cc2F)N1CC(C)(C)F] | (1R,3R)-1-(2,6-difluoro-4-(2-(pyrrolidin-1-yl)ethoxy)phenyl)-2-(2-fluoro-2-methylpropyl)-3-methyl-2,3,4,9-tetrahydro-1H-pyrido[3,4-b]indole | 0.000171 | −71.7 |
| 118 | 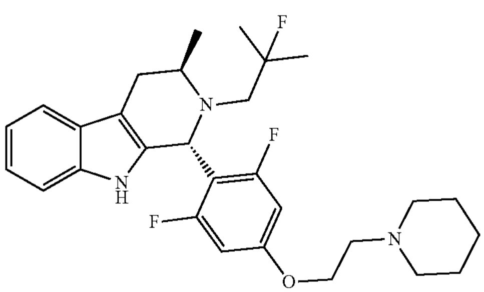 [SMILES: C[C@@H]1Cc2c([nH]c3ccccc23)[C@@H](c2c(F)cc(OCCN3CCCCC3)cc2F)N1CC(C)(C)F] | (1R,3R)-1-(2,6-difluoro-4-(2-(piperidin-1-yl)ethoxy)phenyl)-2-(2-fluoro-2-methylpropyl)-3-methyl-2,3,4,9-tetrahydro-1H-pyrido[3,4-b]indole | 0.000488 | −72.2 |
| 119 | 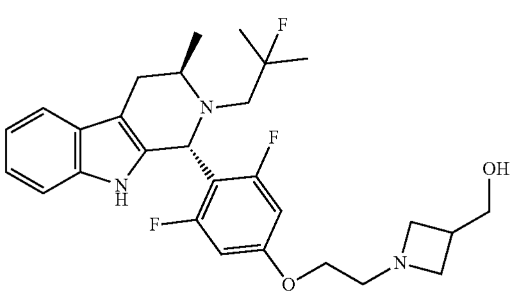 [SMILES: C[C@@H]1Cc2c([nH]c3ccccc23)[C@@H](c2c(F)cc(OCCN3CC(CO)C3)cc2F)N1CC(C)(C)F] | (1-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)azetidin-3-yl)methanol | 0.00198 | −71.3 |

TABLE 1-continued

| No. | Structure | Name | ER-alpha MCF7 HCS EC$_{50}$ (μM) | ER-alpha MCF7 HCS S$_{inf}$ (%) |
|---|---|---|---|---|
| 120 | 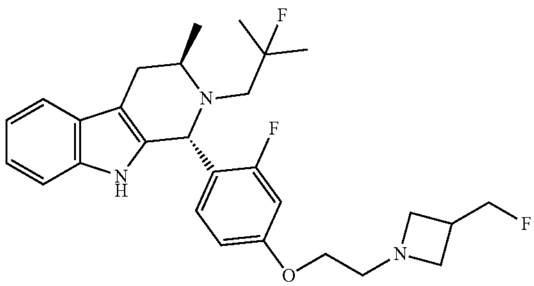 [SMILES: C[C@@H]1Cc2c([nH]c3ccccc23)[C@@H](c2ccc(OCCN3CC(CF)C3)cc2F)N1CC(C)(C)F] | (1R,3R)-2-(2-fluoro-2-methylpropyl)-1-(2-fluoro-4-(2-(3-(fluoromethyl)azetidin-1-yl)ethoxy)phenyl)-3-methyl-2,3,4,9-tetrahydro-1H-pyrido[3,4-b]indole | 0.0000562 | −96.3 |
| 121 | 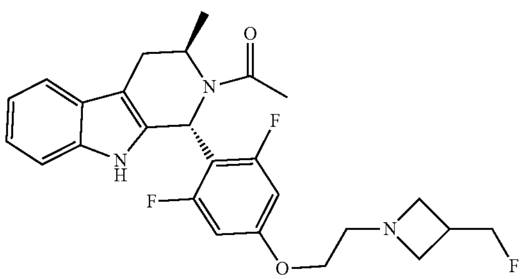 [SMILES: CC(=O)N1[C@H](c2c(F)cc(OCCN3CC(CF)C3)cc2F)c2[nH]c3ccccc3c2C[C@H]1C] | 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)ethanone | 0.008 | −91 |
| 122 | 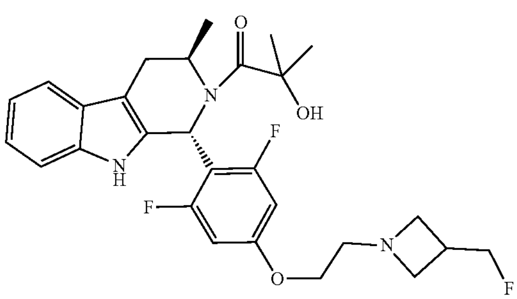 [SMILES: C[C@@H]1Cc2c([nH]c3ccccc23)[C@@H](c2c(F)cc(OCCN3CC(CF)C3)cc2F)N1C(=O)C(C)(C)O] | 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-hydroxy-2-methylpropan-1-one | 0.0014 | −97.8 |
| 123 | 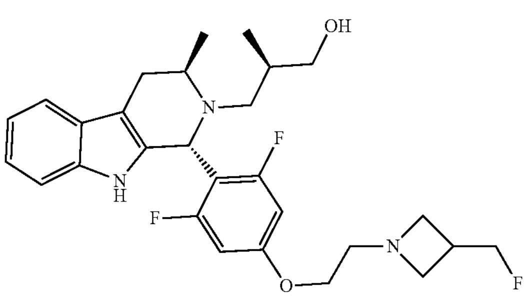 [SMILES: C[C@@H](CO)CN1[C@H](c2c(F)cc(OCCN3CC(CF)C3)cc2F)c2[nH]c3ccccc3c2C[C@H]1C] | (R)-3-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-methylpropan-1-ol | 0.00104 | −96.1 |

TABLE 1-continued

| No. | Structure | Name | ER-alpha MCF7 HCS EC$_{50}$ (μM) | ER-alpha MCF7 HCS S$_{inf}$(%) |
|---|---|---|---|---|
| 124 | 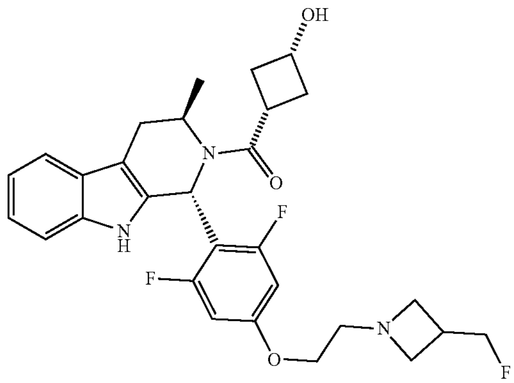 | ((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)((1s,3S)-3-hydroxycyclobutyl)methanone | 0.135 | −75 |
| 125 | 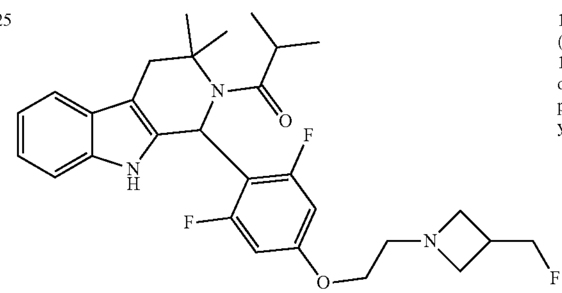 | 1-(1-(2,6-difluoro-4-(2-(3-(fluoromethyl)azetidin-1-yl)ethoxy)phenyl)-3,3-dimethyl-3,4-dihydro-1H-pyrido[3,4-b]indol-2(9H)-yl)-2-methylpropan-1-one | 0.0744 | −90 |
| 126 | 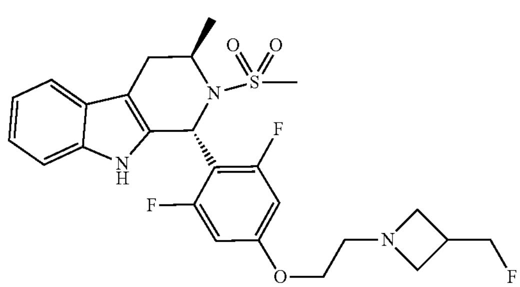 [SMILES: C[C@@H]1Cc2c([nH]c3ccccc23)[C@@H](c2c(F)cc(OCCN3CC(CF)C3)cc2F)N1S(C)(=O)=O] | (1R,3R)-1-(2,6-difluoro-4-(2-(3-(fluoromethyl)azetidin-1-yl)ethoxy)phenyl)-3-methyl-2-tetrahydro-1H-pyrido[3,4-(methylsulfonyl)-2,3,4,9-b]indole | 0.000469 | −94.4 |

TABLE 2

| No. | Structure | Name | ER-alpha MCF7 HCS EC$_{50}$ (μM) | LCMS [M + H]$^+$ |
|-----|-----------|------|----------------------------------|------------------|
| 127 | 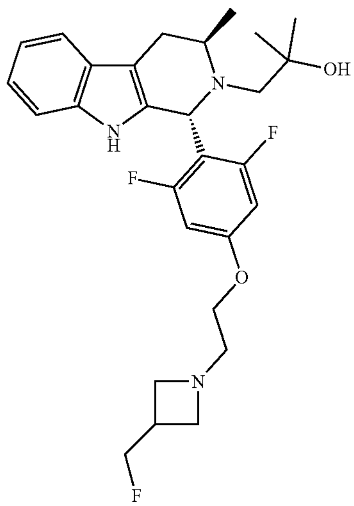 [SMILES: C[C@@H]1Cc2c([nH]c3ccccc23)[C@@H](c2c(F)cc(OCCN3CC(CF)C3)cc2F)N1CC(C)(C)O] | 1-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2-methyl-propan-2-ol | 0.000641 | 502.6 |
| 128 | 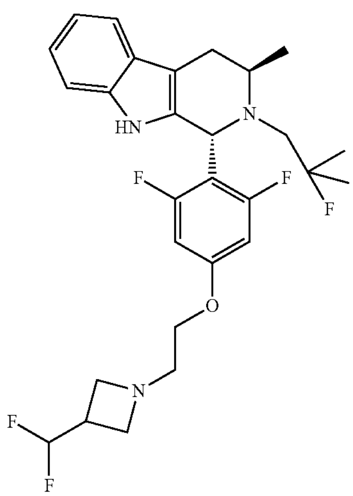 [SMILES: C[C@@H]1Cc2c([nH]c3ccccc23)[C@@H](c2c(F)cc(OCCN3CC(C(F)F)C3)cc2F)N1CC(C)(C)F] | (1R,3R)-1-[4-[2-[3-(difluoromethyl)azetidin-1-yl]ethoxy]-2,6-difluoro-phenyl]-2-(2-fluoro-2-methyl-propyl)-3-methyl-1,3,4,9-tetrahydropyrido[3,4-b]indole | 0.000064 | 522.3 |
| 129 | 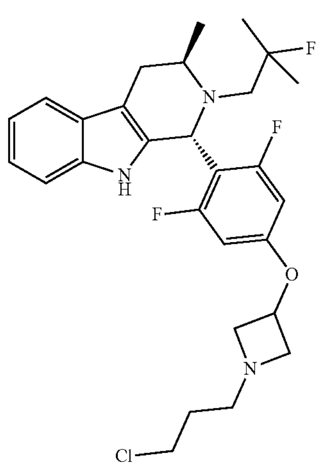 [SMILES: C[C@@H]1Cc2c([nH]c3ccccc23)[C@@H](c2c(F)cc(OC3CN(CCCCl)C3)cc2F)N1CC(C)(C)F] | (1R,3R)-1-[4-[1-(3-chloropropyl)azetidin-3-yl]oxy-2,6-difluoro-phenyl]-2-(2-fluoro-2-methyl-propyl)-3-methyl-1,3,4,9-tetrahydropyrido[3,4-b]indole | 0.00017 | 522.2 |

TABLE 2-continued

| No. | Structure | Name | ER-alpha MCF7 HCS EC$_{50}$ (μM) | LCMS [M + H]$^+$ |
|---|---|---|---|---|
| 130 | 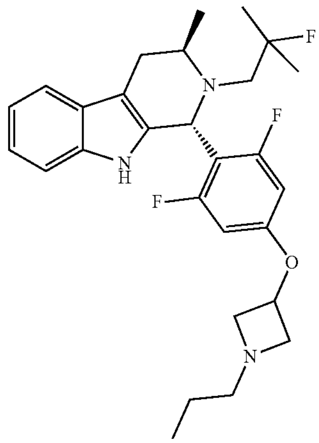 [SMILES: CCCN1CC(Oc2cc(F)c([C@@H]3c4[nH]c5ccccc5c4C[C@@H](C)N3CC(C)(C)F)c(F)c2)C1] | (1R,3R)-1-[2,6-difluoro-4-(1-propylazetidin-3-yl)oxy-phenyl]-2-(2-fluoro-2-methyl-propyl)-3-methyl-1,3,4,9-tetrahydropyrido[3,4-b]indole | 0.0000504 | 486.3 |
| 131 | 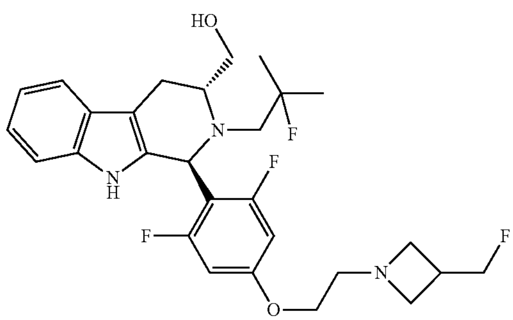 [SMILES: CC(C)(F)CN1[C@@H](CO)Cc2c([nH]c3ccccc23)[C@@H]1c1c(F)cc(OCCN2CC(CF)C2)cc1F] | ((1S,3R)-1-(2,6-difluoro-4-(2-(3-(fluoromethyl)azetidin-1-yl)ethoxy)phenyl)-2-(2-fluoro-2-methylpropyl)-2,3,4,9-tetrahydro-1H-pyrido[3,4-b]indol-3-yl)methanol | 0.000146 | 520.3 |
| 132 | 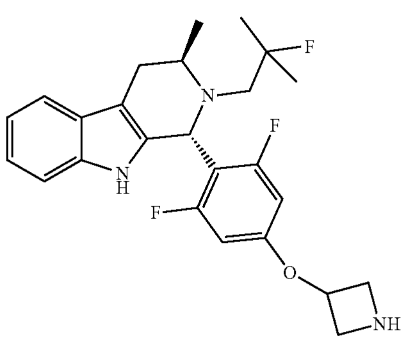 [SMILES: C[C@@H]1Cc2c([nH]c3ccccc23)[C@@H](c2c(F)cc(OC3CNC3)cc2F)N1CC(C)(C)F] | (1R,3R)-1-[4-(azetidin-3-yloxy)-2,6-difluoro-phenyl]-2-(2-fluoro-2-methyl-propyl)-3-methyl-1,3,4,9-tetrahydropyrido[3,4-b]indole | 0.00031 | 444.2 |

TABLE 2-continued

| No. | Structure | Name | ER-alpha MCF7 HCS EC$_{50}$ (μM) | LCMS [M + H]$^+$ |
|---|---|---|---|---|
| 133 | 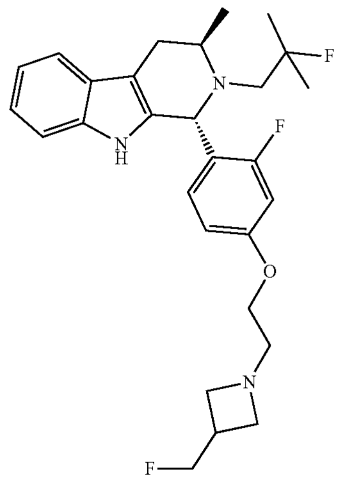 [SMILES: C[C@@H]1Cc2c([nH]c3ccccc23)[C@@H](c2ccc(OCCN3CC(CF)C3)cc2F)N1CC(C)(C)F] | (1R,3R)-2-(2-fluoro-2-methylpropyl)-1-(2-fluoro-4-(2-(3-(fluoromethyl)azetidin-1-yl)ethoxy)phenyl)-3-methyl-2,3,4,9-tetrahydro-1H-pyrido[3,4-b]indole | 0.0000562 | 486.3 |
| 134 | 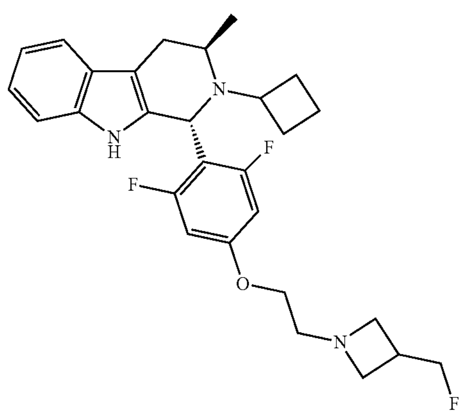 [SMILES: C[C@@H]1Cc2c([nH]c3ccccc23)[C@@H](c2c(F)cc(OCCN3CC(CF)C3)cc2F)N1C1CCC1] | (1R,3R)-2-cyclobutyl-1-[2,6-difluoro-4-[2-[3-(fluoromethyl)azetidin-1-yl]ethoxy]phenyl]-3-methyl-1,3,4,9-tetrahydropyrido[3,4-b]indole | 0.000542 | 484.3 |
| 135 | 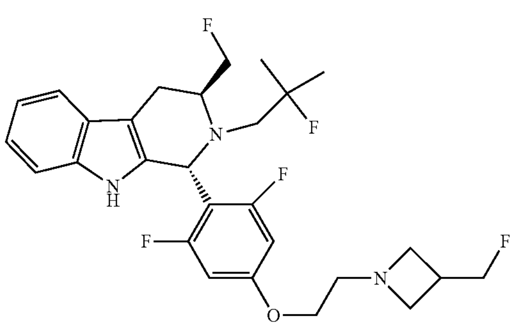 [SMILES: CC(C)(F)CN1[C@H](CF)Cc2c([nH]c3ccccc23)[C@H]1c1c(F)cc(OCCN2CC(CF)C2)cc1F] | (1R,3S)-1-[2,6-difluoro-4-[2-[3-(fluoromethyl)azetidin-1-yl]ethoxy]phenyl]-3-(fluoromethyl)-2-(2-fluoro-2-methyl-propyl)-1,3,4,9-tetrahydropyrido[3,4-b]indole | 0.0000973 | 522.3 |

TABLE 2-continued

| No. | Structure | Name | ER-alpha MCF7 HCS $EC_{50}$ (μM) | LCMS [M + H]+ |
|---|---|---|---|---|
| 136 | 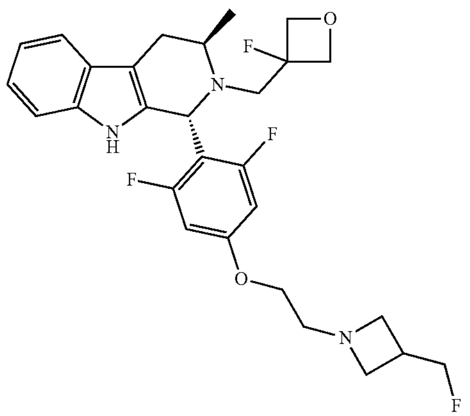 [SMILES: C[C@@H]1Cc2c([nH]c3ccccc23)[C@@H](c2c(F)cc(OCCN3CC(CF)C3)cc2F)N1CC1(F)COC1] | (1R,3R)-1-[2,6-difluoro-4-[2-[3-(fluoromethyl)azetidin-1-yl]ethoxy]phenyl]-2-[(3-fluorooxetan-3-yl)methyl]-3-methyl-1,3,4,9-tetrahydropyrido[3,4-b]indole | 0.000114 | 518.3 |
| 137 | 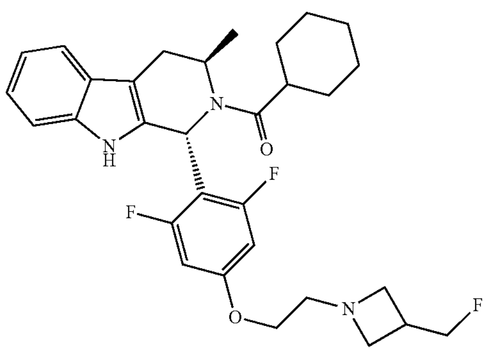 [SMILES: C[C@@H]1Cc2c([nH]c3ccccc23)[C@@H](c2c(F)cc(OCCN3CC(CF)C3)cc2F)N1C(=O)C1CCCCC1] | cyclohexyl((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)methanone | 0.028 | 540.4 |
| 138 | 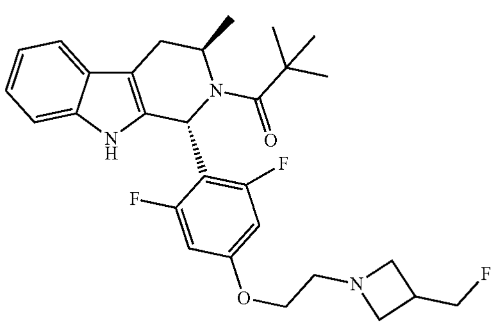 [SMILES: C[C@@H]1Cc2c([nH]c3ccccc23)[C@@H](c2c(F)cc(OCCN3CC(CF)C3)cc2F)N1C(=O)C(C)(C)C] | 1-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2,2-dimethyl-propan-1-one | 0.000491 | 514.3 |
| 139 | 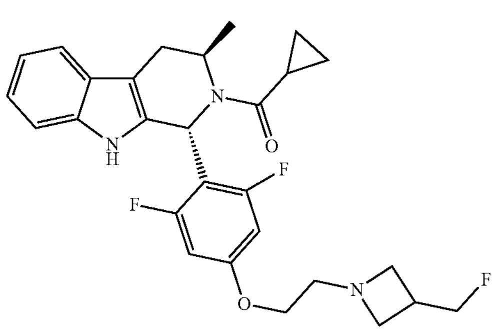 [SMILES: C[C@@H]1Cc2c([nH]c3ccccc23)[C@@H](c2c(F)cc(OCCN3CC(CF)C3)cc2F)N1C(=O)C1CC1] | cyclopropyl((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)methanone | 0.00248 | 498.2 |

TABLE 2-continued

| No. | Structure | Name | ER-alpha MCF7 HCS EC$_{50}$ (μM) | LCMS [M + H]$^+$ |
|---|---|---|---|---|
| 140 | 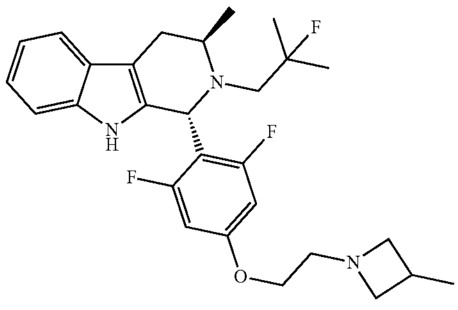 [SMILES: CC1CN(CCOc2cc(F)c([C@@H]3c4[nH]c5ccccc5c4C[C@@H](C)N3CC(C)(C)F)c(F)c2)C1] | (1R,3R)-1-[2,6-difluoro-4-[2-(3-methylazetidin-1-yl)ethoxy]phenyl]-2-(2-fluoro-2-methyl-propyl)-3-methyl-1,3,4,9-tetrahydropyrido[3,4-b]indole | 0.00013 | 486.4 |
| 141 | 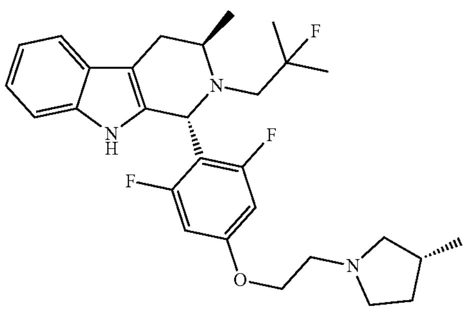 [SMILES: C[C@@H]1CCN(CCOc2cc(F)c([C@@H]3c4[nH]c5ccccc5c4C[C@@H](C)N3CC(C)(C)F)c(F)c2)C1] | (1R,3R)-1-(2,6-difluoro-4-(2-((R)-3-methylpyrrolidin-1-yl)ethoxy)phenyl)-2-(2-fluoro-2-methylpropyl)-3-methyl-2,3,4,9-tetrahydro-1H-pyrido[3,4-b]indole | 0.000151 | 500.2 |
| 142 | 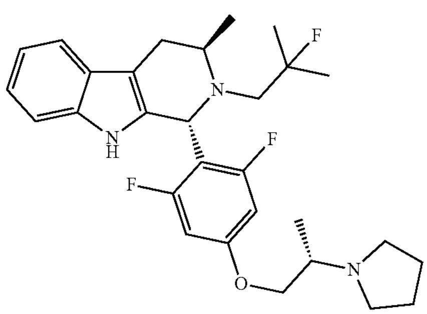 [SMILES: C[C@@H]1Cc2c([nH]c3ccccc23)[C@@H](c2c(F)cc(OC[C@H](C)N3CCCC3)cc2F)N1CC(C)(C)F] | (1R,3R)-1-[2,6-difluoro-4-[(2S)-2-pyrrolidin-1-ylpropoxy]phenyl]-2-(2-fluoro-2-methyl-propyl)-3-methyl-1,3,4,9-tetrahydropyrido[3,4-b]indole | 0.000090 | 500.3 |
| 143 | 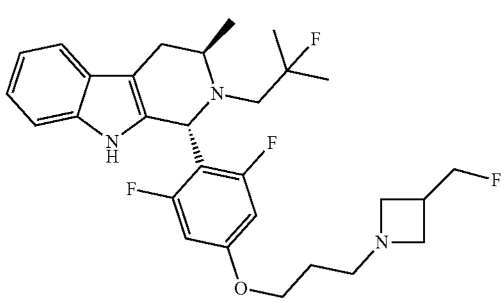 [SMILES: C[C@@H]1Cc2c([nH]c3ccccc23)[C@@H](c2c(F)cc(OCCCN3CC(CF)C3)cc2F)N1CC(C)(C)F] | (1R,3R)-1-[2,6-difluoro-4-[3-[3-(fluoromethyl)azetidin-1-yl]propoxy]phenyl]-2-(2-fluoro-2-methyl-propyl)-3-methyl-1,3,4,9-tetrahydropyrido[3,4-b]indole | 0.000078 | 518.4 |

TABLE 2-continued

| No. | Structure | Name | ER-alpha MCF7 HCS EC$_{50}$ (μM) | LCMS [M + H]$^+$ |
|---|---|---|---|---|
| 144 | 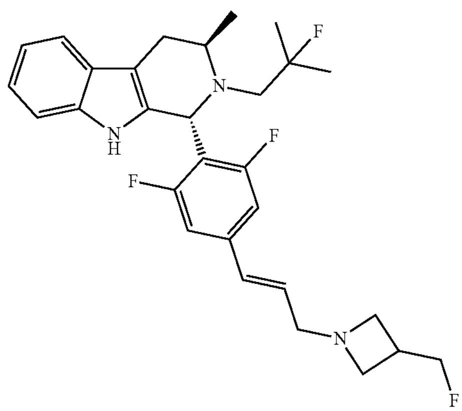 [SMILES: C[C@@H]1Cc2c([nH]c3ccccc23)[C@@H](c2c(F)cc(/C=C/CN3CC(CF)C3)cc2F)N1CC(C)(C)F] | (1R,3R)-1-[2,6-difluoro-4-[(E)-3-[3-(fluoromethyl)azetidin-1-yl]prop-1-enyl]phenyl]-2-(2-fluoro-2-methyl-propyl)-3-methyl-1,3,4,9-tetrahydropyrido[3,4-b]indole | 0.000144 | 500.1 |
| 145 | 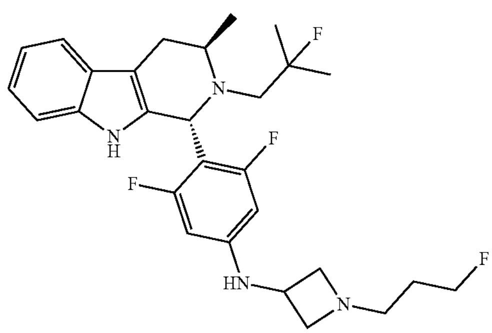 [SMILES: C[C@@H]1Cc2c([nH]c3ccccc23)[C@@H](c2c(F)cc(NC3CN(CCCF)C3)cc2F)N1CC(C)(C)F] | N-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1-(3-fluoropropyl)azetidin-3-amine | 0.000096 | 503.3 |
| 146 | 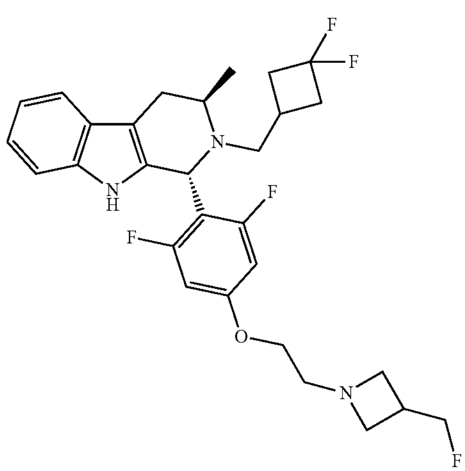 [SMILES: C[C@@H]1Cc2c([nH]c3ccccc23)[C@@H](c2c(F)cc(OCCN3CC(CF)C3)cc2F)N1CC1CC(F)(F)C1] | (1R,3R)-2-[(3,3-difluorocyclobutyl)methyl]-1-[2,6-difluoro-4-[2-[3-(fluoromethyl)azetidin-1-yl]ethoxy]phenyl]-3-methyl-1,3,4,9-tetrahydropyrido[3,4-b]indole | 0.01 | 534.3 |

TABLE 2-continued

| No. | Structure | Name | ER-alpha MCF7 HCS EC$_{50}$ (μM) | LCMS [M + H]$^+$ |
|---|---|---|---|---|
| 147 | 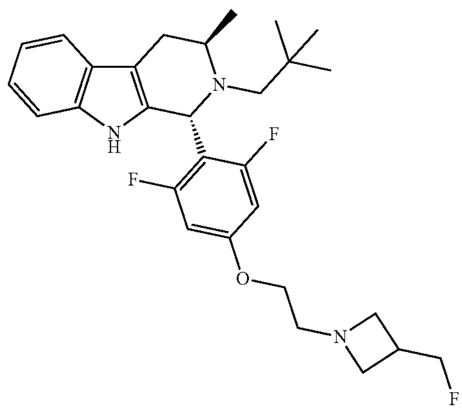 [SMILES: C[C@@H]1Cc2c([nH]c3ccccc23)[C@@H](c2c(F)cc(OCCN3CC(CF)C3)cc2F)N1CC(C)(C)C] | (1R,3R)-1-[2,6-difluoro-4-[2-[3-(fluoromethyl)azetidin-1-yl]ethoxy]phenyl]-2-(2,2-dimethylpropyl)-3-methyl-1,3,4,9-tetrahydropyrido[3,4-b]indole | 0.000698 | 500.3 |
| 148 | 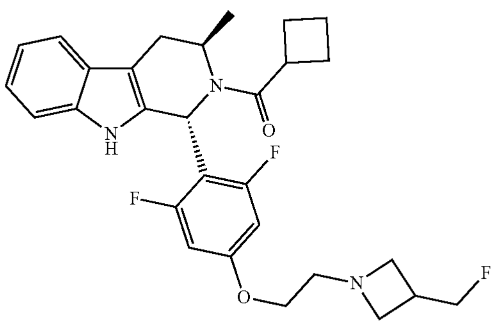 [SMILES: C[C@@H]1Cc2c([nH]c3ccccc23)[C@@H](c2c(F)cc(OCCN3CC(CF)C3)cc2F)N1C(=O)C1CCC1] | cyclobutyl-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]methanone | 0.00147 | 512.3 |
| 149 | 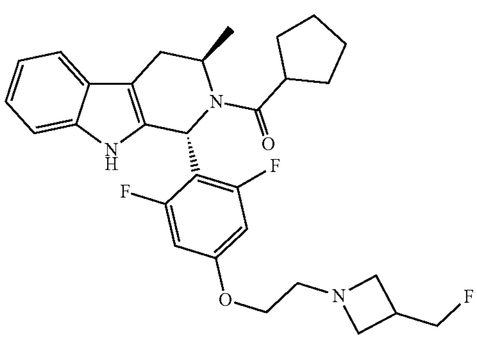 [SMILES: C[C@@H]1Cc2c([nH]c3ccccc23)[C@@H](c2c(F)cc(OCCN3CC(CF)C3)cc2F)N1C(=O)C1CCCC1] | cyclopentyl-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]methanone | 0.00216 | 526.4 |
| 150 | 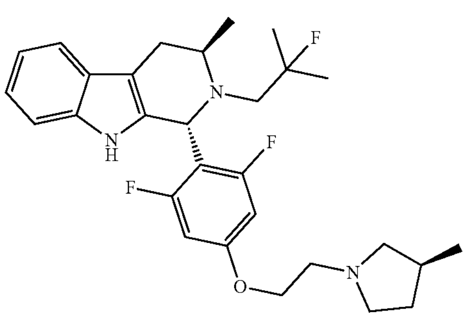 [SMILES: C[C@H]1CCN(CCOc2cc(F)c([C@@H]3c4[nH]c5ccccc5c4C[C@@H](C)N3CC(C)(C)F)c(F)c2)C1] | (1R,3R)-1-[2,6-difluoro-4-[2-[(3S)-3-methylpyrrolidin-1-yl]ethoxy]phenyl]-2-(2-fluoro-2-methyl-propyl)-3-methyl-1,3,4,9-tetrahydropyrido[3,4-b]indole | 0.000483 | 500.2 |

TABLE 2-continued

| No. | Structure | Name | ER-alpha MCF7 HCS EC$_{50}$ (μM) | LCMS [M + H]$^+$ |
|---|---|---|---|---|
| 151 | 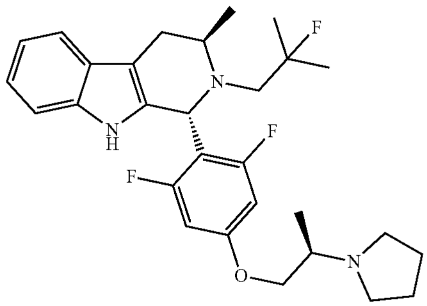 [SMILES: C[C@H](COc1cc(F)c([C@@H]2c3[nH]c4ccccc4c3C[C@@H](C)N2CC(C)(C)F)c(F)c1)N1CCCC1] | (1R,3R)-1-[2,6-difluoro-4-[(2R)-2-pyrrolidin-1-ylpropoxy]phenyl]-2-(2-fluoro-2-methyl-propyl)-3-methyl-1,3,4,9-tetrahydropyrido[3,4-b]indole | 0.000156 | 500.1 |
| 152 | 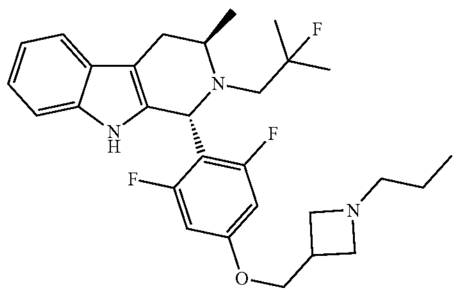 [SMILES: CCCN1CC(COc2cc(F)c([C@@H]3c4[nH]c5ccccc5c4C[C@@H](C)N3CC(C)(C)F)c(F)c2)C1] | (1R,3R)-1-[2,6-difluoro-4-[(1-propylazetidin-3-yl)methoxy]phenyl]-2-(2-fluoro-2-methyl-propyl)-3-methyl-1,3,4,9-tetrahydropyrido[3,4-b]indole | 0.000362 | 500.3 |
| 153 | 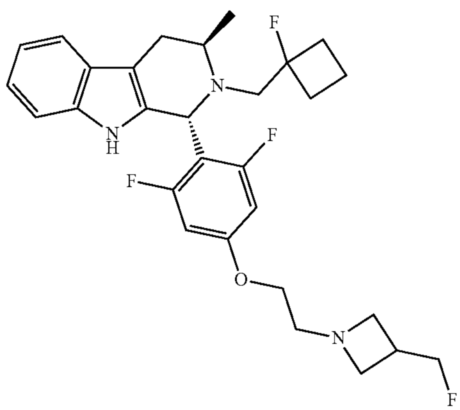 [SMILES: C[C@@H]1Cc2c([nH]c3ccccc23)[C@@H](c2c(F)cc(OCCN3CC(CF)C3)cc2F)N1CC1(F)CCC1] | (1R,3R)-1-[2,6-difluoro-4-[2-[3-(fluoromethyl)azetidin-1-yl]ethoxy]phenyl]-2-[(1-fluorocyclobutyl)methyl]-3-methyl-1,3,4,9-tetrahydropyrido[3,4-b]indole | 0.000221 | 516.3 |
| 154 | 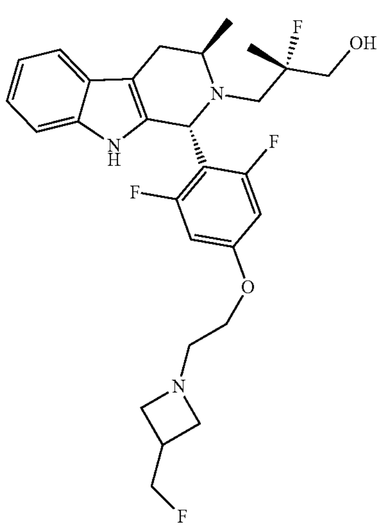 [SMILES: C[C@@H]1Cc2c([nH]c3ccccc23)[C@@H](c2c(F)cc(OCCN3CC(CF)C3)cc2F)N1C[C@](C)(F)CO] | (S)-3-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-fluoro-2-methylpropan-1-ol | 0.0000333 | 520.3 |

TABLE 2-continued

| No. | Structure | Name | ER-alpha MCF7 HCS EC$_{50}$ (μM) | LCMS [M + H]$^+$ |
|---|---|---|---|---|
| 155 | 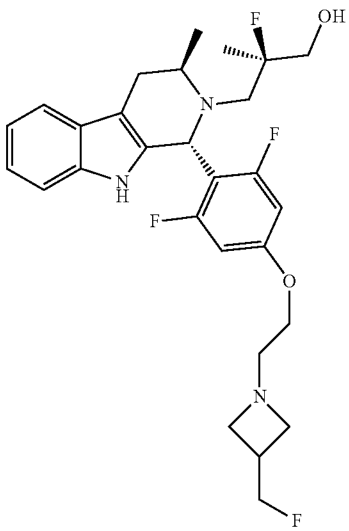 [SMILES: C[C@@H]1Cc2c([nH]c3ccccc23)[C@@H](c2c(F)cc(OCCN3CC(CF)C3)cc2F)N1C[C@@](C)(F)CO] | (2R)-3-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2-fluoro-2-methyl-propan-1-ol | 0.0000799 | 520.3 |
| 156 | 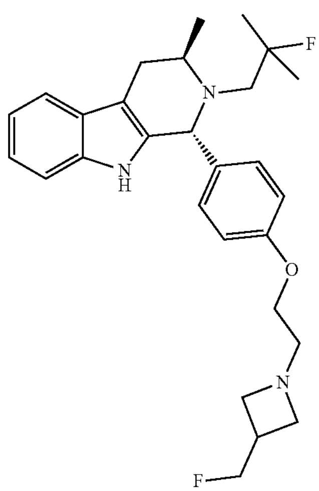 [SMILES: C[C@@H]1Cc2c([nH]c3ccccc23)[C@@H](c2ccc(OCCN3CC(CF)C3)cc2)N1CC(C)(C)F] | (1R,3R)-1-[4-[2-[3-(fluoromethyl)azetidin-1-yl]ethoxy]phenyl]-2-(2-fluoro-2-methyl-propyl)-3-methyl-1,3,4,9-tetrahydropyrido[3,4-b]indole | 0.000335 | 468.3 |
| 157 | 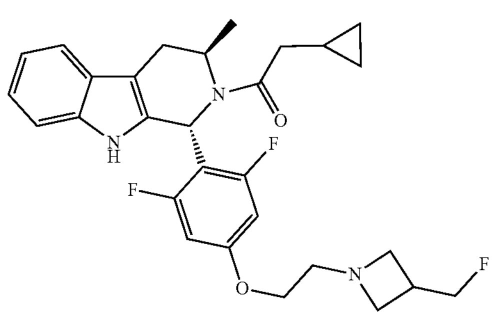 [SMILES: C[C@@H]1Cc2c([nH]c3ccccc23)[C@@H](c2c(F)cc(OCCN3CC(CF)C3)cc2F)N1C(=O)CC1CC1] | 2-cyclopropyl-1-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]ethanone | 0.005 | 512.4 |

TABLE 2-continued

| No. | Structure | Name | ER-alpha MCF7 HCS EC$_{50}$ (μM) | LCMS [M + H]$^+$ |
|---|---|---|---|---|
| 158 | 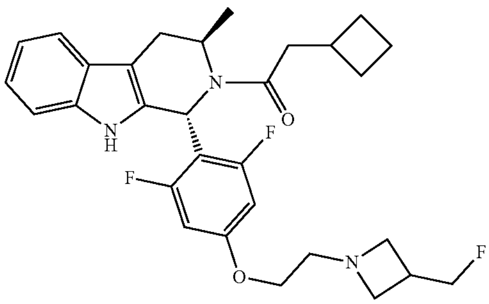 [SMILES: C[C@@H]1Cc2c([nH]c3ccccc23)[C@@H](c2c(F)cc(OCCN3CC(CF)C3)cc2F)N1C(=O)CC1CCC1] | 2-cyclobutyl-1-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]ethanone | 0.01 | 526.4 |
| 159 | 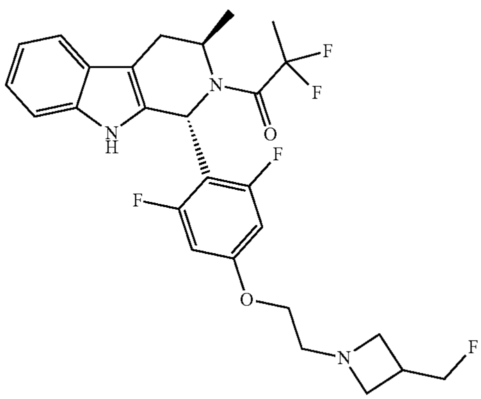 [SMILES: C[C@@H]1Cc2c([nH]c3ccccc23)[C@@H](c2c(F)cc(OCCN3CC(CF)C3)cc2F)N1C(=O)C(C)(F)F] | 1-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2,2-difluoro-propan-1-one | 0.000147 | 522.3 |
| 160 | 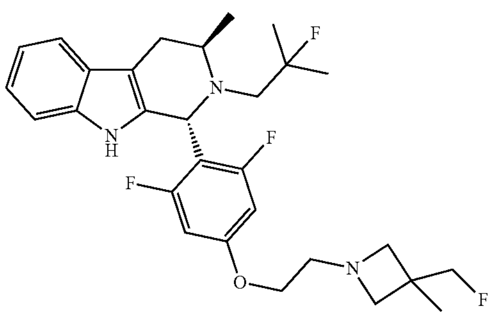 [SMILES: C[C@@H]1Cc2c([nH]c3ccccc23)[C@@H](c2c(F)cc(OCCN3CC(C)(CF)C3)cc2F)N1CC(C)(C)F] | (1R,3R)-1-[2,6-difluoro-4-[2-[3-(fluoromethyl)-3-methyl-azetidin-1-yl]ethoxy]phenyl]-2-(2-fluoro-2-methyl-propyl)-3-methyl-1,3,4,9-tetrahydropyrido[3,4-b]indole | 0.000285 | 518.4 |
| 161 | 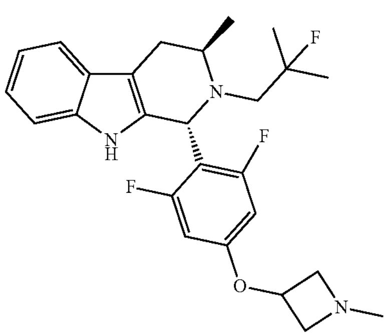 [SMILES: C[C@@H]1Cc2c([nH]c3ccccc23)[C@@H](c2c(F)cc(OC3CN(C)C3)cc2F)N1CC(C)(C)F] | (1R,3R)-1-[2,6-difluoro-4-(1-methylazetidin-3-yl)oxy-phenyl]-2-(2-fluoro-2-methyl-propyl)-3-methyl-1,3,4,9-tetrahydropyrido[3,4-b]indole | 0.0000413 | 458.3 |

TABLE 2-continued

| No. | Structure | Name | ER-alpha MCF7 HCS EC$_{50}$ (μM) | LCMS [M + H]$^+$ |
|---|---|---|---|---|
| 162 | 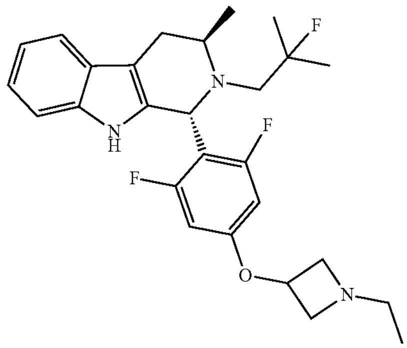 [SMILES: CCN1CC(Oc2cc(F)c([C@@H]3c4[nH]c5ccccc5c4C[C@@H](C)N3CC(C)(C)F)c(F)c2)C1] | (1R,3R)-1-[4-(1-ethylazetidin-3-yl)oxy-2,6-difluoro-phenyl]-2-(2-fluoro-2-methyl-propyl)-3-methyl-1,3,4,9-tetrahydropyrido[3,4-b]indole | 0.0000528 | 472.2 |
| 163 | 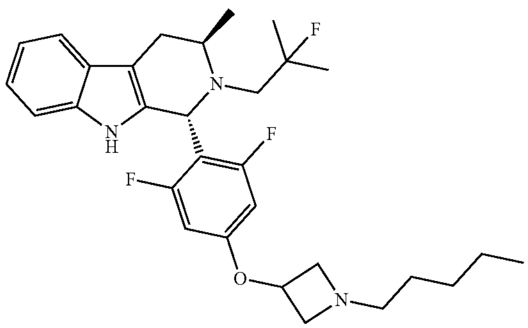 [SMILES: CCCCCN1CC(Oc2cc(F)c([C@@H]3c4[nH]c5ccccc5c4C[C@@H](C)N3CC(C)(C)F)c(F)c2)C1] | (1R,3R)-1-[2,6-difluoro-4-(1-pentylazetidin-3-yl)oxy-phenyl]-2-(2-fluoro-2-methyl-propyl)-3-methyl-1,3,4,9-tetrahydropyrido[3,4-b]indole | 0.000457 | 513.9 |
| 164 | 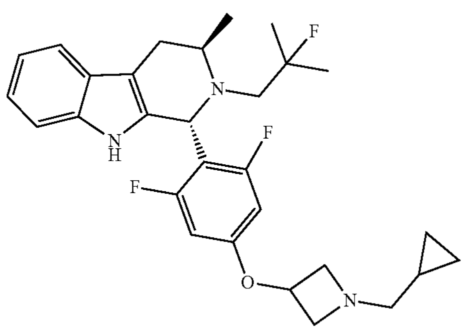 [SMILES: C[C@@H]1Cc2c([nH]c3ccccc23)[C@@H](c2c(F)cc(OC3CN(CC4CC4)C3)cc2F)N1CC(C)(C)F] | (1R,3R)-1-[4-[1-(cyclopropylmethyl)azetidin-3-yl]oxy-2,6-difluoro-phenyl]-2-(2-fluoro-2-methyl-propyl)-3-methyl-1,3,4,9-tetrahydropyrido[3,4-b]indole | 0.000216 | 498.4 |
| 165 | 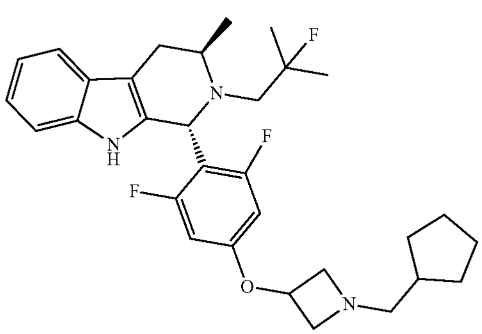 [SMILES: C[C@@H]1Cc2c([nH]c3ccccc23)[C@@H](c2c(F)cc(OC3CN(CC4CCCC4)C3)cc2F)N1CC(C)(C)F] | (1R,3R)-1-[4-[1-(cyclopentylmethyl)azetidin-3-yl]oxy-2,6-difluoro-phenyl]-2-(2-fluoro-2-methyl-propyl)-3-methyl-1,3,4,9-tetrahydropyrido[3,4-b]indole | 0.002 | 526.5 |

TABLE 2-continued

| No. | Structure | Name | ER-alpha MCF7 HCS EC$_{50}$ (μM) | LCMS [M + H]$^+$ |
|---|---|---|---|---|
| 166 | 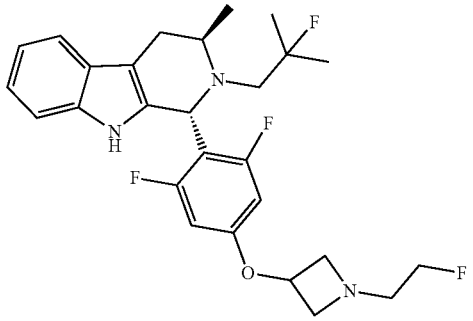 [SMILES: C[C@@H]1Cc2c([nH]c3ccccc23)[C@@H](c2c(F)cc(OC3CN(CCF)C3)cc2F)N1CC(C)(C)F] | (1R,3R)-1-[2,6-difluoro-4-[1-(2-fluoroethyl)azetidin-3-yl]oxy-phenyl]-2-(2-fluoro-2-methyl-propyl)-3-methyl-1,3,4,9-tetrahydropyrido[3,4-b]indole | 0.000175 | 490.4 |
| 167 | 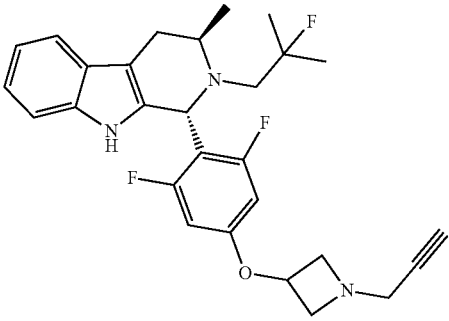 [SMILES: C#CCN1CC(Oc2cc(F)c([C@@H]3c4[nH]c5ccccc5c4C[C@@H](C)N3CC(C)(C)F)c(F)c2)C1] | (1R,3R)-1-[2,6-difluoro-4-(1-prop-2-ynylazetidin-3-yl)oxy-phenyl]-2-(2-fluoro-2-methyl-propyl)-3-methyl-1,3,4,9-tetrahydropyrido[3,4-b]indole | 0.000083 | 482.3 |
| 168 | 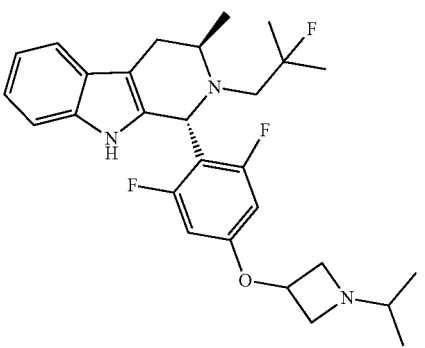 [SMILES: CC(C)N1CC(Oc2cc(F)c([C@@H]3c4[nH]c5ccccc5c4C[C@@H](C)N3CC(C)(C)F)c(F)c2)C1] | (1R,3R)-1-[2,6-difluoro-4-(1-isopropylazetidin-3-yl)oxy-phenyl]-2-(2-fluoro-2-methyl-propyl)-3-methyl-1,3,4,9-tetrahydropyrido[3,4-b]indole | 0.000122 | 486.4 |
| 169 | 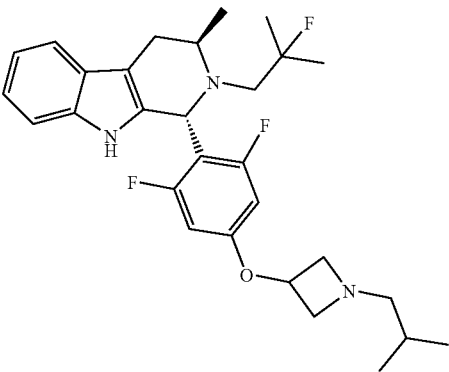 [SMILES: CC(C)CN1CC(Oc2cc(F)c([C@@H]3c4[nH]c5ccccc5c4C[C@@H](C)N3CC(C)(C)F)c(F)c2)C1] | (1R,3R)-1-[2,6-difluoro-4-(1-isobutylazetidin-3-yl)oxy-phenyl]-2-(2-fluoro-2-methyl-propyl)-3-methyl-1,3,4,9-tetrahydropyrido[3,4-b]indole | 0.000409 | 400.3 |

TABLE 2-continued

| No. | Structure | Name | ER-alpha MCF7 HCS EC$_{50}$ (μM) | LCMS [M + H]$^+$ |
|---|---|---|---|---|
| 170 | 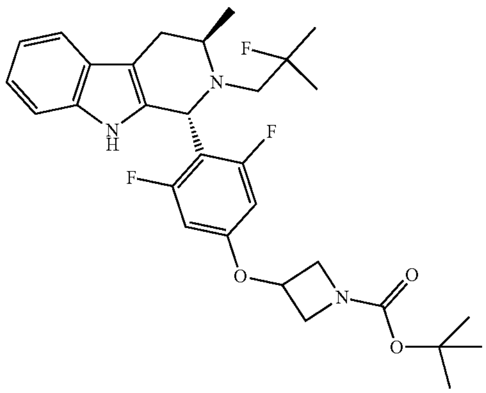 [SMILES: C[C@@H]1Cc2c([nH]c3ccccc23)[C@@H](c2c(F)cc(OC3CN(C(=O)OC(C)(C)C)C3)cc2F)N1CC(C)(C)F] | tert-butyl 3-[3,5-difluoro-4-[(1R,3R)-2-(2-fluoro-2-methyl-propyl)-3-methyl-1,3,4,9-tetrahydropyrido[3,4-b]indol-1-yl]phenoxy]azetidine-1-carboxylate | 0.001 | 544.3 |
| 171 | 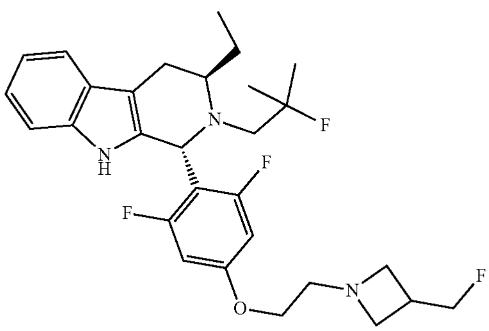 [SMILES: CC[C@@H]1Cc2c([nH]c3ccccc23)[C@@H](c2c(F)cc(OCCN3CC(CF)C3)cc2F)N1CC(C)(C)F] | (1R,3R)-1-(2,6-difluoro-4-(2-(3-(fluoromethyl)azetidin-1-yl)ethoxy)phenyl)-3-ethyl-2-(2-fluoro-2-methylpropyl)-2,3,4,9-tetrahydro-1H-pyrido[3,4-b]indole | 0.000471 | 518.3 |
| 172 | 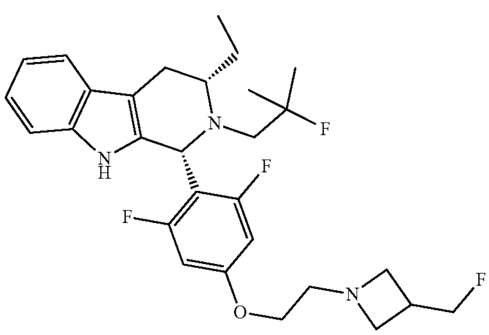 [SMILES: CC[C@H]1Cc2c([nH]c3ccccc23)[C@@H](c2c(F)cc(OCCN3CC(CF)C3)cc2F)N1CC(C)(C)F] | (1R,3S)-1-(2,6-difluoro-4-(2-(3-(fluoromethyl)azetidin-1-yl)ethoxy)phenyl)-3-ethyl-2-(2-fluoro-2-methylpropyl)-2,3,4,9-tetrahydro-1H-pyrido[3,4-b]indole | 0.017 | 518.3 |
| 173 | 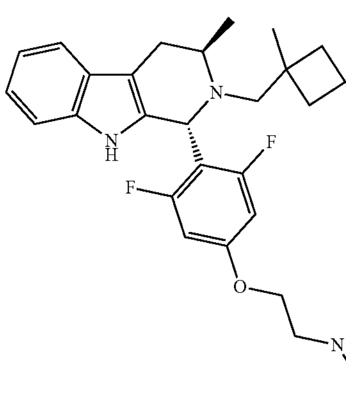 | (1R,3R)-1-[2,6-difluoro-4-[2-[3-(fluoromethyl)azetidin-1-yl]ethoxy]phenyl]-3-methyl-2-[(1-methylcyclobutyl)methyl]-1,3,4,9-tetrahydropyrido[3,4-b]indole | 0.001 | 512.3 |

TABLE 2-continued

| No. | Structure | Name | ER-alpha MCF7 HCS EC$_{50}$ (μM) | LCMS [M + H]$^+$ |
|---|---|---|---|---|
| 174 | 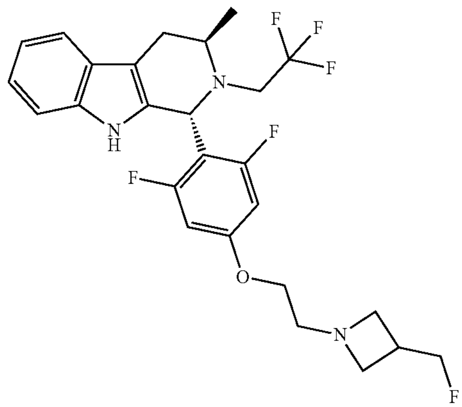 [SMILES: C[C@@H]1Cc2c([nH]c3ccccc23)[C@@H](c2c(F)cc(OCCN3CC(CF)C3)cc2F)N1CC(F)(F)F] | (1R,3R)-1-[2,6-difluoro-4-[2-[3-(fluoromethyl)azetidin-1-yl]ethoxy]phenyl]-3-methyl-2-(2,2,2-trifluoroethyl)-1,3,4,9-tetrahydropyrido[3,4-b]indole | 0.000285 | 512.2 |
| 175 | 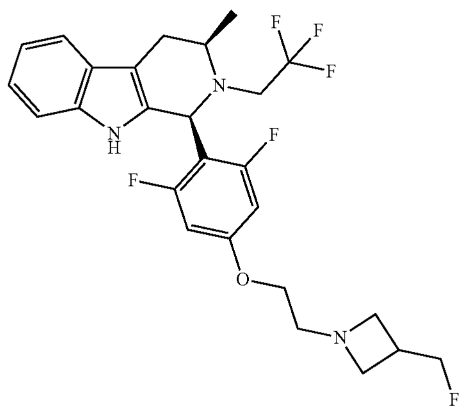 [SMILES: C[C@@H]1Cc2c([nH]c3ccccc23)[C@H](c2c(F)cc(OCCN3CC(CF)C3)cc2F)N1CC(F)(F)F] | (1S,3R)-1-[2,6-difluoro-4-[2-[3-(fluoromethyl)azetidin-1-yl]ethoxy]phenyl]-3-methyl-2-(2,2,2-trifluoroethyl)-1,3,4,9-tetrahydropyrido[3,4-b]indole | 0.014 | 512.2 |
| 176 | 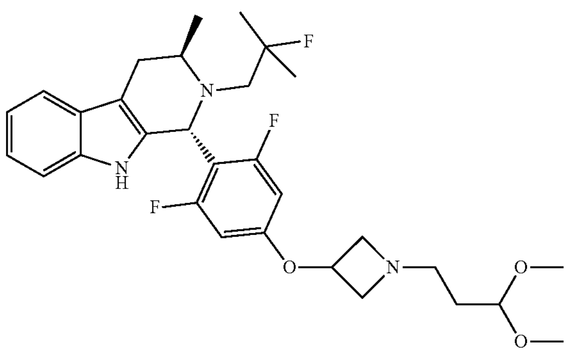 [SMILES: COC(CCN1CC(Oc2cc(F)c([C@@H]3c4[nH]c5ccccc5c4C[C@@H](C)N3CC(C)(C)F)c(F)c2)C1)OC] | (1R,3R)-1-[4-[1-(3,3-dimethoxypropyl)azetidin-3-yl]oxy-2,6-difluoro-phenyl]-2-(2-fluoro-2-methyl-propyl)-3-methyl-1,3,4,9-tetrahydropyrido[3,4-b]indole | 0.000031 | 546.3 |
| 177 | 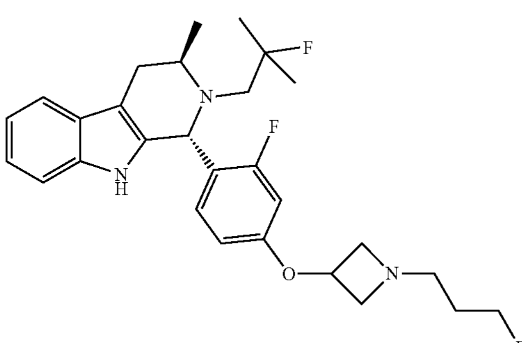 | (1R,3R)-1-[2-fluoro-4-[1-(3-fluoropropyl)azetidin-3-yl]oxy-phenyl]-2-(2-fluoro-2-methyl-propyl)-3-methyl-1,3,4,9-tetrahydropyrido[3,4-b]indole | 0.000164 | 486.3 |

TABLE 2-continued

| No. | Structure | Name | ER-alpha MCF7 HCS EC$_{50}$ (μM) | LCMS [M + H]$^+$ |
|---|---|---|---|---|
| 178 | 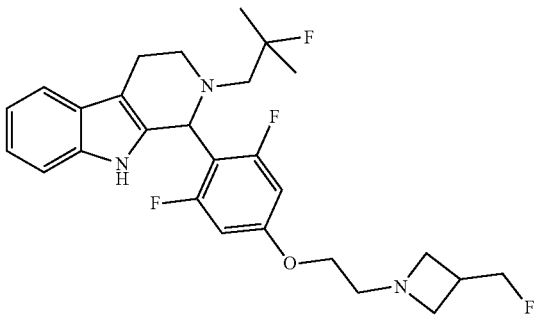 [SMILES: CC(C)(F)CN1CCc2c([nH]c3ccccc23)C1c1c(F)cc(OCCN2CC(CF)C2)cc1F] | 1-[2,6-difluoro-4-[2-[3-(fluoromethyl)azetidin-1-yl]ethoxy]phenyl]-2-(2-fluoro-2-methyl-propyl)-1,3,4,9-tetrahydropyrido[3,4-b]indole | 0.0005 | 490.2 |
| 179 | 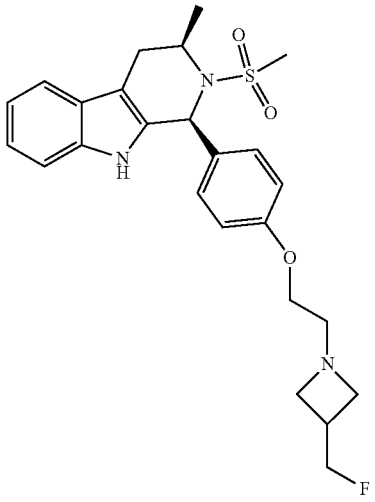 [SMILES: C[C@@H]1Cc2c([nH]c3ccccc23)[C@H](c2ccc(OCCN3CC(CF)C3)cc2)N1S(C)(=O)=O] | (1S,3R)-1-[4-[2-[3-(fluoromethyl)azetidin-1-yl]ethoxy]phenyl]-3-methyl-2-methylsulfonyl-1,3,4,9-tetrahydropyrido[3,4-b]indole | 0.013 | 472.2 |
| 180 | 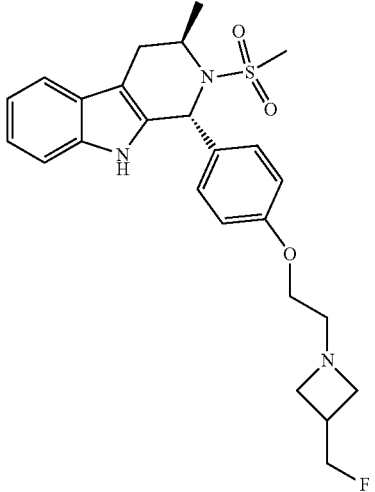 [SMILES: C[C@@H]1Cc2c([nH]c3ccccc23)[C@@H](c2ccc(OCCN3CC(CF)C3)cc2)N1S(C)(=O)=O] | (1R,3R)-1-(4-(2-(3-(fluoromethyl)azetidin-1-yl)ethoxy)phenyl)-3-methyl-2-(methylsulfonyl)-2,3,4,9-tetrahydro-1H-pyrido[3,4-b]indole | 0.000222 | 472.2 |

TABLE 2-continued

| No. | Structure | Name | ER-alpha MCF7 HCS EC$_{50}$ (μM) | LCMS [M + H]$^+$ |
|---|---|---|---|---|
| 181 | 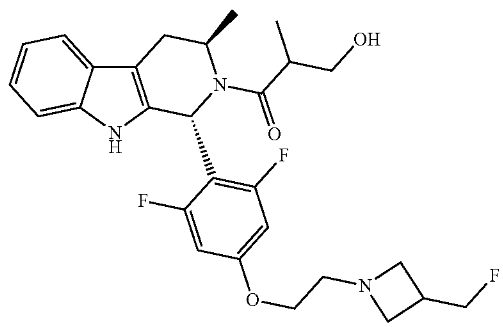 [SMILES: CC(CO)C(=O)N1[C@H](c2c(F)cc(OCCN3CC(CF)C3)cc2F)c2[nH]c3ccccc3c2C[C@H]1C] | 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-3-hydroxy-2-methylpropan-1-one | 0.004 | 516.2 |
| 182 | 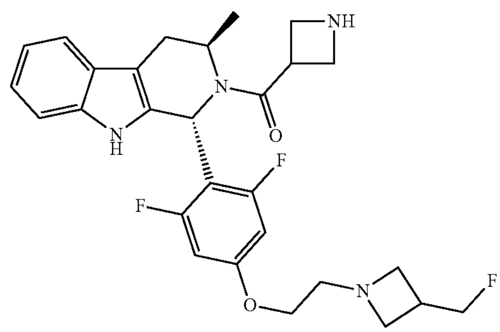 [SMILES: C[C@@H]1Cc2c([nH]c3ccccc23)[C@@H](c2c(F)cc(OCCN3CC(CF)C3)cc2F)N1C(=O)C1CNC1] | azetidin-3-yl-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl] methanone | >0.1 | 513.3 |
| 183 | 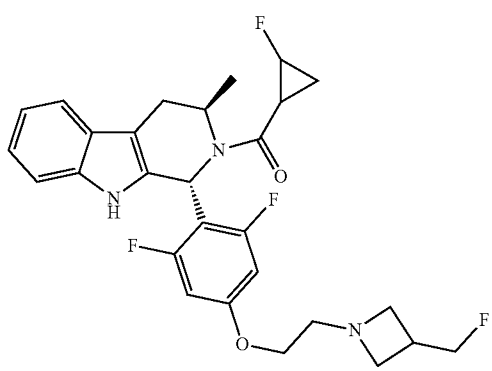 [SMILES: C[C@@H]1Cc2c([nH]c3ccccc23)[C@@H](c2c(F)cc(OCCN3CC(CF)C3)cc2F)N1C(=O)C1CC1F] | ((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)(2-fluorocyclopropyl)methanone | 0.004 | 516.3 |
| 184 | 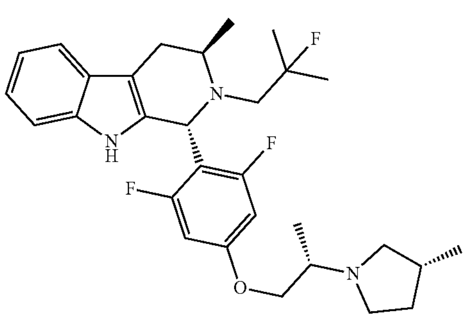 [SMILES: C[C@@H]1CCN([C@@H](C)COc2cc(F)c([C@@H]3c4[nH]c5ccccc5c4C[C@@H](C)N3CC(C)(C)F)c(F)c2)C1] | (1R,3R)-1-[2,6-difluoro-4-[(2S)-2-[(3R)-3-methylpyrrolidin-1-yl]propoxy phenyl]-2-(2-fluoro-2-methyl-propyl)-3-methyl-1,3,4,9-tetrahydropyrido[3,4-b]indole | 0.000494 | 514.4 |

TABLE 2-continued

| No. | Structure | Name | ER-alpha MCF7 HCS EC$_{50}$ (μM) | LCMS [M + H]$^+$ |
|---|---|---|---|---|
| 185 | 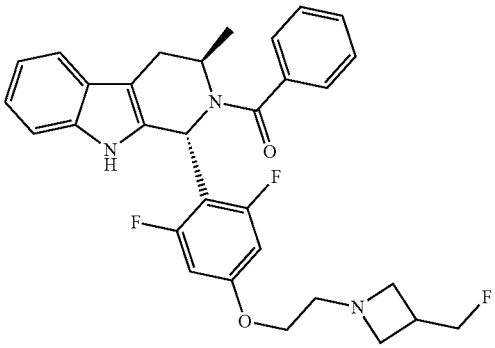 [SMILES: C[C@@H]1Cc2c([nH]c3ccccc23)[C@@H](c2c(F)cc(OCCN3CC(CF)C3)cc2F)N1C(=O)c1ccccc1] | [(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-phenyl-methanone | 0.014 | 534.2 |
| 186 | 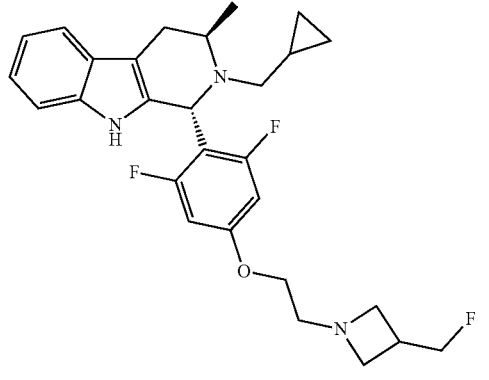 [SMILES: C[C@@H]1Cc2c([nH]c3ccccc23)[C@@H](c2c(F)cc(OCCN3CC(CF)C3)cc2F)N1CC1CC1] | (1R,3R)-2-(cyclopropylmethyl)-1-[2,6-difluoro-4-[2-[3-(fluoromethyl)azetidin-1-yl]ethoxy]phenyl]-3-methyl-1,3,4,9-tetrahydropyrido[3,4-b]indole | 0.002 | 484.4 |
| 187 | 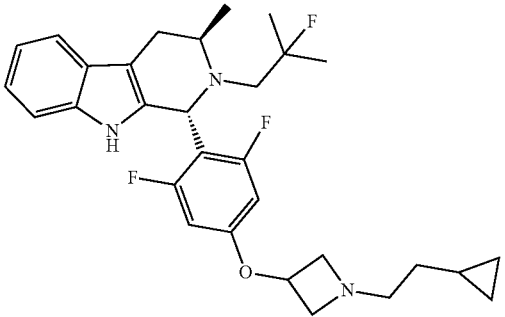 [SMILES: C[C@@H]1Cc2c([nH]c3ccccc23)[C@@H](c2c(F)cc(OC3CN(CCC4CC4)C3)cc2F)N1CC(C)(C)F] | (1R,3R)-1-[4-[1-(2-cyclopropylethyl)azetidin-3-yl]oxy-2,6-difluoro-phenyl]-2-(2-fluoro-2-methyl-propyl)-3-methyl-1,3,4,9-tetrahydropyrido[3,4-b]indole | 0.001 | 512.4 |
| 188 | 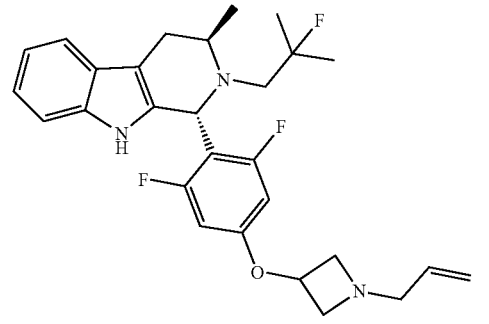 [SMILES: C=CCN1CC(Oc2cc(F)c([C@@H]3c4[nH]c5ccccc5c4C[C@@H](C)N3CC(C)(C)F)c(F)c2)C1] | (1R,3R)-1-[4-(1-allylazetidin-3-yl)oxy-2,6-difluoro-phenyl]-2-(2-fluoro-2-methyl-propyl)-3-methyl-1,3,4,9-tetrahydropyrido[3,4-b]indole | 0.000128 | 484.3 |

TABLE 2-continued

| No. | Structure | Name | ER-alpha MCF7 HCS EC$_{50}$ (μM) | LCMS [M + H]$^+$ |
|---|---|---|---|---|
| 189 | 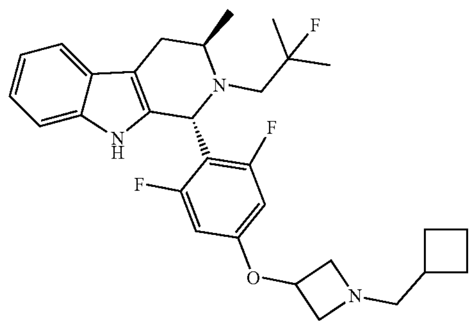 [SMILES: C[C@@H]1Cc2c([nH]c3ccccc23)[C@@H](c2c(F)cc(OC3CN(CC4CCC4)C3)cc2F)N1CC(C)(C)F] | (1R,3R)-1-[4-[1-(cyclobutylmethyl)azetidin-3-yl]oxy-2,6-difluoro-phenyl]-2-(2-fluoro-2-methyl-propyl)-3-methyl-1,3,4,9-tetrahydropyrido[3,4-b]indole | 0.001 | 512.3 |
| 190 | 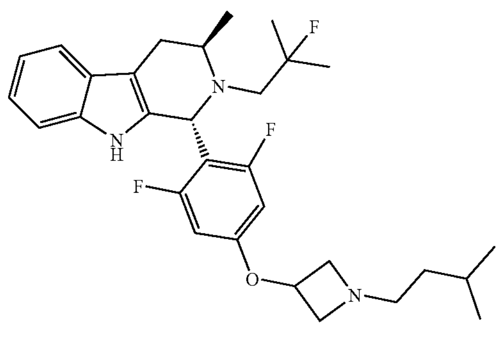 [SMILES: CC(C)CCN1CC(Oc2cc(F)c([C@@H]3c4[nH]c5ccccc5c4C[C@@H](C)N3CC(C)(C)F)c(F)c2)C1] | (1R,3R)-1-[2,6-difluoro-4-(1-isopentylazetidin-3-yl)oxy-phenyl]-2-(2-fluoro-2-methyl-propyl)-3-methyl-1,3,4,9-tetrahydropyrido[3,4-b]indole | 0.002 | 514.3 |
| 191 | 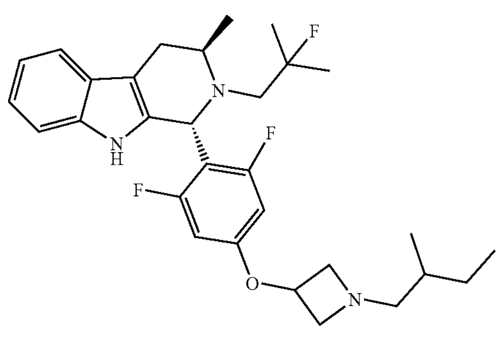 [SMILES: CCC(C)CN1CC(Oc2cc(F)c([C@@H]3c4[nH]c5ccccc5c4C[C@@H](C)N3CC(C)(C)F)c(F)c2)C1] | (1R,3R)-1-(2,6-difluoro-4-((1-(2-methylbutyl)azetidin-3-yl)oxy)phenyl)-2-(2-fluoro-2-methylpropyl)-3-methyl-2,3,4,9-tetrahydro-1H-pyrido[3,4-b]indole | 0.000267 | 514.3 |
| 192 | 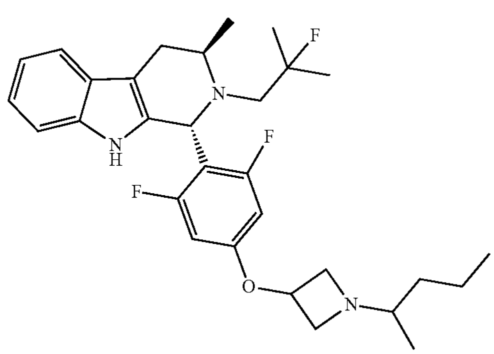 [SMILES: CCCC(C)N1CC(Oc2cc(F)c([C@@H]3c4[nH]c5ccccc5c4C[C@@H](C)N3CC(C)(C)F)c(F)c2)C1] | (1R,3R)-1-(2,6-difluoro-4-((1-(pentan-2-yl)azetidin-3-yl)oxy)phenyl)-2-(2-fluoro-2-methylpropyl)-3-methyl-2,3,4,9-tetrahydro-1H-pyrido[3,4-b]indole | 0.001 | 514.3 |

TABLE 2-continued

| No. | Structure | Name | ER-alpha MCF7 HCS EC$_{50}$ (μM) | LCMS [M + H]$^+$ |
|---|---|---|---|---|
| 193 | 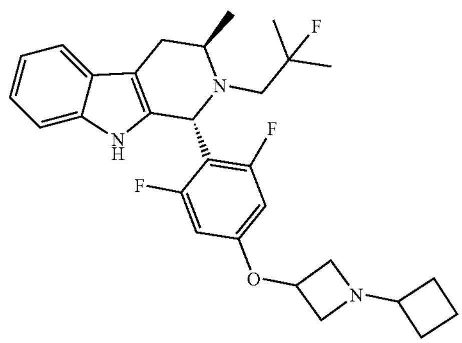 [SMILES: C[C@@H]1Cc2c([nH]c3ccccc23)[C@@H](c2c(F)cc(OC3CN(C4CCC4)C3)cc2F)N1CC(C)(C)F] | (1R,3R)-1-[4-(1-cyclobutylazetidin-3-yl)oxy-2,6-difluoro-phenyl]-2-(2-fluoro-2-methyl-propyl)-3-methyl-1,3,4,9-tetrahydropyrido[3,4-b]indole | 0.000484 | 498.3 |
| 194 | 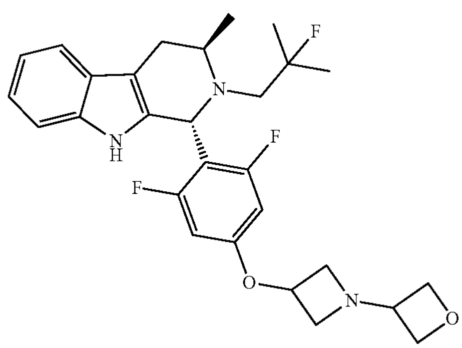 [SMILES: C[C@@H]1Cc2c([nH]c3ccccc23)[C@@H](c2c(F)cc(OC3CN(C4COC4)C3)cc2F)N1CC(C)(C)F] | (1R,3R)-1-[2,6-difluoro-4-[1-(oxetan-3-yl)azetidin-3-yl]oxy-phenyl]-2-(2-fluoro-2-methyl-propyl)-3-methyl-1,3,4,9-tetrahydropyrido[3,4-b]indole | 0.000077 | 500.2 |
| 195 | 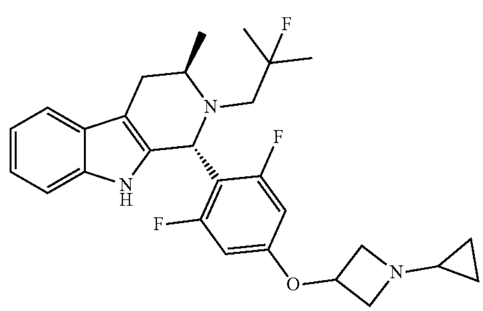 [SMILES: C[C@@H]1Cc2c([nH]c3ccccc23)[C@@H](c2c(F)cc(OC3CN(C4CC4)C3)cc2F)N1CC(C)(C)F] | (1R,3R)-1-[4-(1-cyclopropylazetidin-3-yl)oxy-2,6-difluoro-phenyl]-2-(2-fluoro-2-methyl-propyl)-3-methyl-1,3,4,9-tetrahydropyrido[3,4-b]indole | 0.000165 | 484.3 |
| 196 | 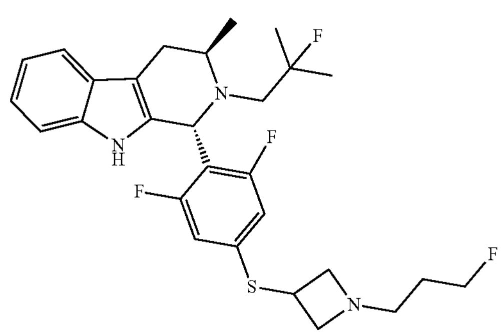 [SMILES: C[C@@H]1Cc2c([nH]c3ccccc23)[C@@H](c2c(F)cc(SC3CN(CCCF)C3)cc2F)N1CC(C)(C)F] | (1R,3R)-1-[2,6-difluoro-4-[1-(3-fluoropropyl)azetidin-3-yl]sulfanyl-phenyl]-2-(2-fluoro-2-methyl-propyl)-3-methyl-1,3,4,9-tetrahydropyrido[3,4-b]indole | 0.000271 | 520.3 |

TABLE 2-continued

| No. | Structure | Name | ER-alpha MCF7 HCS EC$_{50}$ (μM) | LCMS [M + H]$^+$ |
|---|---|---|---|---|
| 197 | 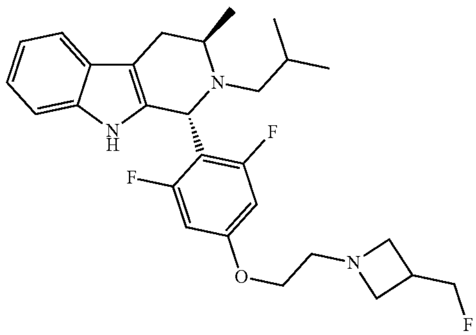 [SMILES: CC(C)CN1[C@H](c2c(F)cc(OCCN3CC(CF)C3)cc2F)c2[nH]c3ccccc3c2C[C@H]1C] | (1R,3R)-1-[2,6-difluoro-4-[2-[3-(fluoromethyl)azetidin-1-yl]ethoxy]phenyl]-2-isobutyl-3-methyl-1,3,4,9-tetrahydropyrido[3,4-b]indole | 0.001 | 486.2 |
| 198 | 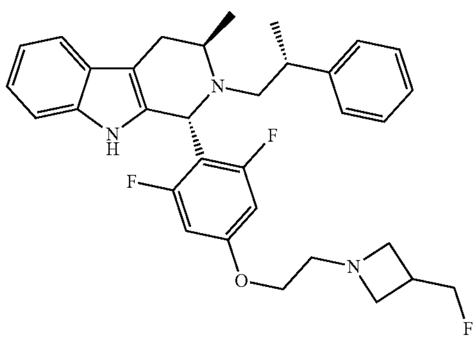 [SMILES: C[C@@H]1Cc2c([nH]c3ccccc23)[C@@H](c2c(F)cc(OCCN3CC(CF)C3)cc2F)N1C[C@H](C)c1ccccc1] | (1R,3R)-1-(2,6-difluoro-4-(2-(3-(fluoromethyl)azetidin-1-yl)ethoxy)phenyl)-3-methyl-2-((R)-2-phenylpropyl)-2,3,4,9-tetrahydro-1H-pyrido[3,4-b]indole | 0.002 | 548.1 |
| 199 | 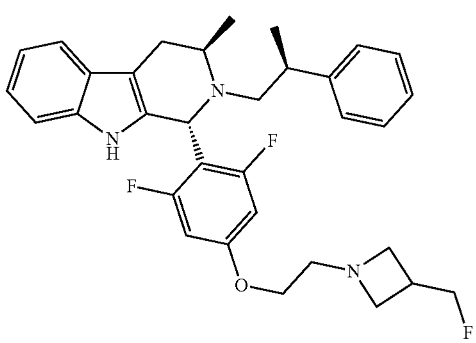 [SMILES: C[C@H](CN1[C@H](c2c(F)cc(OCCN3CC(CF)C3)cc2F)c2[nH]c3ccccc3c2C[C@H]1C)c1ccccc1] | (1R,3R)-1-(2,6-difluoro-4-(2-(3-(fluoromethyl)azetidin-1-yl)ethoxy)phenyl)-3-methyl-2-((S)-2-phenylpropyl)-2,3,4,9-tetrahydro-1H-pyrido[3,4-b]indole | 0.00232 | 548.3 |
| 200 | 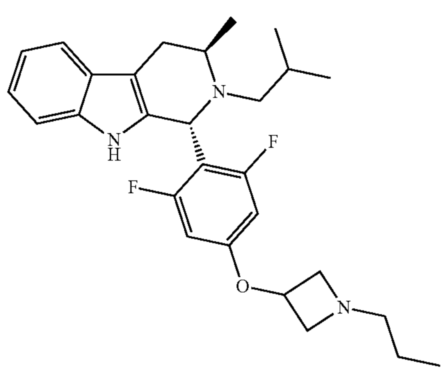 [SMILES: CCCN1CC(Oc2cc(F)c([C@@H]3c4[nH]c5ccccc5c4C[C@@H](C)N3CC(C)C)c(F)c2)C1] | (1R,3R)-1-[2,6-difluoro-4-(1-propylazetidin-3-yl)oxy-phenyl]-2-isobutyl-3-methyl-1,3,4,9-tetrahydropyrido[3,4-b]indole | 0.000408 | 468.3 |

TABLE 2-continued

| No. | Structure | Name | ER-alpha MCF7 HCS EC$_{50}$ (μM) | LCMS [M + H]$^+$ |
|---|---|---|---|---|
| 201 | 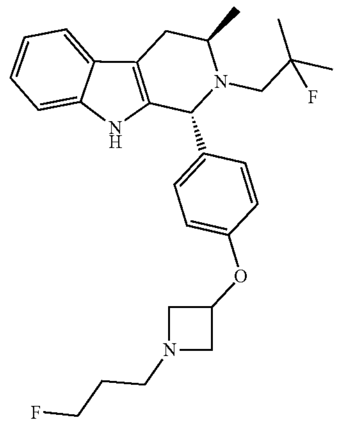 [SMILES: C[C@@H]1Cc2c([nH]c3ccccc23)[C@@H](c2ccc(OC3CN(CCCF)C3)cc2)N1CC(C)(C)F] | (1R,3R)-2-(2-fluoro-2-methyl-propyl)-1-[4-[1-(3-fluoropropyl)azetidin-3-yl]oxyphenyl]-3-methyl-1,3,4,9-tetrahydropyrido[3,4-b]indole | 0.000315 | |
| 202 | 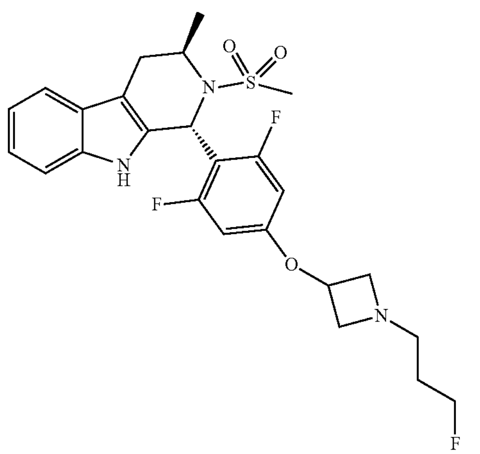 [SMILES: C[C@@H]1Cc2c([nH]c3ccccc23)[C@@H](c2c(F)cc(OC3CN(CCCF)C3)cc2F)N1S(C)(=O)=O] | (1R,3R)-1-[2,6-difluoro-4-[1-(3-fluoropropyl)azetidin-3-yl]oxy-phenyl]-3-methyl-2-methylsulfonyl-1,3,4,9-tetrahydropyrido[3,4-b]indole | 0.0001 | 508.2 |
| 203 | 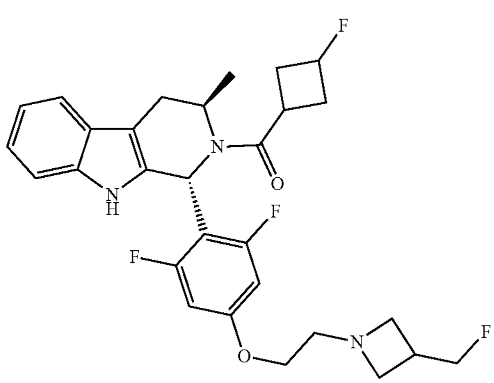 [SMILES: C[C@@H]1Cc2c([nH]c3ccccc23)[C@@H](c2c(F)cc(OCCN3CC(CF)C3)cc2F)N1C(=O)C1CC(F)C1] | [1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-(3-fluorocyclobutyl)methanone | 0.004 | 530.4 |

TABLE 2-continued

| No. | Structure | Name | ER-alpha MCF7 HCS EC$_{50}$ (μM) | LCMS [M + H]$^+$ |
|---|---|---|---|---|
| 204 | 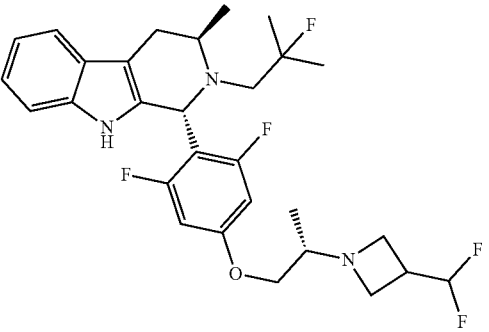 [SMILES: C[C@@H]1Cc2c([nH]c3ccccc23)[C@@H](c2c(F)cc(OC[C@H](C)N3CC(C(F)F)C3)cc2F)N1CC(C)(C)F] | (1R,3R)-1-[4-[(2S)-2-[3-(difluoromethyl)azetidin-1-yl]propoxy]-2,6-difluoro-phenyl]-2-(2-fluoro-2-methyl-propyl)-3-methyl-1,3,4,9-tetrahydropyrido[3,4-b]indole | 0.000371 | 536.4 |
| 205 | 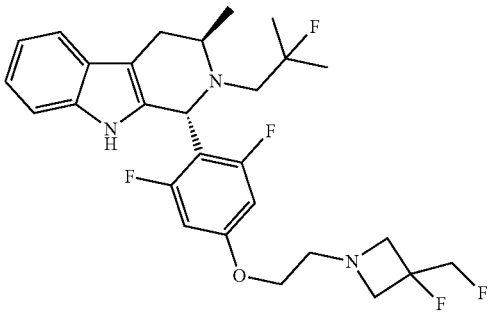 [SMILES: C[C@@H]1Cc2c([nH]c3ccccc23)[C@@H](c2c(F)cc(OCCN3CC(F)(CF)C3)cc2F)N1CC(C)(C)F] | (1R,3R)-1-[2,6-difluoro-4-[2-[3-fluoro-3-(fluoromethyl)azetidin-1-yl]ethoxy]phenyl]-2-(2-fluoro-2-methyl-propyl)-3-methyl-1,3,4,9-tetrahydropyrido[3,4-b]indole | 0.000375 | 522.1 |
| 206 | 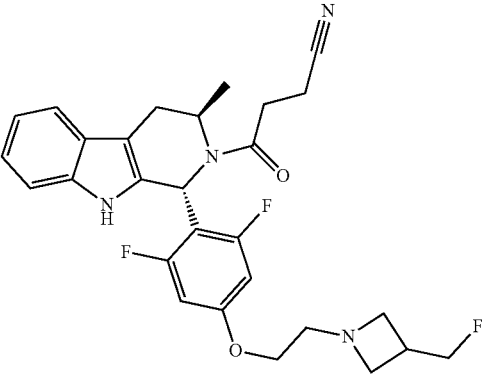 [SMILES: C[C@@H]1Cc2c([nH]c3ccccc23)[C@@H](c2c(F)cc(OCCN3CC(CF)C3)cc2F)N1C(=O)CCC#N] | 4-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-4-oxo-butanenitrile | 0.031 | 511.3 |
| 207 | 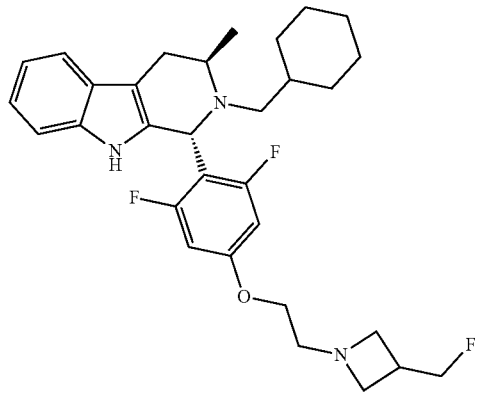 [SMILES: C[C@@H]1Cc2c([nH]c3ccccc23)[C@@H](c2c(F)cc(OCCN3CC(CF)C3)cc2F)N1CC1CCCCC1] | (1R,3R)-2-(cyclohexylmethyl)-1-[2,6-difluoro-4-[2-[3-(fluoromethyl)azetidin-1-yl]ethoxy]phenyl]-3-methyl-1,3,4,9-tetrahydropyrido[3,4-b]indole | 0.013 | 526.4 |

TABLE 2-continued

| No. | Structure | Name | ER-alpha MCF7 HCS EC$_{50}$ (μM) | LCMS [M + H]$^+$ |
|---|---|---|---|---|
| 208 | 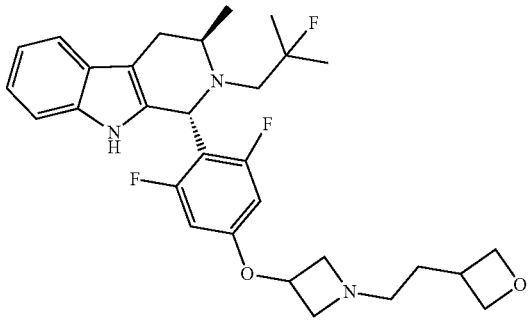 [SMILES: C[C@@H]1Cc2c([nH]c3ccccc23)[C@@H](c2c(F)cc(OC3CN(CCC4COC4)C3)cc2F)N1CC(C)(C)F] | (1R,3R)-1-[2,6-difluoro-4-[1-[2-(oxetan-3-yl)ethyl]azetidin-3-yl]oxy-phenyl]-2-(2-fluoro-2-methyl-propyl)-3-methyl-1,3,4,9-tetrahydropyrido[3,4-b]indole | 0.000066 | 528.3 |
| 209 | 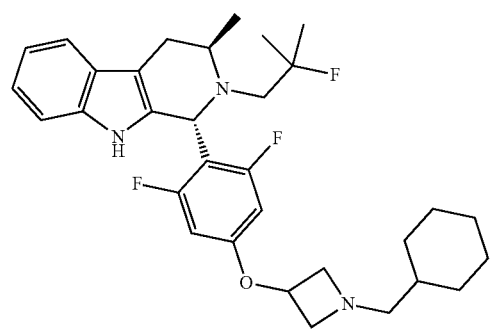 [SMILES: C[C@@H]1Cc2c([nH]c3ccccc23)[C@@H](c2c(F)cc(OC3CN(CC4CCCCC4)C3)cc2F)N1CC(C)(C)F] | (1R,3R)-1-[4-[1-(cyclohexylmethyl)azetidin-3-yl]oxy-2,6-difluoro-phenyl]-2-(2-fluoro-2-methyl-propyl)-3-methyl-1,3,4,9-tetrahydropyrido[3,4-b]indole | 0.008 | 540.3 |
| 210 | 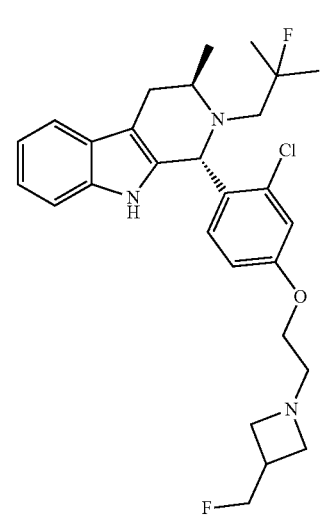 [SMILES: C[C@@H]1Cc2c([nH]c3ccccc23)[C@@H](c2ccc(OCCN3CC(CF)C3)cc2Cl)N1CC(C)(C)F] | (1R,3R)-1-[2-chloro-4-[2-[3-(fluoromethyl)azetidin-1-yl]ethoxy]phenyl]-2-(2-fluoro-2-methyl-propyl)-3-methyl-1,3,4,9-tetrahydropyrido[3,4-b]indole | 0.0001 | 503.2 |
| 211 | 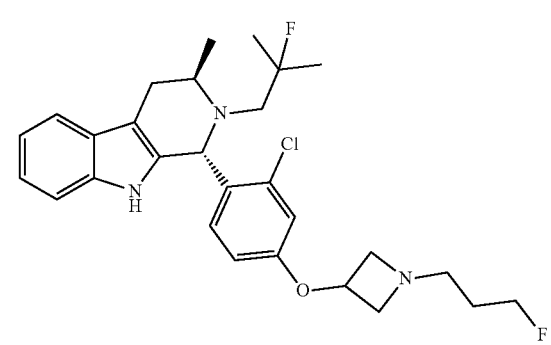 [SMILES: C[C@@H]1Cc2c([nH]c3ccccc23)[C@@H](c2ccc(OC3CN(CCCF)C3)cc2Cl)N1CC(C)(C)F] | (1R,3R)-1-[2-chloro-4-[1-(3-fluoropropyl)azetidin-3-yl]oxy-phenyl]-2-(2-fluoro-2-methyl-propyl)-3-methyl-1,3,4,9-tetrahydropyrido[3,4-b]indole | 0.0002 | 503.2 |

TABLE 2-continued

| No. | Structure | Name | ER-alpha MCF7 HCS EC$_{50}$ (μM) | LCMS [M + H]$^+$ |
|---|---|---|---|---|
| 212 | 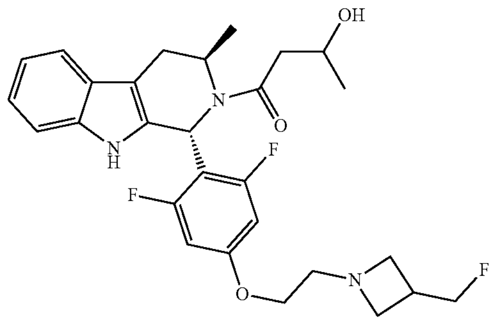 [SMILES: CC(O)CC(=O)N1[C@H](c2c(F)cc(OCCN3CC(CF)C3)cc2F)c2[nH]c3ccccc3c2C[C@H]1C] | 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-3-hydroxybutan-1-one | 0.001 | 538.2 |
| 213 | 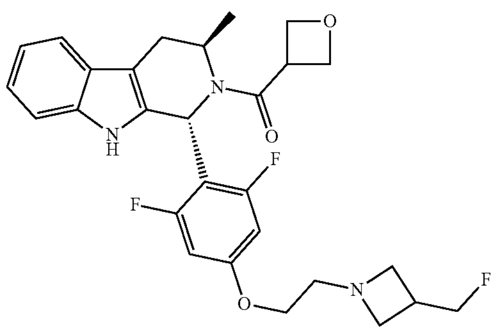 [SMILES: C[C@@H]1Cc2c([nH]c3ccccc23)[C@@H](c2c(F)cc(OCCN3CC(CF)C3)cc2F)N1C(=O)C1COC1] | [(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-(oxetan-3-yl)methanone | 0.004 | 514.2 |
| 214 | 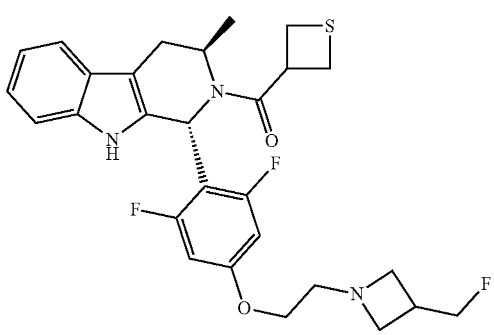 | [(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-(thietan-3-yl)methanone | 0.004 | 530.2 |
| 215 | 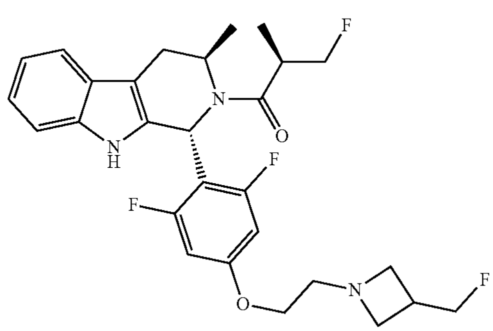 [SMILES: C[C@@H]1Cc2c([nH]c3ccccc23)[C@@H](c2c(F)cc(OCCN3CC(CF)C3)cc2F)N1C(=O)[C@@H](C)CF] | (R)-1-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-3-fluoro-2-methylpropan-1-one | 0.000335 | 518.3 |

TABLE 2-continued

| No. | Structure | Name | ER-alpha MCF7 HCS EC$_{50}$ (μM) | LCMS [M + H]$^+$ |
|---|---|---|---|---|
| 216 | 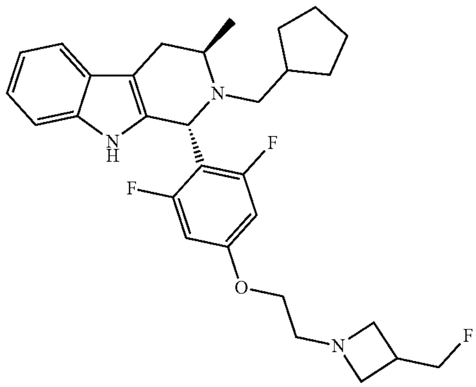 [SMILES: C[C@@H]1Cc2c([nH]c3ccccc23)[C@@H](c2c(F)cc(OCCN3CC(CF)C3)cc2F)N1CC1CCCC1] | (1R,3R)-2-(cyclopentylmethyl)-1-[2,6-difluoro-4-[2-[3-(fluoromethyl)azetidin-1-yl]ethoxy]phenyl]-3-methyl-1,3,4,9-tetrahydropyrido[3,4-b]indole | 0.001 | 512.4 |
| 217 | 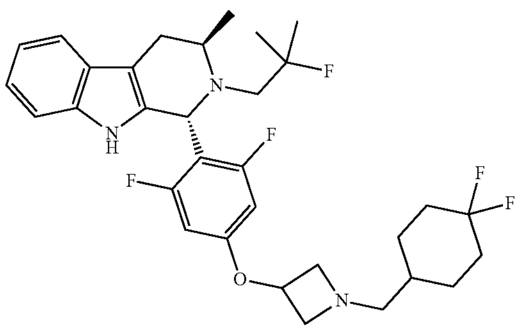 [SMILES: C[C@@H]1Cc2c([nH]c3ccccc23)[C@@H](c2c(F)cc(OC3CN(CC4CCC(F)(F)CC4)C3)cc2F)N1CC(C)(C)F] | (1R,3R)-1-[4-[1-[(4,4-difluorocyclohexyl)methyl]azetidin-3-yl]oxy-2,6-difluoro-phenyl]-2-(2-fluoro-2-methyl-propyl)-3-methyl-1,3,4,9-tetrahydropyrido[3,4-b]indole | 0.002 | 576.3 |
| 218 | 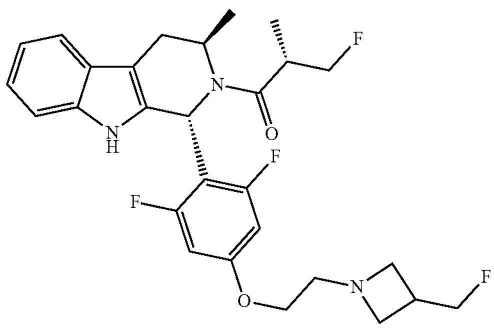 [SMILES: C[C@H](CF)C(=O)N1[C@H](c2c(F)cc(OCCN3CC(CF)C3)cc2F)c2[nH]c3ccccc3c2C[C@H]1C] | (S)-1-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-3-fluoro-2-methylpropan-1-one | 0.000402 | 518.3 |
| 219 | 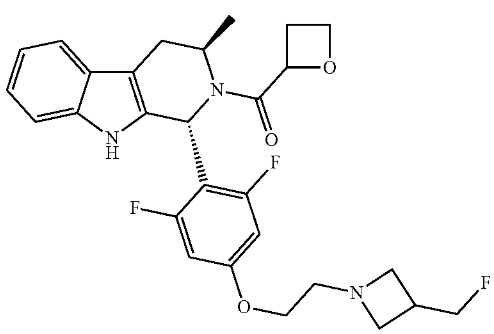 [SMILES: C[C@@H]1Cc2c([nH]c3ccccc23)[C@@H](c2c(F)cc(OCCN3CC(CF)C3)cc2F)N1C(=O)C1CCO1] | ((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)(oxetan-2-yl)methanone | 0.035 | 514.2 |

TABLE 2-continued

| No. | Structure | Name | ER-alpha MCF7 HCS EC$_{50}$ (μM) | LCMS [M + H]$^+$ |
|---|---|---|---|---|
| 220 | 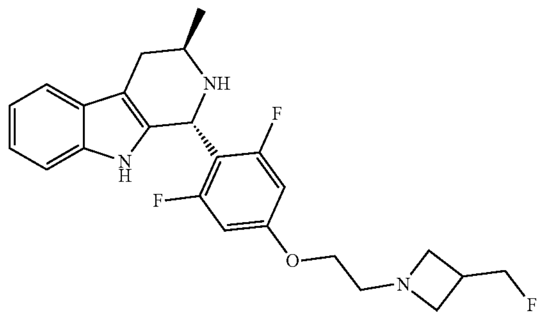 [SMILES: C[C@@H]1Cc2c([nH]c3ccccc23)[C@@H](c2c(F)cc(OCCN3CC(CF)C3)cc2F)N1] | (1R,3R)-1-[2,6-difluoro-4-[2-[3-(fluoromethyl)azetidin-1-yl]ethoxy]phenyl]-3-methyl-2,3,4,9-tetrahydro-1H-pyrido[3,4-b]indole | 0.007 | 430.2 |
| 221 | 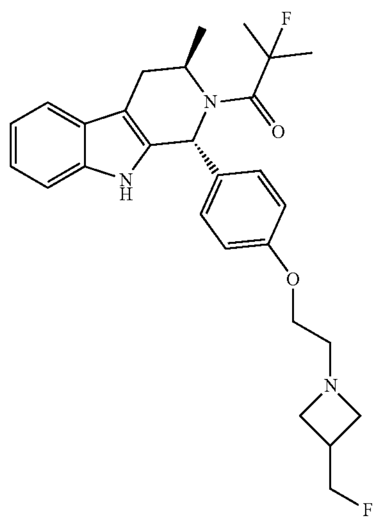 [SMILES: C[C@@H]1Cc2c([nH]c3ccccc23)[C@@H](c2ccc(OCCN3CC(CF)C3)cc2)N1C(=O)C(C)(C)F] | 2-fluoro-1-[(1R,3R)-1-[4-[2-[3-(fluoromethyl)azetidin-1-yl]ethoxy]phenyl]-3-methyl-1,3,4,9-tetrahydropyrido[3,4-b]indol-2-yl]-2-methyl-propan-1-one | 0.18 | 482.3 |
| 222 | 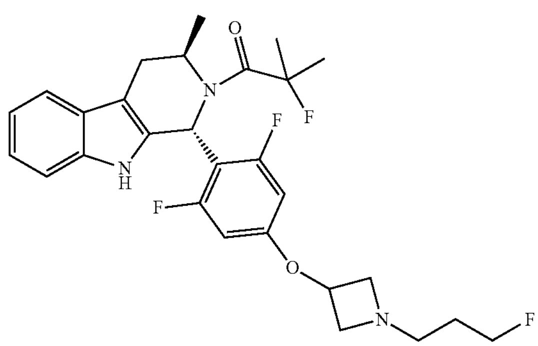 [SMILES: C[C@@H]1Cc2c([nH]c3ccccc23)[C@@H](c2c(F)cc(OC3CN(CCCF)C3)cc2F)N1C(=O)C(C)(C)F] | 1-[(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]-2-fluoro-2-methyl-propan-1-one | 0.0004 | 518.2 |
| 223 | 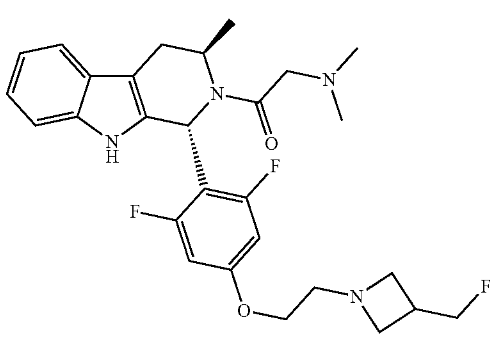 [SMILES: C[C@@H]1Cc2c([nH]c3ccccc23)[C@@H](c2c(F)cc(OCCN3CC(CF)C3)cc2F)N1C(=O)CN(C)C] | 1-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2-(dimethylamino)ethanone | 0.038 | 515.2 |

TABLE 2-continued

| No. | Structure | Name | ER-alpha MCF7 HCS EC$_{50}$ (μM) | LCMS [M + H]$^+$ |
|---|---|---|---|---|
| 224 | 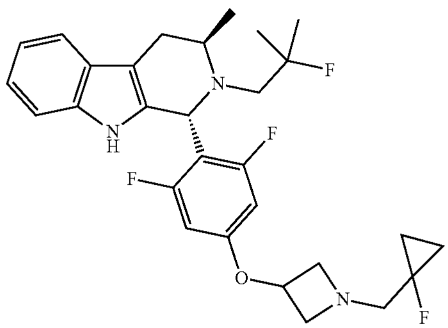 [SMILES: C[C@@H]1Cc2c([nH]c3ccccc23)[C@@H](c2c(F)cc(OC3CN(CC4(F)CC4)C3)cc2F)N1CC(C)(C)F] | (1R,3R)-1-[2,6-difluoro-4-[1-[(1-fluorocyclopropyl)methyl]azetidin-3-yl]oxy-phenyl]-2-(2-fluoro-2-methyl-propyl)-3-methyl-1,3,4,9-tetrahydropyrido[3,4-b]indole | 0.000316 | 516.2 |
| 225 | 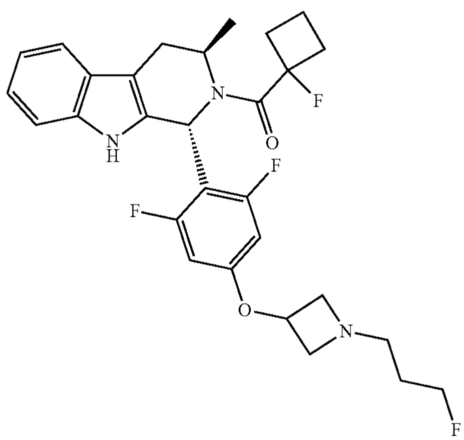 [SMILES: C[C@@H]1Cc2c([nH]c3ccccc23)[C@@H](c2c(F)cc(OC3CN(CCCF)C3)cc2F)N1C(=O)C1(F)CCC1] | [(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]-(1-fluorocyclobutyl)methanone | 0.001 | 530.1 |
| 226 | 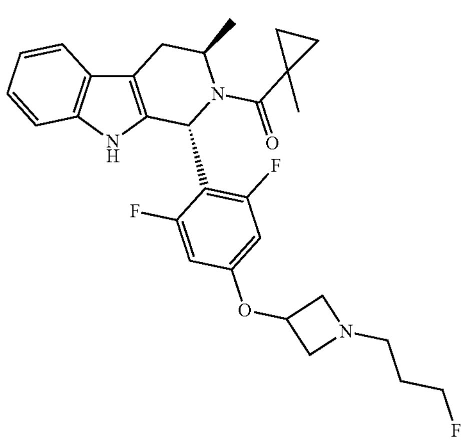 [SMILES: C[C@@H]1Cc2c([nH]c3ccccc23)[C@@H](c2c(F)cc(OC3CN(CCCF)C3)cc2F)N1C(=O)C1(C)CC1] | [(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]-(1-methylcyclopropyl)methanone | 0.002 | 512.1 |

TABLE 2-continued

| No. | Structure | Name | ER-alpha MCF7 HCS EC₅₀ (μM) | LCMS [M + H]⁺ |
|---|---|---|---|---|
| 227 | 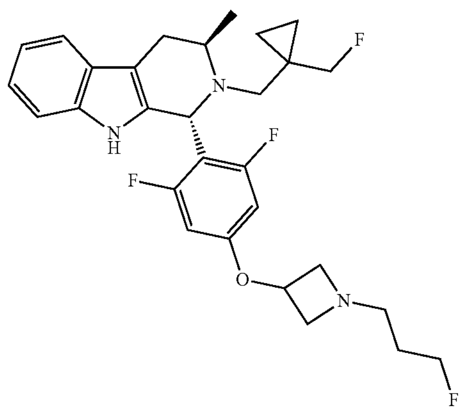 [SMILES: C[C@@H]1Cc2c([nH]c3ccccc23)[C@@H](c2c(F)cc(OC3CN(CCCF)C3)cc2F)N1CC1(CF)CC1] | (1R,3R)-1-[2,6-difluoro-4-[1-(3-fluoropropyl)azetidin-3-yl]oxy-phenyl]-2-[1-(fluoromethyl)cyclopropyl]methyl]-3-methyl-1,3,4,9-tetrahydropyrido[3,4-b]indole | 0.00017 | 516.1 |
| 228 | 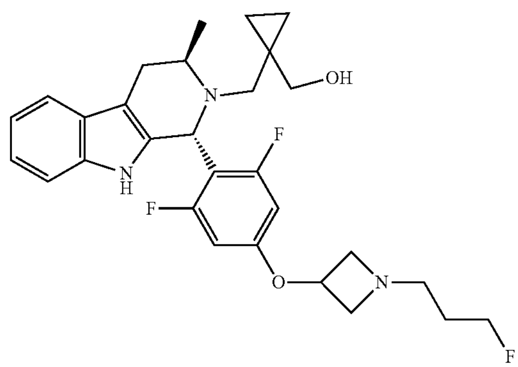 [SMILES: C[C@@H]1Cc2c([nH]c3ccccc23)[C@@H](c2c(F)cc(OC3CN(CCCF)C3)cc2F)N1CC1(CO)CC1] | [1-[[(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]methyl]cyclopropyl]methanol | 0.001 | 514.2 |
| 229 | 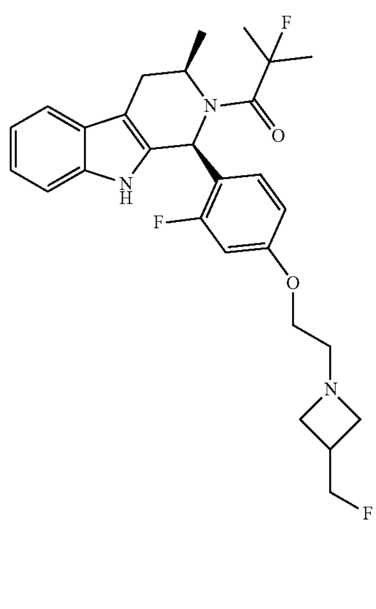 [SMILES: C[C@@H]1Cc2c([nH]c3ccccc23)[C@H](c2ccc(OCCN3CC(CF)C3)cc2F)N1C(=O)C(C)(C)F] | 2-fluoro-1-[(1S,3R)-1-[2-fluoro-4-[2-[3-(fluoromethyl)azetidin-1-yl]ethoxy]phenyl]-3-methyl-1,3,4,9-tetrahydropyrido[3,4-b]indol-2-yl]-2-methyl-propan-1-one | 0.025 | 500.2 |

TABLE 2-continued

| No. | Structure | Name | ER-alpha MCF7 HCS EC$_{50}$ (μM) | LCMS [M + H]$^+$ |
|---|---|---|---|---|
| 230 | 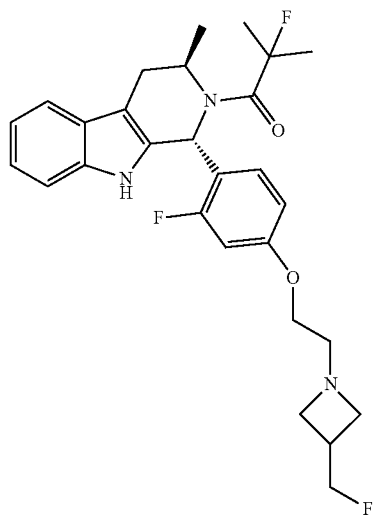 [SMILES: C[C@@H]1Cc2c([nH]c3ccccc23)[C@@H](c2ccc(OCCN3CC(CF)C3)cc2F)N1C(=O)C(C)(C)F] | 2-fluoro-1-[(1R,3R)-1-[2-fluoro-4-[2-[3-(fluoromethyl)azetidin-1-yl]ethoxy]phenyl]-3-methyl-1,3,4,9-tetrahydropyrido[3,4-b]indol-2-yl]-2-methyl-propan-1-one | 0.000068 | 500.2 |
| 231 | 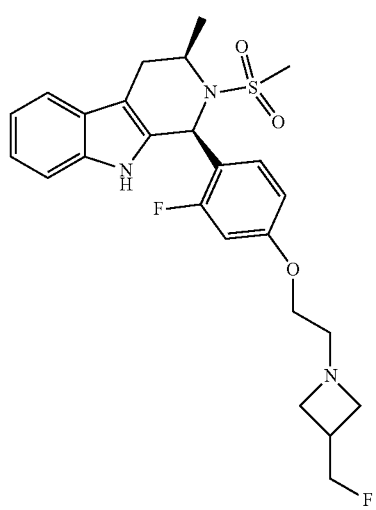 [SMILES: C[C@@H]1Cc2c([nH]c3ccccc23)[C@H](c2ccc(OCCN3CC(CF)C3)cc2F)N1S(C)(=O)=O] | (1S,3R)-1-[2-fluoro-4-[2-[3-(fluoromethyl)azetidin-1-yl]ethoxy]phenyl]-3-methyl-2-methylsulfonyl-1,3,4,9-tetrahydropyrido[3,4-b]indole | 0.024 | 490.2 |
| 232 | 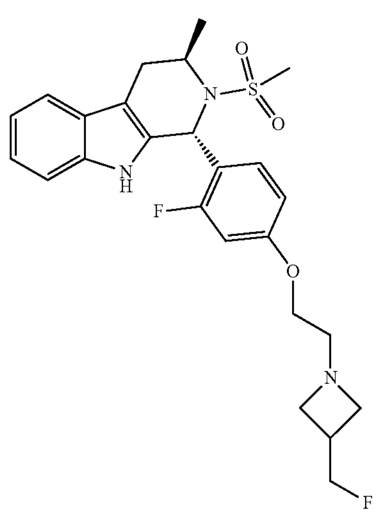 [SMILES: C[C@@H]1Cc2c([nH]c3ccccc23)[C@@H](c2ccc(OCCN3CC(CF)C3)cc2F)N1S(C)(=O)=O] | (1R,3R)-1-[2-fluoro-4-[2-[3-(fluoromethyl)azetidin-1-yl]ethoxy]phenyl]-3-methyl-2-methylsulfonyl-1,3,4,9-tetrahydropyrido[3,4-b]indole | 0.000192 | 490.2 |

TABLE 2-continued

| No. | Structure | Name | ER-alpha MCF7 HCS EC$_{50}$ (μM) | LCMS [M + H]$^+$ |
|---|---|---|---|---|
| 233 | 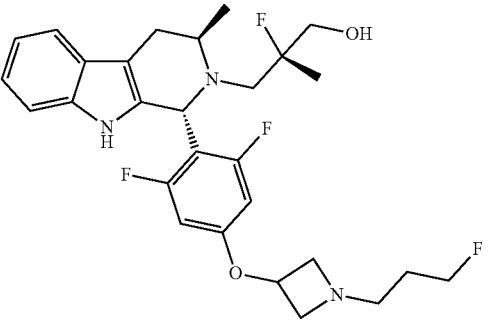 [SMILES: C[C@@H]1Cc2c([nH]c3ccccc23)[C@@H](c2c(F)cc(OC3CN(CCCF)C3)cc2F)N1C[C@](C)(F)CO] | 3-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)-2-fluoro-2-methylpropan-1-ol | 0.000133 | 520.3 |
| 234 | 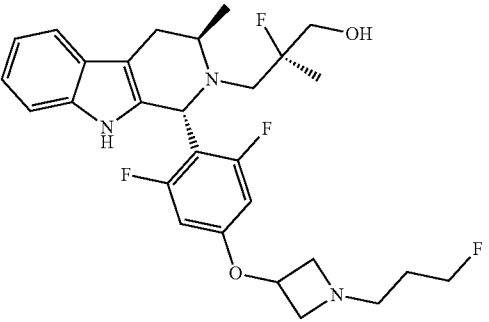 [SMILES: C[C@@H]1Cc2c([nH]c3ccccc23)[C@@H](c2c(F)cc(OC3CN(CCCF)C3)cc2F)N1C[C@@](C)(F)CO] | 3-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)-2-fluoro-2-methylpropan-1-ol | 0.00018 | 520.3 |
| 235 | 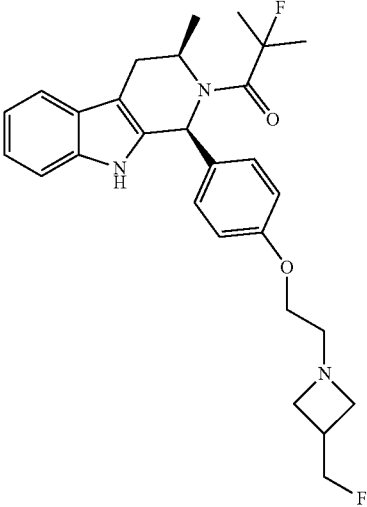 [SMILES: C[C@@H]1Cc2c([nH]c3ccccc23)[C@H](c2ccc(OCCN3CC(CF)C3)cc2)N1C(=O)C(C)(C)F] | 2-fluoro-1-[(1S,3R)-1-[4-[2-[3-(fluoromethyl)azetidin-1-yl]ethoxy]phenyl]-3-methyl-1,3,4,9-tetrahydropyrido[3,4-b]indol-2-yl]-2-methyl-propan-1-one | 0.024 | 482.3 |
| 236 | 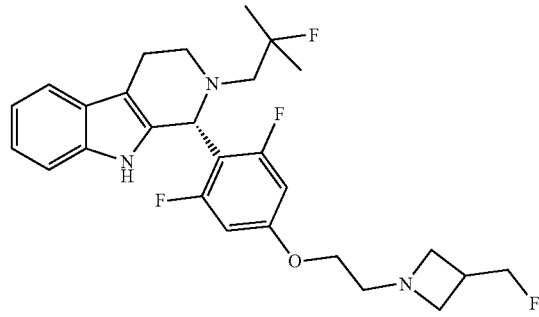 [SMILES: CC(C)(F)CN1CCc2c([nH]c3ccccc23)[C@H]1c1c(F)cc(OCCN2CC(CF)C2)cc1F] | (1R)-1-[2,6-difluoro-4-[2-[3-(fluoromethyl)azetidin-1-yl]ethoxy]phenyl]-2-(2-fluoro-2-methyl-propyl)-1,3,4,9-tetrahydropyrido[3,4-b]indole | 0.000182 | 490.2 |

TABLE 2-continued

| No. | Structure | Name | ER-alpha MCF7 HCS EC$_{50}$ (μM) | LCMS [M + H]$^+$ |
|---|---|---|---|---|
| 237 | 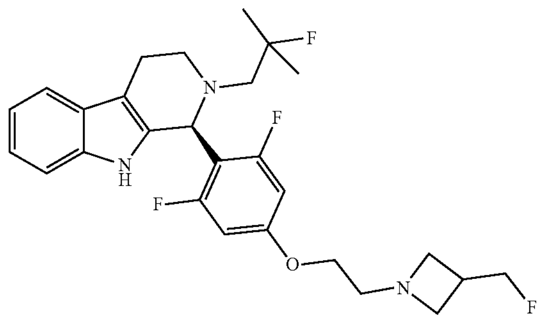 [SMILES: CC(C)(F)CN1CCc2c([nH]c3ccccc23)[C@@H]1c1c(F)cc(OCCN2CC(CF)C2)cc1F] | (1S)-1-[2,6-difluoro-4-[2-[3-(fluoromethyl)azetidin-1-yl]ethoxy]phenyl]-2-(2-fluoro-2-methyl-propyl)-1,3,4,9-tetrahydropyrido[3,4-b]indole | 0.046 | 490.2 |
| 238 | 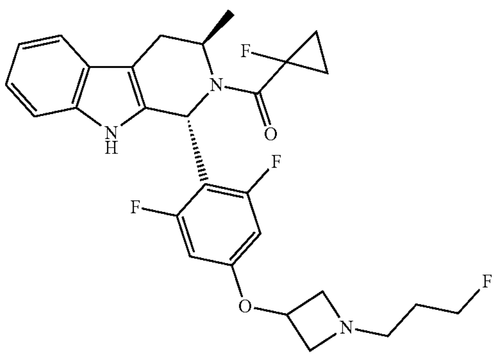 [SMILES: C[C@@H]1Cc2c([nH]c3ccccc23)[C@@H](c2c(F)cc(OC3CN(CCCF)C3)cc2F)N1C(=O)C1(F)CC1] | [(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]-(1-fluorocyclopropyl)methanone | 0.000244 | 516.1 |
| 239 | 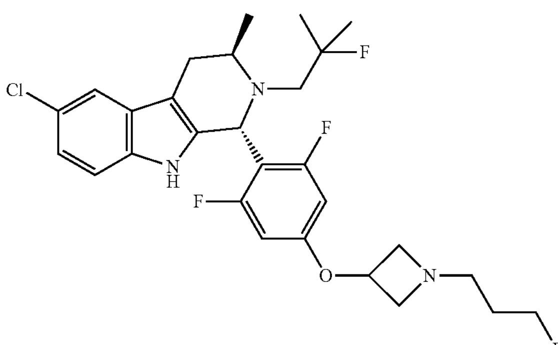 | (1R,3R)-6-chloro-1-(2,6-difluoro-4-((1-(3-fluoropropyl)azetidin-3-yl)oxy)phenyl)-2-(2-fluoro-2-methylpropyl)-3-methyl-2,3,4,9-tetrahydro-1H-pyrido[3,4-b]indole | 0.00156 | 538.1 |
| 240 | 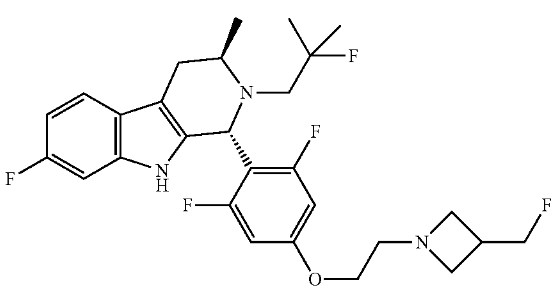 [SMILES: C[C@@H]1Cc2c([nH]c3cc(F)ccc23)[C@@H](c2c(F)cc(OCCN3CC(CF)C3)cc2F)N1CC(C)(C)F] | (1R,3R)-1-(2,6-difluoro-4-(2-(3-(fluoromethyl)azetidin-1-yl)ethoxy)phenyl)-7-fluoro-2-(2-fluoro-2-methylpropyl)-3-methyl-2,3,4,9-tetrahydro-1H-pyrido[3,4-b]indole | 0.000261 | 522.2 |

TABLE 2-continued

| No. | Structure | Name | ER-alpha MCF7 HCS EC$_{50}$ (μM) | LCMS [M + H]$^+$ |
|---|---|---|---|---|
| 241 | 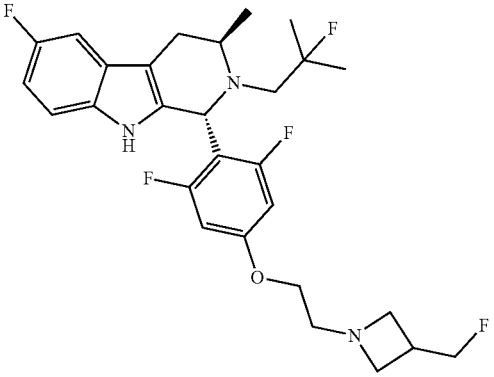 [SMILES: C[C@@H]1Cc2c([nH]c3ccc(F)cc23)[C@@H](c2c(F)cc(OCCN3CC(CF)C3)cc2F)N1CC(C)(C)F] | (1R,3R)-1-(2,6-difluoro-4-(2-(3-(fluoromethyl)azetidin-1-yl)ethoxy)phenyl)-6-fluoro-2-(2-fluoro-2-methylpropyl)-3-methyl-2,3,4,9-tetrahydro-1H-pyrido[3,4-b]indole | 0.000381 | 522.3 |
| 242 | 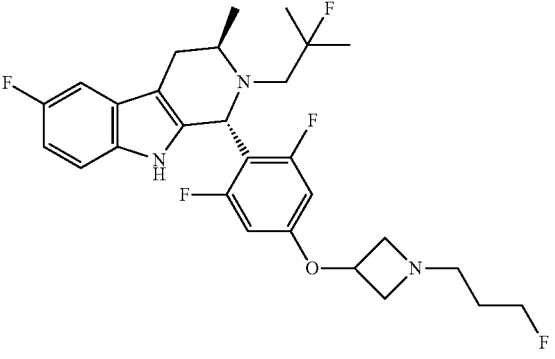 [SMILES: C[C@@H]1Cc2c([nH]c3ccc(F)cc23)[C@@H](c2c(F)cc(OC3CN(CCCF)C3)cc2F)N1CC(C)(C)F] | (1R,3R)-1-(2,6-difluoro-4-((1-(3-fluoropropyl)azetidin-3-yl)oxy)phenyl)-6-fluoro-2-(2-fluoro-2-methylpropyl)-3-methyl-2,3,4,9-tetrahydro-1H-pyrido[3,4-b]indole | 0.00542 | 522.3 |
| 243 | 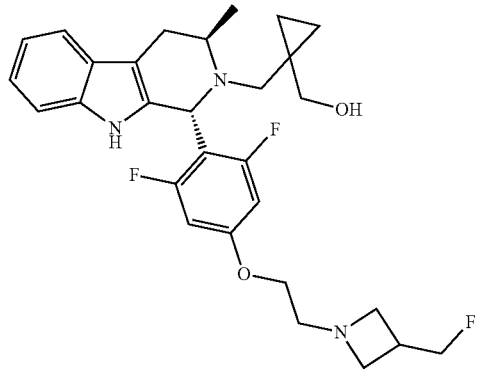 [SMILES: C[C@@H]1Cc2c([nH]c3ccccc23)[C@@H](c2c(F)cc(OCCN3CC(CF)C3)cc2F)N1CC1(CO)CC1] | (1-(((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)methyl)cyclopropyl)methanol | 0.002 | 514.2 |
| 244 | 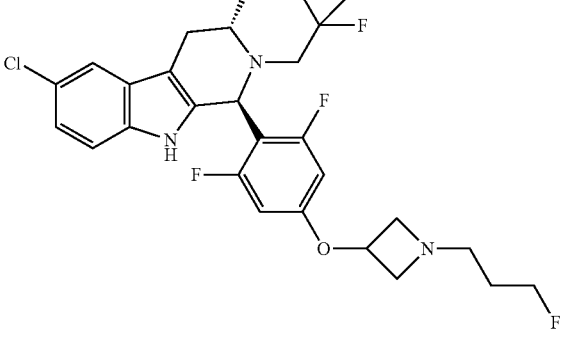 | (1S,3S)-6-chloro-1-(2,6-difluoro-4-((1-(3-fluoropropyl)azetidin-3-yl)oxy)phenyl)-2-(2-fluoro-2-methylpropyl)-3-methyl-2,3,4,9-tetrahydro-1H-pyrido[3,4-b]indole | 0.063 | 538.1 |

TABLE 2-continued

| No. | Structure | Name | ER-alpha MCF7 HCS $EC_{50}$ (μM) | LCMS $[M + H]^+$ |
|---|---|---|---|---|
| 245 | 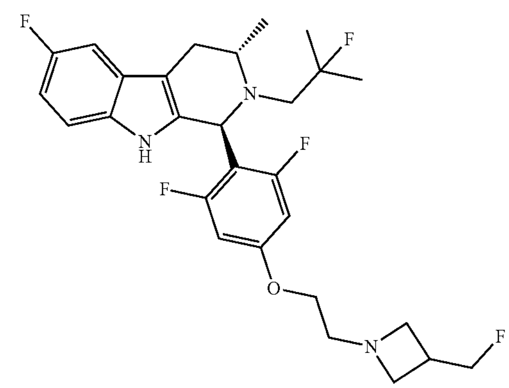 [SMILES: C[C@H]1Cc2c([nH]c3ccc(F)cc23)[C@H](c2c(F)cc(OCCN3CC(CF)C3)cc2F)N1CC(C)(C)F] | (1S,3S)-1-(2,6-difluoro-4-(2-(3-(fluoromethyl)azetidin-1-yl)ethoxy)phenyl)-6-fluoro-2-(2-fluoro-2-methylpropyl)-3-methyl-2,3,4,9-tetrahydro-1H-pyrido[3,4-b]indole | 0.035 | 522.3 |
| 246 | 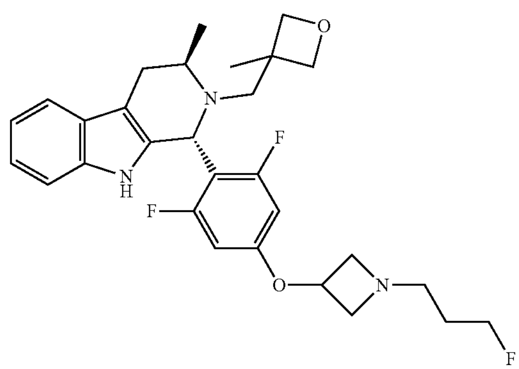 [SMILES: C[C@@H]1Cc2c([nH]c3ccccc23)[C@@H](c2c(F)cc(OC3CN(CCCF)C3)cc2F)N1CC1(C)COC1] | (1R,3R)-1-[2,6-difluoro-4-[1-(3-fluoropropyl)azetidin-3-yl]oxy-phenyl]-3-methyl-2-[(3-methyloxetan-3-yl)methyl]-1,3,4,9-tetrahydropyrido[3,4-b]indole | 0.000358 | 536.1 |
| 247 | 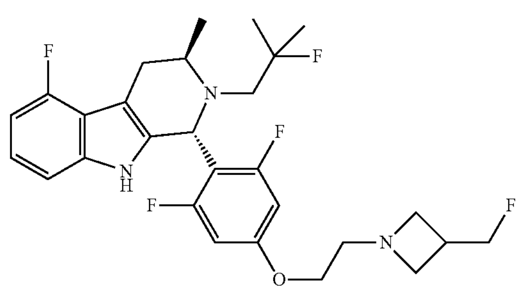 [SMILES: C[C@@H]1Cc2c([nH]c3cccc(F)c23)[C@@H](c2c(F)cc(OCCN3CC(CF)C3)cc2F)N1CC(C)(C)F] | (1R,3R)-1-(2,6-difluoro-4-(2-(3-(fluoromethyl)azetidin-1-yl)ethoxy)phenyl)-5-fluoro-2-(2-fluoro-2-methylpropyl)-3-methyl-2,3,4,9-tetrahydro-1H-pyrido[3,4-b]indole | 0.00434 | 522.2 |
| 248 | 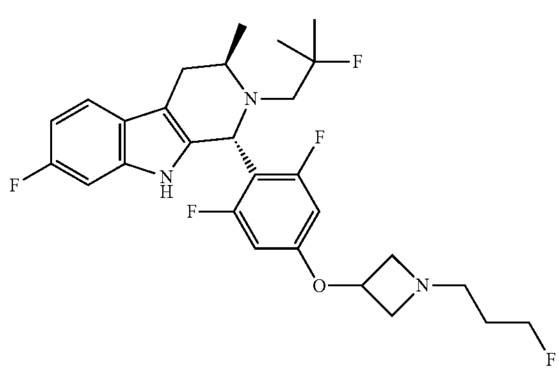 [SMILES: C[C@@H]1Cc2c([nH]c3cc(F)ccc23)[C@@H](c2c(F)cc(OC3CN(CCCF)C3)cc2F)N1CC(C)(C)F] | (1R,3R)-1-(2,6-difluoro-4-((1-(3-fluoropropyl)azetidin-3-yl)oxy)phenyl)-7-fluoro-2-(2-fluoro-2-methylpropyl)-3-methyl-2,3,4,9-tetrahydro-1H-pyrido[3,4-b]indole | 0.000518 | 522.2 |

TABLE 2-continued

| No. | Structure | Name | ER-alpha MCF7 HCS EC50 (μM) | LCMS [M + H]+ |
|---|---|---|---|---|
| 249 | 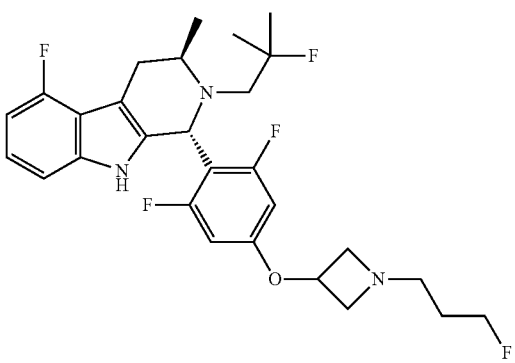 [SMILES: C[C@@H]1Cc2c([nH]c3cccc(F)c23)[C@@H](c2c(F)cc(OC3CN(CCCF)C3)cc2F)N1CC(C)(C)F] | (1R,3R)-1-(2,6-difluoro-4-((1-(3-fluoropropyl)azetidin-3-yl)oxy)phenyl)-5-fluoro-2-(2-fluoro-2-methylpropyl)-3-methyl-2,3,4,9-tetrahydro-1H-pyrido[3,4-b]indole | 0.000511 | 522.2 |
| 250 | 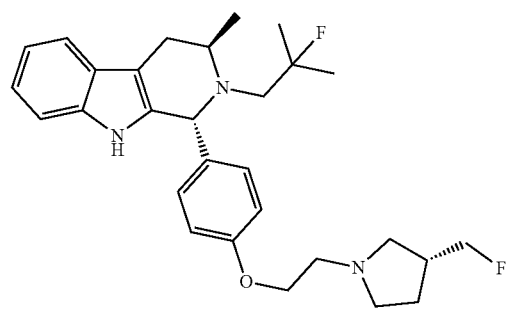 [SMILES: C[C@@H]1Cc2c([nH]c3ccccc23)[C@@H](c2ccc(OCCN3CC[C@@H](CF)C3)cc2)N1CC(C)(C)F] | (1R,3R)-2-(2-fluoro-2-methyl-propyl)-1-[4-[2-[(3R)-3-(fluoromethyl)pyrrolidin-1-yl]ethoxy]phenyl]-3-methyl-1,3,4,9-tetrahydropyrido[3,4-b]indole | 0.000275 | 482.2 |
| 251 | 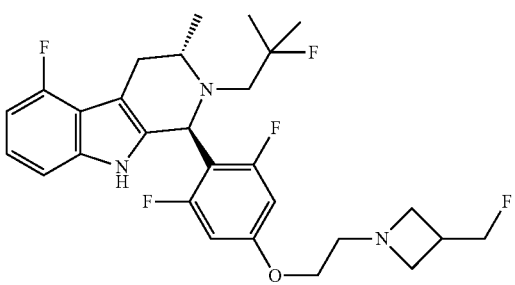 [SMILES: C[C@H]1Cc2c([nH]c3cccc(F)c23)[C@H](c2c(F)cc(OCCN3CC(CF)C3)cc2F)N1CC(C)(C)F] | (1S,3S)-1-(2,6-difluoro-4-(2-(3-(fluoromethyl)azetidin-1-yl)ethoxy)phenyl)-5-fluoro-2-(2-fluoro-2-methylpropyl)-3-methyl-2,3,4,9-tetrahydro-1H-pyrido[3,4-b]indole | 0.021 | 522.2 |
| 252 | 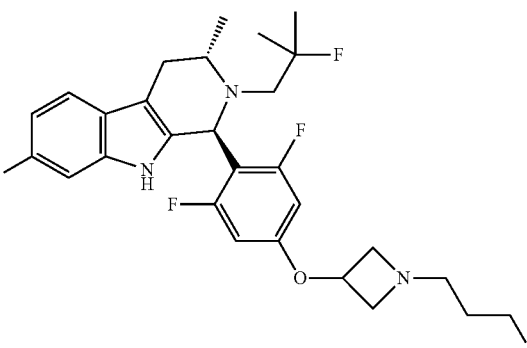 | (1S,3S)-1-(2,6-difluoro-4-((1-(3-fluoropropyl)azetidin-3-yl)oxy)phenyl)-7-fluoro-2-(2-fluoro-2-methylpropyl)-3-methyl-2,3,4,9-tetrahydro-1H-pyrido[3,4-b]indole | 0.05 | 522.3 |

TABLE 2-continued

| No. | Structure | Name | ER-alpha MCF7 HCS EC$_{50}$ (μM) | LCMS [M + H]$^+$ |
|---|---|---|---|---|
| 253 | 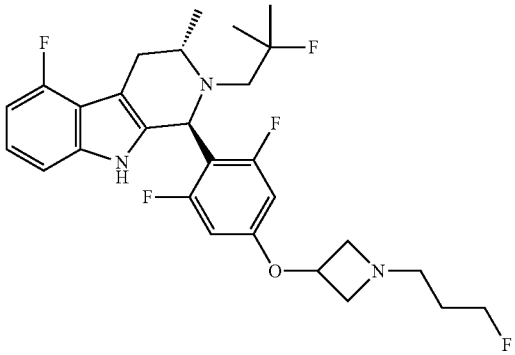 [SMILES: C[C@H]1Cc2c([nH]c3cccc(F)c23)[C@H](c2c(F)cc(OC3CN(CCCF)C3)cc2F)N1CC(C)(C)F] | (1S,3S)-1-(2,6-difluoro-4-((1-(3-fluoropropyl)azetidin-3-yl)oxy)phenyl)-5-fluoro-2-(2-fluoro-2-methylpropyl)-3-methyl-2,3,4,9-tetrahydro-1H-pyrido[3,4-b]indole | 0.035 | 522.2 |
| 254 | 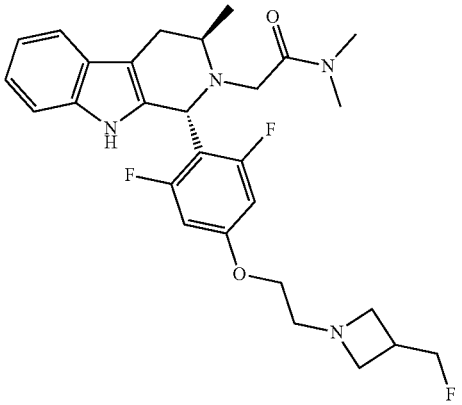 [SMILES: C[C@@H]1Cc2c([nH]c3ccccc23)[C@@H](c2c(F)cc(OCCN3CC(CF)C3)cc2F)N1CC(=O)N(C)C] | 2-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-N,N-dimethyl-acetamide | 0.04 | 515.2 |
| 255 | 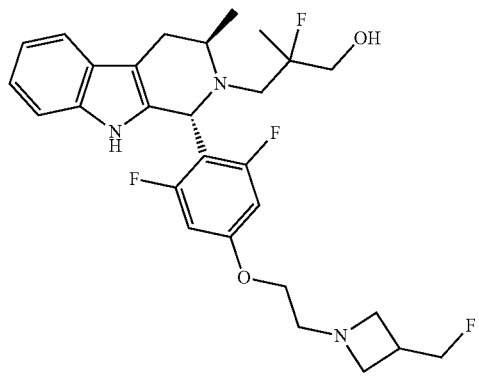 [SMILES: C[C@@H]1Cc2c([nH]c3ccccc23)[C@@H](c2c(F)cc(OCCN3CC(CF)C3)cc2F)N1CC(C)(F)CO] | 3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-2-fluoro-2-methylpropan-1-ol | 0.000010 | 520.2 |

TABLE 2-continued

| No. | Structure | Name | ER-alpha MCF7 HCS EC$_{50}$ (μM) | LCMS [M + H]$^+$ |
|---|---|---|---|---|
| 256 | 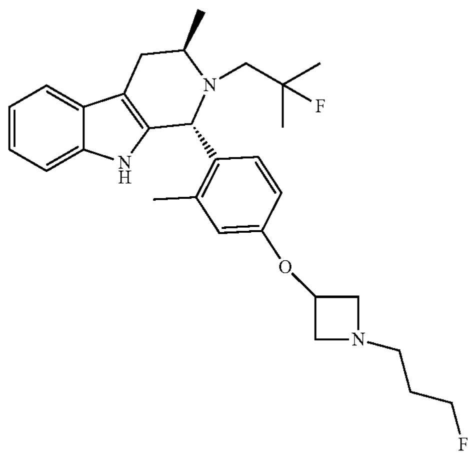 [SMILES: Cc1cc(OC2CN(CCCF)C2)ccc1[C@@H]1c2[nH]c3ccccc3c2C[C@@H](C)N1CC(C)(C)F] | (1R,3R)-2-(2-fluoro-2-methyl-propyl)-1-[4-[1-(3-fluoropropyl)azetidin-3-yl]oxy-2-methyl-phenyl]-3-methyl-1,3,4,9-tetrahydropyrido[3,4-b]indole | 0.00169 | |
| 257 | 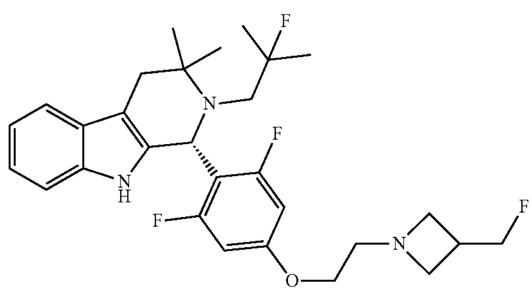 [SMILES: CC(C)(F)CN1[C@H](c2c(F)cc(OCCN3CC(CF)C3)cc2F)c2[nH]c3ccccc3c2CC1(C)C] | (1R)-1-[2,6-difluoro-4-[2-[3-(fluoromethyl)azetidin-1-yl]ethoxy]phenyl]-2-(2-fluoro-2-methyl-propyl)-3,3-dimethyl-4,9-dihydro-1H-pyrido[3,4-b]indole | 0.00109 | 518.3 |
| 258 | 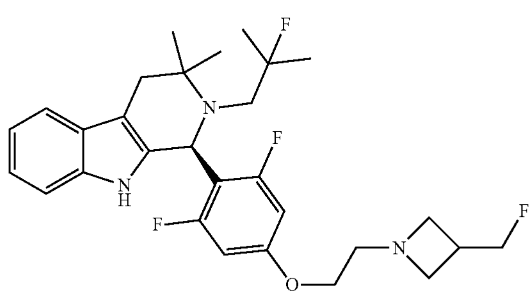 [SMILES: CC(C)(F)CN1[C@@H](c2c(F)cc(OCCN3CC(CF)C3)cc2F)c2[nH]c3ccccc3c2CC1(C)C] | (S)-1-(2,6-difluoro-4-(2-(3-(fluoromethyl)azetidin-1-yl)ethoxy)phenyl)-2-(2-fluoro-2-methylpropyl)-3,3-dimethyl-2,3,4,9-tetrahydro-1H-pyrido[3,4-b]indole | 0.031 | 518.3 |
| 259 | 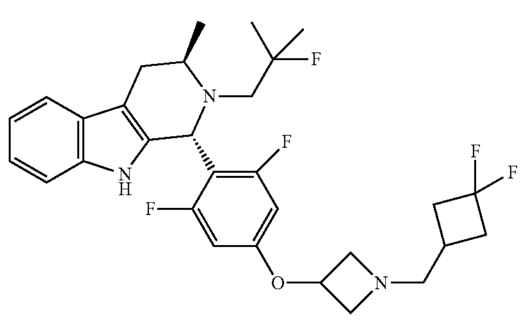 [SMILES: C[C@@H]1Cc2c([nH]c3ccccc23)[C@@H](c2c(F)cc(OC3CN(CC4CC(F)(F)C4)C3)cc2F)N1CC(C)(C)F] | (1R,3R)-1-[4-[1-[(3,3-difluorocyclobutyl)methyl]azetidin-3-yl]oxy-2,6-difluoro-phenyl]-2-(2-fluoro-2-methyl-propyl)-3-methyl-1,3,4,9-tetrahydropyrido[3,4-b]indole | 0.000444 | 538.3 |

TABLE 2-continued

| No. | Structure | Name | ER-alpha MCF7 HCS EC$_{50}$ (μM) | LCMS [M + H]$^+$ |
|---|---|---|---|---|
| 260 | 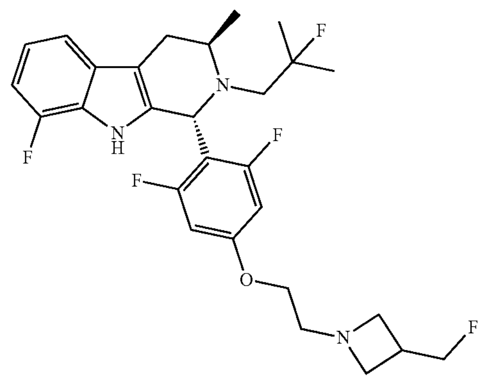 [SMILES: C[C@@H]1Cc2c([nH]c3c(F)cccc23)[C@@H](c2c(F)cc(OCCN3CC(CF)C3)cc2F)N1CC(C)(C)F] | (1R,3R)-1-(2,6-difluoro-4-(2-(3-(fluoromethyl)azetidin-1-yl)ethoxy)phenyl)-8-fluoro-2-(2-fluoro-2-methylpropyl)-3-methyl-2,3,4,9-tetrahydro-1H-pyrido[3,4-b]indole | 0.000881 | 522.3 |
| 261 | 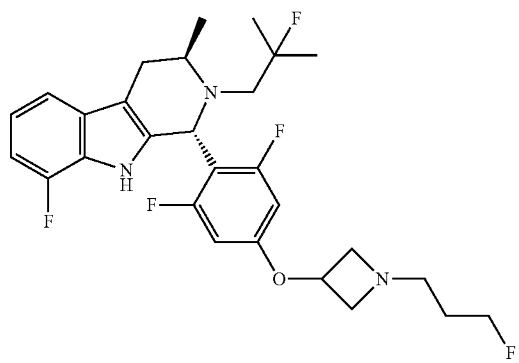 [SMILES: C[C@@H]1Cc2c([nH]c3c(F)cccc23)[C@@H](c2c(F)cc(OC3CN(CCCF)C3)cc2F)N1CC(C)(C)F] | (1R,3R)-1-(2,6-difluoro-4-((1-(3-fluoropropyl)azetidin-3-yl)oxy)phenyl)-8-fluoro-2-(2-fluoro-2-methylpropyl)-3-methyl-2,3,4,9-tetrahydro-1H-pyrido[3,4-b]indole | 0.00028 | 522.3 |
| 262 | 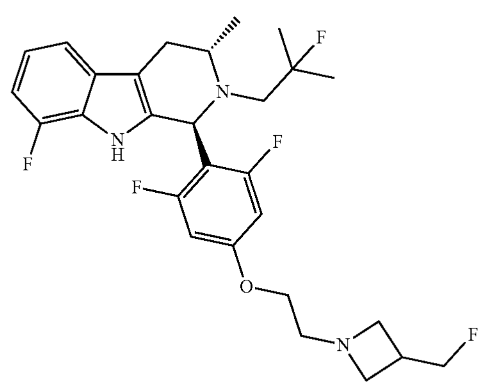 [SMILES: C[C@H]1Cc2c([nH]c3c(F)cccc23)[C@H](c2c(F)cc(OCCN3CC(CF)C3)cc2F)N1CC(C)(C)F] | (1S,3S)-1-(2,6-difluoro-4-(2-(3-(fluoromethyl)azetidin-1-yl)ethoxy)phenyl)-8-fluoro-2-(2-fluoro-2-methylpropyl)-3-methyl-2,3,4,9-tetrahydro-1H-pyrido[3,4-b]indole | 0.026 | 522.3 |
| 263 | 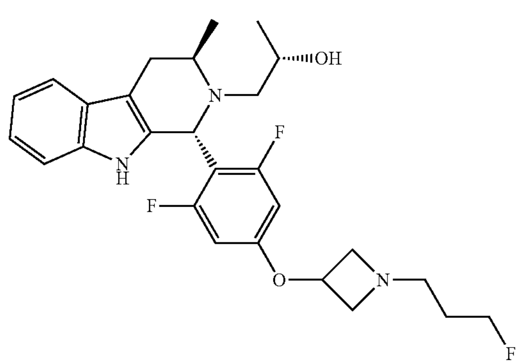 [SMILES: C[C@H](O)CN1[C@H](c2c(F)cc(OC3CN(CCCF)C3)cc2F)c2[nH]c3ccccc3c2C[C@H]1C] | (S)-1-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)propan-2-ol | 0.000359 | 488.3 |

TABLE 2-continued

| No. | Structure | Name | ER-alpha MCF7 HCS EC$_{50}$ (μM) | LCMS [M + H]$^+$ |
|---|---|---|---|---|
| 264 | 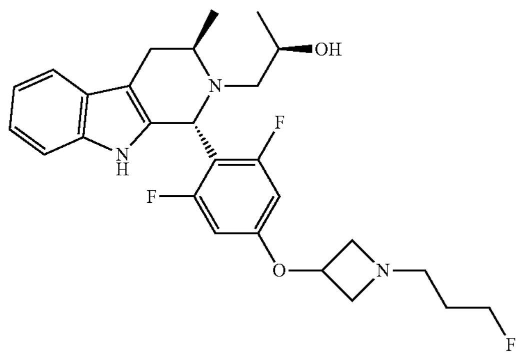 [SMILES: C[C@@H]1Cc2c([nH]c3ccccc23)[C@@H](c2c(F)cc(OC3CN(CCCF)C3)cc2F)N1C[C@@H](C)O] | (R)-1-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)propan-2-ol | 0.000969 | 488.3 |
| 265 | 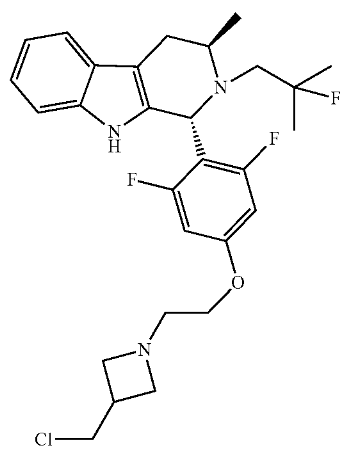 [SMILES: C[C@@H]1Cc2c([nH]c3ccccc23)[C@@H](c2c(F)cc(OCCN3CC(CCl)C3)cc2F)N1CC(C)(C)F] | (1R,3R)-1-[4-[2-[3-(chloromethyl)azetidin-1-yl]ethoxy]-2,6-difluoro-phenyl]-2-(2-fluoro-2-methyl-propyl)-3-methyl-1,3,4,9-tetrahydropyrido[3,4-b]indole | 0.0017 | 521.2 |
| 266 | 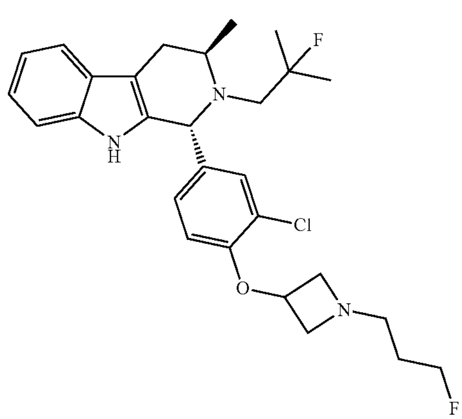 [SMILES: C[C@@H]1Cc2c([nH]c3ccccc23)[C@@H](c2ccc(OC3CN(CCCF)C3)c(Cl)c2)N1CC(C)(C)F] | (1R,3R)-1-[3-chloro-4-[1-(3-fluoropropyl)azetidin-3-yl]oxy-phenyl]-2-(2-fluoro-2-methyl-propyl)-3-methyl-1,3,4,9-tetrahydropyrido[3,4-b]indole | 0.01 | 503.2 |

TABLE 2-continued

| No. | Structure | Name | ER-alpha MCF7 HCS EC$_{50}$ (μM) | LCMS [M + H]$^+$ |
|---|---|---|---|---|
| 267 | 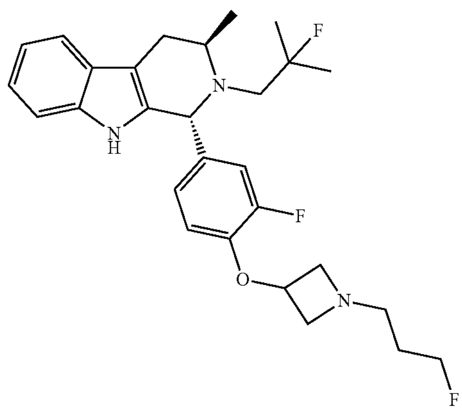 [SMILES: C[C@@H]1Cc2c([nH]c3ccccc23)[C@@H](c2ccc(OC3CN(CCCF)C3)c(F)c2)N1CC(C)(C)F] | (1R,3R)-1-[3-fluoro-4-[1-(3-fluoropropyl)azetidin-3-yl]oxy-phenyl]-2-(2-fluoro-2-methyl-propyl)-3-methyl-1,3,4,9-tetrahydropyrido[3,4-b]indole | 0.000744 | 486.3 |
| 268 | 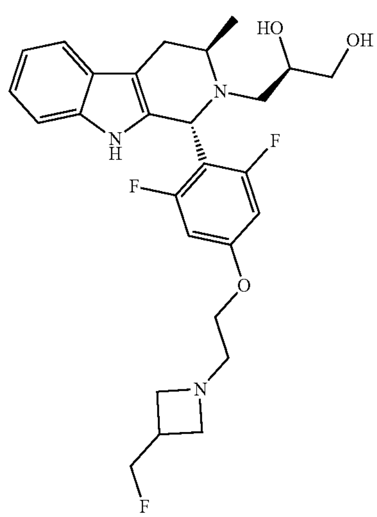 [SMILES: C[C@@H]1Cc2c([nH]c3ccccc23)[C@@H](c2c(F)cc(OCCN3CC(CF)C3)cc2F)N1C[C@@H](O)CO] | (2R)-3-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]propane-1,2-diol | 0.008 | 504.2 |
| 269 | 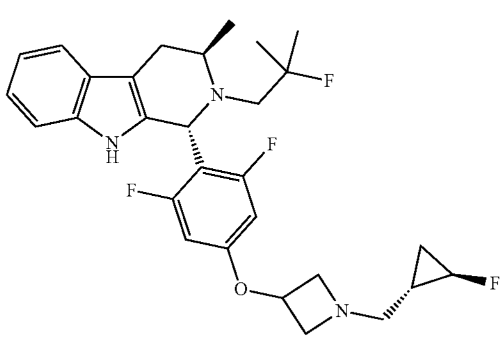 [SMILES: C[C@@H]1Cc2c([nH]c3ccccc23)[C@@H](c2c(F)cc(OC3CN(C[C@@H]4C[C@H]4F)C3)cc2F)N1CC(C)(C)F] | (1R,3R)-1-[2,6-difluoro-4-[1-[[(1S,2R)-2-fluorocyclopropyl]methyl]azetidin-3-yl]oxy-phenyl]-2-(2-fluoro-2-methyl-propyl)-3-methyl-1,3,4,9-tetrahydropyrido[3,4-b]indole | 0.001 | 516.3 |

TABLE 2-continued

| No. | Structure | Name | ER-alpha MCF7 HCS EC$_{50}$ (μM) | LCMS [M + H]$^+$ |
|---|---|---|---|---|
| 270 | 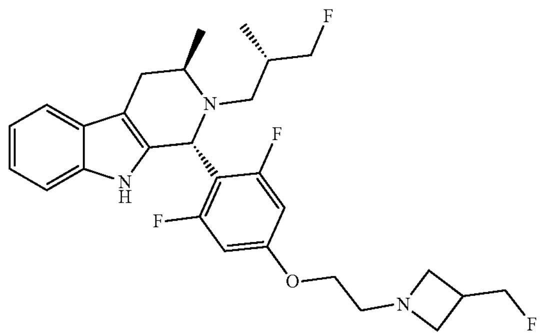 [SMILES: C[C@H](CF)CN1[C@H](c2c(F)cc(OCCN3CC(CF)C3)cc2F)c2[nH]c3ccccc3c2C[C@H]1C] | (1R,3R)-1-(2,6-difluoro-4-(2-(3-(fluoromethyl)azetidin-1-yl)ethoxy)phenyl)-2-((S)-3-fluoro-2-methylpropyl)-3-methyl-2,3,4,9-tetrahydro-1H-pyrido[3,4-b]indole | 0.000459 | 504.3 |
| 271 | 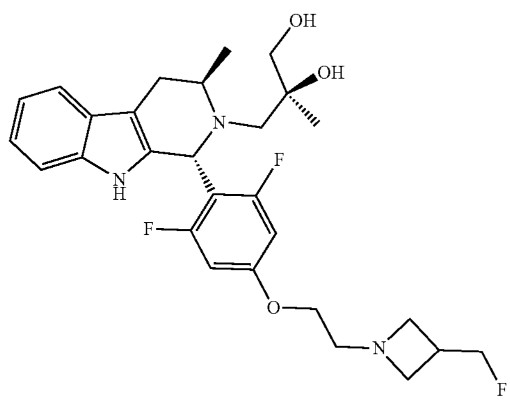 [SMILES: C[C@@H]1Cc2c([nH]c3ccccc23)[C@@H](c2c(F)cc(OCCN3CC(CF)C3)cc2F)N1C[C@](C)(O)CO] | (S)-3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-2-methylpropane-1,2-diol | 0.005 | 518.3 |
| 272 | 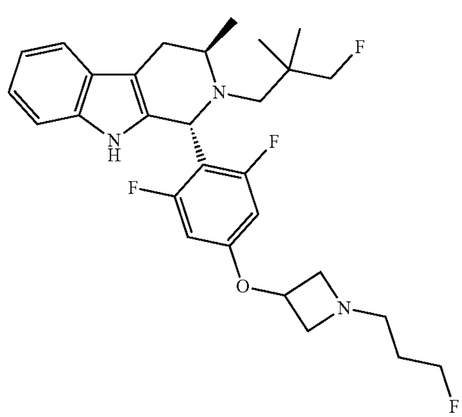 [SMILES: C[C@@H]1Cc2c([nH]c3ccccc23)[C@@H](c2c(F)cc(OC3CN(CCCF)C3)cc2F)N1CC(C)(C)CF] | (1R,3R)-1-[2,6-difluoro-4-[1-(3-fluoropropyl)azetidin-3-yl]oxy-phenyl]-2-(3-fluoro-2,2-dimethyl-propyl)-3-methyl-1,3,4,9-tetrahydropyrido[3,4-b]indole | 0.000685 | 518.3 |
| 273 | 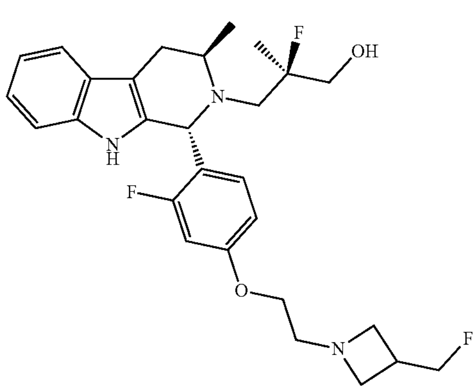 [SMILES: C[C@@H]1Cc2c([nH]c3ccccc23)[C@@H](c2ccc(OCCN3CC(CF)C3)cc2F)N1C[C@@](C)(F)CO] | (R)-2-fluoro-3-((1R,3R)-1-(2-fluoro-4-(2-(3-(fluoromethyl)azetidin-1-yl)ethoxy)phenyl)-3-methyl-1,3,4,9-tetrahydro-2H-pyrido[3,4-b]indol-2-yl)-2-methylpropan-1-ol | 0.00028 | 502.2 |

TABLE 2-continued

| No. | Structure | Name | ER-alpha MCF7 HCS EC$_{50}$ (μM) | LCMS [M + H]$^+$ |
|---|---|---|---|---|
| 274 | 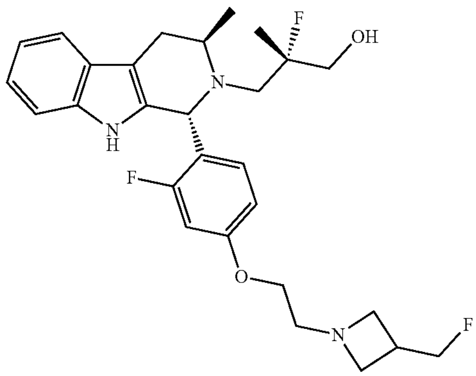 [SMILES: C[C@@H]1Cc2c([nH]c3ccccc23)[C@@H](c2ccc(OCCN3CC(CF)C3)cc2F)N1C[C@](C)(F)CO] | (S)-2-fluoro-3-((1R,3R)-1-(2-fluoro-4-(2-(3-(fluoromethyl)azetidin-1-yl)ethoxy)phenyl)-3-methyl-1,3,4,9-tetrahydro-2H-pyrido[3,4-b]indol-2-yl)-2-methylpropan-1-ol | 0.000253 | 524.1 |
| 275 | 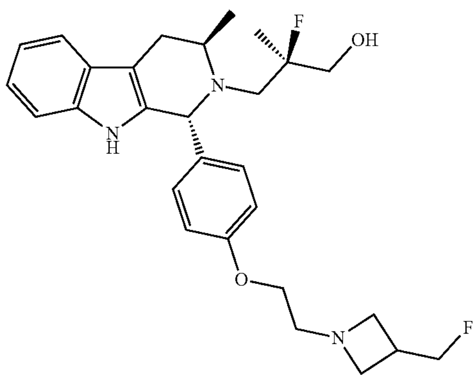 [SMILES: C[C@@H]1Cc2c([nH]c3ccccc23)[C@@H](c2ccc(OCCN3CC(CF)C3)cc2)N1C[C@@](C)(F)CO] | (R)-2-fluoro-3-((1R,3R)-1-(4-(2-(3-(fluoromethyl)azetidin-1-yl)ethoxy)phenyl)-3-methyl-1,3,4,9-tetrahydro-2H-pyrido[3,4-b]indol-2-yl)-2-methylpropan-1-ol | 0.000166 | 484.2 |
| 276 | 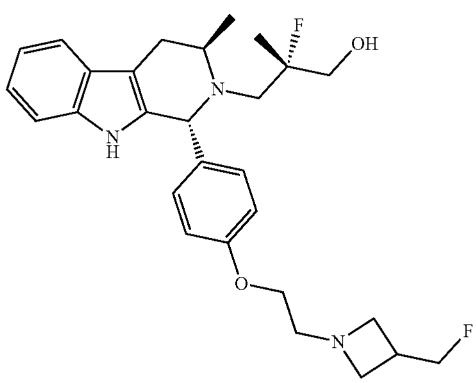 [SMILES: C[C@@H]1Cc2c([nH]c3ccccc23)[C@@H](c2ccc(OCCN3CC(CF)C3)cc2)N1C[C@](C)(F)CO] | (S)-2-fluoro-3-((1R,3R)-1-(4-(2-(3-(fluoromethyl)azetidin-1-yl)ethoxy)phenyl)-3-methyl-1,3,4,9-tetrahydro-2H-pyrido[3,4-b]indol-2-yl)-2-methylpropan-1-ol | 0.000309 | 484.2 |
| 277 | 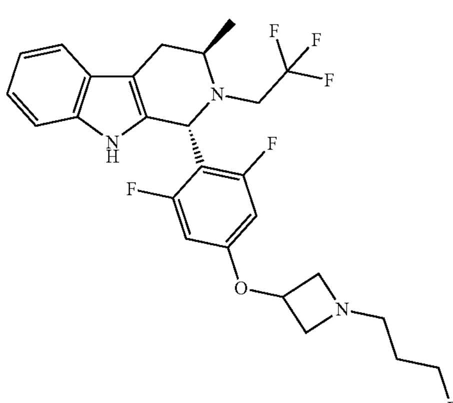 | (1R,3R)-1-[2,6-difluoro-4-[1-(3-fluoropropyl)azetidin-3-yl]oxy-phenyl]-3-methyl-2-(2,2,2-trifluoroethyl)-1,3,4,9-tetrahydropyrido[3,4-b]indole | 0.000090 | 512.2 |

TABLE 2-continued

| No. | Structure | Name | ER-alpha MCF7 HCS EC$_{50}$ (μM) | LCMS [M + H]$^+$ |
|---|---|---|---|---|
| 278 | 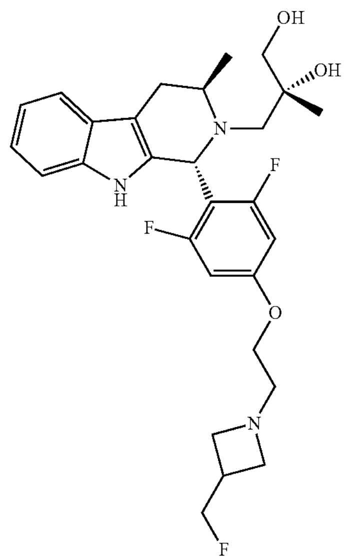 [SMILES: C[C@@H]1Cc2c([nH]c3ccccc23)[C@@H](c2c(F)cc(OCCN3CC(CF)C3)cc2F)N1C[C@@](C)(O)CO] | (2R)-3-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2-methyl-propane-1,2-diol | 0.00031 | 518.3 |
| 279 | 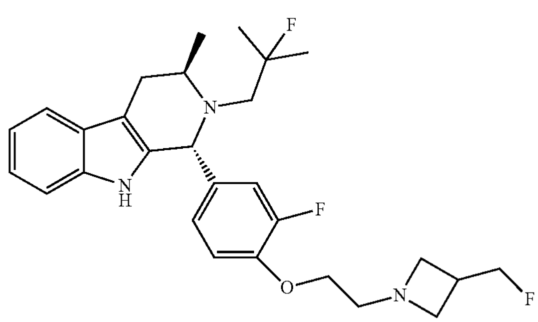 [SMILES: C[C@@H]1Cc2c([nH]c3ccccc23)[C@@H](c2ccc(OCCN3CC(CF)C3)c(F)c2)N1CC(C)(C)F] | (1R,3R)-2-(2-fluoro-2-methylpropyl)-1-(3-fluoro-4-(2-(3-(fluoromethyl)azetidin-1-yl)ethoxy)phenyl)-3-methyl-2,3,4,9-tetrahydro-1H-pyrido[3,4-b]indole | 0.00016 | 486.3 |
| 280 | 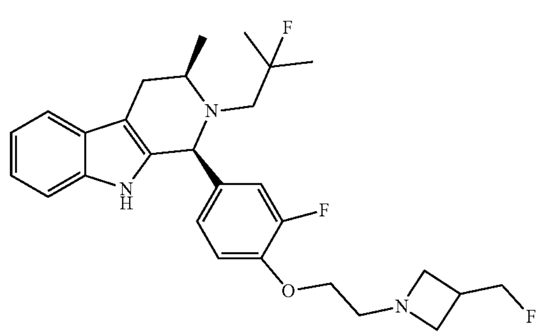 [SMILES: C[C@@H]1Cc2c([nH]c3ccccc23)[C@H](c2ccc(OCCN3CC(CF)C3)c(F)c2)N1CC(C)(C)F] | (1S,3R)-2-(2-fluoro-2-methylpropyl)-1-(3-fluoro-4-(2-(3-(fluoromethyl)azetidin-1-yl)ethoxy)phenyl)-3-methyl-2,3,4,9-tetrahydro-1H-pyrido[3,4-b]indole | 0.006 | 486.3 |

TABLE 2-continued

| No. | Structure | Name | ER-alpha MCF7 HCS EC$_{50}$ (μM) | LCMS [M + H]$^+$ |
|---|---|---|---|---|
| 281 | 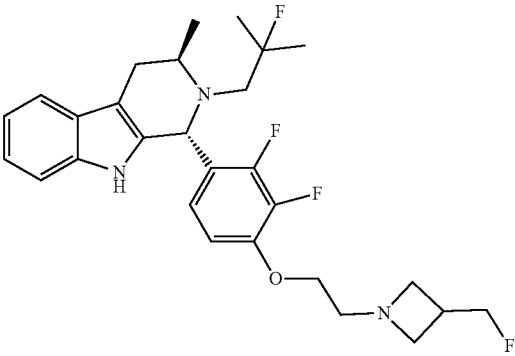 [SMILES: C[C@@H]1Cc2c([nH]c3ccccc23)[C@@H](c2ccc(OCCN3CC(CF)C3)c(F)c2F)N1CC(C)(C)F] | (1R,3R)-1-(2,3-difluoro-4-(2-(3-(fluoromethyl)azetidin-1-yl)ethoxy)phenyl)-2-(2-fluoro-2-methylpropyl)-3-methyl-2,3,4,9-tetrahydro-1H-pyrido[3,4-b]indole | 0.000183 | 504.3 |
| 282 | 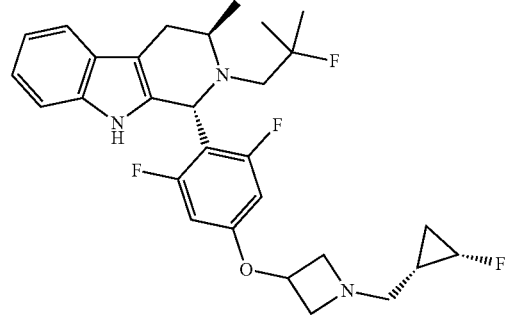 [SMILES: C[C@@H]1Cc2c([nH]c3ccccc23)[C@@H](c2c(F)cc(OC3CN(C[C@@H]4C[C@@H]4F)C3)cc2F)N1CC(C)(C)F] | (1R,3R)-1-(2,6-difluoro-4-((1-(((1S,2S)-2-fluorocyclopropyl)methyl)azetidin-3-yl)oxy)phenyl)-2-(2-fluoro-2-methylpropyl)-3-methyl-2,3,4,9-tetrahydro-1H-pyrido[3,4-b]indole | 0.001 | 516.3 |
| 283 | 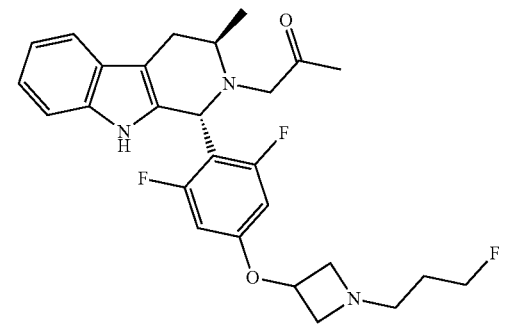 [SMILES: CC(=O)CN1[C@H](c2c(F)cc(OC3CN(CCCF)C3)cc2F)c2[nH]c3ccccc3c2C[C@H]1C] | 1-[(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]propan-2-one | 0.001 | 486.3 |
| 284 | 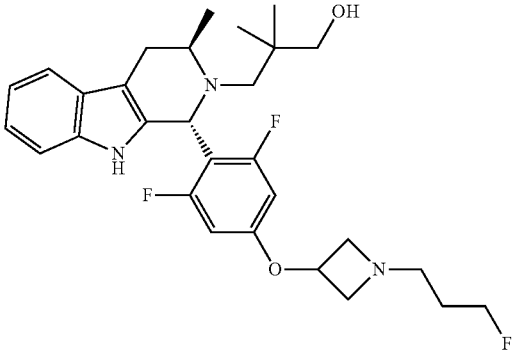 [SMILES: C[C@@H]1Cc2c([nH]c3ccccc23)[C@@H](c2c(F)cc(OC3CN(CCCF)C3)cc2F)N1CC(C)(C)CO] | 3-[(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]-2,2-dimethyl-propan-1-ol | 0.000382 | 516.3 |

TABLE 2-continued

| No. | Structure | Name | ER-alpha MCF7 HCS EC$_{50}$ (μM) | LCMS [M + H]$^+$ |
|---|---|---|---|---|
| 285 | 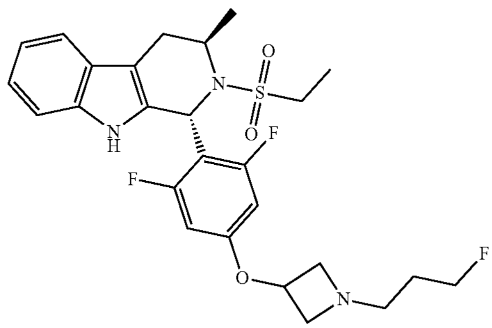 [SMILES: CCS(=O)(=O)N1[C@H](c2c(F)cc(OC3CN(CCCF)C3)cc2F)c2[nH]c3ccccc3c2C[C@H]1C] | (1R,3R)-1-[2,6-difluoro-4-[1-(3-fluoropropyl)azetidin-3-yl]oxy-phenyl]-2-ethylsulfonyl-3-methyl-1,3,4,9-tetrahydropyrido[3,4-b]indole | 0.002 | 522.1 |
| 286 | 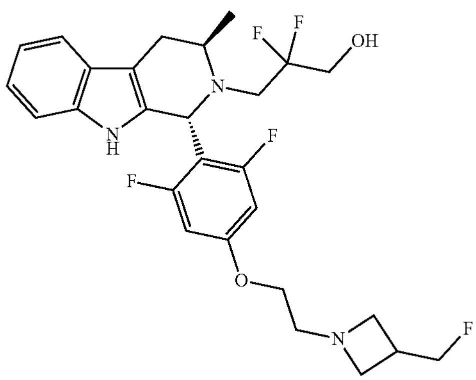 [SMILES: C[C@@H]1Cc2c([nH]c3ccccc23)[C@@H](c2c(F)cc(OCCN3CC(CF)C3)cc2F)N1CC(F)(F)CO] | 3-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2,2-difluoro-propan-1-ol | 0.0000978 | 524.1 |
| 287 | 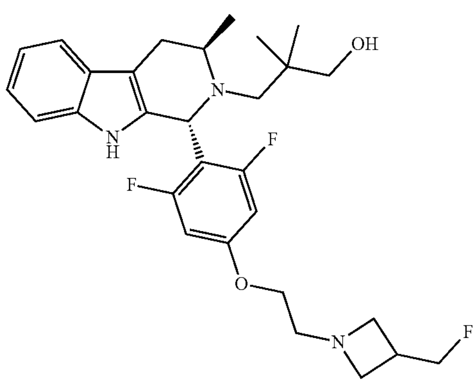 [SMILES: C[C@@H]1Cc2c([nH]c3ccccc23)[C@@H](c2c(F)cc(OCCN3CC(CF)C3)cc2F)N1CC(C)(C)CO] | 3-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2,2-dimethyl-propan-1-ol | 0.001 | 516.3 |
| 288 | 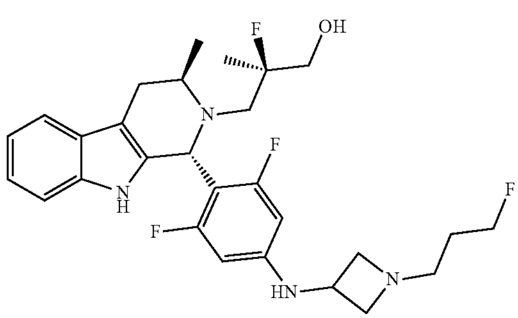 [SMILES: C[C@@H]1Cc2c([nH]c3ccccc23)[C@@H](c2c(F)cc(NC3CN(CCCF)C3)cc2F)N1C[C@@](C)(F)CO] | (R)-3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2-fluoro-2-methylpropan-1-ol | 0.0000528 | 519.3 |

TABLE 2-continued

| No. | Structure | Name | ER-alpha MCF7 HCS EC$_{50}$ (μM) | LCMS [M + H]$^+$ |
|---|---|---|---|---|
| 289 | 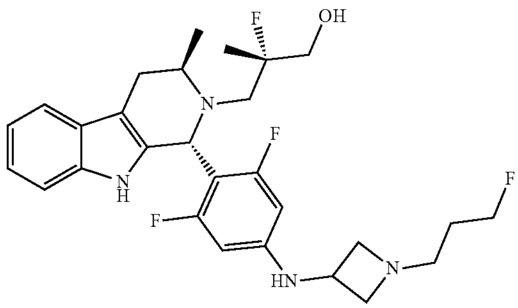 [SMILES: C[C@@H]1Cc2c([nH]c3ccccc23)[C@@H](c2c(F)cc(NC3CN(CCCF)C3)cc2F)N1C[C@](C)(F)CO] | (S)-3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2-fluoro-2-methylpropan-1-ol | 0.000199 | 519.3 |
| 290 | 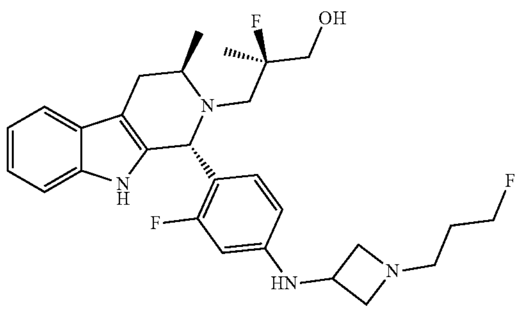 [SMILES: C[C@@H]1Cc2c([nH]c3ccccc23)[C@@H](c2ccc(NC3CN(CCCF)C3)cc2F)N1C[C@@](C)(F)CO] | (R)-2-fluoro-3-((1R,3R)-1-(2-fluoro-4-((1-(3-fluoropropyl)azetidin-3-yl)amino)phenyl)-3-methyl-1,3,4,9-tetrahydro-2H-pyrido[3,4-b]indol-2-yl)-2-methylpropan-1-ol | 0.000497 | 501.3 |
| 291 | 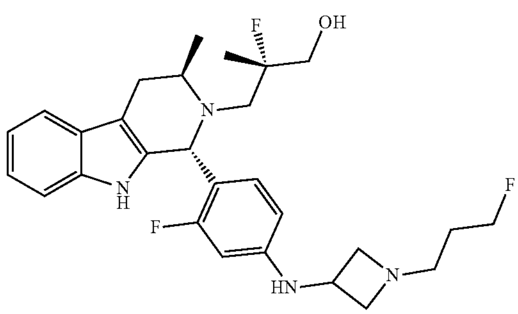 [SMILES: C[C@@H]1Cc2c([nH]c3ccccc23)[C@@H](c2ccc(NC3CN(CCCF)C3)cc2F)N1C[C@](C)(F)CO] | (S)-2-fluoro-3-((1R,3R)-1-(2-fluoro-4-((1-(3-fluoropropyl)azetidin-3-yl)amino)phenyl)-3-methyl-1,3,4,9-tetrahydro-2H-pyrido[3,4-b]indol-2-yl)-2-methylpropan-1-ol | 0.00013 | 501.3 |
| 292 | 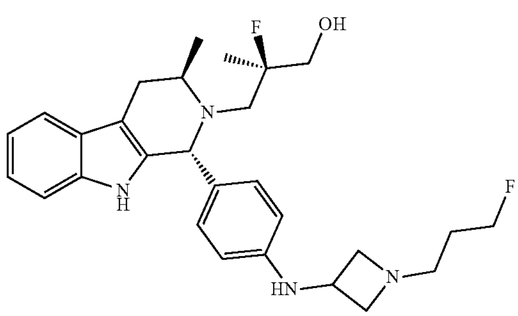 [SMILES: C[C@@H]1Cc2c([nH]c3ccccc23)[C@@H](c2ccc(NC3CN(CCCF)C3)cc2)N1C[C@@](C)(F)CO] | (R)-2-fluoro-3-((1R,3R)-1-(4-((1-(3-fluoropropyl)azetidin-3-yl)amino)phenyl)-3-methyl-1,3,4,9-tetrahydro-2H-pyrido[3,4-b]indol-2-yl)-2-methylpropan-1-ol | 0.002 | 483.3 |
| 293 | 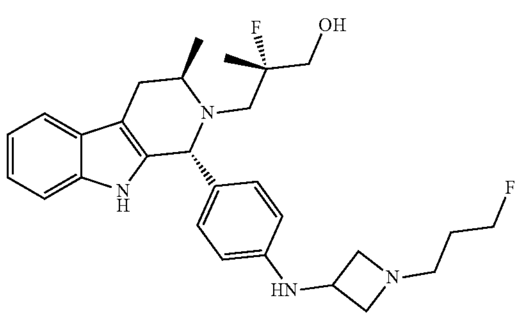 [SMILES: C[C@@H]1Cc2c([nH]c3ccccc23)[C@@H](c2ccc(NC3CN(CCCF)C3)cc2)N1C[C@](C)(F)CO] | (S)-2-fluoro-3-((1R,3R)-1-(4-((1-(3-fluoropropyl)azetidin-3-yl)amino)phenyl)-3-methyl-1,3,4,9-tetrahydro-2H-pyrido[3,4-b]indol-2-yl)-2-methylpropan-1-ol | 0.00015 | 483.3 |

TABLE 2-continued

| No. | Structure | Name | ER-alpha MCF7 HCS EC$_{50}$ (μM) | LCMS [M + H]$^+$ |
|---|---|---|---|---|
| 294 | 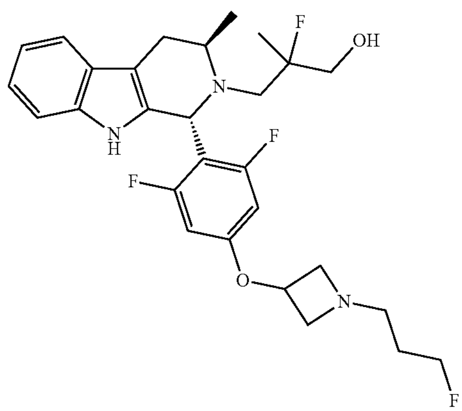 [SMILES: C[C@@H]1Cc2c([nH]c3ccccc23)[C@@H](c2c(F)cc(OC3CN(CCCF)C3)cc2F)N1CC(C)(F)CO] | 3-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)-2-fluoro-2-methylpropan-1-ol | | 520.3 |
| 295 | 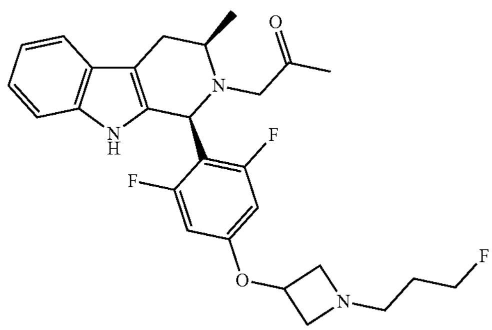 [SMILES: CC(=O)CN1[C@@H](c2c(F)cc(OC3CN(CCCF)C3)cc2F)c2[nH]c3ccccc3c2C[C@H]1C] | 1-((1S,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)propan-2-one | 0.021 | 486.2 |
| 296 | 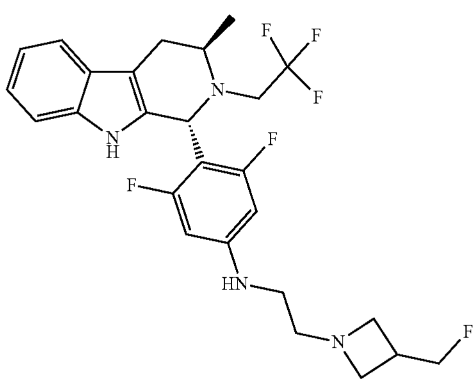 [SMILES: C[C@@H]1Cc2c([nH]c3ccccc23)[C@@H](c2c(F)cc(NCCN3CC(CF)C3)cc2F)N1CC(F)(F)F] | 3,5-difluoro-N-(2-(3-(fluoromethyl)azetidin-1-yl)ethyl)-4-((1R,3R)-3-methyl-2-(2,2,2-trifluoroethyl)-2,3,4,9-tetrahydro-1H-pyrido[3,4-b]indol-1-yl)aniline | 0.0002 | 511.2 |
| 297 | 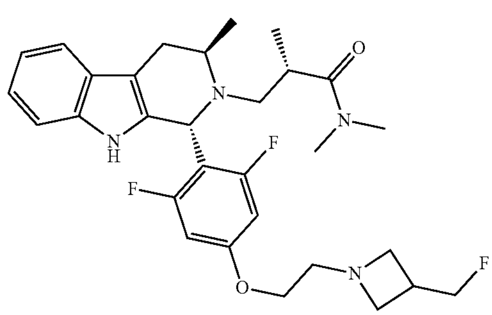 [SMILES: C[C@@H]1Cc2c([nH]c3ccccc23)[C@@H](c2c(F)cc(OCCN3CC(CF)C3)cc2F)N1C[C@H](C)C(=O)N(C)C] | (S)-3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-N,N,2-trimethylpropanamide | 0.018 | 543.3 |

TABLE 2-continued

| No. | Structure | Name | ER-alpha MCF7 HCS EC$_{50}$ (μM) | LCMS [M + H]$^+$ |
|---|---|---|---|---|
| 298 | 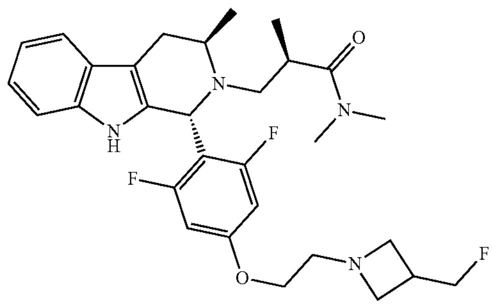 [SMILES: C[C@H](CN1[C@H](c2c(F)cc(OCCN3CC(CF)C3)cc2F)c2[nH]c3ccccc3c2C[C@H]1C)C(=O)N(C)C] | (R)-3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-N,N,2-trimethylpropanamide | 0.005 | 543.3 |
| 299 | 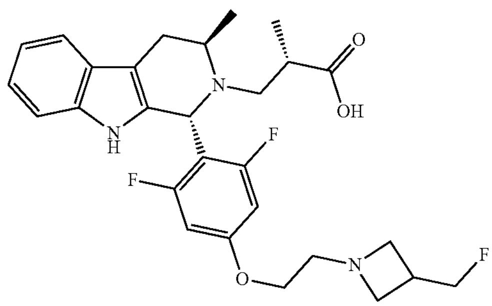 [SMILES: C[C@@H]1Cc2c([nH]c3ccccc23)[C@@H](c2c(F)cc(OCCN3CC(CF)C3)cc2F)N1C[C@H](C)C(=O)O] | (S)-3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-2-methylpropanoic acid | 0.003 | 516.2 |
| 300 | 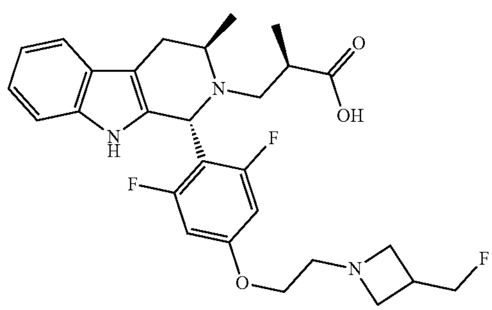 [SMILES: C[C@H](CN1[C@H](c2c(F)cc(OCCN3CC(CF)C3)cc2F)c2[nH]c3ccccc3c2C[C@H]1C)C(=O)O] | (R)-3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-2-methylpropanoic acid | 0.001 | 516.2 |
| 301 | 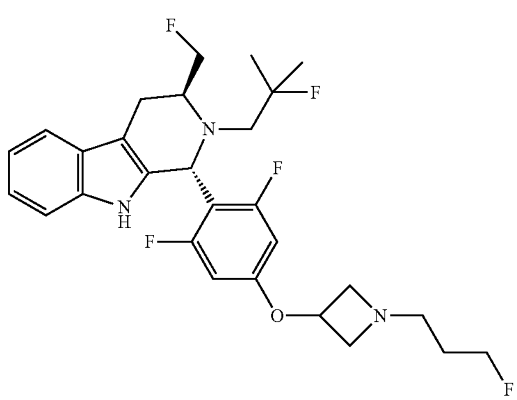 [SMILES: CC(C)(F)CN1[C@H](CF)Cc2c([nH]c3ccccc23)[C@H]1c1c(F)cc(OC2CN(CCCF)C2)cc1F] | (1R,3S)-1-(2,6-difluoro-4-((1-(3-fluoropropyl)azetidin-3-yl)oxy)phenyl)-2-(2-fluoro-2-methylpropyl)-3-(fluoromethyl)-2,3,4,9-tetrahydro-1H-pyrido[3,4-b]indole | 0.0000881 | 522.2 |

TABLE 2-continued

| No. | Structure | Name | ER-alpha MCF7 HCS EC$_{50}$ (μM) | LCMS [M + H]$^+$ |
|---|---|---|---|---|
| 302 | 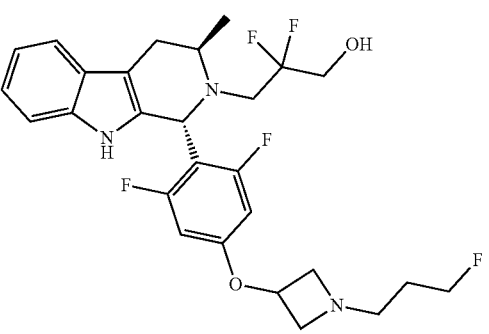 [SMILES: C[C@@H]1Cc2c([nH]c3ccccc23)[C@@H](c2c(F)cc(OC3CN(CCCF)C3)cc2F)N1CC(F)(F)CO] | 3-((1R,3R)-1-(2,6-difluoro-4-((1-(3-fluoropropyl)azetidin-3-yl)oxy)phenyl)-3-methyl-3,4-dihydro-1H-pyrido[3,4-b]indol-2(9H)-yl)-2,2-difluoropropan-1-ol | 0.00012 | 524.1 |
| 303 | 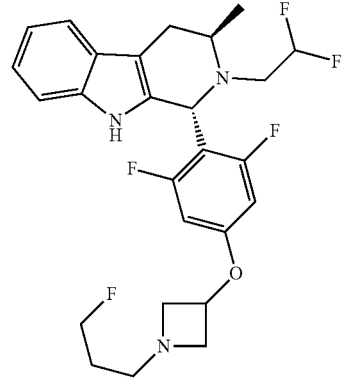 [SMILES: C[C@@H]1Cc2c([nH]c3ccccc23)[C@@H](c2c(F)cc(OC3CN(CCCF)C3)cc2F)N1CC(F)F] | (1R,3R)-2-(2,2-difluoroethyl)-1-[2,6-difluoro-4-[1-(3-fluoropropyl)azetidin-3-yl]oxy-phenyl]-3-methyl-1,3,4,9-tetrahydropyrido[3,4-b]indole | 0.0000482 | 494.2 |
| 304 | 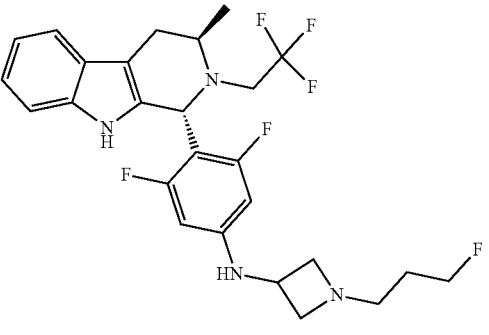 [SMILES: C[C@@H]1Cc2c([nH]c3ccccc23)[C@@H](c2c(F)cc(NC3CN(CCCF)C3)cc2F)N1CC(F)(F)F] | N-(3,5-difluoro-4-((1R,3R)-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine | 0.000224 | 511.2 |
| 305 | 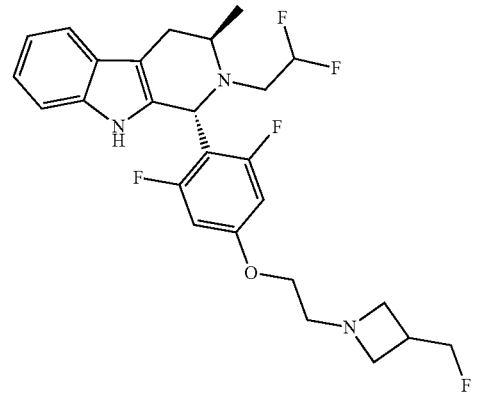 [SMILES: C[C@@H]1Cc2c([nH]c3ccccc23)[C@@H](c2c(F)cc(OCCN3CC(CF)C3)cc2F)N1CC(F)F] | (1R,3R)-2-(2,2-difluoroethyl)-1-[2,6-difluoro-4-[2-[3-(fluoromethyl)azetidin-1-yl]ethoxy]phenyl]-3-methyl-1,3,4,9-tetrahydropyrido[3,4-b]indole | 0.000216 | 494.2 |

TABLE 2-continued

| No. | Structure | Name | ER-alpha MCF7 HCS EC$_{50}$ (μM) | LCMS [M + H]$^+$ |
|---|---|---|---|---|
| 306 | 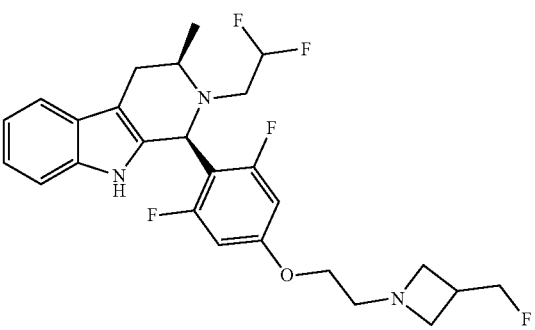 [SMILES: C[C@@H]1Cc2c([nH]c3ccccc23)[C@H](c2c(F)cc(OCCN3CC(CF)C3)cc2F)N1CC(F)F] | (1S,3R)-2-(2,2-difluoroethyl)-1-[2,6-difluoro-4-[2-[3-(fluoromethyl)azetidin-1-yl]ethoxy]phenyl]-3-methyl-1,3,4,9-tetrahydropyrido[3,4-b]indole | 0.003 | 494.2 |
| 307 | 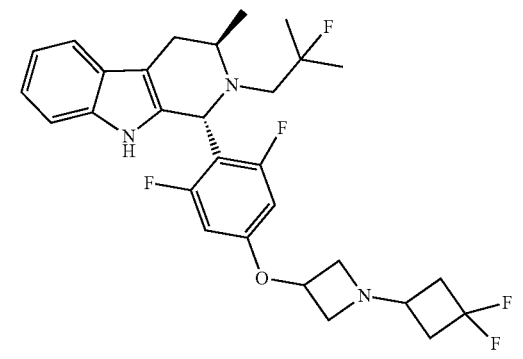 [SMILES: C[C@@H]1Cc2c([nH]c3ccccc23)[C@@H](c2c(F)cc(OC3CN(C4CC(F)(F)C4)C3)cc2F)N1CC(C)(C)F] | (1R,3R)-1-[4-[1-(3,3-difluorocyclobutyl)azetidin-3-yl]oxy-2,6-difluoro-phenyl]-2-(2-fluoro-2-methyl-propyl)-3-methyl-1,3,4,9-tetrahydropyrido[3,4-b]indole | 0.000193 | 534.1 |
| 308 | 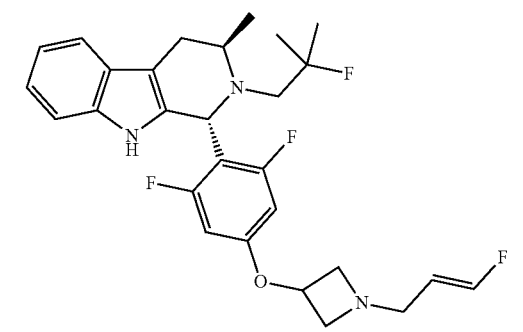 [SMILES: C[C@@H]1Cc2c([nH]c3ccccc23)[C@@H](c2c(F)cc(OC3CN(C/C=C/F)C3)cc2F)N1CC(C)(C)F] | (1R,3R)-1-[2,6-difluoro-4-[1-[(E)-3-fluoroallyl]azetidin-3-yl]oxy-phenyl]-2-(2-fluoro-2-methyl-propyl)-3-methyl-1,3,4,9-tetrahydropyrido[3,4-b]indole | 0.000127 | 502.3 |
| 309 | 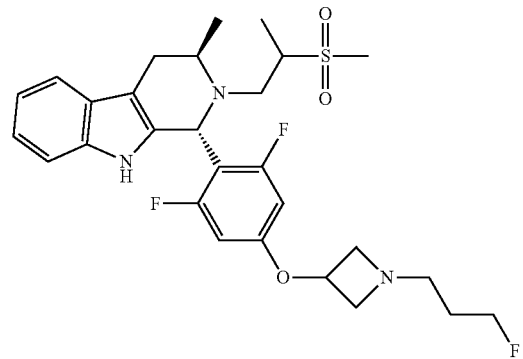 [SMILES: CC(CN1[C@H](c2c(F)cc(OC3CN(CCCF)C3)cc2F)c2[nH]c3ccccc3c2C[C@H]1C)S(C)(=O)=O] | (1R,3R)-1-(2,6-difluoro-4-((1-(3-fluoropropyl)azetidin-3-yl)oxy)phenyl)-3-methyl-2-(2-(methylsulfonyl)propyl)-2,3,4,9-tetrahydro-1H-pyrido[3,4-b]indole | 0.006 | 550.3 |

TABLE 2-continued

| No. | Structure | Name | ER-alpha MCF7 HCS EC$_{50}$ (μM) | LCMS [M + H]$^+$ |
|---|---|---|---|---|
| 310 | 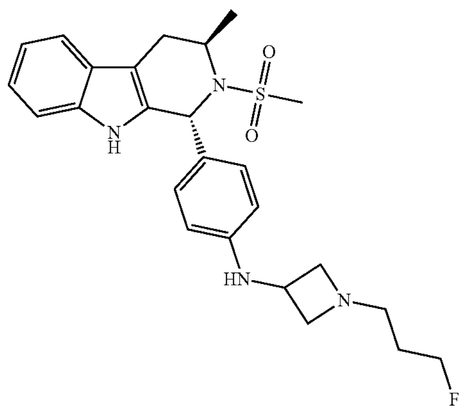 [SMILES: C[C@@H]1Cc2c([nH]c3ccccc23)[C@@H](c2ccc(NC3CN(CCCF)C3)cc2)N1S(C)(=O)=O] | 1-(3-fluoropropyl)-N-[4-[(1R,3R)-3-methyl-2-methylsulfonyl-1,3,4,9-tetrahydropyrido[3,4-b]indol-1-yl]phenyl]azetidin-3-amine | 0.000708 | 471.2 |
| 311 | 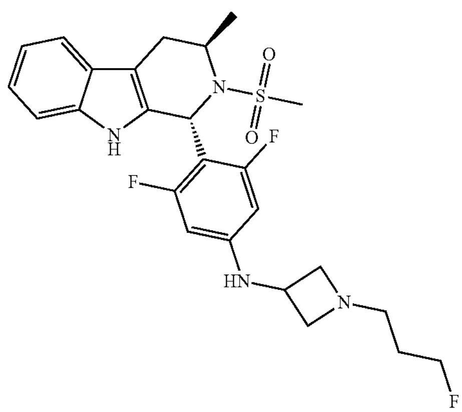 [SMILES: C[C@@H]1Cc2c([nH]c3ccccc23)[C@@H](c2c(F)cc(NC3CN(CCCF)C3)cc2F)N1S(C)(=O)=O] | N-[3,5-difluoro-4-[(1R,3R)-3-methyl-2-methylsulfonyl-1,3,4,9-tetrahydropyrido[3,4-b]indol-1-yl]phenyl]-1-(3-fluoropropyl)azetidin-3-amine | 0.000248 | 507.2 |
| 312 | 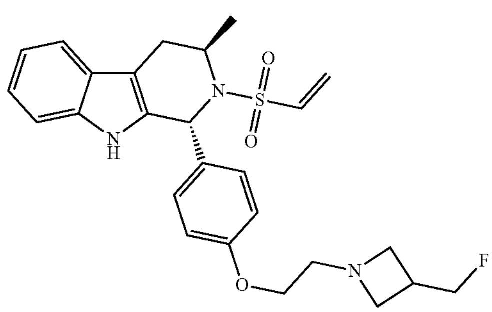 [SMILES: C=CS(=O)(=O)N1[C@H](c2ccc(OCCN3CC(CF)C3)cc2)c2[nH]c3ccccc3c2C[C@H]1C] | (1R,3R)-1-[4-[2-[3-(fluoromethyl)azetidin-1-yl]ethoxy]phenyl]-3-methyl-2-vinylsulfonyl-1,3,4,9-tetrahydropyrido[3,4-b]indole | 0.002 | 484.1 |
| 313 | 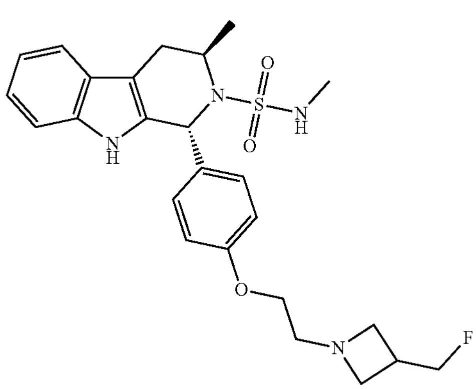 [SMILES: CNS(=O)(=O)N1[C@H](c2ccc(OCCN3CC(CF)C3)cc2)c2[nH]c3ccccc3c2C[C@H]1C] | (1R,3R)-1-[4-[2-[3-(fluoromethyl)azetidin-1-yl]ethoxy]phenyl]-N,3-dimethyl-1,3,4,9-tetrahydropyrido[3,4-b]indole-2-sulfonamide | 0.001 | 487.4 |

TABLE 2-continued

| No. | Structure | Name | ER-alpha MCF7 HCS EC$_{50}$ (μM) | LCMS [M + H]$^+$ |
|---|---|---|---|---|
| 314 | 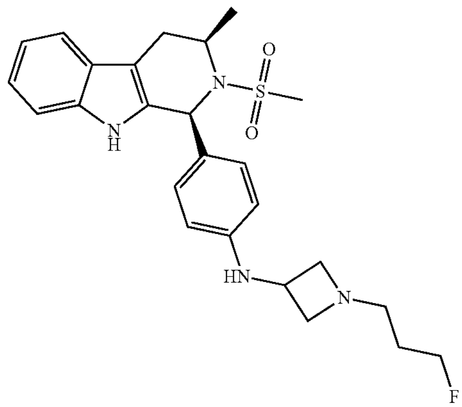 [SMILES: C[C@@H]1Cc2c([nH]c3ccccc23)[C@H](c2ccc(NC3CN(CCCF)C3)cc2)N1S(C)(=O)=O] | 1-(3-fluoropropyl)-N-[4-[(1S,3R)-3-methyl-2-methylsulfonyl-1,3,4,9-tetrahydropyrido[3,4-b]indol-1-yl]phenyl]azetidin-3-amine | 0.009 | 471.3 |
| 315 | 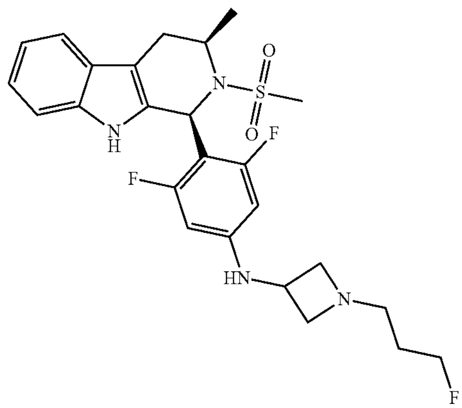 [SMILES: C[C@@H]1Cc2c([nH]c3ccccc23)[C@H](c2c(F)cc(NC3CN(CCCF)C3)cc2F)N1S(C)(=O)=O] | N-[3,5-difluoro-4-[(1S,3R)-3-methyl-2-methylsulfonyl-1,3,4,9-tetrahydropyrido[3,4-b]indol-1-yl]phenyl]-1-(3-fluoropropyl)azetidin-3-amine | 0.002 | 507.1 |
| 316 | 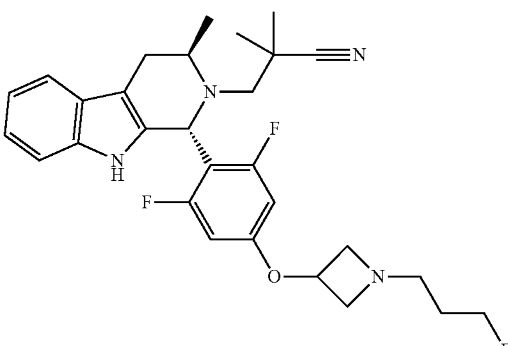 | 3-[(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]-2,2-dimethyl-propanenitrile | 0.0000724 | 511.2 |
| 317 | 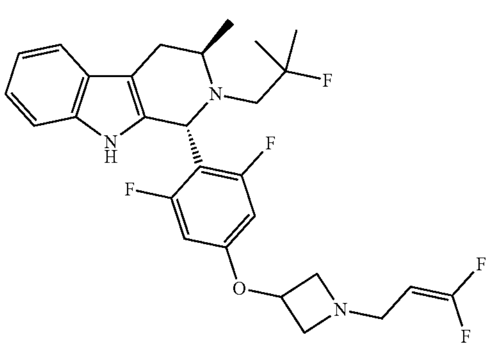 [SMILES: C[C@@H]1Cc2c([nH]c3ccccc23)[C@@H](c2c(F)cc(OC3CN(CC=C(F)F)C3)cc2F)N1CC(C)(C)F] | (1R,3R)-1-[4-[1-(3,3-difluoroallyl)azetidin-3-yl]oxy-2,6-difluoro-phenyl]-2-(2-fluoro-2-methyl-propyl)-3-methyl-1,3,4,9-tetrahydropyrido[3,4-b]indole | 0.000181 | 520.1 |

TABLE 2-continued

| No. | Structure | Name | ER-alpha MCF7 HCS EC$_{50}$ (μM) | LCMS [M + H]$^+$ |
|---|---|---|---|---|
| 318 | 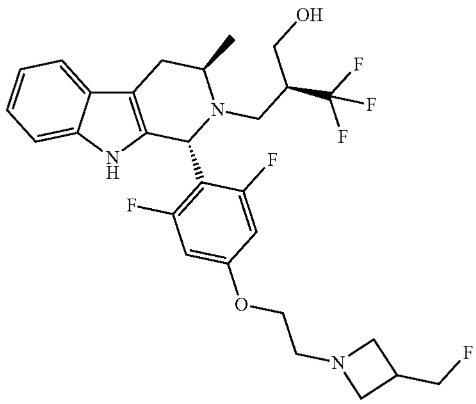 [SMILES: C[C@@H]1Cc2c([nH]c3ccccc23)[C@@H](c2c(F)cc(OCCN3CC(CF)C3)cc2F)N1C[C@@H](CO)C(F)(F)F] | (S)-2-(((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)methyl)-3,3,3-trifluoropropan-1-ol | 0.001 | 556.2 |
| 319 | 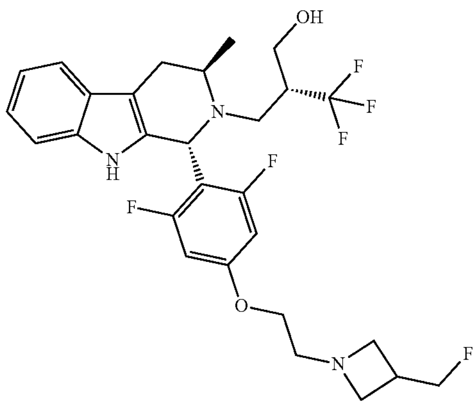 [SMILES: C[C@@H]1Cc2c([nH]c3ccccc23)[C@@H](c2c(F)cc(OCCN3CC(CF)C3)cc2F)N1C[C@H](CO)C(F)(F)F] | (R)-2-(((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)methyl)-3,3,3-trifluoropropan-1-ol | 0.00043 | 556.2 |
| 320 | 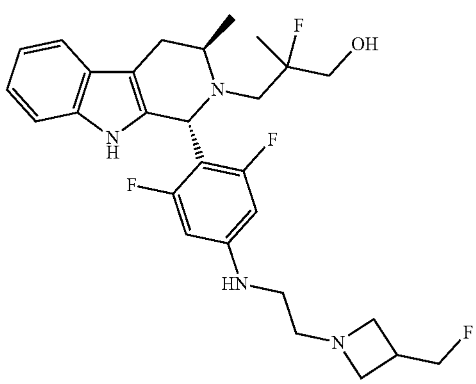 [SMILES: C[C@@H]1Cc2c([nH]c3ccccc23)[C@@H](c2c(F)cc(NCCN3CC(CF)C3)cc2F)N1CC(C)(F)CO] | 3-((1R,3R)-1-(2,6-difluoro-4-((2-(3-(fluoromethyl)azetidin-1-yl)ethyl)amino)phenyl)-3-methyl-1,3,4,9-tetrahydro-2H-pyrido[3,4-b]indol-2-yl)-2-fluoro-2-methylpropan-1-ol | 0.00027 | 519.2 |
| 321 | 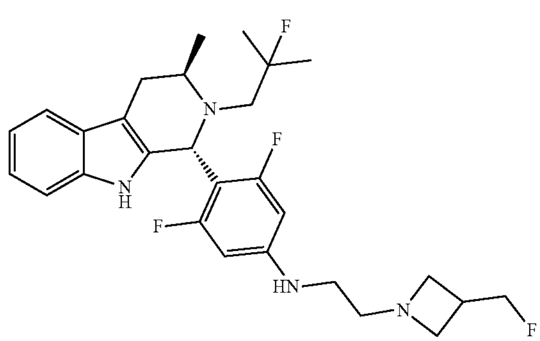 [SMILES: C[C@@H]1Cc2c([nH]c3ccccc23)[C@@H](c2c(F)cc(NCCN3CC(CF)C3)cc2F)N1CC(C)(C)F] | 3,5-difluoro-N-[2-[3-(fluoromethyl)azetidin-1-yl]ethyl]-4-[(1R,3R)-2-(2-fluoro-2-methyl-propyl)-3-methyl-1,3,4,9-tetrahydropyrido[3,4-b]indol-1-yl]aniline | 0.000222 | 503.2 |

TABLE 2-continued

| No. | Structure | Name | ER-alpha MCF7 HCS EC$_{50}$ (μM) | LCMS [M + H]$^+$ |
|---|---|---|---|---|
| 322 | 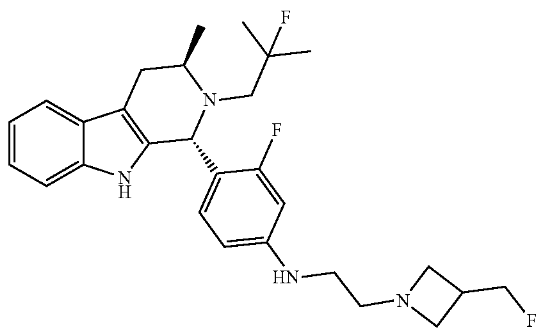 [SMILES: C[C@@H]1Cc2c([nH]c3ccccc23)[C@@H](c2ccc(NCCN3CC(CF)C3)cc2F)N1CC(C)(C)F] | 3-fluoro-N-[2-[3-(fluoromethyl)azetidin-1-yl]ethyl]-4-[(1R,3R)-2-(2-fluoro-2-methyl-propyl)-3-methyl-1,3,4,9-tetrahydropyrido[3,4-b]indol-1-yl]aniline | 0.0000253 | 485.2 |
| 323 | 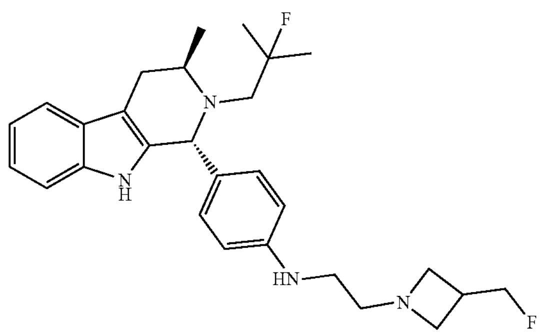 [SMILES: C[C@@H]1Cc2c([nH]c3ccccc23)[C@@H](c2ccc(NCCN3CC(CF)C3)cc2)N1CC(C)(C)F] | N-[2-[3-(fluoromethyl)azetidin-1-yl]ethyl]-4-[(1R,3R)-2-(2-fluoro-2-methyl-propyl)-3-methyl-1,3,4,9-tetrahydropyrido[3,4-b]indol-1-yl]aniline | 0.000215 | 467.2 |
| 324 | 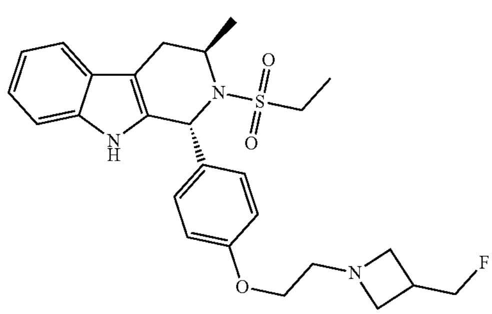 [SMILES: CCS(=O)(=O)N1[C@H](c2ccc(OCCN3CC(CF)C3)cc2)c2[nH]c3ccccc3c2C[C@H]1C] | (1R,3R)-2-ethylsulfonyl-1-[4-[2-[3-(fluoromethyl)azetidin-1-yl]ethoxy]phenyl]-3-methyl-1,3,4,9-tetrahydropyrido[3,4-b]indole | 0.000198 | 486.2 |
| 325 | 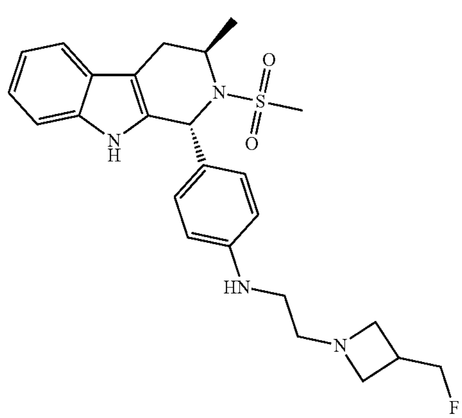 [SMILES: C[C@@H]1Cc2c([nH]c3ccccc23)[C@@H](c2ccc(NCCN3CC(CF)C3)cc2)N1S(C)(=O)=O] | N-[2-[3-(fluoromethyl)azetidin-1-yl]ethyl]-4-[(1R,3R)-3-methyl-2-methylsulfonyl-1,3,4,9-tetrahydropyrido[3,4-b]indol-1-yl]aniline | 0.001 | 471.1 |

TABLE 2-continued

| No. | Structure | Name | ER-alpha MCF7 HCS EC$_{50}$ (μM) | LCMS [M + H]$^+$ |
|---|---|---|---|---|
| 326 | 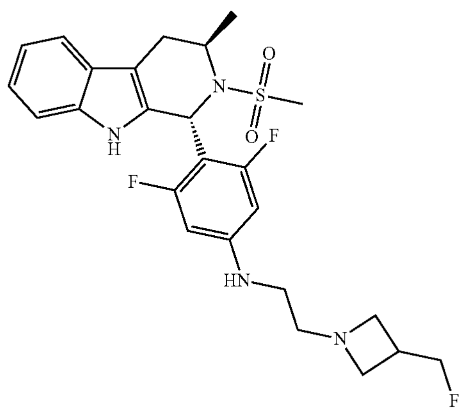 [SMILES: C[C@@H]1Cc2c([nH]c3ccccc23)[C@@H](c2c(F)cc(NCCN3CC(CF)C3)cc2F)N1S(C)(=O)=O] | 3,5-difluoro-N-[2-[3-(fluoromethyl)azetidin-1-yl]ethyl]-4-[(1R,3R)-3-methyl-2-methylsulfonyl-1,3,4,9-tetrahydropyrido[3,4-b]indol-1-yl]aniline | 0.000305 | 507.2 |
| 327 | 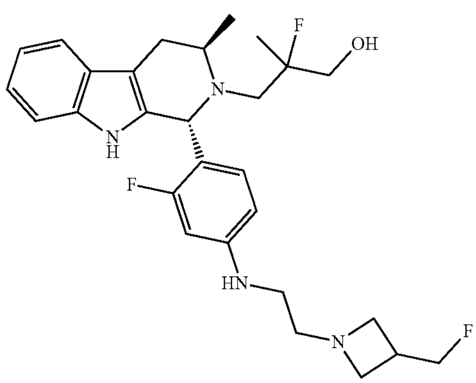 [SMILES: C[C@@H]1Cc2c([nH]c3ccccc23)[C@@H](c2ccc(NCCN3CC(CF)C3)cc2F)N1CC(C)(F)CO] | 2-fluoro-3-((1R,3R)-1-(2-fluoro-4-((2-(3-(fluoromethyl)azetidin-1-yl)ethyl)amino)phenyl)-3-methyl-1,3,4,9-tetrahydro-2H-pyrido[3,4-b]indol-2-yl)-2-methylpropan-1-ol | 0.000347 | 501.2 |
| 328 | 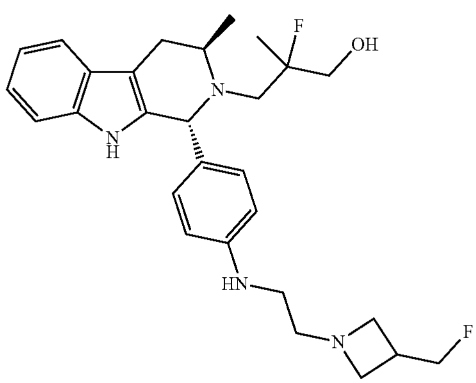 [SMILES: C[C@@H]1Cc2c([nH]c3ccccc23)[C@@H](c2ccc(NCCN3CC(CF)C3)cc2)N1CC(C)(F)CO] | 2-fluoro-3-((1R,3R)-1-(4-((2-(3-(fluoromethyl)azetidin-1-yl)ethyl)amino)phenyl)-3-methyl-1,3,4,9-tetrahydro-2H-pyrido[3,4-b]indol-2-yl)-2-methylpropan-1-ol | 0.000167 | 483.3 |
| 329 | 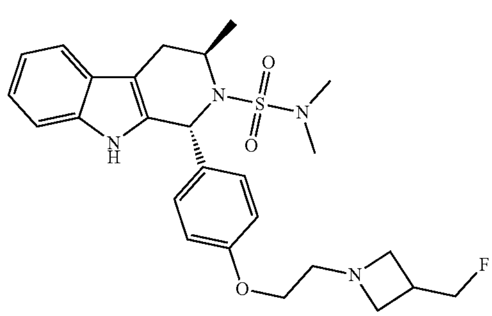 [SMILES: C[C@@H]1Cc2c([nH]c3ccccc23)[C@@H](c2ccc(OCCN3CC(CF)C3)cc2)N1S(=O)(=O)N(C)C] | (1R,3R)-1-[4-[2-[3-(fluoromethyl)azetidin-1-yl]ethoxy]phenyl]-N,N,3-trimethyl-1,3,4,9-tetrahydropyrido[3,4-b]indole-2-sulfonamide | 0.001 | 523.1 |

TABLE 2-continued

| No. | Structure | Name | ER-alpha MCF7 HCS EC$_{50}$ (μM) | LCMS [M + H]$^+$ |
|---|---|---|---|---|
| 330 | 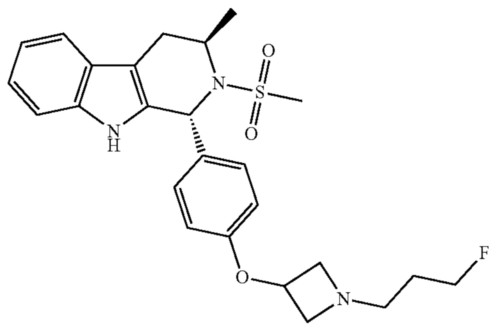 [SMILES: C[C@@H]1Cc2c([nH]c3ccccc23)[C@@H](c2ccc(OC3CN(CCCF)C3)cc2)N1S(C)(=O)=O] | (1R,3R)-1-[4-[1-(3-fluoropropyl)azetidin-3-yl]oxyphenyl]-3-methyl-2-methylsulfonyl-1,3,4,9-tetrahydropyrido[3,4-b]indole | 0.002 | 472.2 |
| 331 | 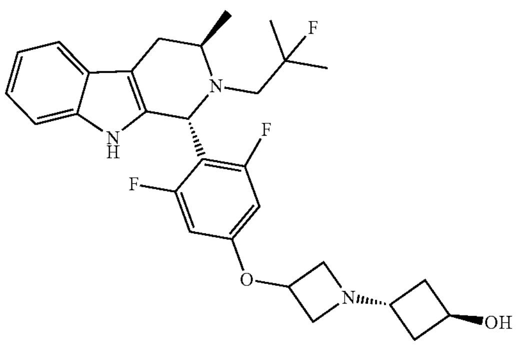 [SMILES: C[C@@H]1Cc2c([nH]c3ccccc23)[C@@H](c2c(F)cc(OC3CN([C@H]4C[C@H](O)C4)C3)cc2F)N1CC(C)(C)F] | 3-[3-[3,5-difluoro-4-[(1R,3R)-2-(2-fluoro-2-methyl-propyl)-3-methyl-1,3,4,9-tetrahydropyrido[3,4-b]indol-1-yl]phenoxy]azetidin-1-yl]cyclobutanol | 0.000236 | 514.2 |
| 332 | 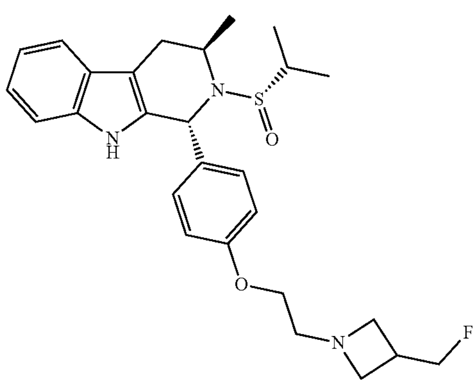 [SMILES: CC(C)[S@](=O)N1[C@H](c2ccc(OCCN3CC(CF)C3)cc2)c2[nH]c3ccccc3c2C[C@H]1C] | (1R,3R)-1-(4-(2-(3-(fluoromethyl)azetidin-1-yl)ethoxy)phenyl)-2-((S)-isopropylsulfinyl)-3-methyl-2,3,4,9-tetrahydro-1H-pyrido[3,4-b]indole | 0.008 | 484.2 |
| 333 | 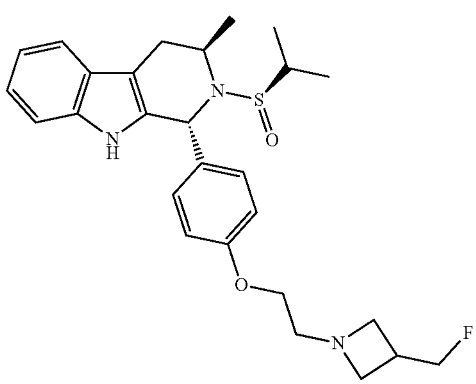 [SMILES: CC(C)[S@@](=O)N1[C@H](c2ccc(OCCN3CC(CF)C3)cc2)c2[nH]c3ccccc3c2C[C@H]1C] | (1R,3R)-1-(4-(2-(3-(fluoromethyl)azetidin-1-yl)ethoxy)phenyl)-2-((R)-isopropylsulfinyl)-3-methyl-2,3,4,9-tetrahydro-1H-pyrido[3,4-b]indole | 0.048 | 484.2 |

TABLE 2-continued

| No. | Structure | Name | ER-alpha MCF7 HCS EC$_{50}$ (μM) | LCMS [M + H]$^+$ |
|---|---|---|---|---|
| 334 | 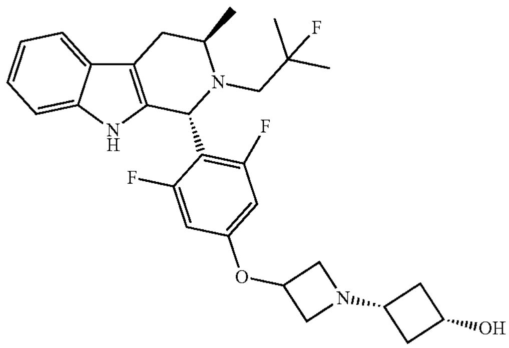 [SMILES: C[C@@H]1Cc2c([nH]c3ccccc23)[C@@H](c2c(F)cc(OC3CN([C@H]4C[C@@H](O)C4)C3)cc2F)N1CC(C)(C)F] | (1S,3s)-3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)azetidin-1-yl)cyclobutanol | 0.00013 | 514.2 |
| 335 | 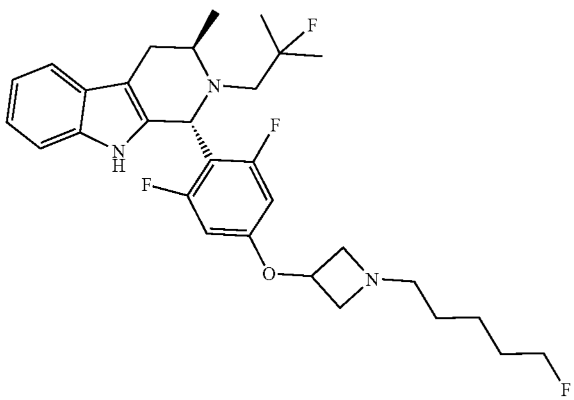 [SMILES: C[C@@H]1Cc2c([nH]c3ccccc23)[C@@H](c2c(F)cc(OC3CN(CCCCCF)C3)cc2F)N1CC(C)(C)F] | (1R,3R)-1-[2,6-difluoro-4-[1-(5-fluoropentyl)azetidin-3-yl]oxy-phenyl]-2-(2-fluoro-2-methyl-propyl)-3-methyl-1,3,4,9-tetrahydropyrido[3,4-b]indole | 0.000442 | 532.3 |
| 336 | 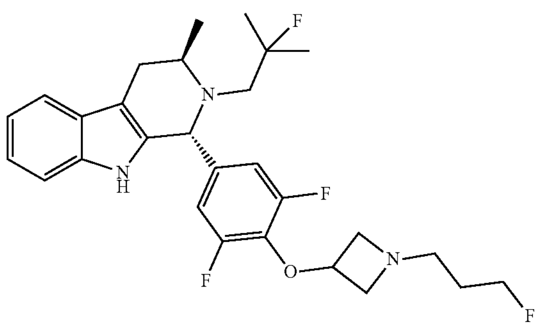 [SMILES: C[C@@H]1Cc2c([nH]c3ccccc23)[C@@H](c2cc(F)c(OC3CN(CCCF)C3)c(F)c2)N1CC(C)(C)F] | (1R,3R)-1-[3,5-difluoro-4-[1-(3-fluoropropyl)azetidin-3-yl]oxy-phenyl]-2-(2-fluoro-2-methyl-propyl)-3-methyl-1,3,4,9-tetrahydropyrido[3,4-b]indole | 0.000263 | 504.3 |
| 337 | 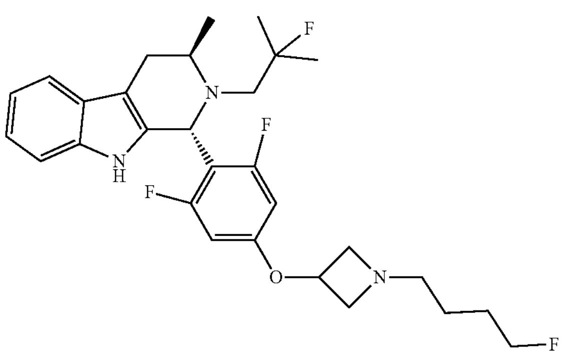 [SMILES: C[C@@H]1Cc2c([nH]c3ccccc23)[C@@H](c2c(F)cc(OC3CN(CCCCF)C3)cc2F)N1CC(C)(C)F] | (1R,3R)-1-[2,6-difluoro-4-[1-(4-fluorobutyl)azetidin-3-yl]oxy-phenyl]-2-(2-fluoro-2-methyl-propyl)-3-methyl-1,3,4,9-tetrahydropyrido[3,4-b]indole | 0.000387 | 518.3 |

TABLE 2-continued

| No. | Structure | Name | ER-alpha MCF7 HCS EC$_{50}$ (μM) | LCMS [M + H]$^+$ |
|---|---|---|---|---|
| 338 | 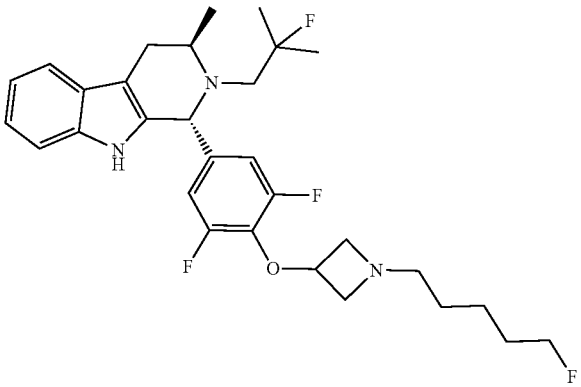 [SMILES: C[C@@H]1Cc2c([nH]c3ccccc23)[C@@H](c2cc(F)c(OC3CN(CCCCCF)C3)c(F)c2)N1CC(C)(C)F] | (1R,3R)-1-[3,5-difluoro-4-[1-(5-fluoropentyl)azetidin-3-yl]oxy-phenyl]-2-(2-fluoro-2-methyl-propyl)-3-methyl-1,3,4,9-tetrahydropyrido[3,4-b]indole | 0.001 | 532.2 |
| 339 | 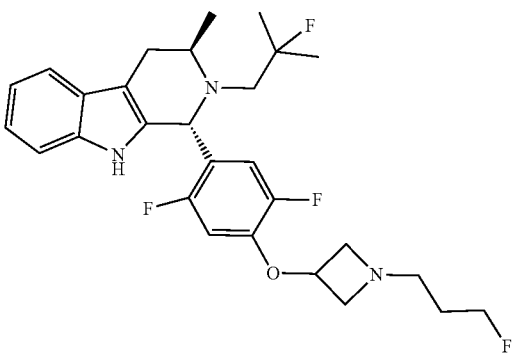 [SMILES: C[C@@H]1Cc2c([nH]c3ccccc23)[C@@H](c2cc(F)c(OC3CN(CCCF)C3)cc2F)N1CC(C)(C)F] | (1R,3R)-1-[2,5-difluoro-4-[1-(3-fluoropropyl)azetidin-3-yl]oxy-phenyl]-2-(2-fluoro-2-methyl-propyl)-3-methyl-1,3,4,9-tetrahydropyrido[3,4-b]indole | 0.001 | 504.2 |
| 340 | 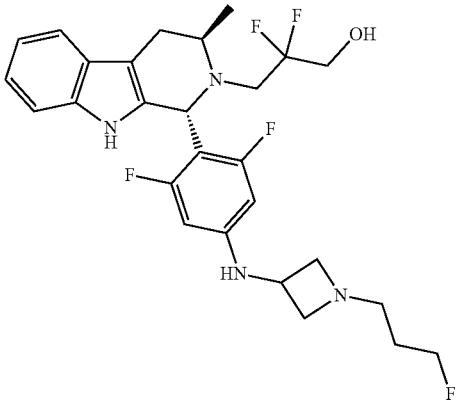 [SMILES: C[C@@H]1Cc2c([nH]c3ccccc23)[C@@H](c2c(F)cc(NC3CN(CCCF)C3)cc2F)N1CC(F)(F)CO] | 3-[(1R,3R)-1-[2,6-difluoro-4-[[1-(3-fluoropropyl)azetidin-3-yl]amino]phenyl]-3-methyl-1,3,4,9-tetrahydropyrido[3,4-b]indol-2-yl]-2,2-difluoro-propan-1-ol | 0.000203 | 523.2 |
| 341 | 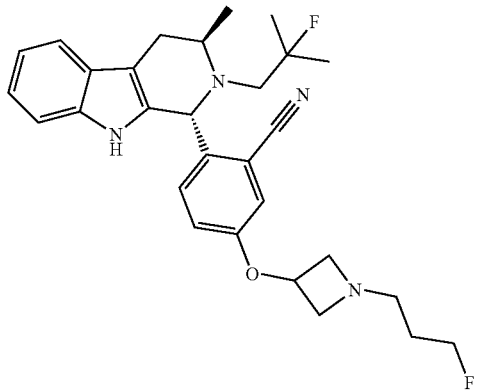 [SMILES: C[C@@H]1Cc2c([nH]c3ccccc23)[C@@H](c2ccc(OC3CN(CCCF)C3)cc2C#N)N1CC(C)(C)F] | 3-[(1R,3R)-1-[2,6-difluoro-4-[2-[3-(fluoromethyl)azetidin-1-yl]ethylamino]phenyl]-3-methyl-1,3,4,9-tetrahydropyrido[3,4-b]indol-2-yl]-2,2-difluoro-propan-1-ol | 0.000348 | 545.2 |

TABLE 2-continued

| No. | Structure | Name | ER-alpha MCF7 HCS EC$_{50}$ (μM) | LCMS [M + H]$^+$ |
|---|---|---|---|---|
| 342 | 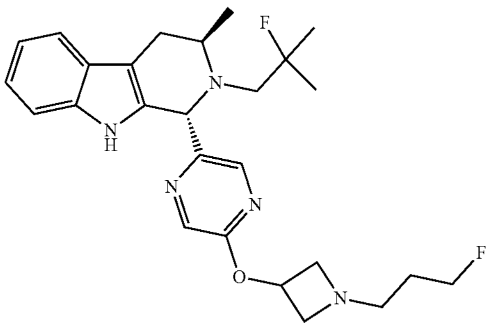 [SMILES: C[C@@H]1Cc2c([nH]c3ccccc23)[C@@H](c2cnc(OC3CN(CCCF)C3)cn2)N1CC(C)(C)F] | (1S,3R)-2-(2-fluoro-2-methylpropyl)-1-(5-((1-(3-fluoropropyl)azetidin-3-yl)oxy)pyrazin-2-yl)-3-methyl-2,3,4,9-tetrahydro-1H-pyrido[3,4-b]indole | 0.000619 | 470.3 |
| 343 | 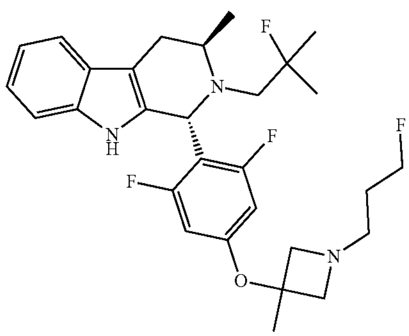 [SMILES: C[C@@H]1Cc2c([nH]c3ccccc23)[C@@H](c2c(F)cc(OC3(C)CN(CCCF)C3)cc2F)N1CC(C)(C)F] | (1R,3R)-1-(2,6-difluoro-4-((1-(3-fluoropropyl)-3-methylazetidin-3-yl)oxy)phenyl)-2-(2-fluoro-2-methylpropyl)-3-methyl-2,3,4,9-tetrahydro-1H-pyrido[3,4-b]indole | 0.0002 | 518.3 |
| 344 | 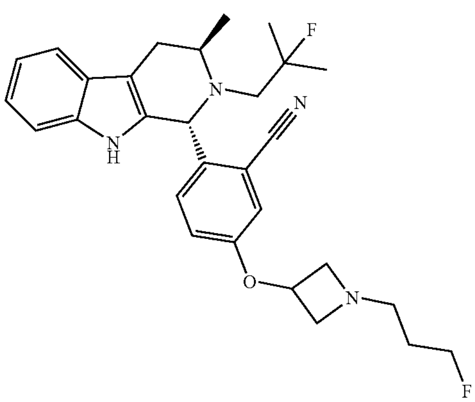 [SMILES: C[C@@H]1Cc2c([nH]c3ccccc23)[C@@H](c2ccc(OC3CN(CCCF)C3)cc2C#N)N1CC(C)(C)F] | 2-[(1R,3R)-2-(2-fluoro-2-methyl-propyl)-3-methyl-1,3,4,9-tetrahydropyrido[3,4-b]indol-1-yl]-5-[1-(3-fluoropropyl)azetidin-3-yl]oxy-benzonitrile | 0.000347 | 493.3 |
| 345 | 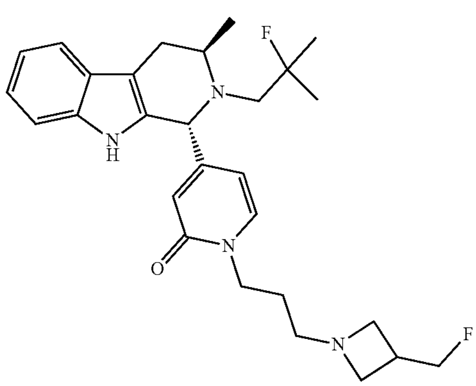 [SMILES: C[C@@H]1Cc2c([nH]c3ccccc23)[C@@H](c2ccn(CCCN3CC(CF)C3)c(=O)c2)N1CC(C)(C)F] | 4-((1R,3R)-2-(2-fluoro-2-methylpropyl)-3-methyl-2,3,4,9-tetrahydro-1H-pyrido[3,4-b]indol-1-yl)-1-(3-(3-(fluoromethyl)azetidin-1-yl)propyl)pyridin-2(1H)-one | 0.0123 | 483.3 |

TABLE 2-continued

| No. | Structure | Name | ER-alpha MCF7 HCS EC$_{50}$ (μM) | LCMS [M + H]$^+$ |
|---|---|---|---|---|
| 346 | 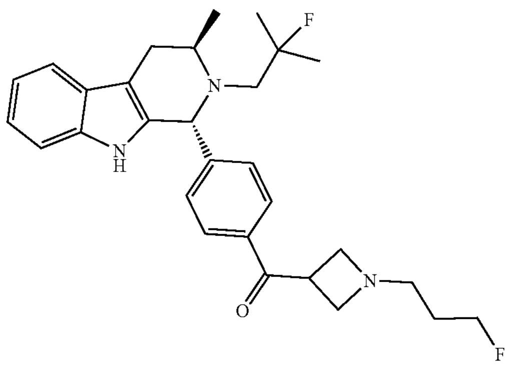 [SMILES: C[C@@H]1Cc2c([nH]c3ccccc23)[C@@H](c2ccc(C(=O)C3CN(CCCF)C3)cc2)N1CC(C)(C)F] | [4-[(1R,3R)-2-(2-fluoro-2-methyl-propyl)-3-methyl-1,3,4,9-tetrahydropyrido[3,4-b]indol-1-yl]phenyl]-[1-(3-fluoropropyl)azetidin-3-yl]methanone | 0.000399 | 480.2 |
| 347 | 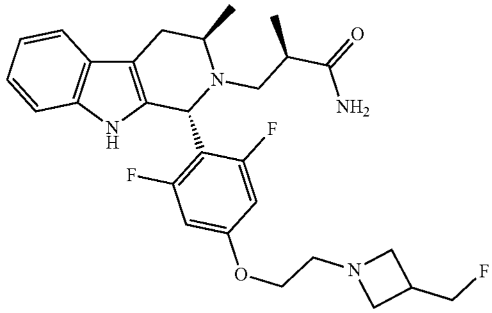 [SMILES: C[C@H](CN1[C@H](c2c(F)cc(OCCN3CC(CF)C3)cc2F)c2[nH]c3ccccc3c2C[C@H]1C)C(N)=O] | (R)-3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-2-methylpropanamide | 0.014 | 515.3 |
| 348 | 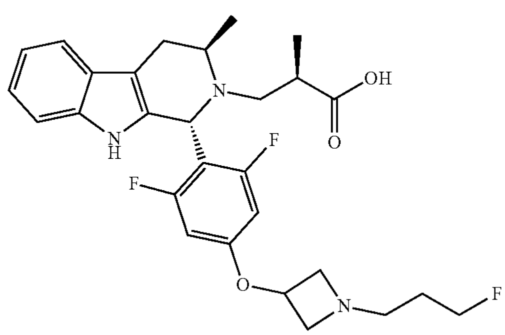 [SMILES: C[C@H](CN1[C@H](c2c(F)cc(OC3CN(CCCF)C3)cc2F)c2[nH]c3ccccc3c2C[C@H]1C)C(=O)O] | (R)-3-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)-2-methylpropanoic acid | 0.001 | 516.2 |
| 349 | 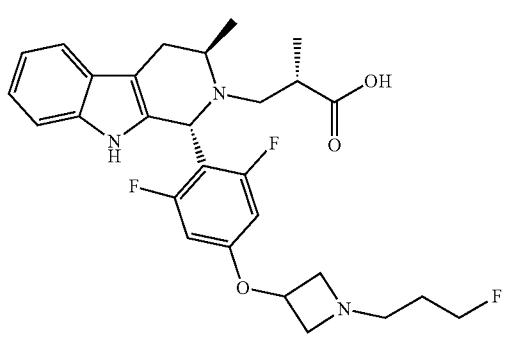 [SMILES: C[C@@H]1Cc2c([nH]c3ccccc23)[C@@H](c2c(F)cc(OC3CN(CCCF)C3)cc2F)N1C[C@H](C)C(=O)O] | (S)-3-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)-2-methylpropanoic acid | 0.00203 | 515.2 |

TABLE 2-continued

| No. | Structure | Name | ER-alpha MCF7 HCS EC$_{50}$ (μM) | LCMS [M + H]$^+$ |
|---|---|---|---|---|
| 350 | 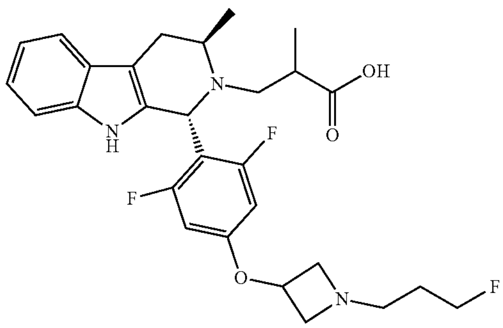 [SMILES: CC(CN1[C@H](c2c(F)cc(OC3CN(CCCF)C3)cc2F)c2[nH]c3ccccc3c2C[C@H]1C)C(=O)O] | 3-[1-[2,6-difluoro-4-[1-(3-fluoropropyl)azetidin-3-yl]oxy-phenyl]-3-methyl-1,3,4,9-tetrahydropyrido[3,4-b]indol-2-yl]-2-methyl-propanoic acid | 0.014 | 516.2 |
| 351 | 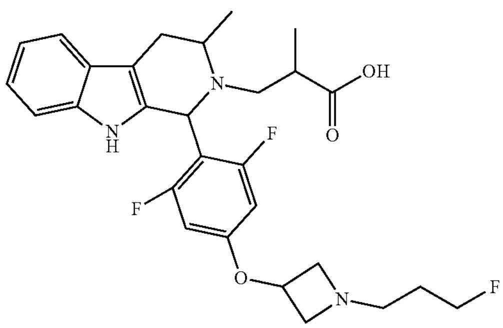 [SMILES: CC(CN1C(C)Cc2c([nH]c3ccccc23)C1c1c(F)cc(OC2CN(CCCF)C2)cc1F)C(=O)O] | 3-[1-[2,6-difluoro-4-[1-(3-fluoropropyl)azetidin-3-yl]oxy-phenyl]-3-methyl-1,3,4,9-tetrahydropyrido[3,4-b]indol-2-yl]-2-methyl-propanoic acid | 0.033 | 516.2 |
| 352 | 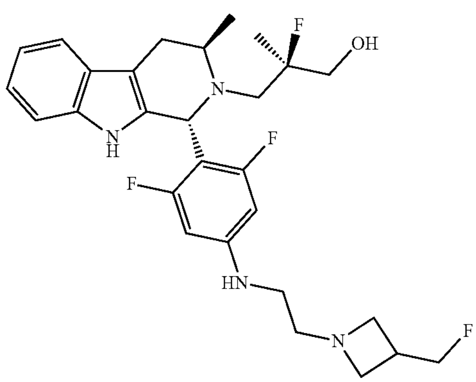 [SMILES: C[C@@H]1Cc2c([nH]c3ccccc23)[C@@H](c2c(F)cc(NCCN3CC(CF)C3)cc2F)N1C[C@@](C)(F)CO] | (R)-3-((1R,3R)-1-(2,6-difluoro-4-((2-(3-(fluoromethyl)azetidin-1-yl)ethyl)amino)phenyl)-3-methyl-1,3,4,9-tetrahydro-2H-pyrido[3,4-b]indol-2-yl)-2-fluoro-2-methylpropan-1-ol | 0.000685 | 519.3 |
| 353 | 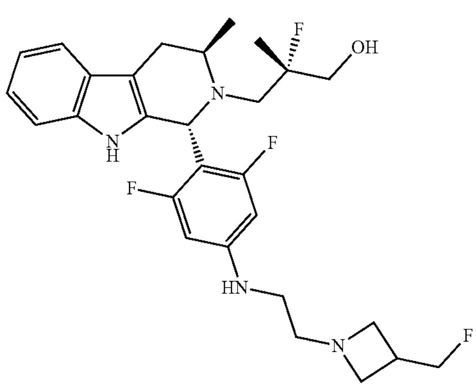 [SMILES: C[C@@H]1Cc2c([nH]c3ccccc23)[C@@H](c2c(F)cc(NCCN3CC(CF)C3)cc2F)N1C[C@](C)(F)CO] | (S)-3-((1R,3R)-1-(2,6-difluoro-4-((2-(3-(fluoromethyl)azetidin-1-yl)ethyl)amino)phenyl)-3-methyl-1,3,4,9-tetrahydro-2H-pyrido[3,4-b]indol-2-yl)-2-fluoro-2-methylpropan-1-ol | 0.000033 | 519.3 |

TABLE 2-continued

| No. | Structure | Name | ER-alpha MCF7 HCS $EC_{50}$ (μM) | LCMS [M + H]$^+$ |
|---|---|---|---|---|
| 354 | 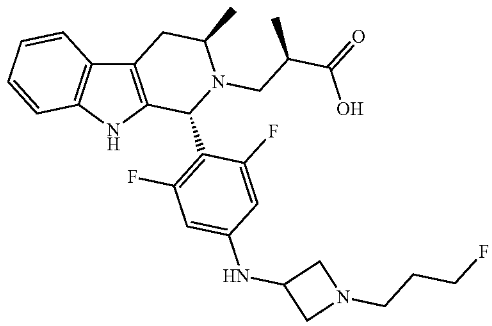 [SMILES: C[C@H](CN1[C@H](c2c(F)cc(NC3CN(CCCF)C3)cc2F)c2[nH]c3ccccc3c2C[C@H]1C)C(=O)O] | (2R)-3-[(1R,3R)-1-[2,6-difluoro-4-[[1-(3-fluoropropyl)azetidin-3-yl]amino]phenyl]-3-methyl-1,3,4,9-tetrahydropyrido[3,4-b]indol-2-yl]-2-methyl-propanoic acid | 0.001 | 514.2 |
| 355 | 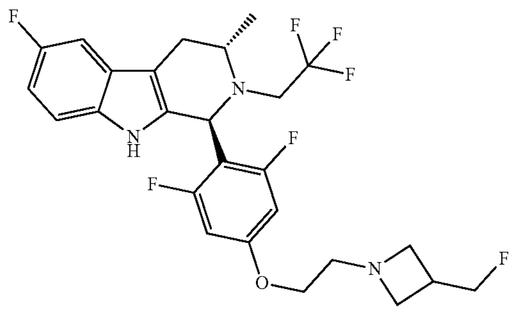 [SMILES: C[C@H]1Cc2c([nH]c3ccc(F)cc23)[C@H](c2c(F)cc(OCCN3CC(CF)C3)cc2F)N1CC(F)(F)F] | (1S,3S)-1-(2,6-difluoro-4-(2-(3-(fluoromethyl)azetidin-1-yl)ethoxy)phenyl)-6-fluoro-3-methyl-2-(2,2,2-trifluoroethyl)-2,3,4,9-tetrahydro-1H-pyrido[3,4-b]indole | 0.0292 | 530.2 |
| 356 | 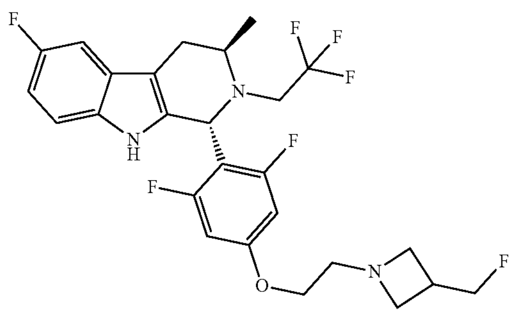 [SMILES: C[C@@H]1Cc2c([nH]c3ccc(F)cc23)[C@@H](c2c(F)cc(OCCN3CC(CF)C3)cc2F)N1CC(F)(F)F] | (1R,3R)-1-(2,6-difluoro-4-(2-(3-(fluoromethyl)azetidin-1-yl)ethoxy)phenyl)-6-fluoro-3-methyl-2-(2,2,2-trifluoroethyl)-2,3,4,9-tetrahydro-1H-pyrido[3,4-b]indole | 0.000509 | 530.2 |
| 357 | 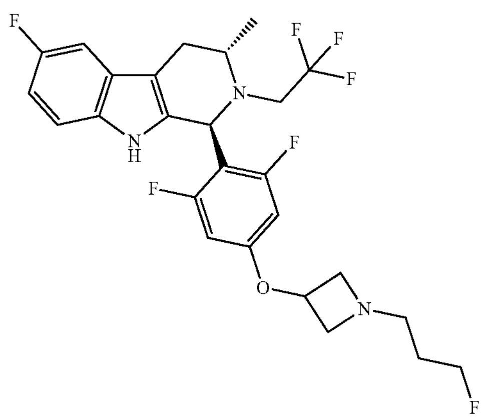 [SMILES: C[C@H]1Cc2c([nH]c3ccc(F)cc23)[C@H](c2c(F)cc(OC3CN(CCCF)C3)cc2F)N1CC(F)(F)F] | (1S,3S)-1-(2,6-difluoro-4-((1-(3-fluoropropyl)azetidin-3-yl)oxy)phenyl)-6-fluoro-3-methyl-2-(2,2,2-trifluoroethyl)-2,3,4,9-tetrahydro-1H-pyrido[3,4-b]indole | 0.0261 | 529.5 |

TABLE 2-continued

| No. | Structure | Name | ER-alpha MCF7 HCS EC$_{50}$ (μM) | LCMS [M + H]$^+$ |
|---|---|---|---|---|
| 358 | 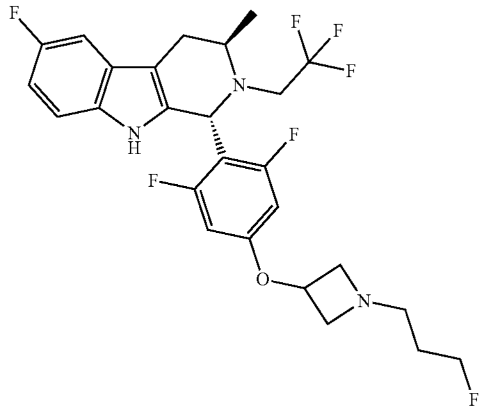 [SMILES: C[C@@H]1Cc2c([nH]c3ccc(F)cc23)[C@@H](c2c(F)cc(OC3CN(CCCF)C3)cc2F)N1CC(F)(F)F] | (1R,3R)-1-(2,6-difluoro-4-((1-(3-fluoropropyl)azetidin-3-yl)oxy)phenyl)-6-fluoro-3-methyl-2-(2,2,2-trifluoroethyl)-2,3,4,9-tetrahydro-1H-pyrido[3,4-b]indole | 0.000417 | 529.5 |
| 359 | 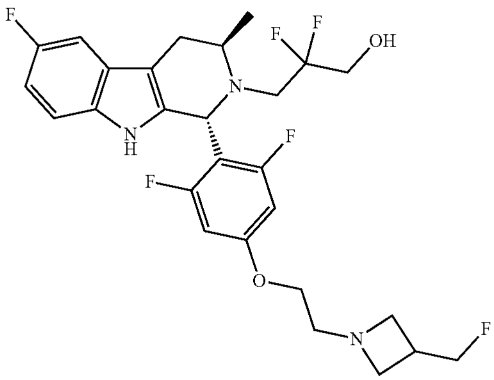 [SMILES: C[C@@H]1Cc2c([nH]c3ccc(F)cc23)[C@@H](c2c(F)cc(OCCN3CC(CF)C3)cc2F)N1CC(F)(F)CO] | 3-((1R,3R)-1-(2,6-difluoro-4-(2-(3-(fluoromethyl)azetidin-1-yl)ethoxy)phenyl)-6-fluoro-3-methyl-1,3,4,9-tetrahydro-2H-pyrido[3,4-b]indol-2-yl)-2,2-difluoropropan-1-ol | 0.000552 | 541.5 |
| 360 | 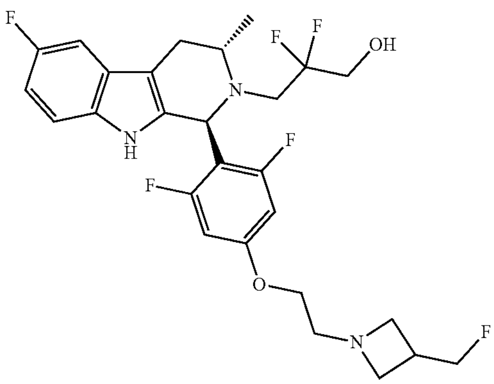 [SMILES: C[C@H]1Cc2c([nH]c3ccc(F)cc23)[C@H](c2c(F)cc(OCCN3CC(CF)C3)cc2F)N1CC(F)(F)CO] | 3-((1S,3S)-1-(2,6-difluoro-4-(2-(3-(fluoromethyl)azetidin-1-yl)ethoxy)phenyl)-6-fluoro-3-methyl-1,3,4,9-tetrahydro-2H-pyrido[3,4-b]indol-2-yl)-2,2-difluoropropan-1-ol | 0.009 | 541.5 |
| 361 | 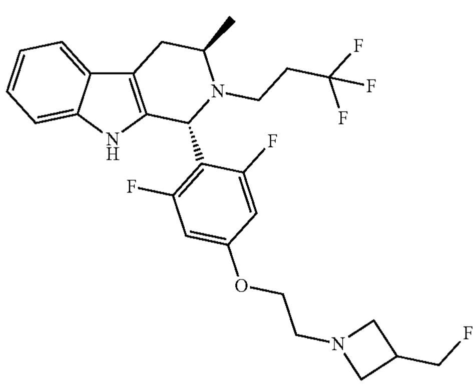 [SMILES: C[C@@H]1Cc2c([nH]c3ccccc23)[C@@H](c2c(F)cc(OCCN3CC(CF)C3)cc2F)N1CCC(F)(F)F] | (1R,3R)-1-[2,6-difluoro-4-[2-[3-(fluoromethyl)azetidin-1-yl]ethoxy]phenyl]-3-methyl-2-(3,3,3-trifluoropropyl)-1,3,4,9-tetrahydropyrido[3,4-b]indole | 0.003 | 525.5 |

TABLE 2-continued

| No. | Structure | Name | ER-alpha MCF7 HCS EC$_{50}$ (μM) | LCMS [M + H]$^+$ |
|---|---|---|---|---|
| 362 | 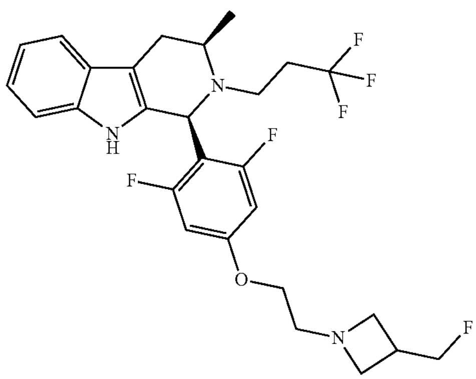 [SMILES: C[C@@H]1Cc2c([nH]c3ccccc23)[C@H](c2c(F)cc(OCCN3CC(CF)C3)cc2F)N1CCC(F)(F)F] | (1S,3R)-1-[2,6-difluoro-4-[2-[3-(fluoromethyl)azetidin-1-yl]ethoxy]phenyl]-3-methyl-2-(3,3,3-trifluoropropyl)-1,3,4,9-tetrahydropyrido[3,4-b]indole | >0.1 | 526.2 |
| 363 | 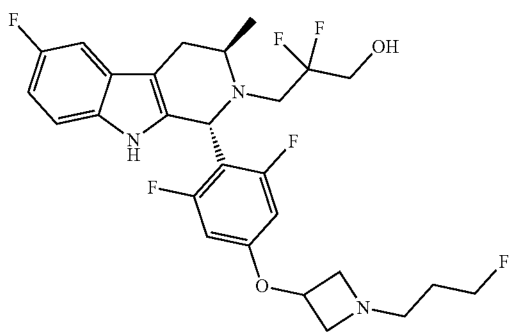 [SMILES: C[C@@H]1Cc2c([nH]c3ccc(F)cc23)[C@@H](c2c(F)cc(OC3CN(CCCF)C3)cc2F)N1CC(F)(F)CO] | 3-((1R,3R)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2,2-difluoropropan-1-ol | 0.000166 | 542.1 |
| 364 | 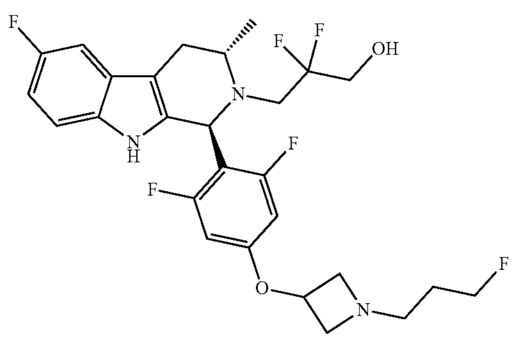 [SMILES: C[C@H]1Cc2c([nH]c3ccc(F)cc23)[C@H](c2c(F)cc(OC3CN(CCCF)C3)cc2F)N1CC(F)(F)CO] | 3-((1S,3S)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2,2-difluoropropan-1-ol | 0.009 | 542.1 |
| 365 | 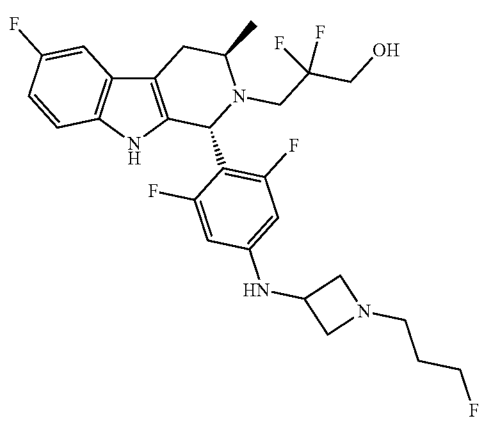 [SMILES: C[C@@H]1Cc2c([nH]c3ccc(F)cc23)[C@@H](c2c(F)cc(NC3CN(CCCF)C3)cc2F)N1CC(F)(F)CO] | 3-((1R,3R)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2,2-difluoropropan-1-ol | 0.000233 | 541.2 |

TABLE 2-continued

| No. | Structure | Name | ER-alpha MCF7 HCS EC$_{50}$ (μM) | LCMS [M + H]$^+$ |
|---|---|---|---|---|
| 366 | 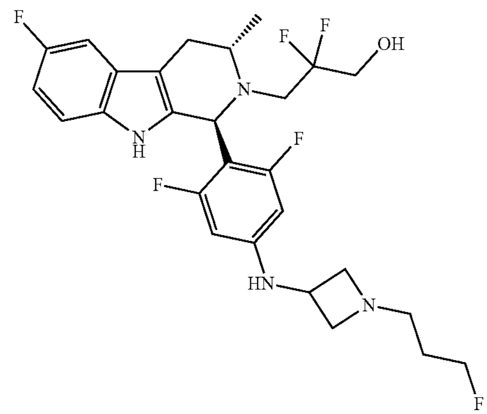 [SMILES: C[C@H]1Cc2c([nH]c3ccc(F)cc23)[C@H](c2c(F)cc(NC3CN(CCCF)C3)cc2F)N1CC(F)(F)CO] | 3-((1S,3S)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2,2-difluoropropan-1-ol | 0.004 | 541.2 |
| 367 | 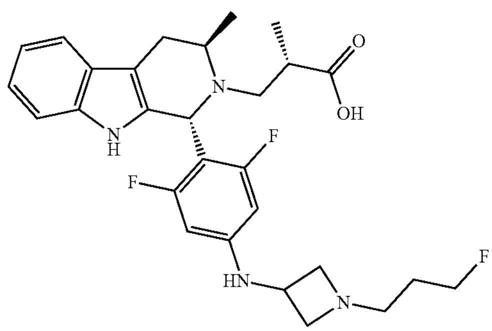 [SMILES: C[C@@H]1Cc2c([nH]c3ccccc23)[C@@H](c2c(F)cc(NC3CN(CCCF)C3)cc2F)N1C[C@H](C)C(=O)O] | (2S)-3-[(1R,3R)-1-[2,6-difluoro-4-[[1-(3-fluoropropyl)azetidin-3-yl]amino]phenyl]-3-methyl-1,3,4,9-tetrahydropyrido[3,4-b]indol-2-yl]-2-methyl-propanoic acid | 0.008 | 515.3 |
| 368 | 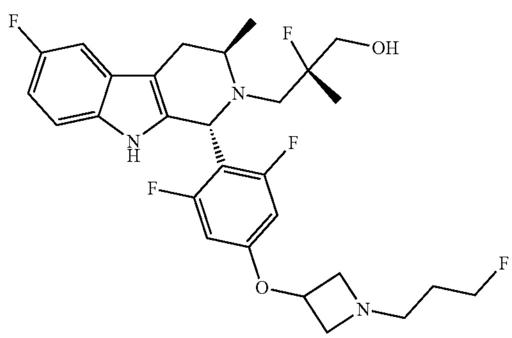 [SMILES: C[C@@H]1Cc2c([nH]c3ccc(F)cc23)[C@@H](c2c(F)cc(OC3CN(CCCF)C3)cc2F)N1C[C@](C)(F)CO] | 3-((1R,3R)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2-fluoro-2-methylpropan-1-ol | 0.000546 | 538.3 |
| 369 | 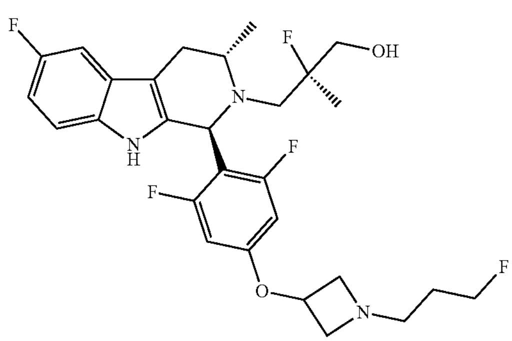 [SMILES: C[C@H]1Cc2c([nH]c3ccc(F)cc23)[C@H](c2c(F)cc(OC3CN(CCCF)C3)cc2F)N1C[C@@](C)(F)CO] | 3-((1S,3S)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2-fluoro-2-methylpropan-1-ol | 0.024 | 538.3 |

TABLE 2-continued

| No. | Structure | Name | ER-alpha MCF7 HCS EC$_{50}$ (μM) | LCMS [M + H]$^+$ |
|---|---|---|---|---|
| 370 | 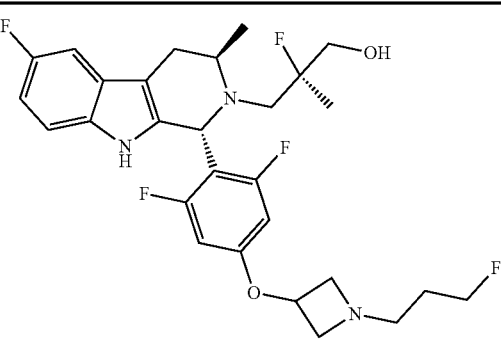 | 3-((1R,3R)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2-fluoro-2-methylpropan-1-ol | 0.000203 | 538.3 |
| 371 | 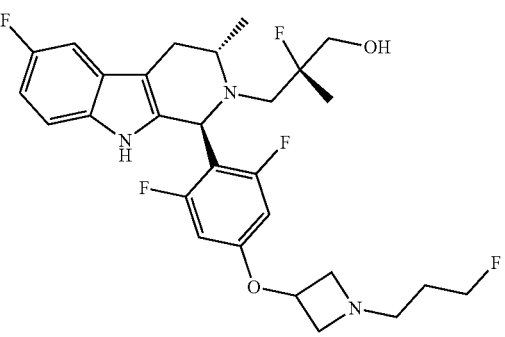 [SMILES: C[C@H]1Cc2c([nH]c3ccc(F)cc23)[C@H](c2c(F)cc(OC3CN(CCCF)C3)cc2F)N1C[C@](C)(F)CO] | 3-((1S,3S)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2-fluoro-2-methylpropan-1-ol | 0.009 | 538.3 |
| 372 | 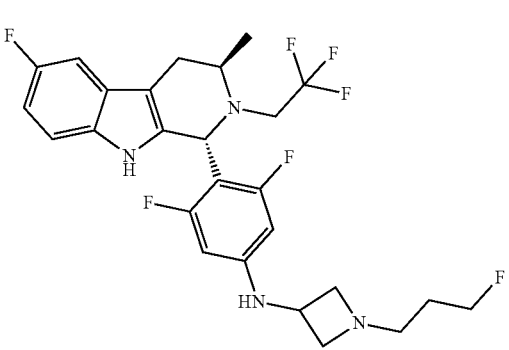 [SMILES: C[C@@H]1Cc2c([nH]c3ccc(F)cc23)[C@@H](c2c(F)cc(NC3CN(CCCF)C3)cc2F)N1CC(F)(F)F] | N-(3,5-difluoro-4-((1R,3R)-6-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine | 0.000198 | 529.2 |
| 373 | 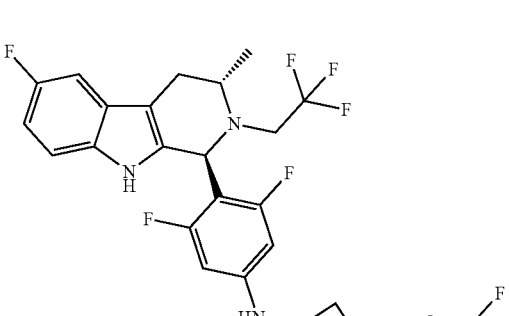 | N-(3,5-difluoro-4-((1S,3S)-6-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine | 0.018 | 529.2 |

TABLE 2-continued

| No. | Structure | Name | ER-alpha MCF7 HCS EC$_{50}$ (μM) | LCMS [M + H]$^+$ |
|---|---|---|---|---|
| 374 | 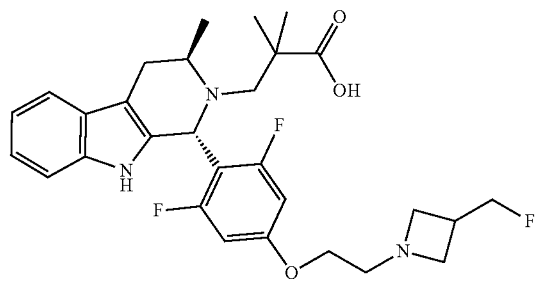 [SMILES: C[C@@H]1Cc2c([nH]c3ccccc23)[C@@H](c2c(F)cc(OCCN3CC(CF)C3)cc2F)N1CC(C)(C)C(=O)O] | 3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-2,2-dimethylpropanoic acid | 0.00155 | 530.3 |
| 375 | 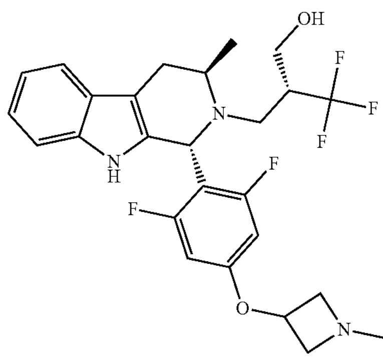 | (R)-2-(((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)methyl)-3,3,3-trifluoropropan-1-ol | 0.000764 | 556.2 |
| 376 | 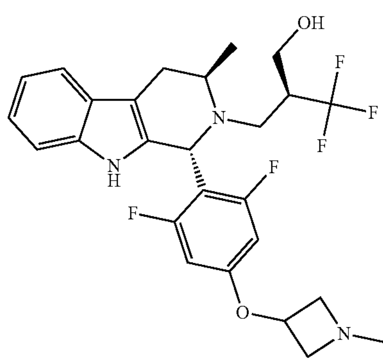 | (S)-2-(((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)methyl)-3,3,3-trifluoropropan-1-ol | 0.001 | 556.2 |
| 377 | 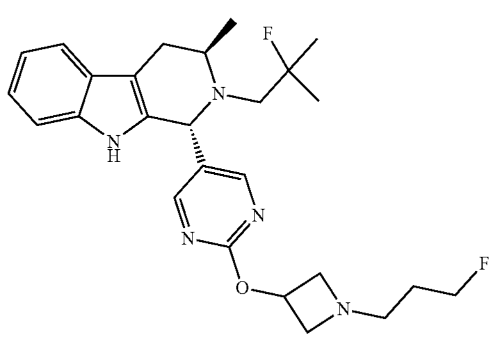 [SMILES: C[C@@H]1Cc2c([nH]c3ccccc23)[C@@H](c2cnc(OC3CN(CCCF)C3)nc2)N1CC(C)(C)F] | (1R,3R)-2-(2-fluoro-2-methylpropyl)-1-(2-((1-(3-fluoropropyl)azetidin-3-yl)oxy)pyrimidin-5-yl)-3-methyl-2,3,4,9-tetrahydro-1H-pyrido[3,4-b]indole | 0.0005 | 470.3 |

TABLE 2-continued

| No. | Structure | Name | ER-alpha MCF7 HCS EC$_{50}$ (μM) | LCMS [M + H]$^+$ |
|---|---|---|---|---|
| 378 | 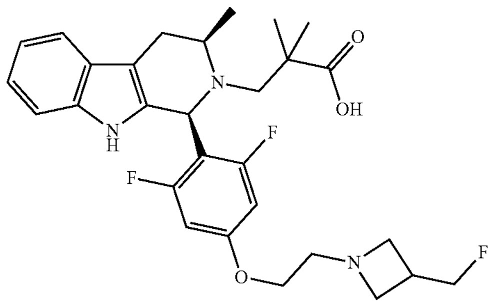 [SMILES: C[C@@H]1Cc2c([nH]c3ccccc23)[C@H](c2c(F)cc(OCCN3CC(CF)C3)cc2F)N1CC(C)(C)C(=O)O] | 3-[(1S,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2,2-dimethyl-propanoic acid | 0.028 | 530.3 |
| 379 | 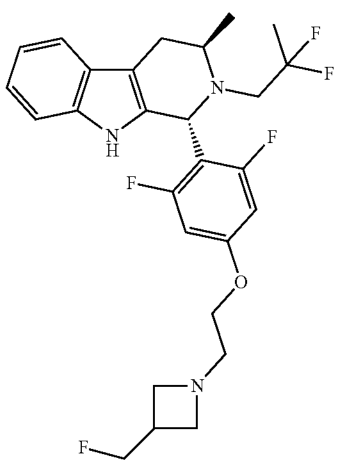 [SMILES: C[C@@H]1Cc2c([nH]c3ccccc23)[C@@H](c2c(F)cc(OCCN3CC(CF)C3)cc2F)N1CC(C)(F)F] | (1R,3R)-1-(2,6-difluoro-4-(2-(3-(fluoromethyl)azetidin-1-yl)ethoxy)phenyl)-2-(2,2-difluoropropyl)-3-methyl-2,3,4,9-tetrahydro-1H-pyrido[3,4-b]indole | 0.00028 | 508.2 |
| 380 | 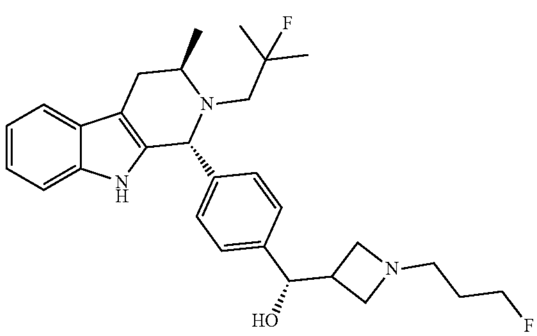 [SMILES: C[C@@H]1Cc2c([nH]c3ccccc23)[C@@H](c2ccc([C@@H](O)C3CN(CCCF)C3)cc2)N1CC(C)(C)F] | (S)-(4-((1R,3R)-2-(2-fluoro-2-methylpropyl)-3-methyl-2,3,4,9-tetrahydro-1H-pyrido[3,4-b]indol-1-yl)phenyl)(1-(3-fluoropropyl)azetidin-3-yl)methanol | 0.000188 | 482.3 |
| 381 | 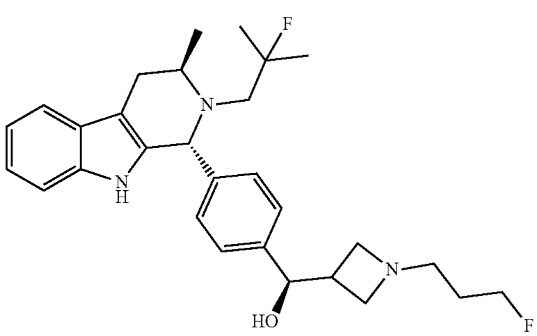 [SMILES: C[C@@H]1Cc2c([nH]c3ccccc23)[C@@H](c2ccc([C@H](O)C3CN(CCCF)C3)cc2)N1CC(C)(C)F] | (R)-(4-((1R,3R)-2-(2-fluoro-2-methylpropyl)-3-methyl-2,3,4,9-tetrahydro-1H-pyrido [3,4-b]indol-1-yl)phenyl)(1-(3-fluoropropyl)azetidin-3-yl)methanol | 0.000605 | 482.3 |

TABLE 2-continued

| No. | Structure | Name | ER-alpha MCF7 HCS EC$_{50}$ (μM) | LCMS [M + H]$^+$ |
|---|---|---|---|---|
| 382 | 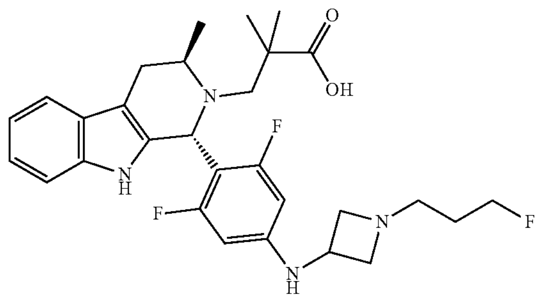 [SMILES: C[C@@H]1Cc2c([nH]c3ccccc23)[C@@H](c2c(F)cc(NC3CN(CCCF)C3)cc2F)N1CC(C)(C)C(=O)O] | 3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2,2-dimethylpropanoic acid | 0.00101 | 528.2 |
| 383 | 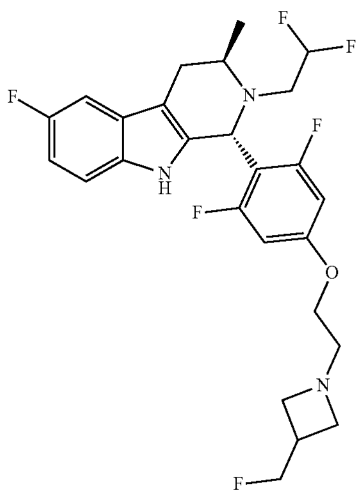 [SMILES: C[C@@H]1Cc2c([nH]c3ccc(F)cc23)[C@@H](c2c(F)cc(OCCN3CC(CF)C3)cc2F)N1CC(F)F] | (1R,3R)-1-(2,6-difluoro-4-(2-(3-(fluoromethyl)azetidin-1-yl)ethoxy)phenyl)-2-(2,2-difluoroethyl)-6-fluoro-3-methyl-2,3,4,9-tetrahydro-1H-pyrido[3,4-b]indole | 0.00028 | 512.2 |
| 384 | 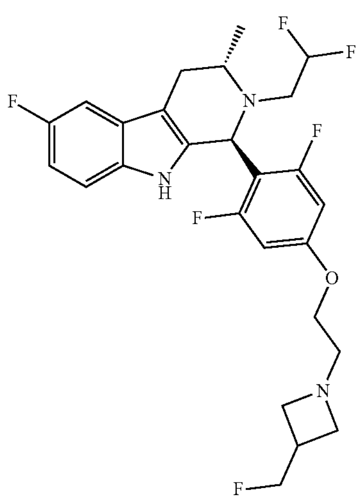 [SMILES: C[C@H]1Cc2c([nH]c3ccc(F)cc23)[C@H](c2c(F)cc(OCCN3CC(CF)C3)cc2F)N1CC(F)F] | (1S,3S)-1-(2,6-difluoro-4-(2-(3-(fluoromethyl)azetidin-1-yl)ethoxy)phenyl)-2-(2,2-difluoroethyl)-6-fluoro-3-methyl-2,3,4,9-tetrahydro-1H-pyrido[3,4-b]indole | 0.029 | 512.2 |

TABLE 2-continued

| No. | Structure | Name | ER-alpha MCF7 HCS EC$_{50}$ (μM) | LCMS [M + H]$^+$ |
|---|---|---|---|---|
| 385 | 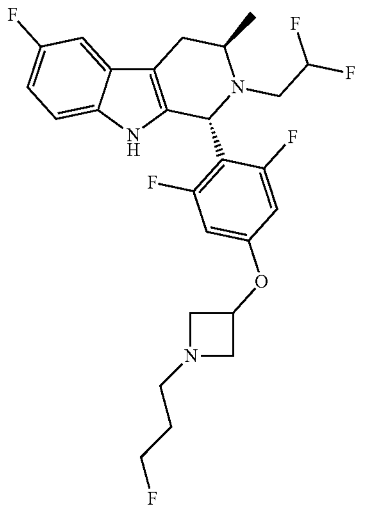 [SMILES: C[C@@H]1Cc2c([nH]c3ccc(F)cc23)[C@@H](c2c(F)cc(OC3CN(CCCF)C3)cc2F)N1CC(F)F] | (1R,3R)-1-(2,6-difluoro-4-((1-(3-fluoropropyl)azetidin-3-yl)oxy)phenyl)-2-(2,2-difluoroethyl)-6-fluoro-3-methyl-2,3,4,9-tetrahydro-1H-pyrido[3,4-b]indole | 0.000074 | 512.2 |
| 386 | 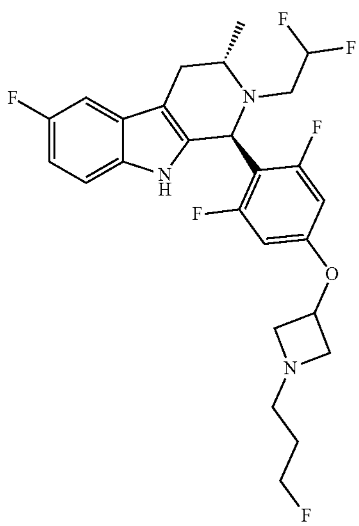 [SMILES: C[C@H]1Cc2c([nH]c3ccc(F)cc23)[C@H](c2c(F)cc(OC3CN(CCCF)C3)cc2F)N1CC(F)F] | (1S,3S)-1-(2,6-difluoro-4-((1-(3-fluoropropyl)azetidin-3-yl)oxy)phenyl)-2-(2,2-difluoroethyl)-6-fluoro-3-methyl-2,3,4,9-tetrahydro-1H-pyrido[3,4-b]indole | 0.023 | 512.2 |
| 387 | 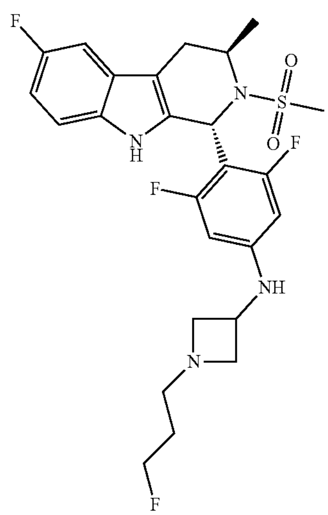 [SMILES: C[C@@H]1Cc2c([nH]c3ccc(F)cc23)[C@@H](c2c(F)cc(NC3CN(CCCF)C3)cc2F)N1S(C)(=O)=O] | N-(3,5-difluoro-4-((1R,3R)-6-fluoro-3-methyl-2-(methylsulfonyl)-2,3,4,9-tetrahydro-1H-pyrido[3,4-b]indol-1-yl)phenyl)-1-(3-fluoropropyl)azetidin-3-amine | 0.000149 | 525.2 |

TABLE 2-continued

| No. | Structure | Name | ER-alpha MCF7 HCS EC$_{50}$ (μM) | LCMS [M + H]$^+$ |
|---|---|---|---|---|
| 388 | 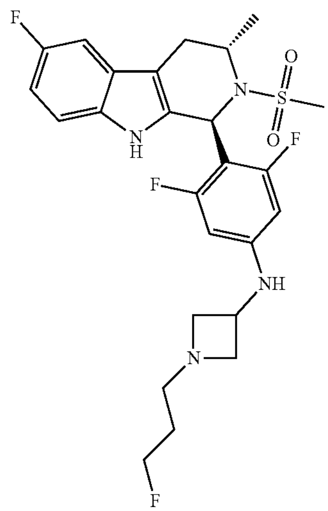 [SMILES: C[C@H]1Cc2c([nH]c3ccc(F)cc23)[C@H](c2c(F)cc(NC3CN(CCCF)C3)cc2F)N1S(C)(=O)=O] | N-(3,5-difluoro-4-((1S,3S)-6-fluoro-3-methyl-2-(methylsulfonyl)-2,3,4,9-tetrahydro-1H-pyrido[3,4-b]indol-1-yl)phenyl)-1-(3-fluoropropyl)azetidin-3-amine | 0.019 | 525.2 |
| 389 | 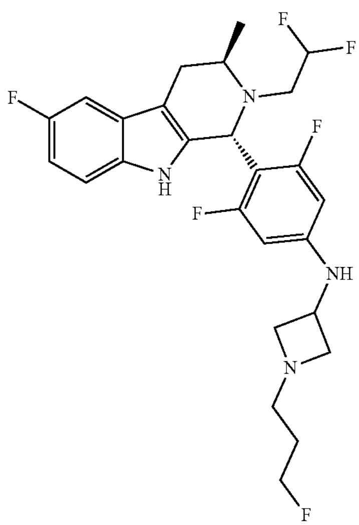 [SMILES: C[C@@H]1Cc2c([nH]c3ccc(F)cc23)[C@@H](c2c(F)cc(NC3CN(CCCF)C3)cc2F)N1CC(F)F] | N-(4-((1R,3R)-2-(2,2-difluoroethyl)-6-fluoro-3-methyl-2,3,4,9-tetrahydro-1H-pyrido[3,4-b]indol-1-yl)-3,5-difluorophenyl)-1-(3-fluoropropyl)azetidin-3-amine | 0.000056 | 511.2 |
| 390 | 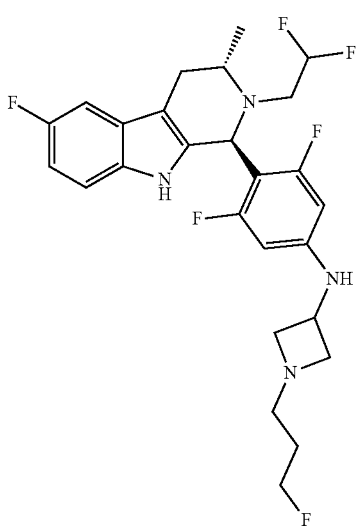 [SMILES: C[C@H]1Cc2c([nH]c3ccc(F)cc23)[C@H](c2c(F)cc(NC3CN(CCCF)C3)cc2F)N1CC(F)F] | N-(4-((1S,3S)-2-(2,2-difluoroethyl)-6-fluoro-3-methyl-2,3,4,9-tetrahydro-1H-pyrido[3,4-b]indol-1-yl)-3,5-difluorophenyl)-1-(3-fluoropropyl)azetidin-3-amine | 0.0097 | 511.2 |

TABLE 2-continued

| No. | Structure | Name | ER-alpha MCF7 HCS EC$_{50}$ (μM) | LCMS [M + H]$^+$ |
|---|---|---|---|---|
| 391 | 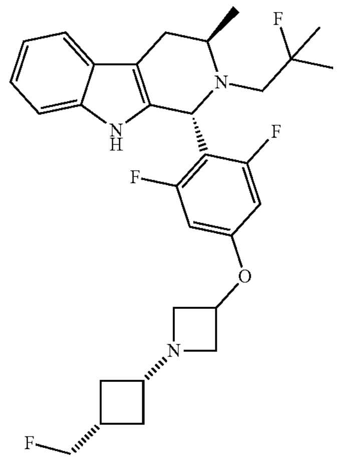 | (1R,3R)-1-(2,6-difluoro-4-((1-cis-(3-(fluoromethyl)cyclobutyl)azetidin-3-yl)oxy)phenyl)-2-(2-fluoro-2-methylpropyl)-3-methyl-2,3,4,9-tetrahydro-1H-pyrido[3,4-b]indole | 0.00015 | 530.3 |
| 392 | 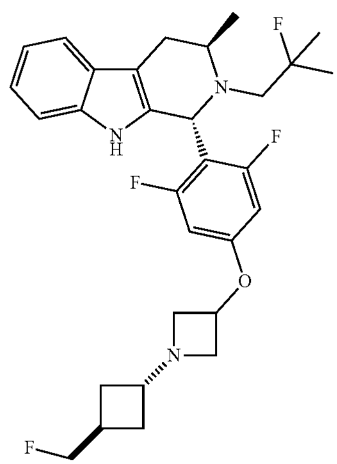 | (1R,3R)-1-(2,6-difluoro-4-((1-trans-(3-(fluoromethyl)cyclobutyl)azetidin-3-yl)oxy)phenyl)-2-(2-fluoro-2-methylpropyl)-3-methyl-2,3,4,9-tetrahydro-1H-pyrido[3,4-b]indole | 0.00044 | 530.3 |
| 393 | 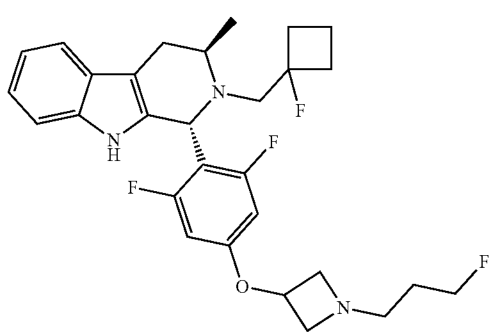 [SMILES: C[C@@H]1Cc2c([nH]c3ccccc23)[C@@H](c2c(F)cc(OC3CN(CCCF)C3)cc2F)N1CC1(F)CCC1] | (1R,3R)-1-(2,6-difluoro-4-((1-(3-fluoropropyl)azetidin-3-yl)oxy)phenyl)-2-((1-fluorocyclobutyl)methyl)-3-methyl-2,3,4,9-tetrahydro-1H-pyrido[3,4-b]indole | 0.000142 | 516.3 |

TABLE 2-continued

| No. | Structure | Name | ER-alpha MCF7 HCS EC$_{50}$ (µM) | LCMS [M + H]$^+$ |
|---|---|---|---|---|
| 394 | 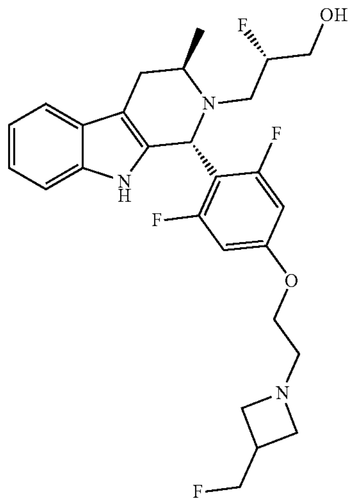 [SMILES: C[C@@H]1Cc2c([nH]c3ccccc23)[C@@H](c2c(F)cc(OCCN3CC(CF)C3)cc2F)N1C[C@H](F)CO] | (S)-3-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-fluoropropan-1-ol | 0.00023 | 506.2 |
| 395 | 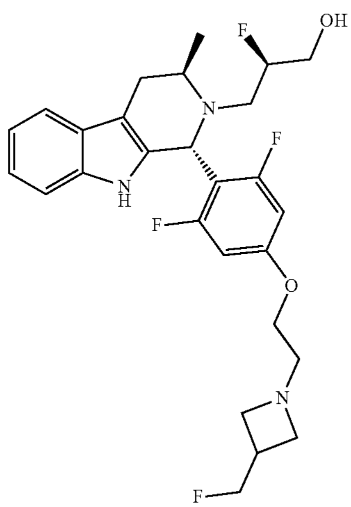 [SMILES: C[C@@H]1Cc2c([nH]c3ccccc23)[C@@H](c2c(F)cc(OCCN3CC(CF)C3)cc2F)N1C[C@@H](F)CO] | (R)-3-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-fluoropropan-1-ol | 0.000053 | 506.2 |
| 396 | 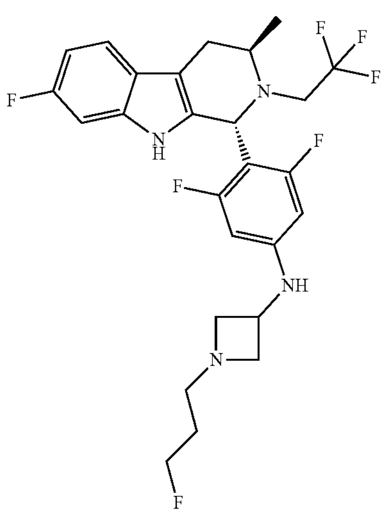 [SMILES: C[C@@H]1Cc2c([nH]c3cc(F)ccc23)[C@@H](c2c(F)cc(NC3CN(CCCF)C3)cc2F)N1CC(F)(F)F] | N-(3,5-difluoro-4-((1R,3R)-7-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine | 0.00011 | 529.2 |

TABLE 2-continued

| No. | Structure | Name | ER-alpha MCF7 HCS EC$_{50}$ (μM) | LCMS [M + H]$^+$ |
|---|---|---|---|---|
| 397 | 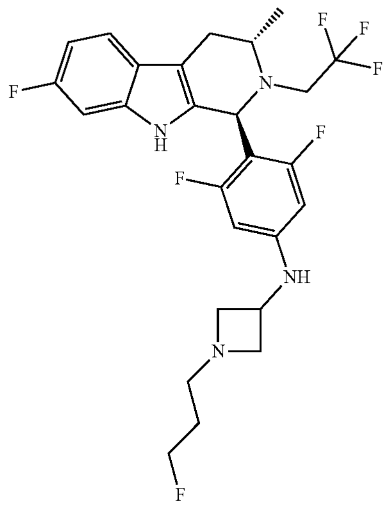 [SMILES: C[C@H]1Cc2c([nH]c3cc(F)ccc23)[C@H](c2c(F)cc(NC3CN(CCCF)C3)cc2F)N1CC(F)(F)F] | N-(3,5-difluoro-4-((1S,3S)-7-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine | 0.033 | 529.2 |
| 398 | 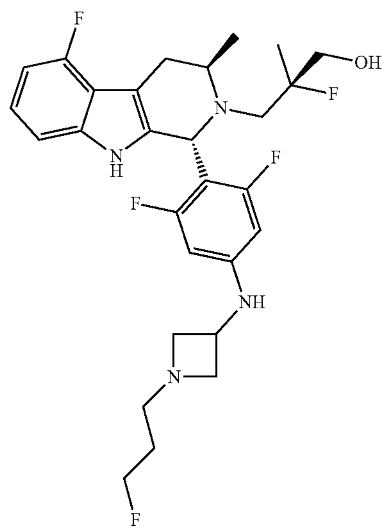 [SMILES: C[C@@H]1Cc2c([nH]c3cccc(F)c23)[C@@H](c2c(F)cc(NC3CN(CCCF)C3)cc2F)N1C[C@](C)(F)CO] | (S)-3-((1R,3R)-1-(2,6-difluoro-4-((1-(3-fluoropropyl)azetidin-3-yl)amino)phenyl)-5-fluoro-3-methyl-3,4-dihydro-1H-pyrido[3,4-b]indol-2(9H)-yl)-2-fluoro-2-methylpropan-1-ol | 0.00011 | 537.3 |
| 399 | 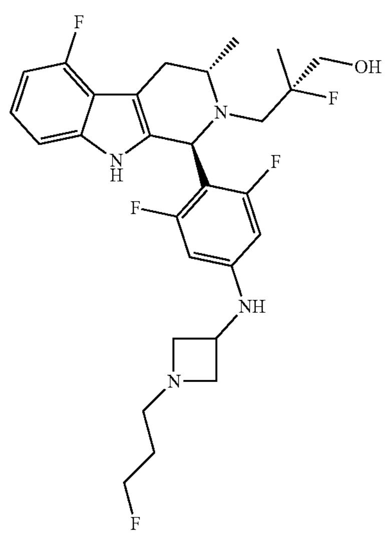 [SMILES: C[C@H]1Cc2c([nH]c3cccc(F)c23)[C@H](c2c(F)cc(NC3CN(CCCF)C3)cc2F)N1C[C@@](C)(F)CO] | (R)-3-((1S,3S)-1-(2,6-difluoro-4-((1-(3-fluoropropyl)azetidin-3-yl)amino)phenyl)-5-fluoro-3-methyl-3,4-dihydro-1H-pyrido[3,4-b]indol-2(9H)-yl)-2-fluoro-2-methylpropan-1-ol | 0.0011 | 537.3 |

TABLE 2-continued

| No. | Structure | Name | ER-alpha MCF7 HCS EC$_{50}$ (μM) | LCMS [M + H]$^+$ |
|---|---|---|---|---|
| 400 | 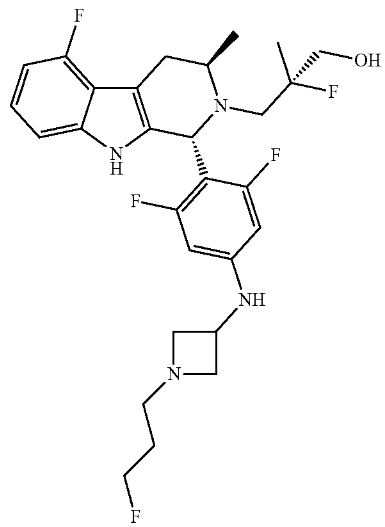 [SMILES: C[C@@H]1Cc2c([nH]c3cccc(F)c23)[C@@H](c2c(F)cc(NC3CN(CCCF)C3)cc2F)N1C[C@@](C)(F)CO] | (R)-3-((1R,3R)-1-(2,6-difluoro-4-((1-(3-fluoropropyl)azetidin-3-yl)amino)phenyl)-5-fluoro-3-methyl-3,4-dihydro-1H-pyrido[3,4-b]indol-2(9H)-yl)-2-fluoro-2-methylpropan-1-ol | 0.000023 | 537.3 |
| 401 | 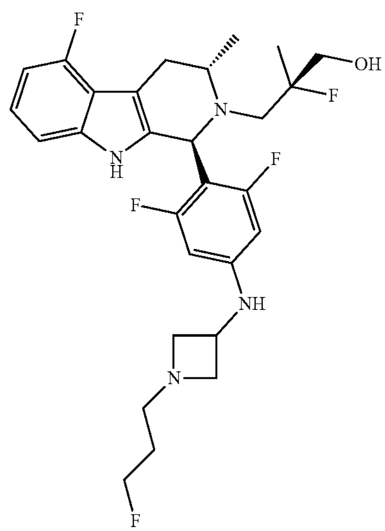 [SMILES: C[C@H]1Cc2c([nH]c3cccc(F)c23)[C@H](c2c(F)cc(NC3CN(CCCF)C3)cc2F)N1C[C@](C)(F)CO] | (S)-3-((1S,3S)-1-(2,6-difluoro-4-((1-(3-fluoropropyl)azetidin-3-yl)amino)phenyl)-5-fluoro-3-methyl-3,4-dihydro-1H-pyrido[3,4-b]indol-2(9H)-yl)-2-fluoro-2-methylpropan-1-ol | 0.0024 | 537.3 |
| 402 | 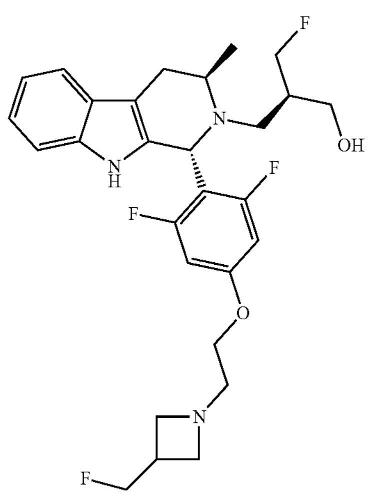 [SMILES: C[C@@H]1Cc2c([nH]c3ccccc23)[C@@H](c2c(F)cc(OCCN3CC(CF)C3)cc2F)N1C[C@H](CO)CF] | (R)-3-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-(fluoromethyl)propan-1-ol | 0.000032 | 520.3 |

TABLE 2-continued

| No. | Structure | Name | ER-alpha MCF7 HCS EC$_{50}$ (µM) | LCMS [M + H]$^+$ |
|---|---|---|---|---|
| 403 | 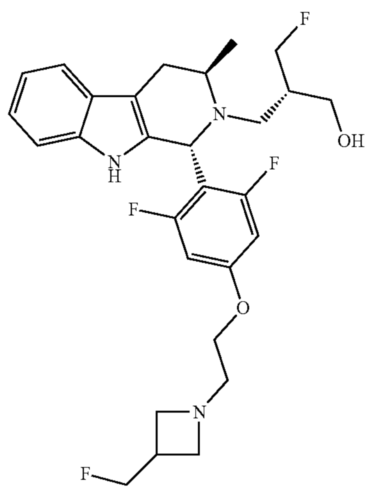 [SMILES: C[C@@H]1Cc2c([nH]c3ccccc23)[C@@H](c2c(F)cc(OCCN3CC(CF)C3)cc2F)N1C[C@@H](CO)CF] | (S)-3-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-(fluoromethyl)propan-1-ol | 0.00013 | 520.3 |
| 404 | 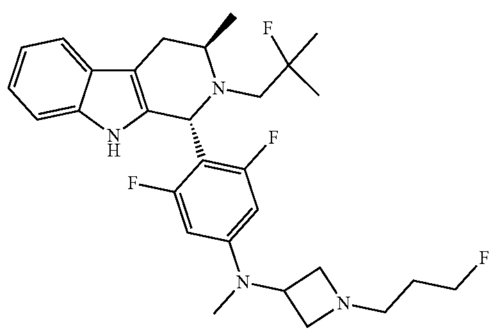 [SMILES: C[C@@H]1Cc2c([nH]c3ccccc23)[C@@H](c2c(F)cc(N(C)C3CN(CCCF)C3)cc2F)N1CC(C)(C)F] | N-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1-(3-fluoropropyl)-N-methylazetidin-3-amine | 0.000745 | 517.3 |
| 405 | 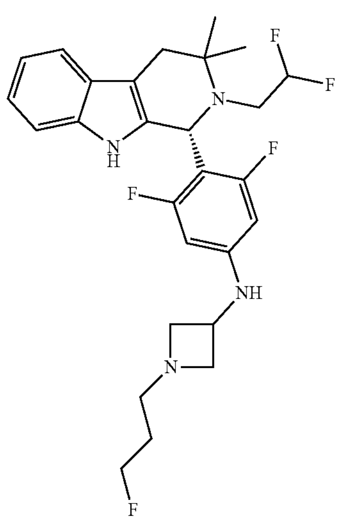 [SMILES: CC1(C)Cc2c([nH]c3ccccc23)[C@@H](c2c(F)cc(NC3CN(CCCF)C3)cc2F)N1CC(F)F] | (R)-N-(4-(2-(2,2-difluoroethyl)-3,3-dimethyl-2,3,4,9-tetrahydro-1H-pyrido[3,4-b]indol-1-yl)-3,5-difluorophenyl)-1-(3-fluoropropyl)azetidin-3-amine | 0.00023 | 517.3 |

TABLE 2-continued

| No. | Structure | Name | ER-alpha MCF7 HCS EC$_{50}$ (μM) | LCMS [M + H]$^+$ |
|---|---|---|---|---|
| 406 | 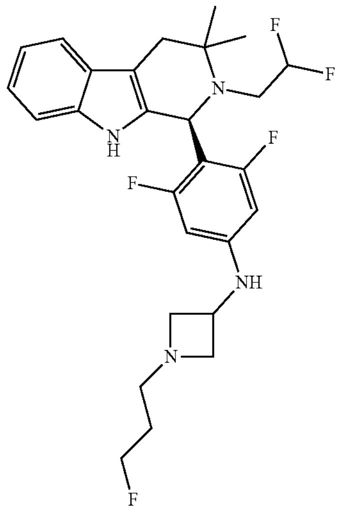 [SMILES: CC1(C)Cc2c([nH]c3ccccc23)[C@H](c2c(F)cc(NC3CN(CCCF)C3)cc2F)N1CC(F)F] | (S)-N-(4-(2-(2,2-difluoroethyl)-3,3-dimethyl-2,3,4,9-tetrahydro-1H-pyrido[3,4-b]indol-1-yl)-3,5-difluorophenyl)-1-(3-fluoropropyl)azetidin-3-amine | 0.0018 | 507.3 |
| 407 | 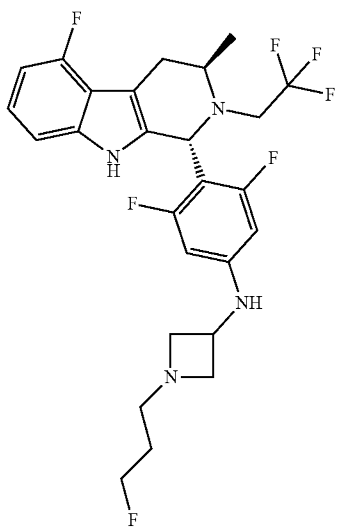 [SMILES: C[C@@H]1Cc2c([nH]c3cccc(F)c23)[C@@H](c2c(F)cc(NC3CN(CCCF)C3)cc2F)N1CC(F)(F)F] | N-(3,5-difluoro-4-((1R,3R)-5-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine | 0.00012 | 529.2 |
| 408 | 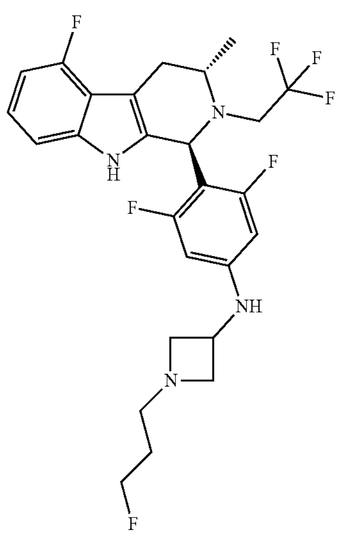 [SMILES: C[C@H]1Cc2c([nH]c3cccc(F)c23)[C@H](c2c(F)cc(NC3CN(CCCF)C3)cc2F)N1CC(F)(F)F] | N-(3,5-difluoro-4-((1S,3S)-5-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine | 0.0063 | 529.2 |

TABLE 2-continued

| No. | Structure | Name | ER-alpha MCF7 HCS EC$_{50}$ (μM) | LCMS [M + H]$^+$ |
|---|---|---|---|---|
| 409 | 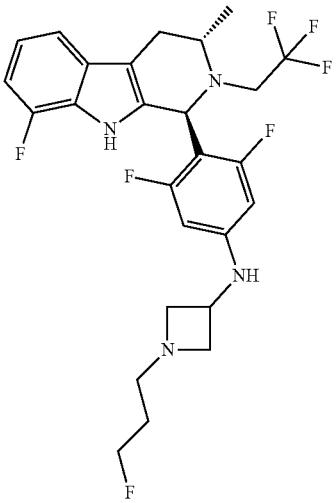 [SMILES: C[C@H]1Cc2c([nH]c3c(F)cccc23)[C@H](c2c(F)cc(NC3CN(CCCF)C3)cc2F)N1CC(F)(F)F] | N-(3,5-difluoro-4-((1S,3S)-8-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine | 0.026 | 529.2 |
| 410 | 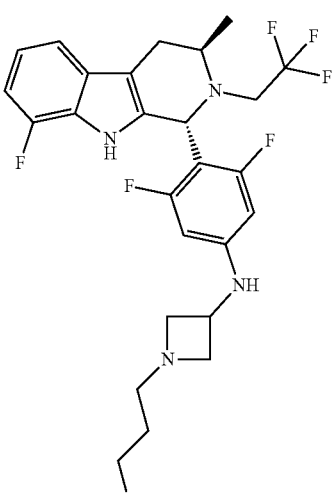 | N-(3,5-difluoro-4-((1R,3R)-8-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine | 0.00012 | 529.2 |
| 411 | 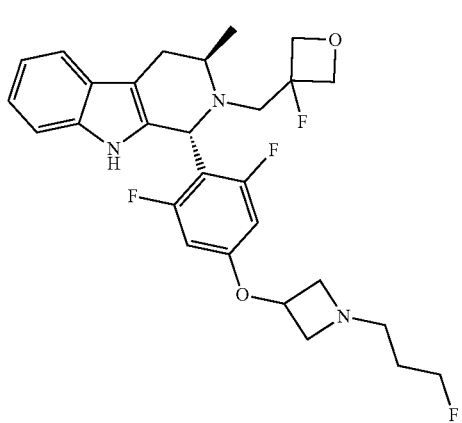 [SMILES: C[C@@H]1Cc2c([nH]c3ccccc23)[C@@H](c2c(F)cc(OC3CN(CCCF)C3)cc2F)N1CC1(F)COC1] | (1R,3R)-1-(2,6-difluoro-4-(1-(3-fluoropropyl)azetidin-3-yloxy)phenyl)-2-((3-fluorooxetan-3-yl)methyl)-3-methyl-2,3,4,9-tetrahydro-1H-pyrido[3,4-b]indole | 0.00007 | 518.3 |

TABLE 2-continued

| No. | Structure | Name | ER-alpha MCF7 HCS EC$_{50}$ (μM) | LCMS [M + H]$^+$ |
|---|---|---|---|---|
| 412 | 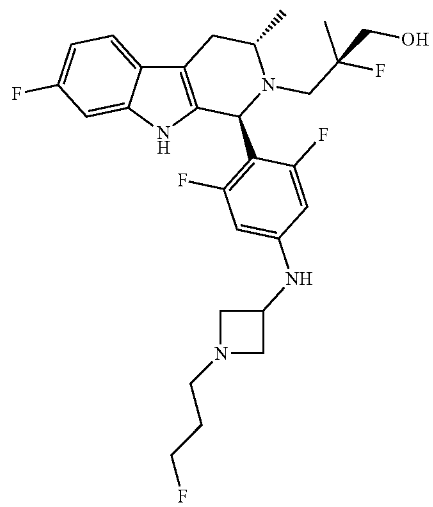 [SMILES: C[C@H]1Cc2c([nH]c3cc(F)ccc23)[C@H](c2c(F)cc(NC3CN(CCCF)C3)cc2F)N1C[C@](C)(F)CO] | (S)-3-((1S,3S)-1-(2,6-difluoro-4-((1-(3-fluoropropyl)azetidin-3-yl)amino)phenyl)-7-fluoro-3-methyl-3,4-dihydro-1H-pyrido[3,4-b]indol-2(9H)-yl)-2-fluoro-2-methylpropan-1-ol | 0.0013 | 537.3 |
| 413 | 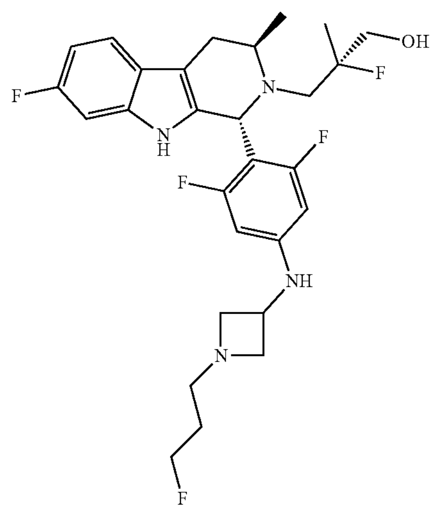 [SMILES: C[C@@H]1Cc2c([nH]c3cc(F)ccc23)[C@@H](c2c(F)cc(NC3CN(CCCF)C3)cc2F)N1C[C@@](C)(F)CO] | (R)-3-((1R,3R)-1-(2,6-difluoro-4-((1-(3-fluoropropyl)azetidin-3-yl)amino)phenyl)-7-fluoro-3-methyl-3,4-dihydro-1H-pyrido[3,4-b]indol-2(9H)-yl)-2-fluoro-2-methylpropan-1-ol | 0.000018 | 537.3 |
| 414 | 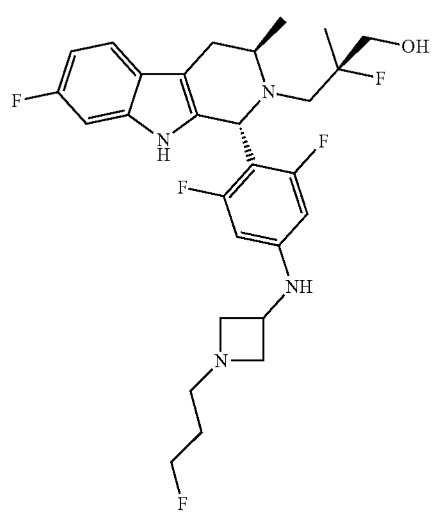 [SMILES: C[C@@H]1Cc2c([nH]c3cc(F)ccc23)[C@@H](c2c(F)cc(NC3CN(CCCF)C3)cc2F)N1C[C@](C)(F)CO] | (S)-3-((1R,3R)-1-(2,6-difluoro-4-((1-(3-fluoropropyl)azetidin-3-yl)amino)phenyl)-7-fluoro-3-methyl-3,4-dihydro-1H-pyrido[3,4-b]indol-2(9H)-yl)-2-fluoro-2-methylpropan-1-ol | 0.00012 | 537.3 |

TABLE 2-continued

| No. | Structure | Name | ER-alpha MCF7 HCS EC$_{50}$ (µM) | LCMS [M + H]$^+$ |
|---|---|---|---|---|
| 415 | 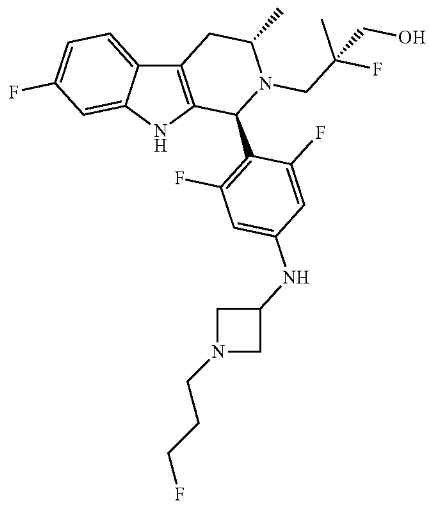 [SMILES: C[C@H]1Cc2c([nH]c3cc(F)ccc23)[C@H](c2c(F)cc(NC3CN(CCCF)C3)cc2F)N1C[C@@](C)(F)CO] | (R)-3-((1S,3S)-1-(2,6-difluoro-4-((1-(3-fluoropropyl)azetidin-3-yl)amino)phenyl)-7-fluoro-3-methyl-3,4-dihydro-1H-pyrido[3,4-b]indol-2(9H)-yl)-2-fluoro-2-methylpropan-1-ol | 0.0095 | 537.3 |
| 416 | 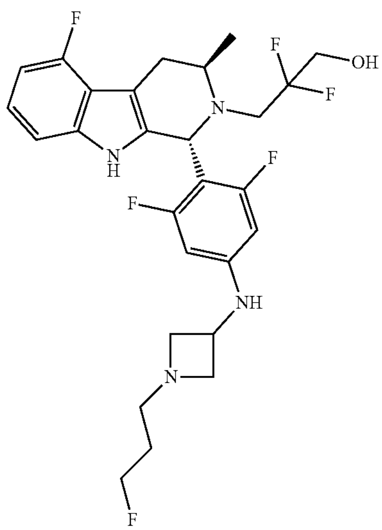 [SMILES: C[C@@H]1Cc2c([nH]c3cccc(F)c23)[C@@H](c2c(F)cc(NC3CN(CCCF)C3)cc2F)N1CC(F)(F)CO] | 3-((1R,3R)-1-(2,6-difluoro-4-((1-(3-fluoropropyl)azetidin-3-yl)amino)phenyl)-5-fluoro-3-methyl-3,4-dihydro-1H-pyrido[3,4-b]indol-2(9H)-yl)-2,2-difluoropropan-1-ol | 0.000024 | 541.2 |
| 417 | 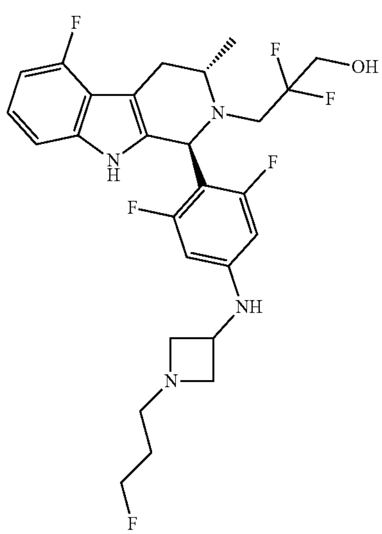 [SMILES: C[C@H]1Cc2c([nH]c3cccc(F)c23)[C@H](c2c(F)cc(NC3CN(CCCF)C3)cc2F)N1CC(F)(F)CO] | 3-((1S,3S)-1-(2,6-difluoro-4-((1-(3-fluoropropyl)azetidin-3-yl)amino)phenyl)-5-fluoro-3-methyl-3,4-dihydro-1H-pyrido[3,4-b]indol-2(9H)-yl)-2,2-difluoropropan-1-ol | 0.0033 | 541.2 |

TABLE 2-continued
| No. | Structure | Name | ER-alpha MCF7 HCS EC$_{50}$ (μM) | LCMS [M + H]$^+$ |
|---|---|---|---|---|
| 418 | 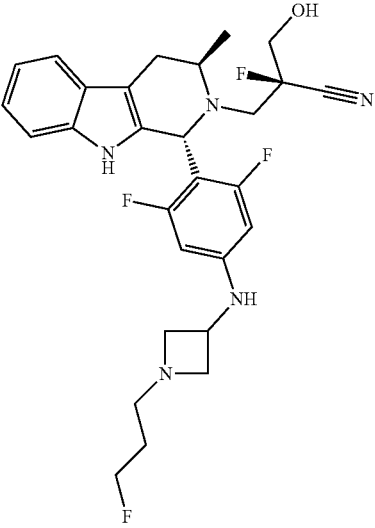 [SMILES: C[C@@H]1Cc2c([nH]c3ccccc23)[C@@H](c2c(F)cc(NC3CN(CCCF)C3)cc2F)N1C[C@@](F)(C#N)CO] | (R)-3-((1R,3R)-1-(2,6-difluoro-4-((1-(3-fluoropropyl)azetidin-3-yl)amino)phenyl)-3-methyl-3,4-dihydro-1H-pyrido[3,4-b]indol-2(9H)-yl)-2-fluoro-2-(hydroxymethyl)propanenitrile | 0.000033 | 530.3 |
| 419 | 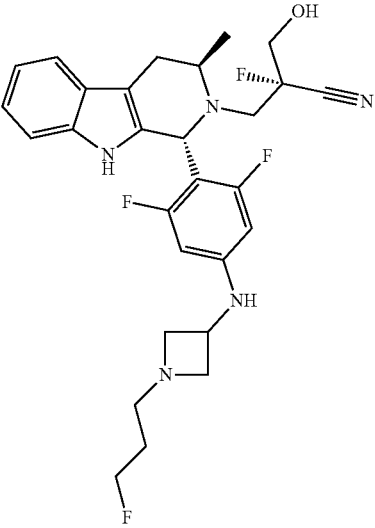 [SMILES: C[C@@H]1Cc2c([nH]c3ccccc23)[C@@H](c2c(F)cc(NC3CN(CCCF)C3)cc2F)N1C[C@](F)(C#N)CO] | (S)-3-((1R,3R)-1-(2,6-difluoro-4-((1-(3-fluoropropyl)azetidin-3-yl)amino)phenyl)-3-methyl-3,4-dihydro-1H-pyrido[3,4-b]indol-2(9H)-yl)-2-fluoro-2-(hydroxymethyl)propanenitrile | 0.000026 | 530.3 |

TABLE 2-continued

| No. | Structure | Name | ER-alpha MCF7 HCS EC$_{50}$ (μM) | LCMS [M + H]$^+$ |
|---|---|---|---|---|
| 420 | 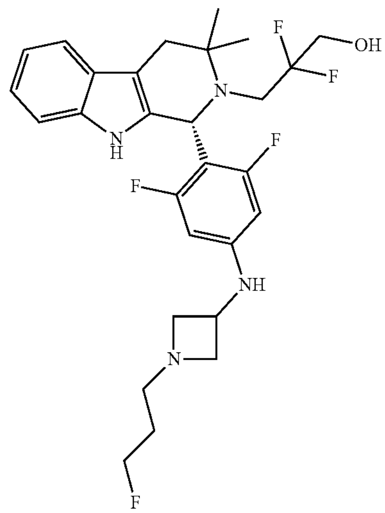 [SMILES: CC1(C)Cc2c([nH]c3ccccc23)[C@@H](c2c(F)cc(NC3CN(CCCF)C3)cc2F)N1CC(F)(F)CO] | (R)-3-(1-(2,6-difluoro-4-((1-(3-fluoropropyl)azetidin-3-yl)amino)phenyl)-3,3-dimethyl-3,4-dihydro-1H-pyrido[3,4-b]indol-2(9H)-yl)-2,2-difluoropropan-1-ol | 0.000117 | 537.3 |
| 421 | 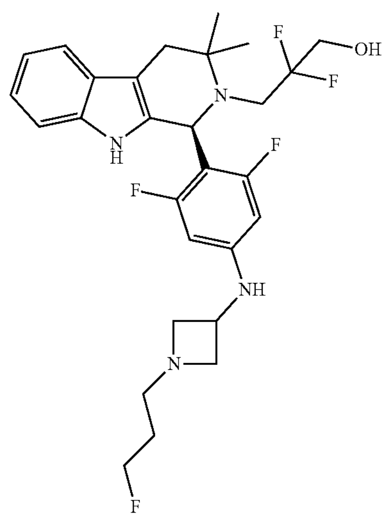 [SMILES: CC1(C)Cc2c([nH]c3ccccc23)[C@H](c2c(F)cc(NC3CN(CCCF)C3)cc2F)N1CC(F)(F)CO] | (S)-3-(1-(2,6-difluoro-4-((1-(3-fluoropropyl)azetidin-3-yl)amino)phenyl)-3,3-dimethyl-3,4-dihydro-1H-pyrido[3,4-b]indol-2(9H)-yl)-2,2-difluoropropan-1-ol | 0.000146 | 537.3 |
| 422 | 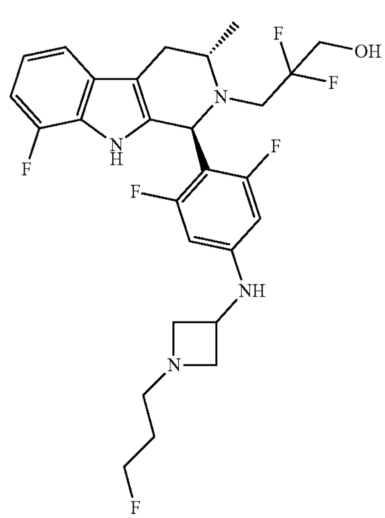 [SMILES: C[C@H]1Cc2c([nH]c3c(F)cccc23)[C@H](c2c(F)cc(NC3CN(CCCF)C3)cc2F)N1CC(F)(F)CO] | 3-((1S,3S)-1-(2,6-difluoro-4-((1-(3-fluoropropyl)azetidin-3-yl)amino)phenyl)-8-fluoro-3-methyl-3,4-dihydro-1H-pyrido[3,4-b]indol-2(9H)-yl)-2,2-difluoropropan-1-ol | 0.0371 | 541.2 |

TABLE 2-continued

| No. | Structure | Name | ER-alpha MCF7 HCS EC$_{50}$ (μM) | LCMS [M + H]$^+$ |
|---|---|---|---|---|
| 423 | 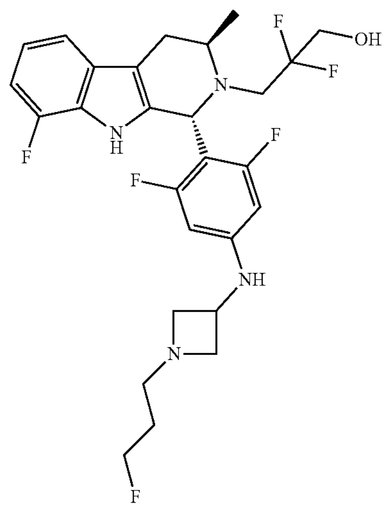 [SMILES: C[C@@H]1Cc2c([nH]c3c(F)cccc23)[C@@H](c2c(F)cc(NC3CN(CCCF)C3)cc2F)N1CC(F)(F)CO] | 3-((1R,3R)-1-(2,6-difluoro-4-((1-(3-fluoropropyl)azetidin-3-yl)amino)phenyl)-8-fluoro-3-methyl-3,4-dihydro-1H-pyrido[3,4-b]indol-2(9H)-yl)-2,2-difluoropropan-1-ol | 0.000089 | 541.2 |
| 424 | 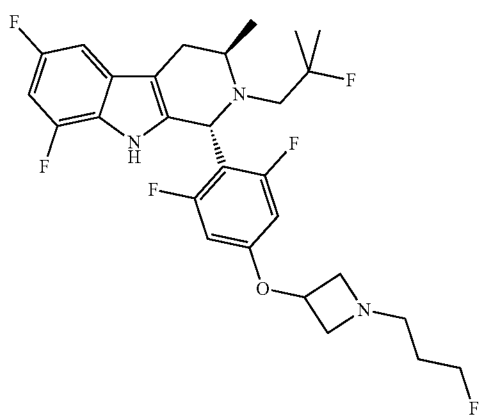 [SMILES: C[C@@H]1Cc2c([nH]c3c(F)cc(F)cc23)[C@@H](c2c(F)cc(OC3CN(CCCF)C3)cc2F)N1CC(C)(C)F] | (1R,3R)-1-(2,6-difluoro-4-(1-(3-fluoropropyl)azetidin-3-yloxy)phenyl)-6,8-difluoro-2-(2-fluoro-2-methylpropyl)-3-methyl-2,3,4,9-tetrahydro-1H-pyrido[3,4-b]indole | 0.0005 | 540.3 |
| 425 | 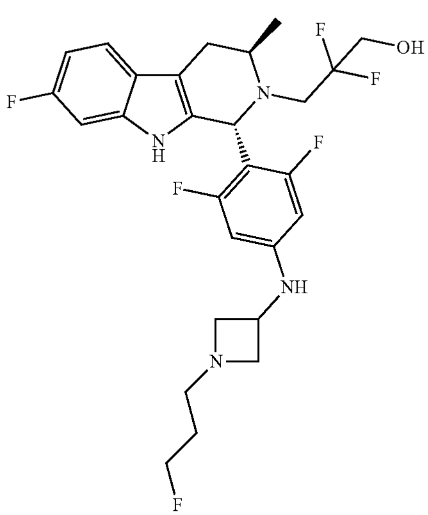 [SMILES: C[C@@H]1Cc2c([nH]c3cc(F)ccc23)[C@@H](c2c(F)cc(NC3CN(CCCF)C3)cc2F)N1CC(F)(F)CO] | 3-((1R,3R)-1-(2,6-difluoro-4-((1-(3-fluoropropyl)azetidin-3-yl)amino)phenyl)-7-fluoro-3-methyl-3,4-dihydro-1H-pyrido[3,4-b]indol-2(9H)-yl)-2,2-difluoropropan-1-ol | 0.000021 | 541.3 |

TABLE 2-continued

| No. | Structure | Name | ER-alpha MCF7 HCS EC$_{50}$ (μM) | LCMS [M + H]$^+$ |
|---|---|---|---|---|
| 426 | 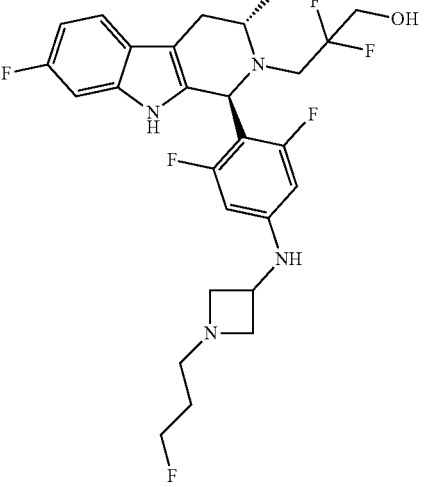 | 3-((1S,3S)-1-(2,6-difluoro-4-((1-(3-fluoropropyl)azetidin-3-yl)amino)phenyl)-7-fluoro-3-methyl-3,4-dihydro-1H-pyrido[3,4-b]indol-2(9H)-yl)-2,2-difluoropropan-1-ol | 0.00638 | 541.2 |
| 427 | 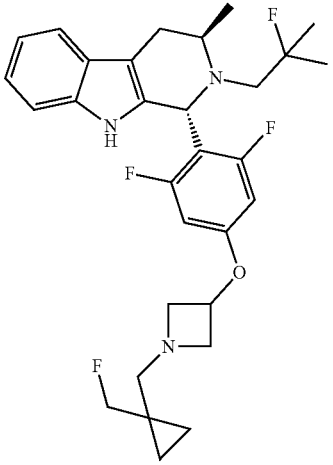 [SMILES: C[C@@H]1Cc2c([nH]c3ccccc23)[C@@H](c2c(F)cc(OC3CN(CC4(CF)CC4)C3)cc2F)N1CC(C)(C)F] | (1R,3R)-1-(2,6-difluoro-4-((1-((1-(fluoromethyl)cyclopropyl)methyl)azetidin-3-yl)oxy)phenyl)-2-(2-fluoro-2-methylpropyl)-3-methyl-2,3,4,9-tetrahydro-1H-pyrido[3,4-b]indole | 0.000278 | 530.3 |
| 428 | 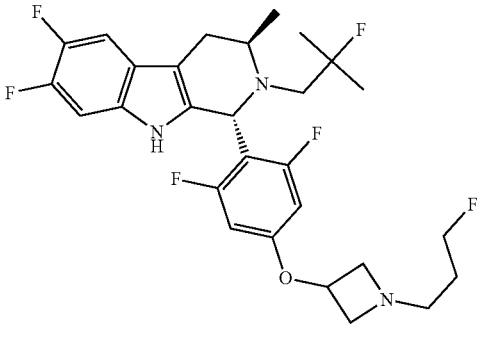 [SMILES: C[C@@H]1Cc2c([nH]c3cc(F)c(F)cc23)[C@@H](c2c(F)cc(OC3CN(CCCF)C3)cc2F)N1CC(C)(C)F] | (1R,3R)-1-(2,6-difluoro-4-(1-(3-fluoropropyl)azetidin-3-yloxy)phenyl)-6, 7-difluoro-2-(2-fluoro-2-methylpropyl)-3-methyl-2,3,4,9-tetrahydro-1H-pyrido[3,4-b]indole | 0.0007 | 540.3 |
| 429 | 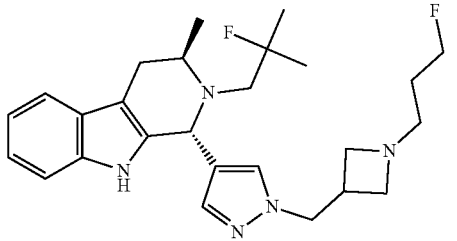 [SMILES: C[C@@H]1Cc2c([nH]c3ccccc23)[C@@H](c2cnn(CC3CN(CCCF)C3)c2)N1CC(C)(C)F] | (1R,3R)-2-(2-fluoro-2-methylpropyl)-1-(1-((1-(3-fluoropropyl)azetidin-3-yl)methyl)-1H-pyrazol-4-yl)-3-methyl-2,3,4,9-tetrahydro-1H-pyrido[3,4-b]indole | 0.00099 | 456.3 |

TABLE 2-continued

| No. | Structure | Name | ER-alpha MCF7 HCS EC$_{50}$ (μM) | LCMS [M + H]$^+$ |
|---|---|---|---|---|
| 430 | 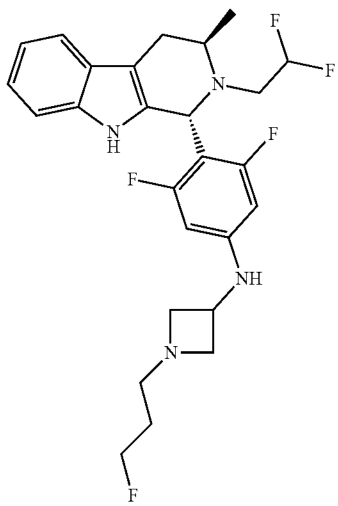 [SMILES: C[C@@H]1Cc2c([nH]c3ccccc23)[C@@H](c2c(F)cc(NC3CN(CCCF)C3)cc2F)N1CC(F)F] | N-[4-[(1R,3R)-2-(2,2-difluoroethyl)-3-methyl-1,3,4,9-tetrahydropyrido[3,4-b]indol-1-yl]-3,5-difluoro-phenyl]-1-(3-fluoropropyl)azetidin-3-amine | 0.000065 | 493.2 |
| 431 | 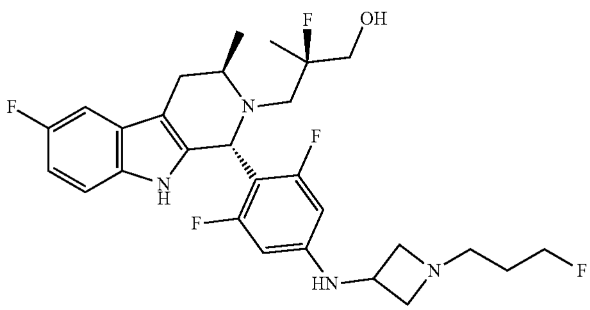 [SMILES: C[C@@H]1Cc2c([nH]c3ccc(F)cc23)[C@@H](c2c(F)cc(NC3CN(CCCF)C3)cc2F)N1C[C@@](C)(F)CO] | (R)-3-((1R,3R)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2-fluoro-2-methylpropan-1-ol | 0.0000943 | 537.3 |
| 432 | 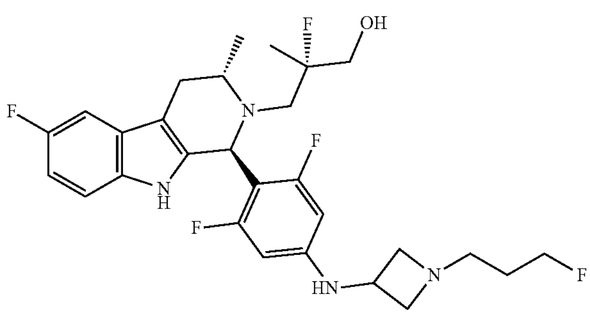 [SMILES: C[C@H]1Cc2c([nH]c3ccc(F)cc23)[C@H](c2c(F)cc(NC3CN(CCCF)C3)cc2F)N1C[C@](C)(F)CO] | (S)-3-((1S,3S)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2-fluoro-2-methylpropan-1-ol | 0.00327 | 537.3 |
| 433 | 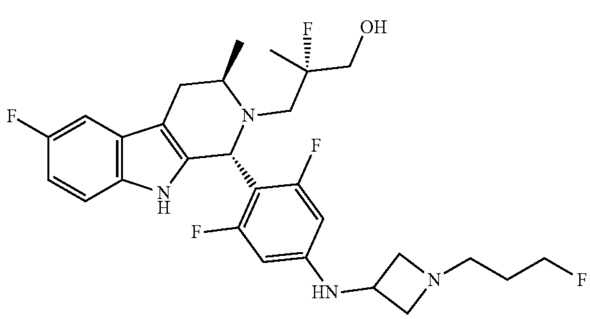 [SMILES: C[C@@H]1Cc2c([nH]c3ccc(F)cc23)[C@@H](c2c(F)cc(NC3CN(CCCF)C3)cc2F)N1C[C@](C)(F)CO] | (S)-3-((1R,3R)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2-fluoro-2-methylpropan-1-ol | 0.0000209 | 537.3 |

TABLE 2-continued

| No. | Structure | Name | ER-alpha MCF7 HCS EC$_{50}$ (μM) | LCMS [M + H]$^+$ |
|---|---|---|---|---|
| 434 | 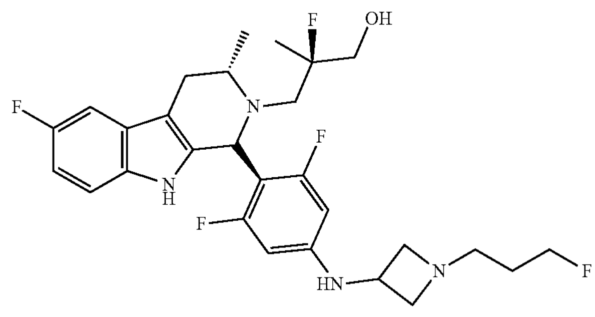 | (R)-3-((1R,3S)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2-fluoro-2-methylpropan-1-ol | 0.000706 | 537.3 |

Administration of Formula I Compounds

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating a human or animal patient suffering from a disease or disorder arising from abnormal cell growth, function or behavior associated with USP7 such as an immune disorder, cardiovascular disease, viral infection, inflammation, a metabolism/endocrine disorder or a neurological disorder, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

Methods of the invention also include treating cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, chronic lymphoid leukemia (CLL), myeloid leukemia, oral cavity and pharynx, non-Hodgkin lymphoma, melanoma, and villous colon adenoma.

PHARMACEUTICAL FORMULATIONS

In order to use a compound of this invention for the therapeutic treatment of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof.

The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-eresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as GDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl di stearate alone or with a wax may be employed.

For treatment of the eye or other external tissues, e.g., mouth and skin, the formulations are preferably applied as a topical ointment or cream containing the active ingredient(s) in an amount of, for example, 0.07S to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizers) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween®60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with additional therapeutic agents for the treatment of a disease or disorder described herein, such as inflammation or a hyperproliferative disorder (e.g., cancer). In certain embodiments, a compound of Formula I is combined in a pharmaceutical combination formulation, or dosing regimen as combination therapy, with an additional, second therapeutic compound that has anti-inflammatory or anti-hyperproliferative properties or that is useful for treating an inflammation, immune-response disorder, or hyperproliferative disorder (e.g., cancer). The additional therapeutic may be a Bcl-2 inhibitor, a JAK inhibitor, a PI3K inhibitor, an mTOR inhibitor, an anti-inflammatory agent, an immunomodulatory agent, chemotherapeutic agent, an apoptosis-enhancer, a neurotropic factor, an agent for treating cardiovascular disease, an agent for treating liver disease, an anti-viral agent, an agent for treating blood disorders, an agent for treating diabetes, and an agent for treating immunodeficiency disorders. The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, tautomer, solvate, metabolite, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I, or a stereoisomer, tautomer, solvate, metabolite, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, or a stereoisomer, tautomer, solvate, metabolite, or pharmaceutically acceptable salt or prodrug thereof, and the use of at least one other cancer treatment method. The amounts of the compound(s) of Formula I and the other pharmaceutically active therapeutic agent(s) and the relative timings of administration will be selected in order to achieve the desired combined therapeutic effect.

In some embodiments, a compound of Formula I, or a pharmaceutically acceptable salt thereof, is used in combination with an aromatase inhibitor, a phosphoinositide 3-kinase (PI3K)/mTOR pathway inhibitor, a CDK 4/6 inhibitor, a HER-2 inhibitor, an EGFR inhibitor, a PD-1 inhibitor, poly ADP-ribose polymerase (PARP) inhibitor, a histone deacetylase (HDAC) inhibitor, an HSP90 inhibitor, a VEGFR inhibitor, an AKT inhibitor, chemotherapy, or any combination thereof.

In some embodiments, a pharmaceutical composition comprising a compound of Formula I, or a pharmaceutically acceptable salt thereof, is administered in combination with a therapeutic agent selected from paclitaxel, anastrozole, exemestane, cyclophosphamide, epirubicin, fulvestrant, letrozole, gemcitabine, trastuzumab (HERCEPTIN®, Genentech), trastuzumab emtansine (KADCYLA®, Genentech), pegfilgrastim, filgrastim, tamoxifen, docetaxel, toremifene, vinorelbine, capecitabine, and ixabepilone.

In some embodiments, a compound of Formula I, or a pharmaceutically acceptable salt thereof, is used in combination with hormone blocking therapy, chemotherapy, radiation therapy, monoclonal antibodies, or combinations thereof.

Hormone blocking therapy includes the use of agents that block the production of estrogens or block the estrogen receptors. In some embodiments, hormone blocking therapy includes the use of estrogen receptor modulators and/or aromatase inhibitors. Estrogen receptor modulators include triphenylethylene derivatives (e.g. tamoxifen, toremifene, droloxifene, 3-hydroxytamoxifen, idoxifene, TAT-59 (a phosphorylated derivative of 4-hydroxytamoxifen) and GW5638 (a carboxylic acid derivative of tamoxifen)); non-steroidal estrogen receptor modulators (e.g. raloxifene, LY353381 (SERM3) and LY357489); steroidal estrogen receptor modulators (e.g. ICI-182,780). Aromatase inhibitors include steroidal aromatase inhibitors and non-steroidal aromatase inhibitors. Steroidal aromatase inhibitors include, but are not limited to, such exemestane. Non-steroidal aromatase inhibitors include, but are not limited to, as anastrozole, and letrozole.

In some embodiments, a compound of Formula I, or a pharmaceutically acceptable salt thereof, is administered in combination with a CDK 4/6 inhibitor. In some embodiments, the CDK 4/6 inhibitor is palbociclib (PD-0332991), ribociclib (LEE011) or LY283519. In some embodiments, the CDK 4/6 inhibitor is LEE011. In some embodiments, ribociclib (LEE011) is administered at a dose of about 10 mg per day to about 1000 mg per day. In some embodiments, LEE011 is administered at a dose of about 400 mg per day, about 500 mg per day or about 600 mg per day. In some embodiments, the daily dose of LEE011 is orally administered. In some embodiments, the daily dose of ribociclib (LEE011) is orally administered once a day for three weeks followed by a one week drug holiday where ribociclib (LEE011) is not administered.

In some embodiments, a compound of Formula I, or a pharmaceutically acceptable salt thereof, is administered in combination with a phosphoinositide 3-kinase (PI3K)/mTOR pathway inhibitor. In some embodiments, the a phosphoinositide 3-kinase (PI3K)/mTOR pathway inhibitor is everolimus, temsirolimus, BEZ235 (dactolisib), BYL719 (alpelisib), GDC0032 (taselisib), BKM120 (buparlisib), BGT226, GDC0068 (ipatasertib), GDC-0980 (apitolisib), GDC0941 (pictilisib), INK128 (MLN0128), INK1117, OSI-027, CC-223, AZD8055, SAR245408, SAR245409, PF04691502, WYE125132, GSK2126458, GSK-2636771, BAY806946, PF-05212384, SF1126, PX866, AMG319, ZSTK474, Cal101 (idelalisib), PWT33597, CU-906, AZD-2014 or CUDC-907. In some embodiments, the phosphoinositide 3-kinase (PI3K)/mTOR pathway inhibitor is everolimus. In some embodiments, everolimus is administered at a dose of about 1 mg per day to about 20 mg per day. In some embodiments, everolimus is administered at a dose of about 2.5 mg per day, about 5 mg per day, or about 10 mg per day. In some embodiments, the daily dose of everolimus is administered once a day. In some embodiments, the phosphoinositide 3-kinase (PI3K)/mTOR pathway inhibitor is BKM120 (buparlisib). In some embodiments, BKM120 (buparlisib) is administered at a dose of about 5 mg per day to about 500 mg per day. In some embodiments, BKM120 is administered at a dose of about 50 mg per day to about 100 mg per day. In some embodiments, BKM120 is administered at a dose of about 100 mg per day. In some embodiments, the daily dose of BKM120 is administered once a day. In some embodiments, the phosphoinositide 3-kinase (PI3K)/mTOR pathway inhibitor is BYL719. In some embodiments, BYL719 is administered at a dose of about 25 mg per day to about 1000 mg per day. In some embodiments, BYL719 is administered at a dose of about 250 mg per day or about 350 mg per day. In some embodiments, the daily dose of BYL719 is administered once a day.

Metabolites of Compounds of Formula I

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I, or a stereoisomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Compounds of Formula I may be synthesized by synthetic routes that include processes analogous to those well-known in the chemical arts, particularly in light of the description contained herein, and those for other heterocycles described in; Comprehensive Heterocyclic Chemistry II, Editors Katritzky and Rees, Elsevier, 1997, e.g. Volume 3; Liebigs Annalen der Chemie, (9): 1910-16, (1985); Helvetica Chimica Acta, 41:1052-60, (1958); Arzneimittel-Forschung, 40(12): 1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

The Examples provide exemplary methods for preparing Formula I compounds. Those skilled in the art will appreciate that other synthetic routes may be used to synthesize the Formula I compounds. Although specific starting materials and reagents are depicted and discussed in the Figures and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including; (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See; "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (–) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Formula I compounds can be prepared by the General Procedures of Schemes 1-7.

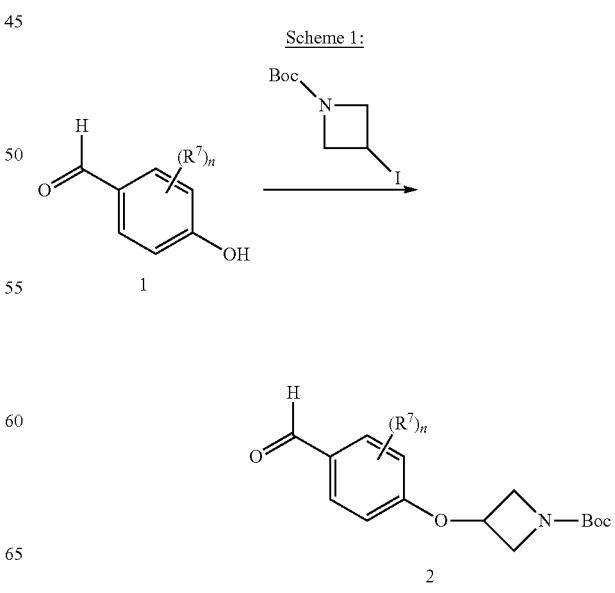

Scheme 1:

-continued

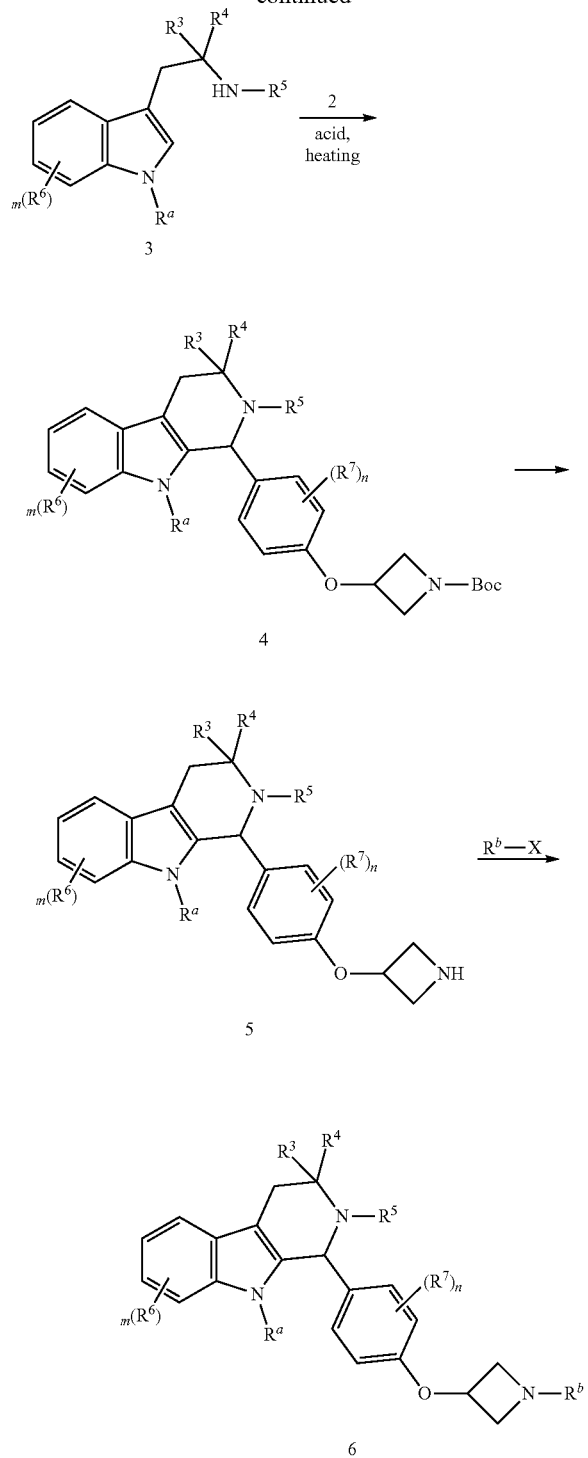

Scheme 2:

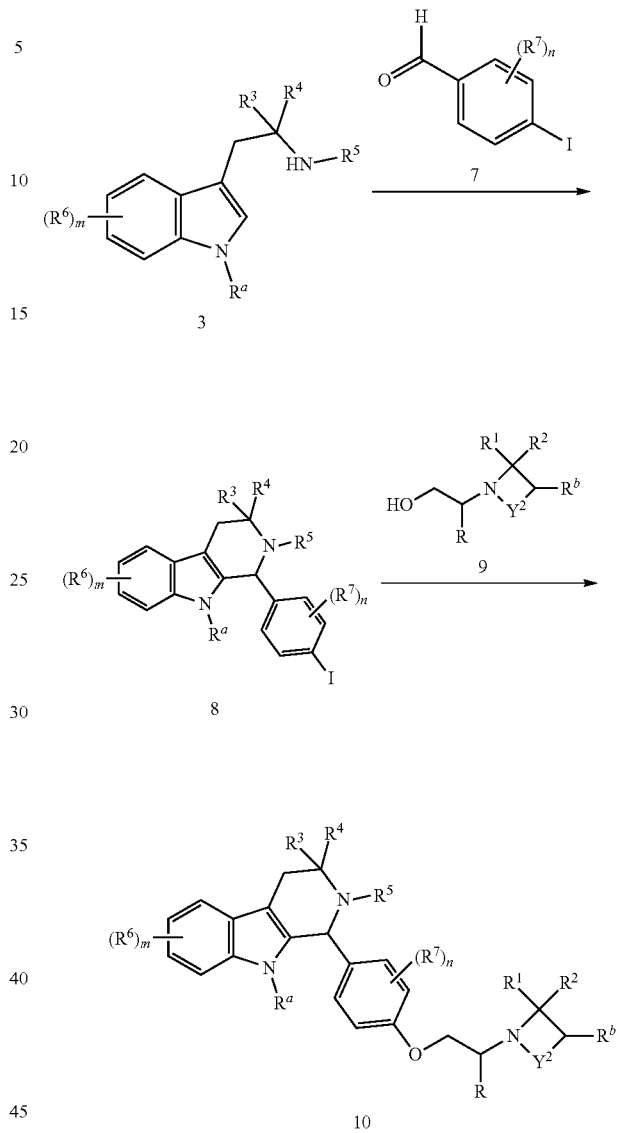

Scheme 1 shows para-hydroxy benzaldehyde intermediate 1 reacted with tert-butyl 3-iodoazetidine-1-carboxylate to give exemplary tert-butyl 3-(4-formylphenoxy)azetidine-1-carboxylate intermediate 2. An exemplary intermediate 1 is 2,6-difluoro-4-hydroxybenzaldehyde. Cyclization of 2 with bicyclic amines 3 gives tricyclic, tetrahydro-pyrido[3,4-b]indol-1-yl azetidine intermediate 4. Acidic deprotection of 4 and alkylation of 5 gives tricyclic, tetrahydro-pyrido[3,4-b]indol-1-yl azetidine intermediate 6.

Scheme 2 shows para-iodo benzaldehyde intermediates 7, such as 2,6-difluoro-4-iodobenzaldehyde, are cyclized with bicyclic amines 3 gives tricyclic, tetrahydro-pyrido[3,4-b]indol-1-yl iodophenyl intermediate 8. Reaction of 8 with alcohol 9 gives tricyclic, tetrahydro-pyrido[3,4-b]indol-1-yl intermediate 10.

Scheme 3:

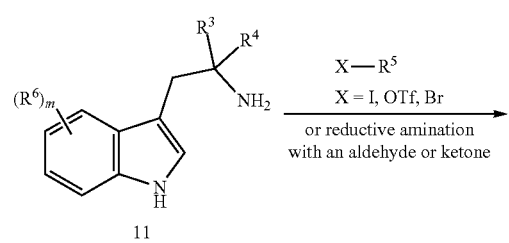

223

-continued

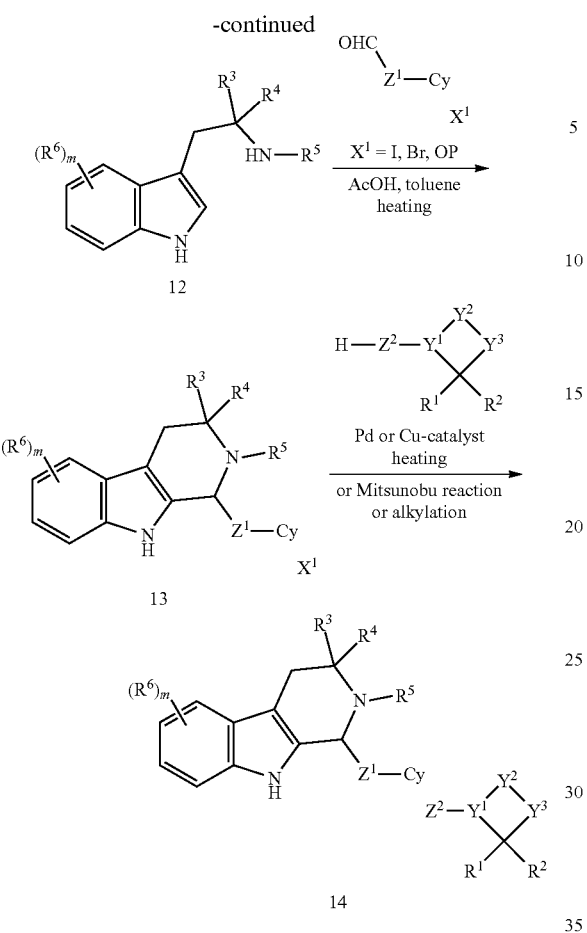

224

-continued

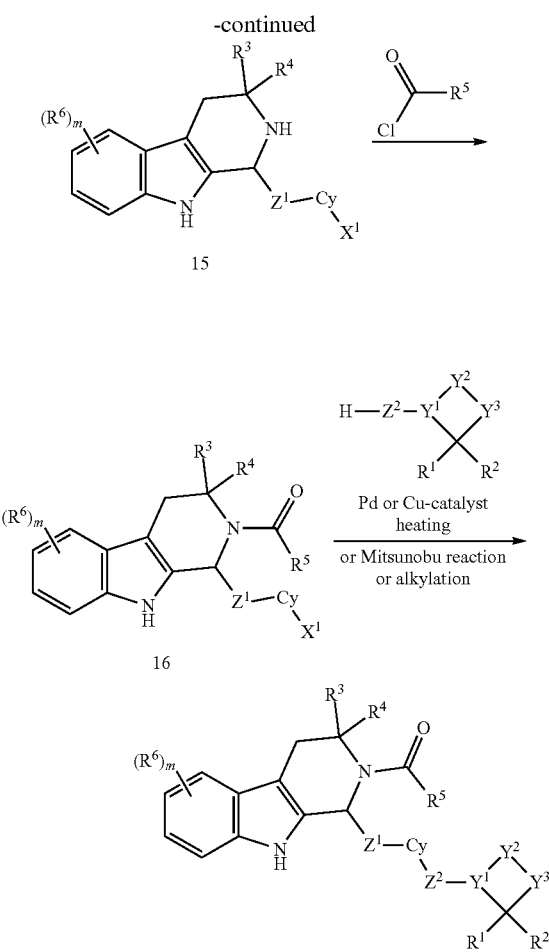

Scheme 3 shows reaction of amine 11 with an alkylating reagent, in which the leaving group could be an iodide, or a bromide, or a triflate, led to intermediate 12. Alternatively, the amine 11 could also react with an aldehyde or ketone to give intermediate 12 through reductive amination reaction. Condensation of intermediate 12 with an aldehyde then produced intermediate 13. The iodide or bromide on the $X^1$ group of Cy could then be coupled with an alcohol, or an amine, or a sulfide, or an olefin through a Pd- or Cu-catalyzed Ullman, or Buchwald, or Heck reaction to give target 14. Alternatively, the protected phenol (OP) on group Cy could be deprotected, and the resulting phenol could be further coupled with an alcohol through a Mitsunobu reaction. Alternatively, the phenol could also be alkylated, with an iodide, or a bromide, or a chloride, or a triflate, or a mesylate, to give tricyclic, tetrahydro-pyrido[3,4-b]indol-1-yl intermediate 14.

Scheme 4 shows Pictet-Spengler cyclization of amine 11 with an aldehyde leads to intermediate 15 where $X^1$ is iodide or bromide. Reaction of amine 15 with an acid chloride produces amide 16. The iodide or bromide $X^1$ group on Cy could then be coupled with an alcohol, or an amine, or a sulfide, or an olefin through a Pd- or Cu-catalyzed Ullman, or Buchwald, or Heck reaction to give intermediate 17. Alternatively, the protected phenol (OP) on group Cy of 16 can be deprotected, and the resulting phenol could be further coupled with an alcohol through a Mitsunobu reaction to give 17. Alternatively, the phenol (OH) can be alkylated, with an iodode, a bromide, a chloride, a triflate, or a mesylate, to give tricyclic, tetrahydro-pyrido[3,4-b]indol-1-yl amide intermediate 17.

Scheme 4:

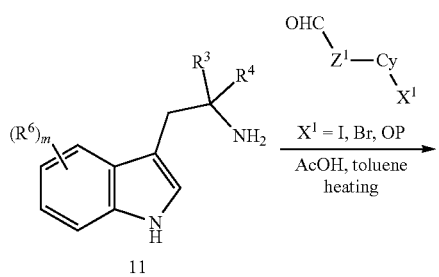

Scheme 5:

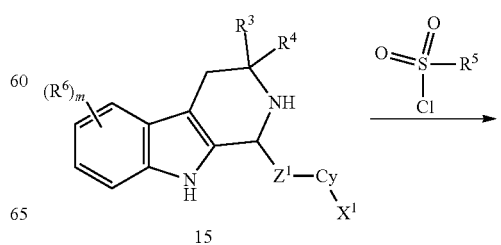

Scheme 7

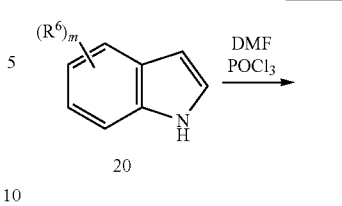

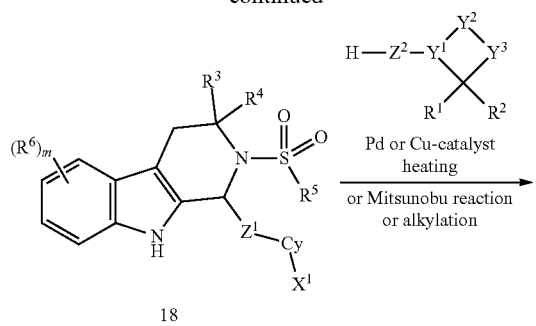

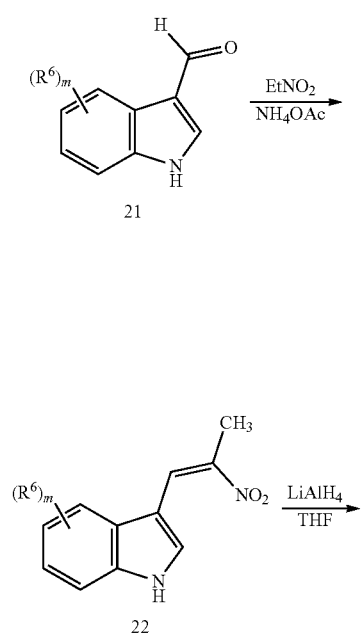

Scheme 5 shows amine 15 can react with a sulfonyl chloride to give sulfonamide 18, which can be converted by Pd- or Cu-catalyzed Ullman, Buchwald, or Heck reaction or by Mitsunobu or alkylation reactions to tricyclic, tetrahydro-pyrido[3,4-b]indol-1-yl sulfonamide intermediate 19.

Scheme 6:

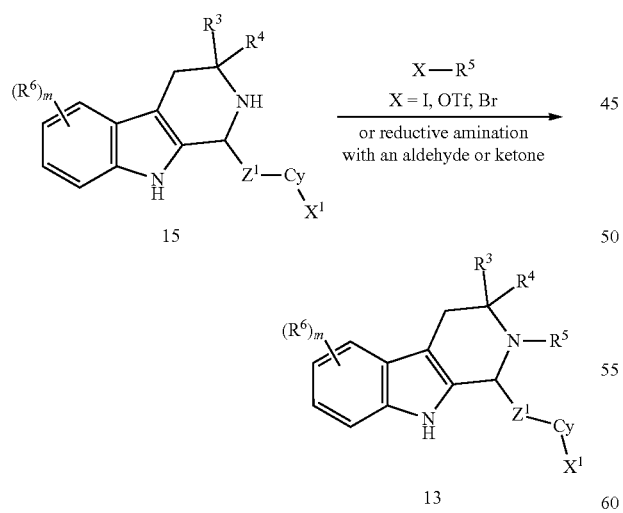

Scheme 6 shows amine 15 can react with an alkylating agent ($R^5$—X) to give intermediate 13. Alternatively amine 15 can react with an aldehyde or ketone and a reducing agent, such as sodium cyanoborohydride, to give intermediate 13.

Scheme 7 shows the general synthetic route for tryptamine 23. A substituted indole 20 is transformed to aldehyde 21, under Vilsmeier reaction conditions. Aldol reaction of aldehyde 21 with nitroethane gives compound 22. Reduction of 22 with lithium aluminum hydride then yields tryptamine 23.

EXAMPLES

Example 101 (1R,3R)-1-(2,6-difluoro-4-((1-(3-fluoropropyl)azetidin-3-yl)oxy)phenyl)-2-(2-fluoro-2-methylpropyl)-3-methyl-2,3,4,9-tetrahydro-1H-pyrido[3,4-b]indole 101

Step 1: 3-(3,5-Difluoro-4-formyl-phenoxy)-azetidine-1-carboxylic acid tert-butyl ester 101c

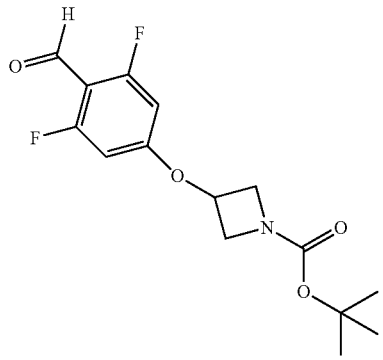

101c

To a solution of 2,6-difluoro-4-hydroxy-benzaldehyde 101a (CAS No.: 532967-21-8, 600 mg, 3.79 mmol) in N,N-dimethyl formamide (25 mL) under argon were added cesium carbonate (3.09 g, 9.48 mmol) and 1-Boc-3-iodo-azetidine 101b (CAS No.: 254454-54-1, 2.68 g, 9.48 mmol). The resulting mixture was heated at 150° C. under microwave heating for 1 h. The reaction mixture was allowed to cool to ambient temperature, the solid removed by filtration, the filter cake was washed with toluene and the filtrate was concentrated in vacuo. The residue was partitioned between EtOAc and water, the organic phase was separated, washed with brine, dried over Na₂SO₄, filtered and concentrated in vacuo. The crude product was adsorbed onto HMN diatomaceous earth (Isolute®, Biotage) and purified by silica gel chromatography (mobile phase: cyclohexane/ethyl acetate, gradient 0% to 30%) to afford 101c as a yellow oil (1.10 g, 93%). ¹H NMR (300 MHz, CDCl₃): δ 10.20 (s, 1H), 6.35 (m, 2H), 4.94-4.86 (m, 1H), 4.34 (ddd, J=1.1, 6.4, 9.8 Hz, 2H), 4.05-3.98 (m, 2H), 1.45 (s, 9H).

Step 2: (2-fluoro-2-methyl-propyl)-[(R)-2-(1H-indol-3-yl)-1-methyl-ethyl]-amine 101d Compound 101d was prepared according to WO 2014/191726, page 78

Step 3: 3-{3,5-difluoro-4-[(1R,3R)-2-(2-fluoro-2-methyl-propyl)-3-methyl-2,3,4,9-tetrahydro-1H-beta-carbolin-1-yl]-phenoxy}-azetidine-1-carboxylic Acid tert-butyl ester 101e

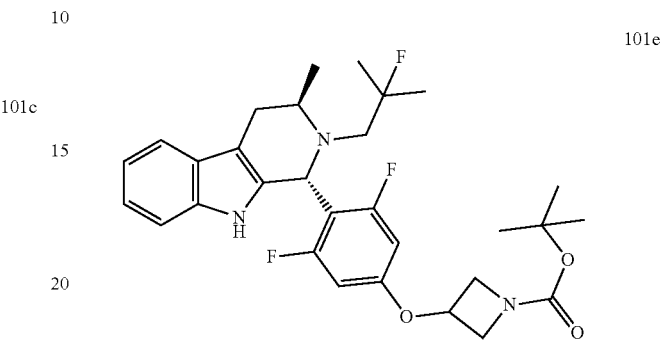

101e

To a solution of (2-fluoro-2-methyl-propyl)-[(R)-2-(1H-indol-3-yl)-1-methyl-ethyl]-amine 101d, prepared according to WO 2014/191726, page 78 (540 mg, 2.17 mmol) in toluene (8 mL) under argon were added 3-(3,5-difluoro-4-formyl-phenoxy)-azetidine-1-carboxylic acid tert-butyl ester 101c (818 mg, 2.61 mmol) and acetic acid (249 μL, 4.34 mmol). The mixture was heated at 80° C. in a sealed tube for 4 h protected from light. The reaction mixture was allowed to cool to room temperature (RT) and concentrated in vacuo. The residue was partitioned between ethyl acetate (EtOAc) and saturated sodium hydrogen carbonate solution. The organic phase was separated, washed with brine, dried over Na₂SO₄, filtered and concentrated in vacuo. The crude product was adsorbed onto HMN diatomaceous earth and purified by silica gel chromatography (mobile phase: cyclohexane/ethyl acetate, gradient 0% to 20%) to afford 101e as an off-white solid (1.10 g, 90%). ¹H NMR (300 MHz, CDCl₃): δ 7.54-7.49 (m, 1H), 7.39 (s, 1H), 7.25-7.19 (m, 1H), 7.15-7.05 (m, 2H), 6.28-6.21 (m, 2H), 5.20 (s, 1H), 4.84-4.76 (m, 1H), 4.33-4.24 (m, 2H), 4.02-3.94 (m, 2H), 3.69-3.61 (m, 1H), 3.12-3.02 (m, 1H), 2.84 (dd, J=15.1, 20.0 Hz, 1H), 2.65-2.56 (m, 1H), 2.38 (dd, J=14.9, 24.7 Hz, 1H), 1.45 (s, 9H), 1.28-1.08 (m, 9H); LCMS: 544.5 [M+H]⁺.

Step 4: (1R,3R)-1-[4-(Azetidin-3-yloxy)-2,6-difluoro-phenyl]-2-(2-fluoro-2-methyl-propyl)-3-methyl-2,3,4,9-tetrahydro-1H-beta-carboline 101f

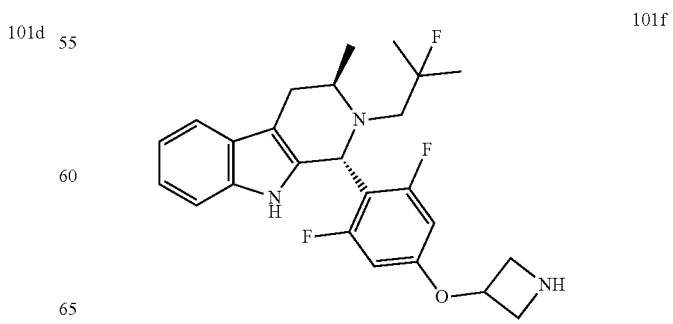

101d

101f

To a mixture of 3-{3,5-difluoro-4-[(1R,3R)-2-(2-fluoro-2-methyl-propyl)-3-methyl-2,3,4,9-tetrahydro-1H-beta-carbolin-1-yl]-phenoxy}-azetidine-1-carboxylic acid tert-butyl ester 101e (840 mg, 1.54 mmol) in dichloromethane (10 mL) under argon was added TFA (1.75 mL, 23.1 mmol) dropwise and the mixture was stirred, protected from light, at RT for 3 h. The reaction mixture was concentrated in vacuo and purified using an SCX-2 cartridge (mobile phase: dichloromethane/methanol 1:1 then 2N ammonia in methanol). Appropriate fractions were combined and evaporated to afford 101f as an off-white solid (54 mg, 8%). $^1$H NMR (300 MHz, CDCl$_3$): δ 7.54-7.49 (m, 1H), 7.41 (s, 1H), 7.25-7.20 (m, 1H), 7.13-7.07 (m, 2H), 6.30-6.22 (m, 2H), 5.19 (s, 1H), 4.96-4.90 (m, 1H), 3.97-3.91 (m, 2H), 3.83-3.78 (m, 2H), 3.71-3.60 (m, 1H), 3.12-3.03 (m, 1H), 2.85 (dd, J=15.1, 19.6 Hz, 1H), 2.64-2.55 (m, 1H), 2.38 (dd, J=15.1, 25.2 Hz, 1H), 1.82 (br. s, 1H), 1.27-1.07 (m, 9H); LCMS: 442.5 [M−H]$^-$.

Step 5: To a mixture of (7R,3R)-1-[4-(azetidin-3-yloxy)-2,6-difluoro-phenyl]-2-(2-fluoro-2-methyl-propyl)-3-methyl-2,3,4,9-tetrahydro-1H-beta-carboline 101f (54 mg, 0.12 mmol) in N,N-dimethylformamide (2 mL) under argon were added 1-bromo-3-fluoropropane (16 μL, 0.16 mmol; CAS No. 352-91-0) and ethyldiisopropylamine (12 μL, 0.24 mmol). The reaction mixture was stirred at RT for 48 h protected from light. The reaction mixture was poured into a mixture of ethyl acetate and water. The organic layer was separated, washed with water and brine, dried over Na$_2$SO$_4$, filtered, and the filtrate concentrated under reduced pressure. The crude product was purified by silica gel chromatography (mobile phase: dichloromethane/methanol, gradient 0% to 5%) and then using a C18 cartridge (acetonitrile, water, formic acid). Appropriate fractions were combined and evaporated to give 101 as a yellow solid (27 mg, 8%). $^1$H NMR (400 MHz, CDCl$_3$): δ 11.12 (br s., 1H), 8.27 (s, 1.3H, formic acid), 7.53-7.47 (m, 2H), 7.24-7.20 (m, 1H), 7.13-7.08 (m, 2H), 6.31-6.25 (m, 2H), 5.20 (s, 1H), 4.96-4.89 (m, 1H), 4.56 (dd, J=5.6, 5.6 Hz, 1H), 4.44 (dd, J=5.6, 5.6 Hz, 1H), 4.33-4.24 (m, 2H), 3.64 (dd, J=4.8, 11.1 Hz, 1H), 3.49-3.47 (m, 1H), 3.07-2.97 (m, 3H), 2.84 (dd, J=15.0, 20.3 Hz, 1H), 2.64-2.58 (m, 1H), 2.38 (dd, J=15.0, 24.5 Hz, 1H), 1.99-1.83 (m, 2H), 1.27-1.08 (m, 9H); LCMS: 504.3 [M+H]$^+$.

Example 102 (1R,3R)-1-(2,6-difluoro-4-(2-(3-(fluoromethyl)azetidin-1-yl)ethoxy)phenyl)-2-(2-fluoro-2-methylpropyl)-3-methyl-2,3,4,9-tetrahydro-1H-pyrido[3,4-b]indole 102

Step 1: (1R,3R)-1-(2,6-Difluoro-4-iodo-phenyl)-2-(2-fluoro-2-methyl-propyl)-3-methyl-2,3,4,9-tetrahydro-1H-beta-carboline 102b To a solution of (2-fluoro-2-methyl-propyl)-[(R)-2-(1H-indol-3-yl)-1-methyl-ethyl]-amine 101d, prepared according to WO 2014/191726, page 78, (50 mg, 0.20 mmol) in toluene (170 μL) under argon was added 2,6-difluoro-4-iodo-benzaldehyde 102a (CAS No.: 1160573-10-3, 65 mg, 0.24 mmol) followed by acetic acid (23 μL, 0.40 mmol). The resulting mixture was stirred at 80° C. in a sealed tube for 5 h then allowed to cool to RT. The mixture was purified on an SCX-2 cartridge (mobile phase: dichloromethane/methanol 9:1 then 2 N ammonia in methanol). Appropriate fractions were combined, evaporated and the crude product was purified by silica gel chromatography (mobile phase: cyclohexane/ethyl acetate, gradient 0% to 30%) to afford 102b as a yellow solid (89 mg, 89%). $^1$H NMR (400 MHz, CDCl$_3$): δ 7.54-7.50 (m, 1H), 7.39 (s, 1H), 7.25-7.21 (m, 3H), 7.16-7.08 (m, 2H), 5.26 (s, 1H), 3.67-3.60 (m, 1H), 3.06 (ddd, J=1.5, 4.9, 15.2 Hz, 1H), 2.86 (dd, J=15.2, 21.5 Hz, 1H), 2.61 (ddd, J=1.5, 4.4, 15.2 Hz, 1H), 2.39 (dd, J=15.2, 24.0 Hz, 1H), 1.29-1.15 (m, 6H), 1.10 (d, J=6.4 Hz, 3H); LCMS: 497.0 [M−H]$^-$.

Step 2: A mixture of (1R,3R)-1-(2,6-Difluoro-4-iodophenyl)-2-(2-fluoro-2-methyl-propyl)-3-methyl-2,3,4,9-tetrahydro-1H-beta-carboline 102b (82 mg, 0.16 mmol), 2-(3-fluoromethyl-azetidin-1-yl)-ethanol 102c, prepared according to WO 2013/090836, page 124 (44 mg, 0.33 mmol; CAS No.: 1443984-69-7, WO 2013/090836), copper iodide (6.2 mg, 0.03 mmol), and potassium carbonate (68 mg, 0.49 mmol) in butyronitrile (600 μL) was degassed with three vacuum/argon cycles. The reaction mixture was heated at 135° C. for 24 h, allowed to cool to room temperature and diluted with ethyl acetate. The solid was removed from the reaction mixture by filtration through Celite and the solid was washed with ethyl acetate. The combined filtrate was washed with water (three times) and brine, dried over Na$_2$SO$_4$, filtered, and concentrated under reduced pressure. The crude product was purified by silica gel chromatography (mobile phase: 0-7% methanol/dichloromethane). Appropriate fractions were collected and evaporated to give 102 as a yellow solid (17.2 mg, 21%). $^1$H NMR (400 MHz, DMSO-d$_6$): δ 10.51 (s, 1H), 7.39 (d, J=73 Hz, 1H), 7.18 (d, J=7.8 Hz, 1H), 7.01-6.91 (m, 2H), 6.64 (d, J=11.2 Hz, 2H), 5.11 (s, 1H), 4.56 (d, J=5.9 Hz, 1H), 4.44 (d, J=5.4 Hz, 1H), 3.92 (s, 2H), 3.54-3.47 (m, 2H), 3.06-2.66 (m, 6H), 2.59-2.53 (m, 2H, partially under DMSO-d6), 2.40-2.27 (m, 2H), 1.25-1.09 (m, 6H), 1.04 (d, J=6.4 Hz, 3H); LCMS: 502.3 [M−H]$^-$.

Example 103 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-methylpropan-1-one 103

Step 1: (1R,3R)-1-(2,6-difluoro-4-iodophenyl)-3-methyl-2,3,4,9-tetrahydro-1H-pyrido[3,4-b]indole 103b

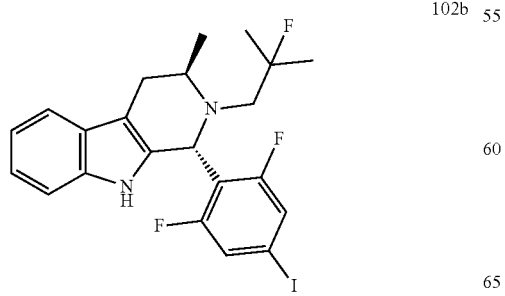

102b

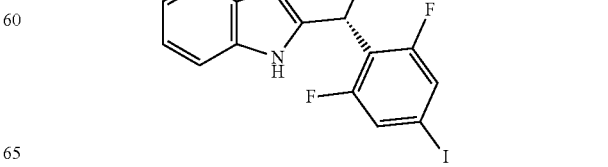

103b

To a microwave vial was added (2R)-1-(1H-indol-3-yl) propan-2-amine 103a (710 mg, 3.67 mmol), followed by 2,6-difluoro-4-iodo-benzaldehyde (1.1 g, 4.03 mmol) and acetonitrile (2.6 mL). The reaction was placed under a nitrogen atmosphere and TFA (0.5 mL, 7.0 mmol) was added. Then the reaction was heated to 130° C. in a microwave for 1 h and then quenched with a saturated aq. NaHCO$_3$ solution. The mixture was extracted DCM (3×100 mL), dried with MgSO$_4$, filtered and concentrated. The crude product was purified by flash column chromatography over silica gel (0-100% EtOAc/Hexanes) to yield 103b (450 mg, 29%). $^1$H NMR (400 MHz, deuterochloroform-d): δ 7.60-7.48 (m, 2H), 7.27 (d, J=7.3 Hz, 2H), 7.17-7.08 (m, 2H), 5.63 (s, 1H), 3.45 (dq, J=12.7, 6.2 Hz, 1H), 2.99 (ddd, J=15.5, 4.6, 1.3 Hz, 1H), 2.52 (ddd, J=15.5, 7.3, 1.8 Hz, 1H), 1.29 (d, J=6.5 Hz, 3H).

Step 2: 1-((1R,3R)-1-(2,6-difluoro-4-iodophenyl)-3-methyl-3,4-dihydro-1H-pyrido[3,4-b]indol-2(9H)-yl)-2-methylpropan-1-one 103c

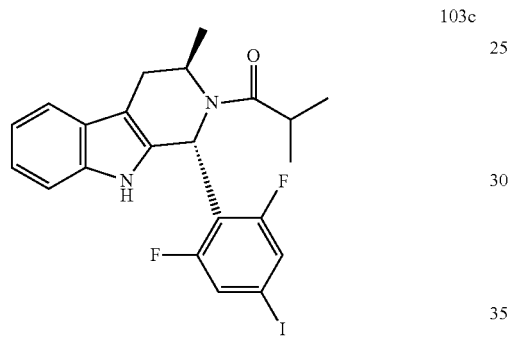

103c

To a round-bottom flask (RBF) was added (1R,3R)-1-(2,6-difluoro-4-iodo-phenyl)-3-methyl-2,3,4,9-tetrahydro-1H-pyrido[3,4-b]indole 103b (50 mg, 0.12 mmol), followed by sodium bicarbonate (50 mg, 0.59 mmol), and chloroform (0.8 mL). 2-Methylpropanoyl chloride (31 mg, 0.2947 mmol) was added and the reaction was heated to 45° C. for 1 h (hour). Diisopropylethylamine (Hunig's base, 0.1 mL, 0.59 mmol) was added and the reaction was stirred until LC-MS indicated that the starting materials were consumed. Aqueous saturated solution (10 mL) of sodium bicarbonate was added. The reaction mixture is then extracted with DCM (3×50 mL), dried over MgSO$_4$, filtered and concentrated. Crude product was purified by flash column chromatography on silica gel (0-100% EtOAc/Hexanes) to give 103c (51 mg, 88%). $^1$H NMR (400 MHz, DMSO-d$_6$): δ 10.74 (s, 1H), 7.46 (d, J=7.8 Hz, 1H), 7.39 (d, J=9.2 Hz, 2H), 7.24 (dt, J=8.0, 1.0 Hz, 1H), 7.01 (dddd, J=26.4, 8.0, 7.0, 1.2 Hz, 2H), 6.10 (s, 1H), 4.88-4.71 (m, 1H), 3.17 (dd, J=14.9, 5.6 Hz, 1H), 3.03 (p, J=6.6 Hz, 1H), 2.84 (d, J=15.2 Hz, 1H), 1.12 (d, J=6.5 Hz, 2H), 1.06-0.92 (m, 6H).

Step 3: To a 5 mL microwave vial was added 1-[(1R,3R)-1-(2,6-difluoro-4-iodo-phenyl)-3-methyl-1,3,4,9-tetrahydropyrido[3,4-b]indol-2-yl]-2-methyl-propan-1-one 103c (51 mg, 0.10 mmol), followed by 2-[3-(fluoromethyl)azetidin-1-yl]ethanol 102c, prepared according to WO 2013/090836, page 124 (27 mg, 0.21 mmol), copper iodide (8 mg, 0.04 mmol), potassium carbonate (43 mg, 0.31 mmol). The vial was sealed and butyronitrile (0.7 mL) was added. The reaction was then heated to 135° C. overnight and then cooled to room temperature. The reaction mixture was then filtered through Celite, eluting with EtOAc. The combined filtrate was then concentrated and purified by reverse phase HPLC to yield 103 (16 mg, 31%). $^1$H NMR (400 MHz, DMSO-d$_6$): δ 10.48 (s, 1H), 7.51-7.39 (m, 1H), 7.32-7.22 (m, 1H), 7.09-6.90 (m, 2H), 6.51 (d, J=11.0 Hz, 2H), 6.11 (s, 1H), 4.89-4.71 (m, 1H), 4.55 (d, J=6.1 Hz, 1H), 4.43 (d, J=6.0 Hz, 1H), 3.94 (q, J=5.4 Hz, 2H), 3.59-3.38 (m, 2H), 3.24-3.18 (m, 2H), 3.04-2.97 (m, 2H), 2.87-2.74 (m, 4H), 1.12 (d, J=6.4 Hz, 3H), 0.98 (dd, J=10.3, 6.7 Hz, 6H); LCMS: 500.3 [M+H]$^+$ Example 104 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-fluoro-2-methylpropan-1-one 104

Step 1: 1-((1R,3R)-1-(2,6-difluoro-4-iodophenyl)-3-methyl-3,4-dihydro-1H-pyrido[3,4-b]indol-2(9H)-yl)-2-fluoro-2-methylpropan-1-one 104a

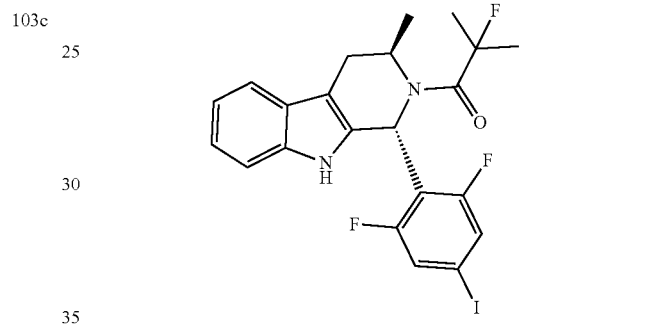

104a

To a round bottom flask was added (1R,3R)-1-(2,6-difluoro-4-iodo-phenyl)-3-methyl-2,3,4,9-tetrahydro-1H-pyrido[3,4-b]indole 103b (100 mg, 0.24 mmol), followed by 2-fluoro-2-methyl-propanoyl chloride (0.59 mL of a 1 M solution in CHCl$_3$, prepared from the reaction of the corresponding acid with oxalyl chloride), sodium bicarbonate (99 mg, 1.2 mmol) and chloroform (1.6 mL). Then the reaction was then heated to 45° C. for 1 h and then Hunig's base (0.2 mL, 1.2 mmol) was added. The reaction was stirred until monitoring the reaction by LC-MS indicated that all starting materials were consumed. The reaction was quenched with a saturated aqueous solution of sodium bicarbonate. The mixture was then extracted with DCM (3×50 mL), dried with MgSO$_4$, filtered and concentrated. The resulting crude product was purified by silica gel column chromatography (0-100% EtOAC/Hexanes) to give 104a (95 mg, 79%). $^1$H NMR (400 MHz, DMSO-d$_6$): δ 7.54-7.31 (m, 3H), 7.28-7.21 (m, 1H), 7.04 (ddd, J=8.1, 7.1, 1.3 Hz, 1H), 6.98 (td, J=7.5, 7.0, 1.1 Hz, 1H), 6.08 (s, 1H), 5.14 (s, 1H), 3.14 (dd, J=15.4, 4.6 Hz, 1H), 2.81 (d, J=15.2 Hz, 1H), 1.51 (dd, J=35.4, 21.8 Hz, 6H), 1.17 (dt, J=3.1 Hz, 3H); LCMS: 513.0 [M+H]$^+$.

Step 2: To a 5 mL microwave vial was added 1-[(1R,3R)-1-(2,6-difluoro-4-iodo-phenyl)-3-methyl-1,3,4,9-tetrahydropyrido[3,4-b]indol-2-yl]-2-fluoro-2-methyl-propan-1-one 104a (29 mg, 0.056 mmol), followed by 2-[3-(fluoromethyl)azetidin-1-yl]ethanol (15 mg, 0.11 mmol), copper iodide (4 mg., 0.023 mmol), potassium carbonate (24 mg, 0.17 mmol), and butyronitrile (0.37 mL). The solution was degassed for 5 min and then heated to 135° C. overnight. When monitoring the reaction by LC-MS indicated that all starting materials were consumed, the crude mixture was cooled to room temperature, filtered through Celite®. The Celite plug was further washed with EtOAc, and combined filtrate was concentrated and purified by reverse phase HPLC to give 104 (9 mg, 31%). $^1$H NMR (400 MHz, DMSO-d$_6$, 350K): δ 10.69 (s, 1H), 7.54-7.38 (m, 1H), 7.31-7.17 (m, 1H), 7.00 (dtd, J=24.8, 7.1, 1.2 Hz, 2H), 6.55 (d, J=12.0 Hz, 1H), 6.03 (s, 1H), 5.21-5.05 (m, 1H), 4.54 (d, J=6.2 Hz, 1H), 4.42 (d, J=6.2 Hz, 1H), 3.87 (t, J=5.4 Hz, 2H), 3.30-3.25 (m, 2H), 3.15 (dd, J=15.3, 4.7 Hz, 1H), 2.96 (t, J=6.5 Hz, 2H), 2.79 (d, J=15.1 Hz, 1H), 2.75-2.62 (m, 3H), 1.55 (d, J=21.8 Hz, 2H), 1.45 (d, J=21.8 Hz, 2H), 1.15 (d, J=6.4 Hz, 2H); LCMS: 518.2 [M+H]$^+$.

Example 105 (1R,3R)-1-(4-(2-(3-(difluoromethyl) azetidin-1-yl)ethoxy)-2,6-difluorophenyl)-2-(2-fluoro-2-methylpropyl)-3-methyl-2,3,4,9-tetrahydro-1H-pyrido[3,4-b]indole 105

Step 1: 2-(3,5-difluoro-4-formylphenoxy)ethyl acetate 105a

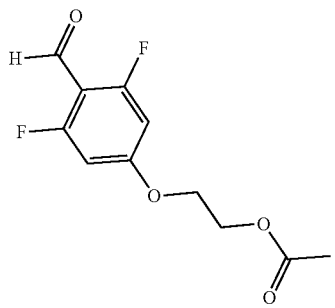

A solution of 2,6-difluoro-4-hydroxy-benzaldehyde (CAS No.: 532967-21-8, 300 mg, 1.89 mmol) and 2-bromo-ethylacetate (CAS No.: 927-68-4, 0.22 mL, 2 mmol) in acetonitrile (5 mL) and N,N-dimethylformamide (1 mL) was heated at 80° C. for 24 h. A further portion of 2-bromo-ethylacetate (0.11 mL, 1 mmol) was added, and heating continued at 80° C. for additional 30 h. The reaction mixture was allowed to cool to ambient temperature. The residue was partitioned between EtOAc and a saturated solution of sodium bicarbonate. The aqueous layer was extracted with further portions of EtOAc. The combined organic layer was separated, dried over MgSO$_4$, filtered and concentrated in vacuo. The crude product was purified by silica gel column chromatography (mobile phase: cyclohexane/ethyl acetate, gradient 0% to 33%) to afford 105a as a white powder (213 mg, 45%). $^1$H NMR (300 MHz, CDCl$_3$): δ 10.20 (s, 1H), 6.51 (d, J=10.4 Hz, 2H), 4.44 (t, J=4.7 Hz, 2H), 4.22 (t, J=4.7 Hz, 2H), 2.11 (s, 3H).

Step 2: 2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl acetate 105b

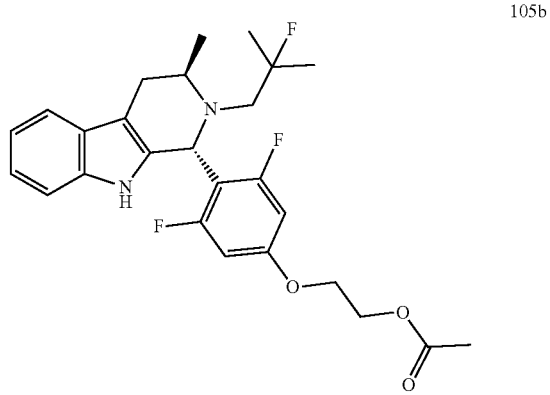 [SMILES: CC(=O)OCCOc1cc(F)c([C@@H]2c3[nH]c4ccccc4c3C[C@@H](C)N2CC(C)(C)F)c(F)c1]

To a solution of (2-fluoro-2-methyl-propyl)-[(R)-2-(1H-indol-3-yl)-1-methyl-ethyl]-amine 101d (213 mg, 0.86 mmol) and 2-(3,5-difluoro-4-formylphenoxy)ethyl acetate 105a (210 mg, 0.86 mmol) in toluene (1 mL) under argon, was added glacial acetic acid (0.1 mL, 1.72 mmol). The vessel was sealed, and the reaction mixture was heated at 80° C. for 16 h. The reaction mixture was allowed to cool to ambient temperature. The residue was partitioned between dichloromethane and a saturated solution of sodium bicarbonate. The aqueous layer was extracted with further portions of dichloromethane. The combined organic layer was separated, dried over MgSO$_4$, filtered and concentrated in vacuo. The crude product was purified by silica gel chromatography (mobile phase: cyclohexane/ethyl acetate, gradient 0% to 20%) to afford 105b as a white foam (323 mg, 80%). $^1$H NMR (300 MHz, CDCl$_3$): δ 7.54-7.49 (m, 1H), 7.38 (s, 1H), 7.24-7.19 (m, 1H), 7.14-7.07 (m, 2H), 6.42 (dd, J=13, 3 Hz, 2H), 5.19 (s, 1H), 4.40 (t, J=4.7 Hz, 2H), 4.12 (t, J=4.7 Hz, 2H), 3.70-3.62 (m, 1H), 3.13-3.04 (m, 1H), 2.92-2.79 (dd, J=19, 15 Hz, 1H), 2.65-2.55 (m, 1H), 2.46-2.31 (dd, J=25.0, 15.0 Hz, 1H), 2.10 (s, 3H), 1.24 (d, J=11.0 Hz, 3H), 1.17 (d, J=11.3 Hz, 3H), 1.1 (d, J=6.5 Hz, 3H).

Step 3: 2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethanol 105c

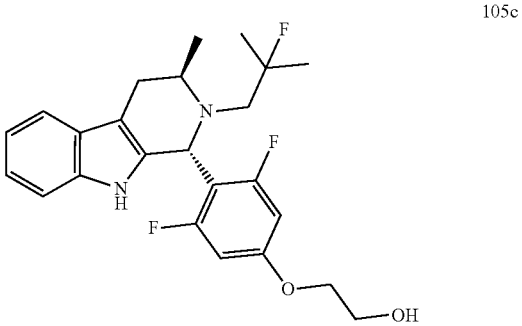 [SMILES: C[C@@H]1Cc2c([nH]c3ccccc23)[C@@H](c2c(F)cc(OCCO)cc2F)N1CC(C)(C)F]

To a solution of 2-(3,5-difluoro-4-((1R,3R)-2-(2-fluoro-2-methylpropyl)-3-methyl-2,3,4,9-tetrahydro-1H-pyrido[3, 4-b]indol-1-yl)phenoxy)ethyl acetate 105b (320 mg, 0.675 mmol) in THF/MeOH (2/1, 6 mL) was added sodium hydroxide (1 N, 4 mL). The reaction mixture was heated at 70° C. for 45 min. The reaction mixture was allowed to cool to ambient temperature, and the solvent was removed in vacuo. The residue was partitioned between dichloromethane and water. The organic layer was separated, dried over MgSO$_4$, filtered and concentrated in vacuo, to afford 105c as a white foam (264 mg, 91%). LCMS: 431.2 [M−H]⁻.

Step 4: (1R,3R)-1-(4-(2-bromoethoxy)-2,6-difluorophenyl)-2-(2-fluoro-2-methylpropyl)-3-methyl-2,3,4,9-tetrahydro-1H-pyrido[3,4-b]indole 105d

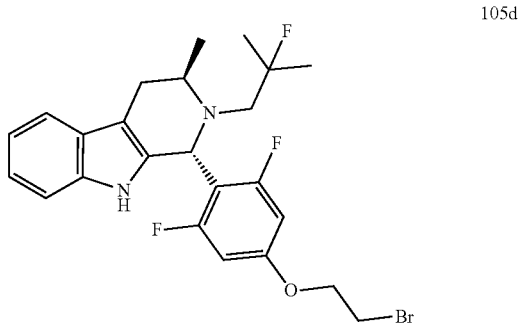 [SMILES: C[C@@H]1Cc2c([nH]c3ccccc23)[C@@H](c2c(F)cc(OCCBr)cc2F)N1CC(C)(C)F]

To a solution of 2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethanol 105c (130 mg, 0.3 mmol) in DCM (2.5 mL) were added triphenylphosphine (94 mg, 0.36 mmol) and carbon tetrabromide (120 mg, 0.36 mmol). The reaction mixture was stirred at room temperature for 1 h, then the solvent was removed in vacuo. The crude product was purified by silica gel column chromatography (mobile phase: cyclohexane/ethyl acetate, gradient 0% to 20%) to afford 105d as a white foam (142 mg, 95%). ¹H NMR (300 MHz, CDCl$_3$): δ 7.54-7.49 (m, 1H), 7.38 (s, 1H), 7.25-7.19 (m, 1H), 7.15-7.07 (m, 2H), 6.42 (dd, J=13.0, 3.0 Hz, 2H), 5.20 (s, 1H), 4.24 (t, J=4.7 Hz, 2H), 3.72-3.59 (m, 3H), 3.12-3.03 (m, 1H), 2.92-2.79 (dd, J=19.4, 15.0 Hz, 1H), 2.64-2.56 (m, 1H), 2.46-2.31 (dd, J=25.0, 15.0 Hz, 1H), 1.24 (d, J=12.1 Hz, 3H), 1.17 (d, J=12 Hz, 3H), 1.10 (d, J=6.5 Hz, 3H).

Step 5: To a solution of (1R,3R)-1-(4-(2-bromoethoxy)-2,6-difluorophenyl)-2-(2-fluoro-2-methylpropyl)-3-methyl-2,3,4,9-tetrahydro-1H-pyrido[3,4-b]indole 105d (62 mg, 0.125 mmol) in acetonitrile (1 mL) were added N,N-diisopropylethylamine (0.064 mL, 0.375 mmol) and 3-(difluoromethyl)azetidine hydrochloride (CAS 1354792-76-9, 27 mg, 0.187 mmol). The reaction mixture was stirred at room temperature for 1 h, then at 45° C. for 4 h. The reaction mixture was allowed to cool to ambient temperature. The residue was partitioned between EtOAc and water. The aqueous layer was extracted with further portions of EtOAc. The combined organic layers were separated, dried over MgSO$_4$, filtered and concentrated in vacuo. The crude product was purified by silica gel column chromatography (mobile phase: dichloromethane/methanol, gradient 0% to 2.5%) to afford 105 as an off-white solid (40 mg, 62%). ¹H NMR (300 MHz, CDCl$_3$): δ 7.54-7.49 (m, 1H), 7.24-7.19 (m, 1H), 7.14-7.06 (m, 2H), 6.38 (dd, J=13.3, 3 Hz, 2H), 6.17-5.76 (dt, J=56.0, 5.1 Hz, 1H), 5.18 (s, 1H), 3.90 (t, J=5.3 Hz, 2H), 3.71-3.63 (m, 1H), 3.46 (t, J=7.8 Hz, 2H), 3.27 (t, J=6.7 Hz, 2H), 3.13-3.04 (m, 1H), 2.92-2.79 (m, 3H), 2.64-2.55 (m, 1H), 2.45-2.30 (dd, J=25.6, 14.9 Hz, 1H), 1.23 (d, J=10.3 Hz, 3H), 1.16 (d, J=12 Hz, 3H), 1.09 (d, J=6.5 Hz, 3H); LCMS: 520.4 [M−H]⁻.

Compounds 106-125 were prepared by the procedures described herein and characterized by LCMS [M+H]⁺:

| | |
|---|---|
| 106 | 520.1 |
| 107 | 486.4 |
| 108 | 532.4 |
| 109 | 518.2 |
| 110 | |
| 111 | 469.2 |
| 112 | 487.3 |
| 113 | 498.3 |
| 114 | 514.3 |
| 115 | 500.3 |
| 116 | 486.3 |
| 117 | 486.1 |
| 118 | 500.2 |
| 119 | 500.2 |
| 120 | 484.2 |
| 121 | 472.2 |
| 122 | 516.2 |
| 123 | 502.3 |
| 124 | 528.3 |
| 125 | 514.3 |

Example 126 (1R,3R)-1-(2,6-difluoro-4-(2-(3-(fluoromethyl)azetidin-1-yl)ethoxy)phenyl)-3-methyl-2-(methylsulfonyl)-2,3,4,9-tetrahydro-1H-pyrido[3,4-b]indole 126

Step 1: (1R,3R)-1-(2,6-difluoro-4-iodophenyl)-3-methyl-2-(methylsulfonyl)-2,3,4,9-tetrahydro-1H-pyrido[3,4-b]indole

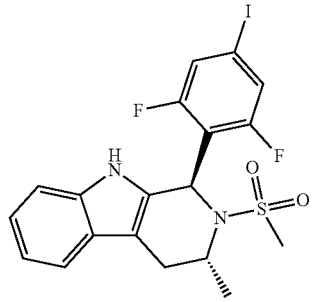 [SMILES: C[C@@H]1Cc2c([nH]c3ccccc23)[C@@H](c2c(F)cc(I)cc2F)N1S(C)(=O)=O]

To a 50-mL round-bottom-flask was added (1R,3R)-1-(2,6-difluoro-4-iodo-phenyl)-3-methyl-2,3,4,9-tetrahydro-1H-pyrido[3,4-b]indole (50 mg, 0.12 mmol) and chloroform (0.15 M, 0.8 mL). Then N,N-diisopropylethylamine (0.06 mL, 0.35 mmol) and methanesulfonyl chloride (0.014 mL, 0.18 mmol) were added sequentially. The reaction was then heated to 45° C. and monitored until LCMS indicated complete consumption of the starting materials. The reaction was cooled to room temperature, quenched with the addition of saturated aq. NH$_4$Cl, extracted with DCM (3×50 mL), dried over MgSO$_4$, filtered and concentrated. The crude product was purified by flash column chromatography over silica gel, eluting with 0-50% iPrOAc/Heptanes to yield the title compound (40 mg, 68% yield). ¹H NMR (400 MHz, DMSO-d$_6$) δ 10.78 (s, 1H), 7.54 (d, J=7.9 Hz, 2H), 7.44 (d, J=7.8 Hz, 1H), 7.22 (d, J=8.1 Hz, 1H), 7.05 (ddd, J=8.2, 7.1, 1.2 Hz, 1H), 7.02-6.95 (m, 1H), 6.18 (s, 1H), 4.43 (q, J=5.6, 5.0 Hz, 1H), 3.09-2.99 (m, 1H), 2.83 (s, 4H), 1.31 (d, J=6.6 Hz, 3H). LCMS: 503.0 [M+H]⁺.

Step 2: To a 5 mL vial was added (1R,3R)-1-(2,6-difluoro-4-iodo-phenyl)-3-methyl-2-methylsulfonyl-1,3,4,9-tetrahydropyrido[3,4-b]indole (40 mg, 0.08 mmol), 2-[3-(fluoromethyl)azetidin-1-yl]ethanol (21 mg, 0.16 mmol), cuprous iodide (6 mg, 0.032 mmol), potassium carbonate (33 mg, 0.24 mmol) and butyronitrile (0.5 mL). The solution was degassed for 5 min and then heated to 135° C. overnight. Once monitoring the reaction by LCMS indicated reaction was complete, the reaction mixture was filtered through Celite, eluting with EtOAc. The filtrate was concentrated and purified by reverse phase HPLC to yield 126 (6 mg, 15% yield). ¹H NMR (400 MHz, DMSO-d₆) δ 10.74 (s, 1H), 7.43 (d, J=7.7 Hz, 1H), 7.24-7.20 (m, 1H), 7.04 (ddd, J=8.2, 7.0, 1.4 Hz, 1H), 6.97 (td, J=7.4, 1.1 Hz, 1H), 6.73-6.64 (m, 2H), 6.15 (s, 1H), 4.55 (d, J=6.2 Hz, 1H), 4.45-4.35 (m, 2H), 3.93 (t, J=5.4 Hz, 2H), 3.30-3.28 (m, 2H), 3.03-2.95 (m, 3H), 2.77 (s, 3H), 2.74-2.65 (m, 4H), 1.33 (dd, J=6.8, 2.1 Hz, 3H). LCMS: 508.2 [M+H]⁺.

Example 145 N-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1-(3-fluoropropyl)azetidin-3-amine 145

Step 1: (1R,3R)-1-(4-Bromo-2,6-difluorophenyl)-2-(2-fluoro-2-methylpropyl)-3-methyl-2,3,4,9-tetrahydro-1H-pyrido[3,4-&]indole

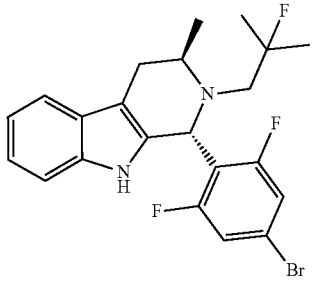 [SMILES: C[C@@H]1Cc2c([nH]c3ccccc23)[C@@H](c2c(F)cc(Br)cc2F)N1CC(C)(C)F]

To a solution of (R)—N-(1-(1H-indol-3-yl)propan-2-yl)-2-fluoro-2-methylpropan-1-amine (500 mg, 2.01 mmol) in toluene (6 mL) was added 4-bromo-2,6-difluorobenzaldehyde (490 mg, 2.21 mmol) and acetic acid (0.58 mL, 10.2 mmol). The reaction mixture was stirred at 80° C. for 16 hours. After being cooled to room temperature, the solution was concentrated and the residue was diluted with EtOAc (40 mL), washed with saturated aqueous NaHCO₃ (10 mL) and water (20 mL). The organic layer was dried over anhydrous Na₂SO₄ and concentrated. The residue was purified by chromatography on silica (solvent gradient: 0-6% EtOAc in petroleum ether) to afford the title compound (800 mg, 88%) as a light yellow solid. ¹H NMR (400 MHz, CDCl₃) δ 7.53 (d, J=7.2 Hz, 1H), 7.41 (s, 1H), 7.24 (d, J=7.2 Hz, 1H), 7.16-7.09 (m, 2H), 7.06 (d, J=8.0 Hz, 2H), 5.27 (s, 1H), 3.73-3.54 (m, 1H), 3.09-3.05 (m, 1H), 2.95-2.76 (m, 1H), 2.64-2.60 (m, 1H), 2.47-2.33 (m, 1H), 1.30-1.17 (m, 6H), 1.11 (d, J=6.4 Hz, 3H).

Step 2: t-Butyl 3-((3,5-difluoro-4-((1R,3R)-2-(2-fluoro-2-methylpropyl)-3-methyl-2,3,4,9-tetrahydro-1H-pyrido[3,4-b]indol-1-yl)phenyl)amino)azetidine-1-carboxylate

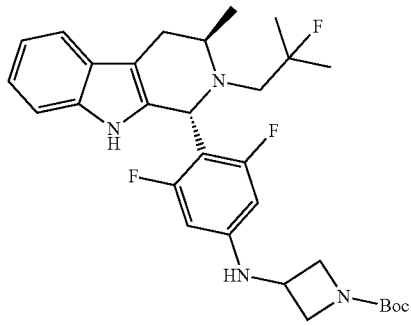 [SMILES: C[C@@H]1Cc2c([nH]c3ccccc23)[C@@H](c2c(F)cc(NC3CN(C(=O)OC(C)(C)C)C3)cc2F)N1CC(C)(C)F]

A mixture of (1R,3R)-1-(4-bromo-2,6-difluorophenyl)-2-(2-fluoro-2-methylpropyl)-3-methyl-2,3,4,9-tetrahydro-1H-pyrido[3,4-b]indole (From Step 1, 800.0 mg, 1.77 mmol), BINAP (110.4 mg, 0.18 mmol), Pd₂(dba)₃ (162.3 mg, 0.18 mmol), t-BuONa (511.0 mg, 5.32 mmol) and t-butyl 3-aminoazetidine-1-carboxylate (457.9 mg, 2.66 mmol) in toluene (10 mL) was stirred at 110° C. under N₂ atmosphere for 16 hours. The reaction mixture was concentrated and was purified with silica gel column (0-5% methanol in DCM) to afford the title compound (900 mg, 94%) as a brown solid. ¹H NMR (400 MHz, CDCl₃) δ 7.51 (d, J=6.4 Hz, 1H), 7.43 (s, 1H), 7.22 (d, J=8.0 Hz, 1H), 7.13-7.05 (m, 2H), 5.97 (d, J=11.2 Hz, 2H), 5.14 (s, 1H), 4.37-4.21 (m, 3H), 4.20-4.01 (m, 1H), 3.78-3.60 (m, 3H), 3.12-3.07 (m, 1H), 2.96-2.77 (m, 1H), 2.63-2.57 (m, 1H), 2.48-2.33 (m, 1H), 1.45 (s, 9H), 1.25-1.17 (m, 6H), 1.10 (d, J=6.0 Hz, 3H)

Step 3: N-(3,5-Difluoro-4-((1R,3R)-2-(2-fluoro-2-methylpropyl)-3-methyl-2,3,4,9-tetrahydro-1H-pyrido[3,4-b]indol-1-yl)phenyl)azetidin-3-amine

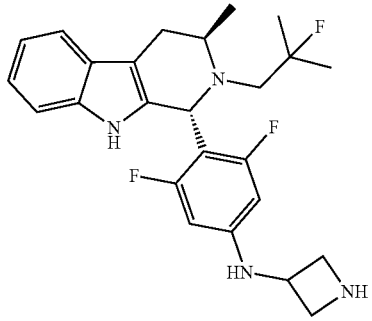 [SMILES: C[C@@H]1Cc2c([nH]c3ccccc23)[C@@H](c2c(F)cc(NC3CNC3)cc2F)N1CC(C)(C)F]

To a mixture of t-butyl 3-((3,5-difluoro-4-((1R,3R)-2-(2-fluoro-2-methylpropyl)-3-methyl-2,3,4,9-tetrahydro-1H-pyrido[3,4-b]indol-1-yl)phenyl)amino)azetidine-1-carboxylate (From Step 2, 0.9 g, 1.66 mmol) in DCM (5 mL) was added TFA (1.8 mL, 24.88 mmol) at −20° C. The resulting mixture was stirred at 0° C. for 16 hours. Aqueous NaHCO₃ solution (80 mL) was added slowly to the reaction mixture and the reaction mixture was then extracted with DCM (100 mL×2). The combined organic layers were dried over anhydrous Na₂SO₄, filtered and concentrated to give the title compound (700 mg, 95%) as a brown solid. The crude product was used for the next step without further purification.

Step 4: To a mixture of N-(3,5-difluoro-4-((1R,3R)-2-(2-fluoro-2-methylpropyl)-3-methyl-2,3,4,9-tetrahydro-1H-pyrido[3,4-A]indol-1-yl)phenyl)azetidin-3-amine (From Step 3, 700.0 mg, 1.58 mmol) and N,N-diisopropylethylamine (613.3 mg, 4.75 mmol) in N,N-dimethylformamide (10 mL) was added 1-bromo-3-fluoropropane (223.0 mg, 1.58 mmol) and the reaction mixture was stirred at 10° C. for 16 hours. The reaction mixture was purified by column (0-10% MeOH in DCM) and further purified by reverse phase chromatography (acetonitrile 66-96%/0.05% NH$_4$OH in water) to afford 145 (280 mg, 35%) as a white solid. $^1$H NMR (400 MHz, CD$_3$OD) δ 7.38 (d, J=7.6 Hz, 1H), 7.17 (d, J=7.6 Hz, 1H), 7.03-6.88 (m, 2H), 6.07 (d, J=11.6 Hz, 2H), 5.10 (s, 1H), 4.54-4.36 (m, 2H), 4.03-4.01 (m, 1H), 3.79-3.71 (m, 2H), 3.69-3.65 (m, 1H), 3.04-3.00 (m, 1H), 2.97-2.91 (m, 2H), 2.87-2.85 (m, 1H), 2.62 (t, J=7.6 Hz, 2H), 2.58-2.55 (m, 1H), 2.48-2.32 (m, 1H), 1.83-1.67 (m, 2H), 1.20-1.11 (m, 6H), 1.08 (d, J=6.8 Hz, 3H).

Example 154 (S)-3-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-fluoro-2-methylpropan-1-ol 154

Step 1: dimethyl 2-fluoro-2-methylmalonate

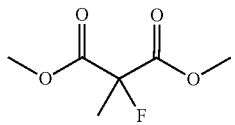

To a 500-mL oven-dried round-bottom flask was added sodium hydride (1.15 equiv., 21 mmol). The reaction reaction was placed under a nitrogen atmosphere and cooled to 0° C. Then THF (63 mL) was added. To this mixture was added dimethyl 2-methylpropanedioate (5.0 g, 34.2 mmol) dropwise and the reaction mixture was stirred for 30 min. Then n-fluorobenzenesulfonimide (1.05 equiv., 19.2 mmol) was added in one portion. The reaction mixture was allowed to warm to room temperature and the reaction mixture solidified, so additional 50 mL of THF was added. After 1.5 h the reaction was quenched with aq. 2 N HCl, diluted with EtOAc (500 mL) and was washed with 3×200 mL 2 N HCl. The organics were separated, dried with MgSO$_4$, filtered, and concentrated. The crude white solid was then taken up in 200 mL heptane, sonicated and filtered through Celite. The filtered solids where then washed with 3×200 mL heptane. The combined filtrate was then concentrated to yield crude desired product (3 g, 53% yield) as a yellow oil. $^1$H NMR (400 MHz, DMSO-d$_6$) δ 3.32 (s, 6H), 1.18 (d, J=6.3 Hz, 3H).

Step 2: 2-fluoro-2-methylpropane-1,3-diol

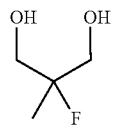

To a 500-mL oven-dried round-bottom flask was added dimethyl 2-fluoro-2-methylpropanedioate (3 g, 18.3 mmol) and THF (90 mL). The reaction mixture was placed under N$_2$ atmosphere and then cooled to 0° C. Then lithium aluminum hydride solution (1 M in THF, 2.75 equiv., 50.3 mmol) was added dropwise and the reaction was warmed to room temperature over 1 h. The reaction was then cooled to 0° C. again and quenched with addition of water (2 mL), followed by 15% NaOH aq. sol. (2 mL) and water (4 mL). The slurry was stirred for 15 min, filtered and concentrated to deliver the crude product (1.4 g, 71% yield). $^1$H NMR (400 MHz, DMSO-d$_6$) δ 4.85 (t, J=5.9 Hz, 2H), 3.45 (d, J=5.9 Hz, 2H), 3.41 (d, J=5.9 Hz, 2H), 1.22-1.15 (d, 3H).

Step 3: 3-(tert-butyldiphenylsilyloxy)-2-fluoro-2-methylpropan-1-ol

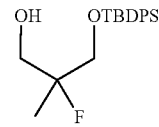

To a 500-mL oven-dried round-bottom flask was added 2-fluoro-2-methyl-propane-1,3-diol (1.47 g, 1.25 equiv., 13.6 mmol), followed by imidazole (1.11 g, 1.5 equiv., 16.4 mmol), tert-butylchlorodiphenylsilane (3.0 g, 10.9 mmol) and chloroform (136 mL). The reaction was stirred overnight and quenched with addition of sat. NH$_4$Cl solution (100 mL). The mixture was extracted with DCM (100 mL), dried with MgSO$_4$, filtered and concentrated. The crude mixture was purified by flash silica gel column chromatography (0-100% iPrOAc/Heptanes) to furnish the desired product (1.26 g, 33% yield). $^1$H NMR (400 MHz, DMSO-d$_6$) δ 7.68-7.60 (m, 4H), 7.51-7.40 (m, 6H), 4.97 (t, J=5.8 Hz, 1H), 3.70 (dd, J=19.4, 1.9 Hz, 2H), 3.52 (ddd, J=18.5, 5.8, 1.8 Hz, 2H), 1.28 (d, J=21.8 Hz, 3H), 1.01 (s, 9H).

Step 4: 3-(tert-butyldiphenylsilyloxy)-2-fluoro-2-methylpropyl trifluoromethanesulfonate

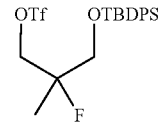

To a 500-mL oven-dried round-bottom flask was added 3-[tert-butyl(diphenyl)silyl]oxy-2-fluoro-2-methyl-propan-1-ol (1.3 g, 3.8 mmol), dichloromethane (63 mL) under a nitrogen atmosphere. The reaction mixture was then cooled to 0° C. and trifluoromethanesulfonic anhydride (1.27 g, 1.2 equiv., 4.5 mmol) was added dropwise. The reaction mixture was then stirred for 2 h and then washed with 2 N HCl and then sat. NaHCO$_3$ solution. The organics were separated, then dried with MgSO$_4$, and filtered through a silica gel plug eluting with DCM. Then the filtrate was concentrated to dryness to yield the crude desired product (1.8 g, 100% yield) and used in the next step without further purification. $^1$H NMR (400 MHz, DMSO-d$_6$) δ 7.66-7.58 (m, 4H), 7.56-7.41 (m, 6H), 5.07-4.81 (m, 2H), 3.88-3.68 (m, 2H), 1.40 (d, J=21.6 Hz, 3H), 1.01 (s, 9H).

Step 5: N—((R)-1-(1H-indol-3-yl)propan-2-yl)-3-(tert-butyldiphenylsilyloxy)-2-fluoro-2-methyl propan-1-amine

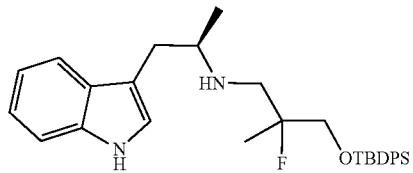

To a 250-mL oven-dried round-bottom flask was added (2R)-1-(1H-indol-3-yl)propan-2-amine (600 mg, 3.1 mmol), N,N-diisopropylethylamine (0.81 mL, 1.5 equiv., 4.65 mmol) and 1,4-dioxane (6 mL) and the reaction mixture was placed under a nitrogen atmosphere. Then [3-[tert-butyl(diphenyl)silyl]oxy-2-fluoro-2-methyl-propyl]trifluoromethanesulfonate (1.95 g, 1.25 equiv., 3.9 mmol) was added and the reaction mixture was heated to 90° C. When LC-MS indicated the consumption of the starting material, the reaction mixture was quenched with sat aq NaHCO₃ and the mixture was extracted with EtOAc (3×200 mL) The combined organics were dried with MgSO₄, filtered and concentrated. Purification by flash silica gel column chromatography (0-100% EtOAc/Hexanes) delivered the title compound (1.2 g, 77% yield). LCMS: 503.3 [M+H]⁺.

Step 6: 3-((R)-1-(1H-indol-3-yl)propan-2-ylamino)-2-fluoro-2-methylpropan-1-ol

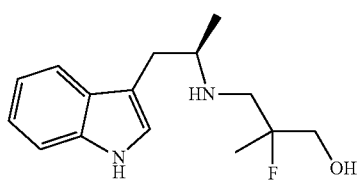 [SMILES: C[C@H](Cc1c[nH]c2ccccc12)NCC(C)(F)CO]

3-[tert-butyl(diphenyl)silyl]oxy-2-fluoro-N-[(1R)-2-(1H-indol-3-yl)-1-methyl-ethyl]-2-methyl-propan-1-amine (1.2 g, 2.4 mmol) was added to 250-mL oven-dried round-bottom flask and then THF (9.6 mL) and tetrabutylammonium fluoride hydrate (3 mL of a 1 M solution in THF) was added. The reaction mixture was allowed to stir at room temperature until LC-MS indicated complete consumption of the starting materials. The reaction mixture was quenched with the addition of water and extracted with 25% IPA in DCM 5×100 mL. The combined organics were then dried with MgSO₄, filtered, and concentrated. Purification by flash column chromatography over silica gel (0-30% 2 N NH₃ in MeOH/DCM) provides the title compound (332 mg, 53% yield). LCMS: 265.1 [M+H]⁺.

Step 7: 3-((1R,3R)-1-(2,6-difluoro-4-iodophenyl)-3-methyl-3,4-dihydro-1H-pyrido[3,4-b]indol-2(9H)-yl)-2-fluoro-2-methylpropan-1-ol

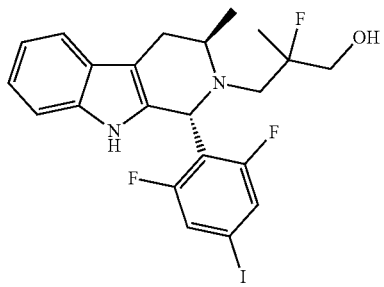 [SMILES: C[C@@H]1Cc2c([nH]c3ccccc23)[C@@H](c2c(F)cc(I)cc2F)N1CC(C)(F)CO]

To a 100-mL round-bottom flask was added 2-fluoro-3-[[(1R)-2-(1H-indol-3-yl)-1-methyl-ethyl]amino]-2-methyl-propan-1-ol (332 mg, 1.26 mmol), 2,6-difluoro-4-iodo-benzaldehyde (370 mg, 1.1 equiv., 1.38 mmol), and toluene (5.5 mL). The reaction was placed under a nitrogen atmosphere and acetic acid (2 M) was added. Then the reaction was allowed to heat to 90° C. for 48 h. The reaction was then quenched with sat. aq. solution of NaHCO₃ and vigorously extracted with iPrOAc (5×100 ml). The organics where then dried with MgSO₄, filtered and concentrated. Purification by flash column chromatography over silica gel (0-100% iPrOAc/heptanes) delivered the title compound (475 mg, 74% yield). LCMS: 515.1 [M+H]⁺.

Step 8: To a 20-mL microwave vial was added 3-[(1R,3R)-1-(2,6-difluoro-4-iodo-phenyl)-3-methyl-1,3,4,9-tetrahydropyrido[3,4-b]indol-2-yl]-2-fluoro-2-methyl-propan-1-ol (400 mg, 0.78 mmol), 2-[3-(fluoromethyl)azetidin-1-yl]ethanol (518 mg, 5 equiv., 3.9 mmol), cuprous iodide (74 mg, 0.5 equiv., 0.39 mmol) and potassium carbonate (644 mg, 6 equiv., 4.7 mmol). The vial was capped and the mixture was placed under an atmosphere of nitrogen. Then butyronitrile (5.2 mL) was added and the mixture was degassed for 10 min. Then reaction mixture was then heated to 135° C. for 16 h, filtered through Celite and purified via chiral reverse phase HPLC to yield two diastereomers. 154 was the second eluting diastereomer (90 mg, 22% yield). 154: ¹H NMR (400 MHz, DMSO-d₆) δ 10.48 (s, 1H), 7.39 (dd, J=7.4, 1.3 Hz, 1H), 7.17 (dd, J=7.6, 1.2 Hz, 1H), 6.96 (dtd, J=20.1, 7.2, 1.3 Hz, 2H), 6.72-6.55 (m, 2H), 5.08 (s, 1H), 4.84 (t, J=5.6 Hz, 1H), 4.56 (d, J=6.2 Hz, 1H), 4.44 (d, J=6.2 Hz, 1H), 3.92 (t, J=5.4 Hz, 2H), 3.55 (q, J=6.0, 5.4 Hz, 1H), 3.03-2.83 (m, 4H), 2.72 (dt, J=13.0, 5.6 Hz, 3H), 2.61-2.51 (m, 2H), 2.45-2.30 (m, 1H), 1.15-0.96 (m, 6H). 2 Protons obscured under the water peak. Chiral SFC: column OX UPC2, isocratic 25% MeOH with 0.1% NH₄OH for 2.5 min. Retention time 1.35 min. LCMS: 520.3 [M+H]⁺.

Example 155 (2R)-3-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2-fluoro-2-methyl-propan-1-ol 155

Following the procedures of Example 154, 155 was the first eluting diastereomer (110 mg, 27% yield). 155. ¹H NMR (400 MHz, DMSO-d₆): δ 10.52 (s, 1H), 7.42-7.34 (m, 1H), 7.21-7.14 (m, 1H), 6.96 (dtd, J=20.9, 7.1, 1.2 Hz, 2H), 6.69-6.58 (m, 2H), 5.12 (s, 1H), 4.81 (t, J=5.8 Hz, 1H), 4.56 (d, J=6.2 Hz, 1H), 4.44 (d, J=6.2 Hz, 1H), 3.93 (t, J=5.4 Hz, 2H), 3.46 (ddd, J=18.2, 11.9, 5.7 Hz, 2H), 3.14 (ddd, J=20.4, 11.9, 5.9 Hz, 2H), 3.03-2.78 (m, 4H), 2.78-2.64 (m, 3H), 2.58-2.51 (m, 2H), 2.47-2.36 (m, 1H), 1.11 (d, J=22.0 Hz, 3H), 1.04 (d, J=6.5 Hz, 3H). 2 Protons obscured under the water peak. Chiral SFC: column OX UPC2, isocratic 25% MeOH with 0.1% NH$_4$OH for 2.5 min. Retention time 0.55 min. LCMS: 520.2 [M+H]$^+$.

Example 174 (1R,3R)-1-[2,6-difluoro-4-[2-[3-(fluoromethyl)azetidin-1-yl]ethoxy]phenyl]-3-methyl-2-(2,2,2-trifluoroethyl)-1,3,4,9-tetrahydropyrido[3,4-b]indole 174

Step 1: (R)-1-(1H-indol-3-yl)-N-(2,2,2-trifluoroethyl)propan-2-amine

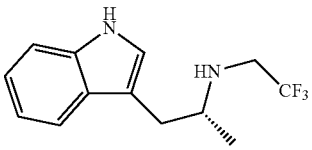 [SMILES: C[C@H](Cc1c[nH]c2ccccc12)NCC(F)(F)F]

The mixture of (2R)-1-(1H-indol-3-yl)propan-2-amine (100 mg, 0.574 mmol), 2,2,2-trifluoroethyl trifluoromethanesulfonate (151 mg, 0.6313 mmol), and N,N-diisopropylethylamine (371 mg, 2.87 mmol) in 1,4-dioxane (3.8261 mL) was heated at 50° C. for 6 h. The reaction mixture was cooled to room temperature, diluted with water, and extracted with EtOAc (2×). The combined organics were dried (Na$_2$SO$_4$), filtered and concentrated. The crude product was purified by silica flash chromatography (0-50% iPrOAc/heptane) to give the title compound (89 mg, 60.5% yield) as colorless oil. $^1$H NMR (Chloroform-d) δ: 8.10-7.92 (m, 1H), 7.62-7.56 (m, 1H), 7.33 (dt, J=8.1, 0.9 Hz, 1H), 7.23-7.16 (m, 1H), 7.15-7.08 (m, 1H), 7.02-6.98 (m, 1H), 3.21-3.09 (m, 3H), 2.83 (dd, J=6.6, 0.8 Hz, 2H), 1.12 (d, J=6.2 Hz, 3H). LCMS (ESI) m/z 257 [M+H]$^+$.

Step 2: (1R,3R)-1-(2,6-difluoro-4-iodophenyl)-3-methyl-2-(2,2,2-trifluoroethyl)-2,3,4,9-tetrahydro-1H-pyrido[3,4-b]indole

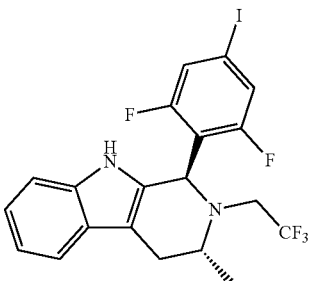

The mixture of (2R)-1-(1H-indol-3-yl)-N-(2,2,2-trifluoroethyl)propan-2-amine (54 mg, 0.211 mmol), 2,6-difluoro-4-iodo-benzaldehyde (62 mg, 0.232 mmol) and acetic acid (110 mg, 1.84 mmol) in toluene (1 mL) was heated at 90° C. for 5 h. The mixture was then concentrated. The residue was partitioned between EtOAc and sat. NaHCO$_3$. The aqueous layer was extracted with EtOAc (2×). The combined organics were dried (Na$_2$SO$_4$), filtered and concentrated to give the title compound as a white solid which was used without purification. LCMS (ESI) m/z 507 [M+H]$^+$.

Step 3: The mixture of (1R,3R)-1-(2,6-difluoro-4-iodophenyl)-3-methyl-2-(2,2,2-trifluoroethyl)-1,3,4,9-tetrahydropyrido[3,4-b]indole (107 mg, 0.211 mmol), 2-[3-(fluoromethyl)azetidin-1-yl]ethanol (84 mg, 0.632 mmol), CuI (16 mg, 0.0843 mmol) and K$_2$CO$_3$ (87 mg, 0.632 mmol) in butyronitrile (1.4 mL) in a microwave vial was purged with N$_2$ for 5 min, and then sealed and heated at 135° C. for 23 h. The mix was filtered through celite, concentrated and purified by prep HPLC to give 174 (51 mg, 47% yield) as a yellow solid. $^1$H NMR (400 MHz, DMSO-d$_6$) δ 10.61 (s, 1H), 7.45-7.35 (m, 1H), 7.20 (dt, J=8.0, 0.9 Hz, 1H), 7.05-6.90 (m, 2H), 6.71-6.59 (m, 2H), 5.20 (s, 1H), 4.50 (dd, J=47.6, 6.2 Hz, 2H), 3.94 (t, J=5.4 Hz, 2H), 3.57-3.35 (m, 2H), 3.31-3.22 (m, 2H), 2.97 (dt, J=16.8, 7.9 Hz, 3H), 2.84 (ddd, J=15.3, 4.9, 1.2 Hz, 1H), 2.77-2.66 (m, 3H), 2.64-2.56 (m, 1H), 1.12 (d, J=6.6 Hz, 3H). LCMS (ESI) m/z 512 [M+H]$^+$.

Example 286 3-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2,2-difluoro-propan-1-ol 286

Step 1: 3-((tert-Butyldiphenylsilyl)oxy)-2,2-difluoropropan-1-ol

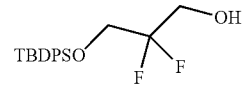

To a stirred solution of 2,2-difluoropropane-1,3-diol (200 mg, 1.78 mmol) in THF (4 mL) was added NaH (60% in mineral oil, 71 mg, 1.78 mmol) on an ice bath and the reaction mixture was stirred for 30 minutes. TBDPSCl (490 mg, 1.78 mmol) was added to the reaction mixture drop wise. Then the reaction mixture was warmed up to 20° C. and the stirring continued for 3 hours. Water (10 mL) was slowly added to the reaction mixture and the resulting mixture was washed with EtOAc (10 mL*2). The combined organic layers were dried over anhydrous Na$_2$SO$_4$, filtered and concentrated. The crude residue was purified by silica gel column chromatography (20% petroleum ether in EtOAc) to afford the title compound (450 mg, 1.28 mmol, 72% yield) as a light yellow oil. $^1$H NMR (400 MHz, CDCl$_3$) δ 7.71-7.64 (m, 4H), 7.44-7.36 (m, 6H), 3.96-3.84 (m, 4H), 1.86 (s, 1H), 1.06 (s, 9H).

Step 2: 3-((tert-Butyl diphenyl si 1 yl)oxy)-2,2-difluoropropyl trifluoromethanesulfonate

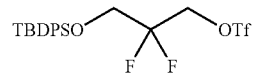

To a stirred solution of 3-[tert-butyl(diphenyl)silyl]oxy-2,2-difluoro-propan-1-ol (From Step 1, 400 mg, 1.14 mmol) and 2,6-lutidine (0.39 mL, 3.42 mmol) in DCM (8 mL) was added Tf$_2$O (0.38 mL, 2.28 mmol) dropwise on an ice bath. The reaction mixture was stirred at 20° C. for 2 hours. The reaction mixture was then poured into ice-water (20 mL)

Step 3: (R)—N-(1-(1H-Indol-3-yl)propan-2-yl)-3-((tert-butyldiphenylsilyl)oxy)-2,2-difluoropropan-1-amine

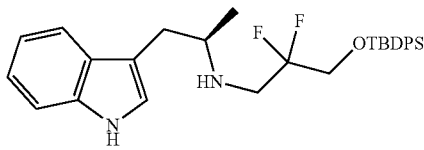

A mixture of [3-[tert-butyl(diphenyl)silyl]oxy-2,2-difluoro-propyl]trifluoromethanesulfonate (From Step 2, 8.31 g, 17.22 mmol), DIPEA (6.1 mL, 34.44 mmol) and (2R)-1-(1H-indol-3-yl)propan-2-amine (3 g, 17.22 mmol) in dioxane (60 mL) was stirred at 90° C. for 12 hours. After being cooled to room temperature, the reaction mixture was diluted with water (100 mL) and was washed with EtOAc (100 mL×2). The combined organic layers were dried over anhydrous Na₂SO₄, filtered and concentrated. The crude residue was purified by silica gel column chromatography (20% EtOAc in petroleum ether) to afford the title compound (7.6 g, 87%) as a yellow oil. LCMS: 507.2 [M+H]⁺.

Step 4: (R)-3-((1-(1H-Indol-3-yl)propan-2-yl)amino)-2,2-difluoropropan-1-ol

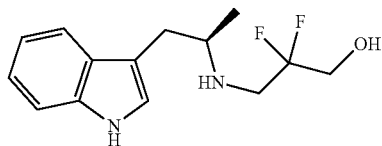 [SMILES: C[C@H](Cc1c[nH]c2ccccc12)NCC(F)(F)CO]

To a stirred solution of (R)—N-(1-(1H-indol-3-yl)propan-2-yl)-3-((tert-butyldiphenylsilyl)oxy)-2,2-difluoropropan-1-amine (From Step 3, 7.6 g, 15 mmol) in THF (100 mL) was added TBAF (1.0 M in THF, 30 mL, 30 mmol). The reaction mixture was stirred at 25° C. for 4 hours and was then diluted with water (200 mL) and was extracted with EtOAc (200 mL×3). The combined organic layers were dried over anhydrous Na₂SO₄, filtered and concentrated. The crude residue was purified by silica gel column chromatography (70% EtOAc in petroleum ether) to afford the title compound (3.5 g, 87%) as a light yellow oil. LCMS: 268.9 [M+H]⁺.

Step 5: 3-((1R,3R)-1-(2,6-Difluoro-4-iodophenyl)-3-methyl-3,4-dihydro-1H-pyrido[3,4-b]indol-2(9H)-yl)-2,2-difluoropropan-1-ol

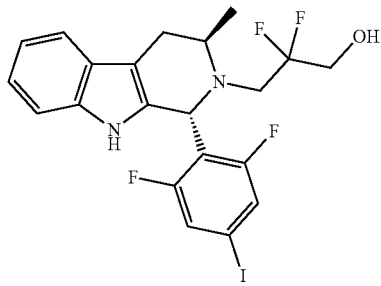 [SMILES: C[C@@H]1Cc2c([nH]c3ccccc23)[C@@H](c2c(F)cc(I)cc2F)N1CC(F)(F)CO]

A mixture of (R)-3-((1-(1H-indol-3-yl)propan-2-yl)amino)-2,2-difluoropropan-1-ol (From Step 4, 2 g, 7.45 mmol), HOAc (1.29 mL, 22.36 mmol) and 2,6-difluoro-4-iodo-benzaldehyde (2 g, 7.45 mmol) in toluene (30 mL) was stirred at 90° C. for 12 hours. After being cooled to room temperature, the reaction mixture was diluted with water (50 mL), washed with EtOAc (50 mL×2). The combined organic layers were dried over anhydrous Na₂SO₄, filtered and concentrated. The crude residue was purified by silica gel column chromatography (20% petroleum ether in EtOAc) to afford the title compound (2.8 g, 73%) as a light yellow solid. ¹H NMR (400 MHz, CDCl₃) δ 7.53-7.49 (m, 2H), 7.30-7.22 (m, 3H), 7.18-7.13 (m, 2H), 5.25 (s, 1H), 3.72-3.68 (m, 3H), 3.24-3.06 (m, 3H), 2.85-2.75 (m, 1H), 2.70-2.66 (m, 1H), 1.18 (d, J=6.8 Hz, 3H).

Step 6: A mixture of 3-((1R,3R)-1-(2,6-difluoro-4-iodophenyl)-3-methyl-3,4-dihydro-1H-pyrido[3,4-b]indol-2 (9H)-yl)-2,2-difluoropropan-1-ol (From Step 5, 1.5 g, 2.89 mmol), 2-[3-(fluoromethyl)azetidin-1-yl]ethanol (1.93 g, 14.47 mmol), CuI (1.65 g, 8.68 mmol) and K₂CO₃ (1.2 g, 8.68 mmol) in n-PrCN (20 mL) was stirred under N₂ atmosphere at 135° C. for 3 hours. After being cooled to room temperature, the reaction mixture was diluted with water (50 mL), washed with DCM (50 mL×2). The combined organic layers were dried over anhydrous Na₂SO₄, filtered and concentrated. The resulting residue was purified by reverse phase chromatography (acetonitrile 50-80%/0.05% NH₄OH in water) to afford 286 (170 mg, 11%) as a white solid. ¹H NMR (400 MHz, CD₃OD) δ 7.41 (d, J=8.0 Hz, 1H), 7.19 (d, J=8.0 Hz, 1H), 7.03-6.94 (m, 2H), 6.54 (d, J=11.2 Hz, 2H), 5.24 (s, 1H), 4.49 (dd, J=47.6, 6.0 Hz, 2H), 4.00-3.98 (m, 2H), 3.83-3.72 (m, 1H), 3.63-3.45 (m, 4H), 3.22-3.13 (m, 3H), 3.02-2.60 (m, 6H), 1.17 (d, J=6.0 Hz, 3H). LCMS: 524.1 [M+H]⁺.

Example 303 (1R,3R)-2-(2,2-difluoroethyl)-1-[2,6-difluoro-4-[1-(3-fluoropropyl)azetidin-3-yl]oxyphenyl]-3-methyl-1,3,4,9-tetrahydropyrido[3,4-b]indole 303

Following the procedures of Example 305, 303 was prepared. LCMS: 494.2 [M+H]⁺.

Example 304 N-(3,5-difluoro-4-((1R,3R)-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine 304

Step 1: (R)-1-(1H-Indol-3-yl)-N-(2,2,2-trifluoroethyl)propan-2-amine

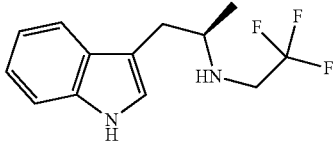 [SMILES: C[C@H](Cc1c[nH]c2ccccc12)NCC(F)(F)F]

To a solution of (2R)-1-(1H-indol-3-yl)propan-2-amine (10.0 g, 57.39 mmol) in 1,4-dioxane (100 mL) was added 2,2,2-trifluoroethyl trifluoromethanesulfonate (13.3 g, 57.39 mmol) and DIPEA (22.2 g, 172.18 mmol). The resulting mixture was stirred at 80° C. for 15 hours. The reaction mixture was concentrated and purified by column chromatography eluted with 0-30% EtOAc in hexanes to give the title compound (14 g, 95.2%) as a light yellow oil. NMR (400 MHz, CDCl$_3$) δ 8.02 (br. s., 1H), 7.60 (d, J=8.0 Hz, 1H), 7.37 (d, J=8.0 Hz, 1H), 7.21 (t, J=8.0 Hz, 1H), 7.16-7.09 (m, 1H), 7.05 (s, 1H), 3.24-3.11 (m, 3H), 2.84 (d, J=6.4 Hz, 2H), 1.14 (d, J=6.4 Hz, 3H).

Step 2: (1R,3R)-1-(4-Bromo-2,6-difluorophenyl)-3-methyl-2-(2,2,2-trifluoroethyl)-2,3,4,9-tetrahydro-1H-pyrido[3,4-b]indole

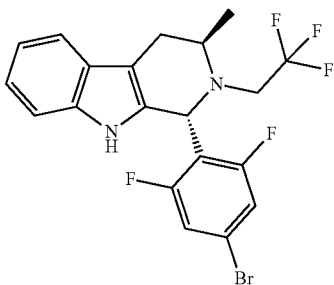 [SMILES: C[C@@H]1Cc2c([nH]c3ccccc23)[C@@H](c2c(F)cc(Br)cc2F)N1CC(F)(F)F]

A mixture of (2R)-1-(1H-Indol-3-yl)-N-(2,2,2-trifluoroethyl)propan-2-amine (From step 1, 14.0 g, 54.63 mmol), 4-bromo-2,6-difluorobenzaldehyde (11.5 g, 51.9 mmol) and acetic acid (6.25 mL, 109.26 mmol) in toluene (150 mL) was stirred at 90° C. for 16 hours. The reaction mixture was cooled to 25° C., concentrated and purified by silica gel column chromatography (0-5% EtOAc in petroleum ether) to afford the title compound and its cis-isomer (24 g, 95.7% yield) (trans:cis=4:1) as a yellow solid. $^1$H NMR (400 MHz, CDCl$_3$) δ 7.52 (d, J=8.4 Hz, 1H), 7.24 (d, J=8.0 Hz, 1H), 7.19-7.05 (m, 4H), 5.69 (s, 0.2H), 5.31 (s, 0.8H), 3.64-3.50 (m, 1H), 3.45-3.17 (m, 1H), 3.10-3.06 (m, 1H), 2.98-2.81 (m, 1H), 2.78-2.59 (m, 1H), 1.41 (d, J=6.4 Hz, 0.6H), 1.18 (d, J=6.4 Hz, 2.4H).

Step 3: tert-Butyl 3-((3,5-difluoro-4-((1R,3R)-3-methyl-2-(2,2,2-trifluoroethyl)-2,3,4,9-tetrahydro-1H-pyrido[3,4-b]indol-1-yl)phenyl)amino)azetidine-1-carboxylate

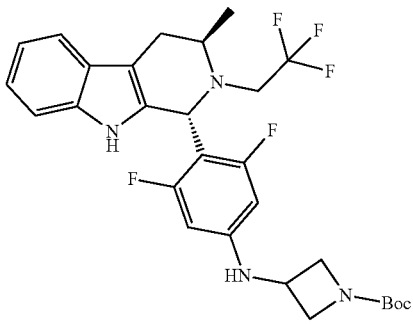 [SMILES: C[C@@H]1Cc2c([nH]c3ccccc23)[C@@H](c2c(F)cc(NC3CN(C(=O)OC(C)(C)C)C3)cc2F)N1CC(F)(F)F]

A mixture of (1R,3R)-1-(4-bromo-2,6-difluorophenyl)-3-methyl-2-(2,2,2-trifluoroethyl)-2,3,4,9-tetrahydro-1H-pyrido[3,4-b]indole (trans:cis=4:1) (From step 2, 23.0 g, 50.08 mmol), Pd$_2$(dba)$_3$ (4.59 g, 5.01 mmol), tert-butyl 3-aminoazetidine-1-carboxylate (12.9 g, 75.12 mmol), Xantphos (5.8 g, 10.02 mmol) and Cs$_2$CO$_3$ (48.9 g, 150.25 mmol) in 1,4-dioxane (250 mL) was stirred at 115° C. under N$_2$ atmosphere for 16 hours. The reaction mixture was filtered through Celite and the filtrate was concentrated and purified by column chromatography (0-30% EtOAc in petroleum ether) to afford the title compound (25 g, 90.7% yield) (trans:cis=4:1) as a light brown solid. $^1$H NMR (400 MHz, CDCl$_3$) δ 7.56-7.37 (m, 1H), 7.24-7.19 (m, 1H), 7.15-7.06 (m, 2H), 6.04-5.94 (m, 2H), 5.57 (s, 0.2H), 5.21 (s, 0.8H), 4.50-4.38 (m, 1H), 4.31-4.21 (m, 2H), 3.74-3.72 (m, 2H), 3.61-3.47 (m, 1H), 3.35-3.17 (m, 1H), 3.10-3.07 (m, 1H), 3.02-2.78 (m, 1H), 2.77-2.55 (m, 1H), 1.44 (s, 9H), 1.39 (d, J=6.4 Hz, 0.6H), 1.16 (d, J=6.4 Hz, 2.4H).

Step 4: N-(3,5-Difluoro-4-((1R,3R)-3-methyl-2-(2,2,2-trifluoroethyl)-2,3,4,9-tetrahydro-1H-pyrido[3,4-b]indol-1-yl)phenyl)azetidin-3-amine

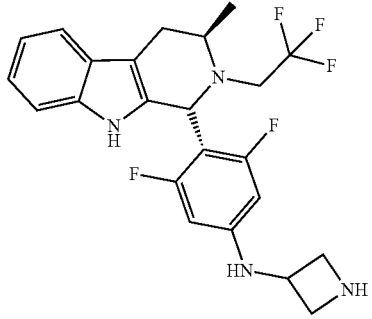

To a solution of tert-butyl 3-((3,5-difluoro-4-((1R,3R)-3-methyl-2-(2,2,2-trifluoroethyl)-2,3,4,9-tetrahydro-1H-pyrido[3,4-b]indol-1-yl)phenyl)amino)azetidine-1-carboxylate (From step 3, 10.0 g, 18.16 mmol) (trans:cis=4:1) in 1,4-dioxane (120 mL) was added sulfuric acid (4.87 mL, 90.82 mmol) at 0° C. The reaction mixture was stirred at 0° C. for 0.5 hours. The reaction mixture was poured into saturated aqueous NaHCO$_3$ (250 mL) and the mixture was extracted with EtOAc (200 mL×2). The combined organic layers were dried over Na₂SO₄ and concentrated to give the title compound (8 g, 97.8% yield) (trans:cis=4:1) as a yellow solid. The crude compound was used for the next step directly.

Step 5: To a mixture of N-(3,5-difluoro-4-((1R,3R)-3-methyl-2-(2,2,2-trifluoroethyl)-2,3,4,9-tetrahydro-1H-pyrido[3,4-b]indol-1-yl)phenyl)azetidin-3-amine (From step 4, trans:cis=4:1, 8.0 g, 17.76 mmol) and DIPEA (8.83 mL, 53.28 mmol) in DMF (80 mL) was added 1-fluoro-3-iodopropane (3.34 g, 17.76 mmol) dropwise. The reaction mixture was stirred at 20° C. for 16 hours. The reaction mixture was diluted with EtOAc (400 mL), washed with brine (200 mL×5). The combined organic layers were dried over Na₂SO₄, filtered, concentrated and purified by column chromatography (10-40% EtOAc in DCM) to afford the desired product (7 g, 77.2% yield) as brown solid. This product was combined with another batch (12.3 g total) and was purified by prep-HPLC (Phenomenex Synergi Max-RP 250*80 mm*10 um acetonitrile 50-80/10 mM NH₄HCO₃ in water) to afford 10 g product (trans:cis=4:1, inseparable on HPLC) as a white solid. This product (trans:cis=4:1) was then further purified by SFC (AD(250 mm*30 mm, 10 μm) base-EtOH 40%) to afford pure 304 (5.9 g, 59% yield) as a white solid. ¹H NMR (400 MHz, CD₃OD) δ 7.40 (d, J=7.6 Hz, 1H), 7.20 (d, J=7.6 Hz, 1H), 7.05-6.91 (m, 2H), 6.09 (d, J=12 Hz, 2H), 5.22 (s, 1H), 4.58-4.35 (m, 2H), 4.07-4.02 (m, 1H), 3.77 (t, J=7.6 Hz, 2H), 3.62-3.50 (m, 1H), 3.39-3.32 (m, 1H), 3.06-2.90 (m, 4H), 2.66-2.55 (m, 3H), 1.87-1.66 (m, 2H), 1.17 (d, J=6.4 Hz, 3H).

Example 305 (1R,3R)-2-(2,2-difluoroethyl)-1-[2,6-difluoro-4-[2-[3-(fluoromethyl)azetidin-1-yl]ethoxy]phenyl]-3-methyl-1,3,4,9-tetrahydropyrido[3,4-b]indole 305

Step 1: (R)—N-(2,2-difluoroethyl)-1-(1H-indol-3-yl)propan-2-amine

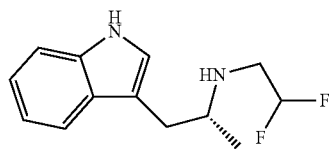 [SMILES: C[C@H](Cc1c[nH]c2ccccc12)NCC(F)F]

A mixture of (2R)-1-(1H-indol-3-yl)propan-2-amine (4.2 g, 24.1 mmol), 2,2-difluoroethyl trifluoromethanesulfonate (5.16 g, 24.1 mmol) and diisopropylamine (8.41 mL, 48.2 mmol) was heated to 80° C. for 3 hours. The reaction was cooled to room temperature, diluted with iPrOAc (150 mL) and was washed with water, brine, dried over sodium sulfate, filtered and concentrated. The crude product was purified by flash column chromatography over silica gel, eluting with 0-5% MeOH/DCM to yield the title compound (5.6 g, 97% yield). ¹H NMR (400 MHz, Chloroform-d) δ 8.03 (s, 1H), 7.63-7.54 (m, 1H), 7.36 (dt, J=8.1, 0.9 Hz, 1H), 7.27-7.17 (m, 1H), 7.12 (ddd, J=8.0, 7.1, 1.1 Hz, 1H), 5.78 (tdd, J=56.6, 4.7, 4.1 Hz, 1H), 3.11-2.76 (m, 5H), 1.12 (d, J=6.2 Hz, 3H); LCMS: 239.15 [M+H]⁺.

Step 2: (1R,3R)-2-(2,2-difluoroethyl)-1-(2,6-difluoro-4-iodo-phenyl)-3-methyl-1,3,4,9-tetrahydropyrido[3,4-b]indole

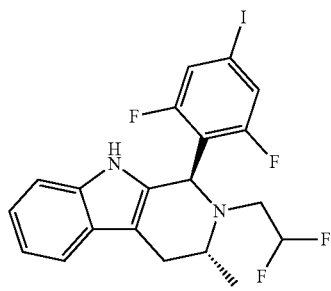 [SMILES: C[C@@H]1Cc2c([nH]c3ccccc23)[C@@H](c2c(F)cc(I)cc2F)N1CC(F)F]

To a solution of (R)—N-(2,2-difluoroethyl)-1-(1H-indol-3-yl)propan-2-amine (5.0 g, 21 mmol) and 2,6-difluoro-4-iodobenzaldehyde (5.2 g, 19 mmol) in toluene (70 ml) was added acetic acid (2.4 mL) and the mixture was heated at 90° C. for 20 h under nitrogen atmosphere. The reaction mixture was cooled and concentrated. The residue was dissolved in iPrOAc and was washed with saturated sodium bicarbonate solution, water, brine, dried over sodium sulfate and concentrated. Purification by flash chromatography (silica gel, 0-15% iPrOAc/heptanes) yielded the title compound (7.8 g, 76%) as a 3:1 mixture of trans:cis isomers. LCMS: 489.0 [M+H]⁺. The mixture was carried on to the next step as is.

Step 3: A mixture of (1R,3R)-2-(2,2-difluoroethyl)-1-(2,6-difluoro-4-iodo-phenyl)-3-methyl-1,3,4,9-tetrahydropyrido[3,4-b]indole (8.0 g, 16.4 mmol), 2-[3-(fluoromethyl)azetidin-1-yl]ethanol (2.62 g, 19.7 mmol), cuprous iodide (0.94 g, 4.9 mmol), potassium carbonate (4.5 g, 32.8 mmol) and butyronitrile (33 mL) was degassed for 5 min and then heated to 140° C. overnight. The reaction mixture was filtered through Celite eluting with iPrOAc. The filtrate was concentrated and purified by reverse phase HPLC and the cis:trans isomers were separated by chiral SFC to yield 305 (3.77 g, 44% yield). ¹H NMR (400 MHz, DMSO-d₆) δ 10.59 (s, 1H), 7.40 (dd, J=7.9, 1.3 Hz, 1H), 7.22-7.14 (m, 1H), 7.04-6.88 (m, 2H), 6.66 (d, J=11.1 Hz, 2H), 6.05-5.61 (m, 1H), 5.17 (d, 1.7 Hz, 1H), 4.50 (dd, J=47.6, 6.2 Hz, 2H), 3.94 (t, J=5.3 Hz, 2H), 3.41-3.32 (m, 2H), 3.15-2.90 (m, 3H), 2.90-2.52 (m, 7H), 1.09 (d, J=6.5 Hz, 3H) LCMS: 494.2 [M+H]⁺.

Example 306 (1S,3R)-2-(2,2-difluoroethyl)-1-[2,6-difluoro-4-[2-[3-(fluoromethyl)azetidin-1-yl]ethoxy]phenyl]-3-methyl-1,3,4,9-tetrahydropyrido[3,4-b]indole 306

Following the procedures of Example 305, 306 was prepared. LCMS: 494.2 [M+H]⁺.

Example 340 3-[(1R,3R)-1-[2,6-difluoro-4-[[1-(3-fluoropropyl)azetidin-3-yl]amino]phenyl]-3-methyl-1,3,4,9-tetrahydropyrido[3,4-b]indol-2-yl]-2,2-difluoro-propan-1-ol 340

Step 1: (R)—N-(1-(1H-Indol-3-yl)propan-2-yl)-3-((tert-butyldiphenylsilyl)oxy)-2,2-difluoropropan-1-amine

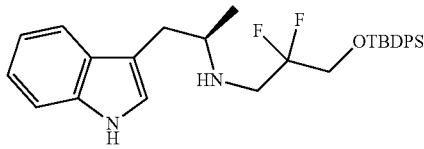

A mixture of (2R)-1-(1H-indol-3-yl)propan-2-amine (29 g, 166.44 mmol), [3-[tert-butyl(diphenyl)silyl]oxy-2,2-difluoro-propyl]trifluoromethanesulfonate (80.31 g, 166.44 mmol) and DIPEA (55.01 mL, 332.87 mmol) in 1,4-dioxane (600 mL) was stirred at 90° C. for 12 hours. The reaction mixture was diluted in water (600 mL) and was extracted with EtOAc (600 mL*2). The combined organic layers were dried over anhydrous Na$_2$SO$_4$, filtered and concentrated. The crude residue was purified by silica gel column chromatography (40% EtOAc in petroleum ether) to afford the title compound (69 g, 82%) as a light yellow oil. $^1$H NMR (400 MHz, CDCl$_3$) δ 7.88 (s, 1H), 7.66 (d, J=7.2 Hz, 4H), 7.60 (d, J=8.0 Hz, 1H), 7.48-7.33 (m, 7H), 7.22-7.08 (m, 2H), 7.01 (s, 1H), 3.86-3.79 (m, 2H), 3.23-3.09 (m, 3H), 2.86-2.80 (m, 2H), 1.13 (d, J=6.4 Hz, 3H), 1.05 (s, 9H). MS: [M+H]$^+$ 507.1.

Step 2: (R)-3-((1-(1H-Indol-3-yl)propan-2-yl)amino)-2,2-difluoropropan-1-ol

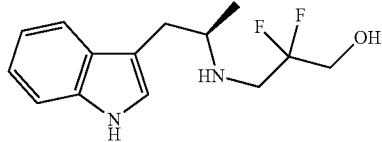 [SMILES: C[C@H](Cc1c[nH]c2ccccc12)NCC(F)(F)CO]

To a stirred solution of (R)—N-(1-(1H-indol-3-yl)propan-2-yl)-3-((tert-butyldiphenylsilyl)oxy)-2,2-difluoropropan-1-amine (From step 1, 69 g, 136.18 mmol) in THF (690 mL) was added 1 M TBAF (272.35 mL, 272.35 mmol) in THF. The mixture was stirred at 25° C. for 4 hours. The reaction mixture was diluted with water (800 mL) and was extracted with EtOAc (800 mL×3). The combined organic layers were concentrated and the crude residue was purified by silica gel column chromatography (50% EtOAc in petroleum ether) to afford the title compound (29 g, 79%) as a light yellow oil.

Step 3: 3-((1R,3R)-1-(4-Bromo-2,6-difluorophenyl)-3-methyl-3,4-dihydro-1H-pyrido[3,4-b]indol-2(9H)-yl)-2,2-difluoropropan-1-ol

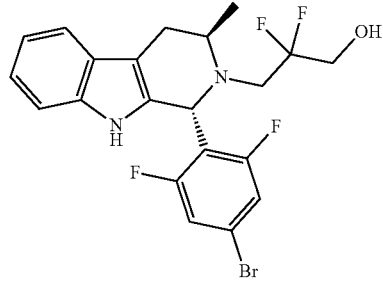 [SMILES: C[C@@H]1Cc2c([nH]c3ccccc23)[C@@H](c2c(F)cc(Br)cc2F)N1CC(F)(F)CO]

A mixture of (R)-3-((1-(1H-indol-3-yl)propan-2-yl)amino)-2,2-difluoropropan-1-ol (From step 2, 20 g, 74.54 mmol), acetic acid (12.91 mL, 223.63 mmol) and 4-bromo-2,6-difluorobenzaldehyde (16.47 g, 74.54 mmol) in toluene (400 mL) was stirred at 90° C. for 12 hours. The reaction mixture was diluted with water (500 mL) and was extracted with EtOAc (500 mL*2). The combined organic layers were dried over anhydrous Na$_2$SO$_4$, filtered and concentrated. The crude residue was purified by silica gel column chromatography (20% EtOAc in petroleum ether) to afford the title compound (24.8 g, 71%, trans/cis=20/1) as a light yellow solid. MS: [M+H]$^+$ 470.9.

Step 4: tert-Butyl 3-((4-((1R,3R)-2-(2,2-difluoro-3-hydroxypropyl)-3-methyl-2,3,4,9-tetrahydro-1H-pyrido[3,4-b]indol-1-yl)-3,5-difluorophenyl)amino)azetidine-1-carboxylate

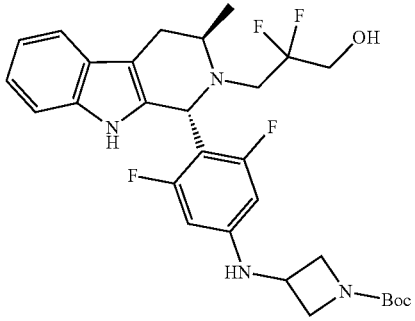 [SMILES: C[C@@H]1Cc2c([nH]c3ccccc23)[C@@H](c2c(F)cc(NC3CN(C(=O)OC(C)(C)C)C3)cc2F)N1CC(F)(F)CO]

A mixture of 3-((1-(4-bromo-2,6-difluorophenyl)-3-methyl-3,4-dihydro-1H-pyrido[3,4-b]indol-2(9H)-yl)-2,2-difluoropropan-1-ol (From step 3, 24.8 g, 52.62 mmol), Pd$_2$(dba)$_3$ (4.82 g, 5.26 mmol), Xantphos (6.09 g, 10.5 2 mmol), Cs$_2$CO$_3$ (51.44 g, 157.86 mmol) and tert-butyl 3-aminoazetidine-1-carboxylate (13.59 g, 78.93 mmol) in 1,4-dioxane (300 mL) was stirred at 110° C. for 3 hours under N$_2$ atmosphere. The reaction mixture was cooled to 25° C. and was diluted with water (500 mL), extracted with EtOAc (500 mL*2). The combined organic layers were dried over anhydrous Na$_2$SO$_4$, filtered and concentrated. The crude residue was purified by silica gel column chromatography (20% petroleum ether in EtOAc) to afford the title compound (20.5 g, 69%, trans/cis=20/1) as a yellow solid. MS: [M+H]$^+$ 563.0.

253

Step 5: 3-((1R,3R)-1-(4-(Azetidin-3-ylamino)-2,6-difluorophenyl)-3-methyl-3,4-dihydro-1H-pyrido[3,4-b]indol-2(9H)-yl)-2,2-difluoropropan-1-ol

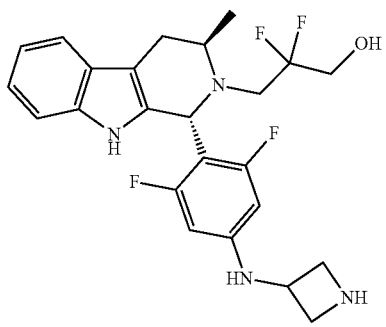 [SMILES: C[C@@H]1Cc2c([nH]c3ccccc23)[C@@H](c2c(F)cc(NC3CNC3)cc2F)N1CC(F)(F)CO]

A solution of tert-butyl 3-((4-((1R,3R)-2-(2,2-difluoro-3-hydroxypropyl)-3-methyl-2,3,4,9-tetrahydro-1H-pyrido[3,4-b]indol-1-yl)-3,5-difluorophenyl)amino)azetidine-1-carboxylate (From step 4, 20.5 g, 36.44 mmol) in 1,4-dioxane (194 mL) was added sulfuric acid (19.42 mL, 364.38 mmol) drop wise on an ice bath. The reaction mixture was stirred at 25° C. for 0.5 hours. The reaction mixture was then poured into saturated aqueous NaHCO₃ solution (800 mL) and was extracted with EtOAc (600 mL*2). The combined organic layers were dried over anhydrous Na₂SO₄, filtered and concentrated to afford the title compound (18 g, crude, trans/cis=20/1) as a yellow solid. The crude residue was carried over to the next step directly. MS: [M+H]⁺ 463.0.

Step 6: A mixture of 3-((1R,3R)-1-(4-(azetidin-3-ylamino)-2,6-difluorophenyl)-3-methyl-3,4-dihydro-1H-pyrido[3,4-b]indol-2(9H)-yl)-2,2-difluoropropan-1-ol (From step 5, 18 g, 38.92 mmol), DIPEA (19.3 mL, 116.76 mmol) and 1-fluoro-3-iodopropane (7.32 g, 38.9 2 mmol) in DMF (180 mL) was stirred at 25° C. for 12 hours. The reaction mixture was diluted with EtOAc (500 mL) and was washed with brine (500 mL×3). The combined organic layers were dried over anhydrous Na₂SO₄, filtered and concentrated. The crude residue was purified by silica gel column chromatography (10% MeOH in DCM) to afford the desired product (7.1 g, 85% purity) as a yellow oil. The resulting residue was further purified by reverse phase chromatography (acetonitrile 40-75/0.05% NH₃OH in water) and chiral SFC (AD 250 mm*50 mm, 10 um; supercritical CO₂/EtOH(0.1% NH₃H₂O)=40/40 at 200 mL/min) to afford 340 (2.85 g, 14%) as a light yellow solid. ¹H NMR (400 MHz, CD₃OD) δ 7.39 (d, J=7.2 Hz, 1H), 7.19 (d, J=8.0 Hz, 1H), 7.01-6.93 (m, 2H), 6.11 (d, J=12.0 Hz, 2H), 5.16 (s, 1H), 4.52-4.38 (m, 2H), 4.05-4.03 (m, 1H), 3.80-3.74 (m, 3H), 3.63-3.42 (m, 2H), 3.20-3.10 (m, 1H), 2.96-2.92 (m, 3H), 2.82-2.71 (m, 1H), 2.64-2.58 (m, 3H), 1.81-1.68 (m, 2H), 1.14 (d, J=6.4 Hz, 3H); MS: [M+H]⁺ 523.2.

254

Example 365 3-((1R,3R)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2,2-difluoropropan-1-ol 365

Step 1: ([3-(tert-Butyl-diphenyl-silanyloxy)-2,2-difluoro-propyl]-[2-(5-fluoro-1H-indol-3-yl)-1-methyl-ethyl]-amine

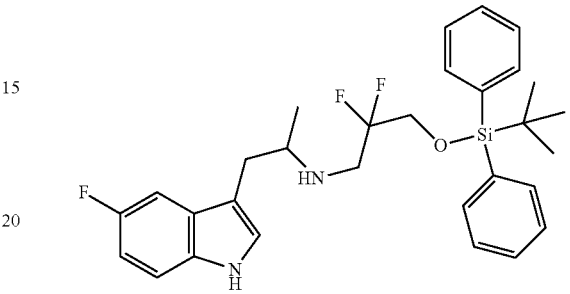

A mixture of [3-[tert-butyl(diphenyl)silyl]oxy-2,2-difluoro-propyl]trifluoromethanesulfonate (From Example 286, Step 2, 43.22 g, 89.6 mmol), DIPEA (19.5 mL, 112.0 mmol) and 2-(5-fluoro-1H-indol-3-yl)-1-methyl-ethylamine (CAS No.: 712-08-3, 14.7 g, 74.7 mmol) in dioxane (140 mL) was stirred at 90° C. for 3 hours. The mixture was cooled to room temperature, diluted with EtOAc and washed with water (×2) and brine, dried over anhydrous Na₂SO₄, filtered and concentrated. The crude residue was purified by silica gel column chromatography (mobile phase: DCM) to afford the title compound (32.8 g, 96%) as a yellow oil. 1H NMR (400 MHz, CDCl₃): δ 7.89 (s, 1H), 7.69-7.61 (m, 4H), 7.48-7.34 (m, 6H), 7.26-7.19 (m, 2H), 7.03-7.02 (m, 1H), 6.93 (dt, J=2.5, 9.0 Hz, 1H), 3.88-3.78 (m, 2H), 3.22-3.03 (m, 3H), 2.84-2.70 (m, 2H), 1.11 (d, J=6.2 Hz, 3H), 1.04 (s, 9H). LCMS: 525.3 [M+H]⁺.

Step 2: 2-[3-(tert-Butyl-diphenyl-silanyloxy)-2,2-difluoro-propyl]-1-(2,6-difluoro-4-iodo-phenyl)-6-fluoro-3-methyl-2,3,4,9-tetrahydro-1H-beta-carboline

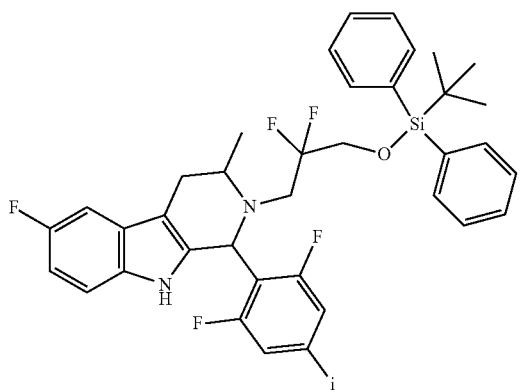

To a solution of [3-(tert-butyl-diphenyl-silanyloxy)-2,2-difluoro-propyl]-[2-(5-fluoro-1H-indol-3-yl)-1-methyl-ethyl]-amine (32.8 g, 62.5 mmol) in toluene (65 mL) was added 4-iodo-2,6-difluorobenzaldehyde (20.1 g, 75.0 mmol) and acetic acid (7.2 mL, 125.0 mmol). On complete addition the reaction mixture was stirred at 90° C. for 14 hours. The mixture was allowed to cool to room temperature, diluted with EtOAc, washed with saturated aqueous NaHCO$_3$ (×3) and brine, dried over anhydrous Na$_2$SO$_4$ and concentrated. The residue was purified by chromatography on silica (mobile phase: toluene in cyclohexane, gradient 10-50%) to afford the title compound (34.9 g, 72%) as an off white foam. $^1$H NMR (400 MHz, CDCl$_3$): δ 7.65-7.60 (m, 4H), 7.46-7.33 (m, 7H), 7.21-7.08 (m, 4H), 6.90-6.84 (m, 1H), 5.27 (s, 1H), 3.99-3.88 (m, 1H), 3.65-3.54 (m, 2H), 3.33-3.20 (m, 1H), 2.93 (ddd, J=1.4, 4.9, 15.2 Hz, 1H), 2.81-2.69 (m, 1H), 2.56-2.51 (m, 1H), 1.14 (d, J=6.6 Hz, 3H), 1.05 (s, 9H). LCMS: 775.2 [M+H]$^+$.

Step 3: 3-(4-{2-[3-(tert-Butyl-diphenyl-silanyloxy)-2,2-difluoro-propyl]-6-fluoro-3-methyl-2,3,4,9-tetrahydro-1H-beta-carbolin-1-yl}-3,5-difluoro-phenylamino)-azetidine-1-carboxylic Acid tert-butyl ester

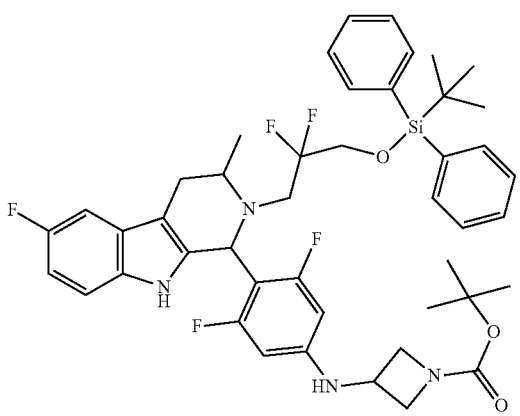

A mixture of 2-[3-(tert-butyl-diphenyl-silanyloxy)-2,2-difluoro-propyl]-1-(2,6-difluoro-4-iodo-phenyl)-6-fluoro-3-methyl-2,3,4,9-tetrahydro-1H-beta-carboline (30.8 g, 39.8 mmol), XantPhos (4.60 g, 7.9 mmol), Pd$_2$(dba)$_3$ (3.64 g, 4.0 mmol), Cs$_2$CO$_3$ (25.9 g, 79.4 mmol) and t-butyl 3-amino-azetidine-1-carboxylate (10.3 g, 59.6 mmol) in 1,4-dioxane (192 mL) was stirred at 115° C. in a sealed vessel under argon for 1.5 hours. The reaction mixture was allowed to cool to room temperature, the residual solid was removed by filtration through a pad of Celite® and the filtrate concentrated. The resultant residue was purified by flash chromatography on silica gel (mobile phase: EtOAc in DCM, gradient 0-5%) to afford the title compound (27.9 g, 76%) as a beige foam. $^1$H NMR (400 MHz, CDCl$_3$): δ 7.67-7.58 (m, 4H), 7.48-7.32 (m, 6H), 7.15-7.06 (m, 2H), 6.88-6.80 (m, 1H), 5.88-5.80 (m, 2H), 5.15 (s, 1H), 4.26-4.09 (m, 2H), 4.03-3.91 (m, 2H), 3.69-3.50 (m, 3H), 3.26-3.14 (m, 1H), 2.95-2.90 (m, 1H), 2.83-2.70 (m, 1H), 2.50 (dd, J=3.3, 15.1 Hz, 1H), 1.44 (s, 9H), 1.13 (d, J=6.5 Hz, 3H), 1.04 (s, 9H). LCMS: 819.4 [M+H]$^+$.

Step 4: Azetidin-3-yl-(4-{2-[3-(tert-butyl-diphenyl-silanyloxy)-2,2-difluoro-propyl]-6-fluoro-3-methyl-2,3,4,9-tetrahydro-1H-beta-carbolin-1-yl}-3,5-difluoro-phenyl)-amine

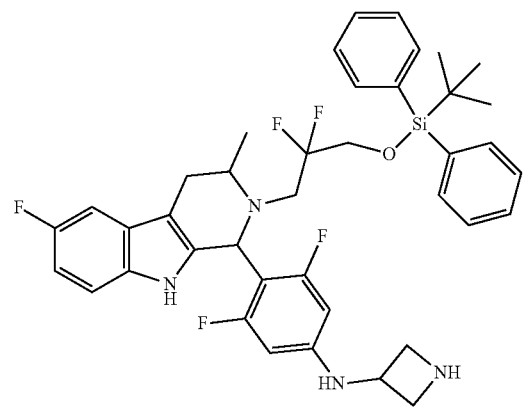 [SMILES: CC1Cc2c([nH]c3ccc(F)cc23)C(c2c(F)cc(NC3CNC3)cc2F)N1CC(F)(F)CO[Si](c1ccccc1)(c1ccccc1)C(C)(C)C]

A pre-mixed ice cooled solution of cc. sulfuric acid (9.1 mL, 170.2 mmol) in dioxane (100 mL) was added slowly to a solution of 3-(4-{2-[3-(tert-butyl-diphenyl-silanyloxy)-2,2-difluoro-propyl]-6-fluoro-3-methyl-2,3,4,9-tetrahydro-1H-beta-carbolin-1-yl}-3,5-difluoro-phenylamino)-azetidine-1-carboxylic acid tert-butyl ester (27.9 g, 34.0 mmol) in dioxane (275 mL) under nitrogen at room temperature. On complete addition, the reaction mixture was for 1 hour at room temperature. EtOAc and water were added and the pH of the aqueous phase adjusted to pH 9 by the addition of solid Na$_2$CO$_3$. The organic layer was separated, washed with brine (×3), dried over Na$_2$SO$_4$, filtered and concentrated in vacuo to afford the title compound (mixture of (R,R) & (S,S) diastereoisomers) as a pale orange foam (26.6 g, ~quant). LCMS: 719.4 [M+H]$^+$.

Step 5: (4-{2-[3-(tert-Butyl-diphenyl-silanyloxy)-2,2-difluoro-propyl]-6-fluoro-3-methyl-2,3,4,9-tetrahydro-1H-beta-carbolin-1-yl}-3,5-difluoro-phenyl)-[1-(3-fluoro-propyl)-azetidin-3-yl]-amine

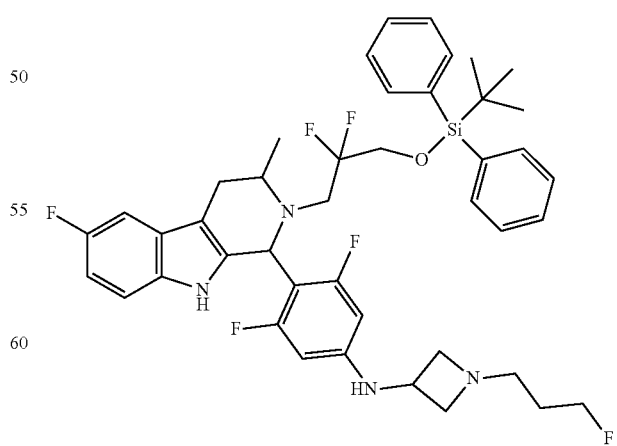

The title compound was prepared from azetidin-3-yl-(4-{2-[3-(tert-butyl-diphenyl-silanyloxy)-2,2-difluoro-propyl]-

6-fluoro-3-methyl-2,3,4,9-tetrahydro-1H-beta-carbolin-1-yl}-3,5-difluoro-phenyl)-amine (26.6 g, 34.0 mmol) and 1-iodo-3-fluoropropane (9.60 g, 51.1 mmol; CAS No.; 462-40-8) following the procedure outlined for the preparation of Example 101. The crude product was purified and purified by silica gel chromatography (mobile phase; dichloromethane/methanol, gradient 0% to 5%) to afford the title compound as a pale brown foam (14.9 g, 56%). $^1$H NMR (400 MHz, CDCl$_3$): δ 7.69-7.56 (m, 4H), 7.50 (s, 1H), 7.47-7.30 (m, 6H), 7.16-7.01 (m, 2H), 6.87-6.81 (m, 1H), 5.92-5.78 (m, 2H), 5.14 (s, 1H), 4.54 (t, J=6.0 Hz, 1H), 4.42 (t, J=6.0 Hz, 1H), 4.18 (d, J=7.0 Hz, 1H), 4.06-3.86 (m, 2H), 3.74-3.47 (m, 4H), 3.30-3.10 (m, 1H), 3.00-2.70 (m, 3H), 2.56 (t, J=7.2 Hz, 2H), 2.53-2.45 (m, 1H), 1.85-1.50 (m, 3H), 1.12 (d, J=6.5 Hz, 3H), 1.04 (s, 9H). LCMS: 779.4 [M+H]$^+$.

Step 6: 3-(1-{2,6-difluoro-4-[1-(3-fluoro-propyl)-azetidin-3-ylamino]-phenyl}-6-fluoro-3-methyl-1,3,4,9-tetrahydro-beta-carbolin-2-yl)-2,2-difluoro-propan-1-ol

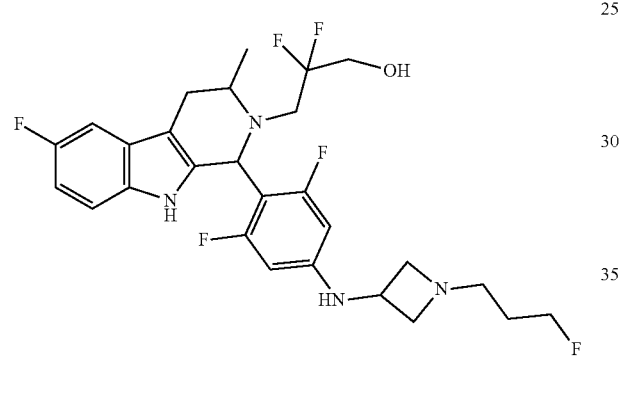

To a mixture of (4-{2-[3-(tert-butyl-diphenyl-silanyloxy)-2,2-difluoro-propyl]-6-fluoro-3-methyl-2,3,4,9-tetrahydro-1H-beta-carbolin-1-yl}-3,5-difluoro-phenyl)-[1-(3-fluoro-propyl)-azetidin-3-yl]-amine (12.1 g, 15.5 mmol) in THF (150 mL) under argon was added a solution of 1M TBAF in THF (23.3 mL) and the reaction mixture was stirred at room temperature for 5 hours. The reaction mixture was diluted with EtOAc and washed with water (×4). The organic layer was dried over Na$_2$SO$_4$, filtered, and concentrated in vacuo. The crude product was purified by silica gel chromatography (mobile phase: 2M ammonia in methanol/TBME, gradient 0.5% to 5%) to afford a mixture of (R,R) and (S,S) 3-(1-{2,6-difluoro-4-[1-(3-fluoro-propyl)-azetidin-3-ylamino]-phenyl}-6-fluoro-3-methyl-1,3,4,9-tetrahydro-beta-carbolin-2-yl)-2,2-difluoro-propan-1-ol. The pair of diastereoisomers were separated by chiral HPLC (ChiralPak IB, 15% EtOH in heptane+0.1% diethylamine). 365 was the second peak isolated by chiral HPLC: (1.90 g, 23%). Peak 2 rt=15 min. $^1$H NMR (400 MHz, CDCl$_3$): δ 7.46 (s, 1H), 7.16-7.08 (m, 2H), 6.86 (dt, J=2.5, 9.0 Hz, 1H), 6.08-6.00 (m, 2H), 5.09 (s, 1H), 4.54 (t, J=5.9 Hz, 1H), 4.43 (t, J=5.9 Hz, 1H), 4.38 (d, J=6.7 Hz, 1H), 4.07-3.97 (m, 1H), 3.80-3.56 (m, 6H), 3.28-3.16 (m, 1H), 3.11-3.02 (m, 1H), 2.97-2.82 (m, 3H), 2.64-2.55 (m, 3H), 1.82-1.67 (m, 2H), 1.16 (d, J=6.5 Hz, 3H). LCMS: 541.4 [M+H]$^+$.

Example 366 3-((1S,3S)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2,2-difluoropropan-1-ol 366

Following the procedures of Example 365, the first peak isolated by chiral HPLC was 366: (1.95 g, 24%). Peak 1 rt=12 min. $^1$H NMR (400 MHz, CDCl$_3$): δ 7.46 (s, 1H), 7.16-7.08 (m, 2H), 6.86 (dt, J=2.5, 9.0 Hz, 1H), 6.08-6.00 (m, 2H), 5.09 (s, 1H), 4.54 (t, J=5.9 Hz, 1H), 4.43 (t, J=5.9 Hz, 1H), 4.38 (d, J=6.7 Hz, 1H), 4.07-3.97 (m, 1H), 3.80-3.56 (m, 6H), 3.28-3.16 (m, 1H), 3.11-3.02 (m, 1H), 2.97-2.82 (m, 3H), 2.64-2.55 (m, 3H), 1.82-1.67 (m, 2H), 1.16 (d, J=6.5 Hz, 3H). LCMS: 541.4 [M+H]$^+$.

Example 368 3-((1R,3R)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2-fluoro-2-methylpropan-1-ol 368

Step 1: [3-(tert-Butyl-diphenyl-silanyloxy)-2-fluoro-2-methyl-propyl]-[2-(5-fluoro-1H-indol-3-yl)-1-methyl-ethyl]-amine

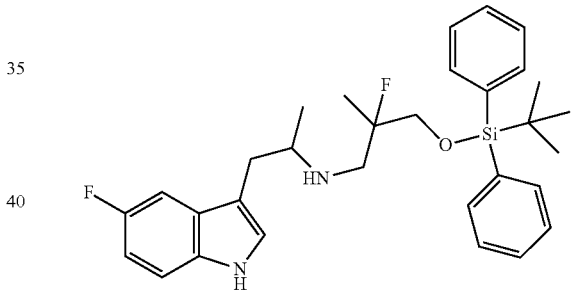

To a solution of 2-(5-fluoro-1H-indol-3-yl)-1-methyl-ethylamine (CAS No.: 712-08-3, 3.61 g, 18.7 mmol)) and DIPEA (4.9 mL, 28.1 mmol) in dioxane (43 mL) under argon was added trifluoro-methanesulfonic acid 3-(tert-butyl-diphenyl-silanyloxy)-2-fluoro-2-methyl-propyl ester, intermediate XX (3.09 g, 9.48 mmol). The resulting mixture was stirred at 90° C. for 6 h. The reaction mixture was partitioned between EtOAc and water. The organic phase was separated and further washed with brine, dried over Na$_2$SO$_4$, filtered and concentrated in vacuo. The crude product was purified by silica gel chromatography (mobile phase: dichloromethane/methanol, gradient 0% to 5%) to afford a mixture of diastereoisomers of the title compound as a yellow oil (8.0 g, 82%). $^1$H NMR (300 MHz, CDCl$_3$): δ 7.82 (br. s, 1H), 7.68-7.63 (m, 4H), 7.52-7.38 (m, 6H), 7.25-7.18 (m, 2H), 7.02-6.98 (m, 1H), 6.92 (dt, J=2.4, 9.1 Hz, 1H), 3.82-3.57 (m, 5H), 3.02-2.65 (m, 6H), 1.33 (d, J=22.0 Hz, 3H), 1.1-1.0 (m, 9H); LCMS: 521.3 [M+H]$^+$.

Step 2: 3-(4-{2-[3-(tert-Butyl-diphenyl-silanyloxy)-2-fluoro-2-methyl-propyl]-6-fluoro-3-methyl-2,3,4,9-tetrahydro-1H-beta-carbolin-1-yl}-3,5-difluoro-phenoxy)-azetidine-1-carboxylic Acid tert-butyl ester

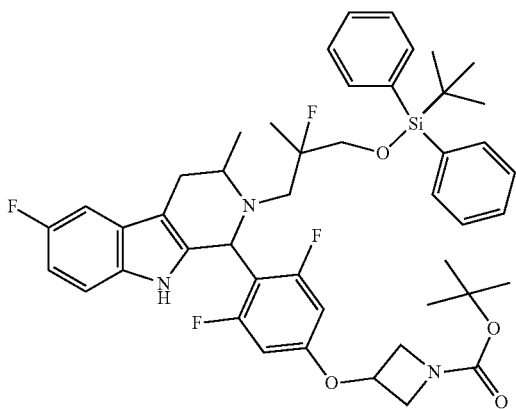 [SMILES: CC1Cc2c([nH]c3ccc(F)cc23)C(c2c(F)cc(OC3CN(C(=O)OC(C)(C)C)C3)cc2F)N1CC(C)(F)CO[Si](c1ccccc1)(c1ccccc1)C(C)(C)C]

The title compound was prepared from [3-(tert-butyl-diphenyl-silanyloxy)-2-fluoro-2-methyl-propyl]-[2-(5-fluoro-1H-indol-3-yl)-1-methyl-ethyl]-amine, intermediate 1a (8 g, 15.3 mmol) and 3-(3,5-difluoro-4-formyl-phenoxy)-azetidine-1-carboxylic acid tert-butyl ester 101c (5.6 g, 18.1 mmol) following the procedure outlined for the preparation of intermediate 101e. The crude product was purified and purified by silica gel chromatography (mobile phase: cyclohexane/ethyl acetate, gradient 0% to 20%) to afford a mixture of diastereoisomers of the title compound as a white foam (8.0 g, 64%). $^1$H NMR (300 MHz, CDCl$_3$): δ 7.65-7.54 (m, 4H), 7.47-7.30 (m, 7H), 7.17-7.08 (m, 2H), 6.84 (dt, J=2.4, 9.0 Hz, 1H), 6.23-6.07 (m, 2H), 5.16 (s, 1H), 4.71-4.63 (m, 1H), 4.29-4.18 (m, 2H), 3.99-3.88 (m, 2H), 3.79 (dd, J=11.5, 16.8 Hz, 1H), 3.64-3.54 (m, 1H), 3.50-3.29 (m, 1H), 3.10-2.83 (m, 2H), 2.69-2.39 (m, 2H), 1.54 (s, 3H), 1.46-1.40 (m, 9H), 1.29-0.98 (m, 12H); LCMS: 816.5 [M+H]$^+$.

Step 3: 1-[4-(Azetidin-3-yloxy)-2,6-difluoro-phenyl]-2-[3-(tert-butyl-diphenyl-silanyloxy)-2-fluoro-2-methyl-propyl]-6-fluoro-3-methyl-2,3,4,9-tetrahydro-1H-beta-carboline

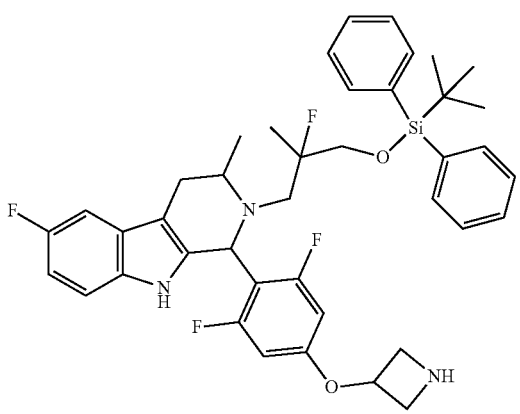 [SMILES: CC1Cc2c([nH]c3ccc(F)cc23)C(c2c(F)cc(OC3CNC3)cc2F)N1CC(C)(F)CO[Si](c1ccccc1)(c1ccccc1)C(C)(C)C]

To a mixture of 3-(4-{2-[3-(tert-butyl-diphenyl-silanyloxy)-2-fluoro-2-methyl-propyl]-6-fluoro-3-methyl-2,3,4,9-tetrahydro-1H-beta-carbolin-1-yl}-3,5-difluoro-phenoxy)-azetidine-1-carboxylic acid tert-butyl ester, intermediate 2a (8.0 g, 9.80 mmol) in dioxane (80 mL) under argon at 0° C. was added dropwise a solution of cc. sulfuric acid (2.62 mL, 49.0 mmol) in dioxane (27 mL) and the mixture, protected from light, was allowed to warm to RT and stirred for 3.5 h. The reaction mixture was diluted with EtOAc and sat. NaHCO$_3$, stirred for 10 min and the layers separated. The organic layer was further washed with sat. NaHCO$_3$, brine, dried over Na$_2$SO$_4$, filtered, and concentrated in vacuo to afford a mixture of diastereoisomers of the title compound as a pale yellow foam (7.05 g, ~quant). $^1$H NMR (300 MHz, CDCl$_3$): $^1$H NMR (300 MHz, CDCl$_3$): δ 7.66-7.54 (m, 4H), 7.47-7.30 (m, 7H), 7.17-7.06 (m, 2H), 6.84 (dt, J=2.4, 9.0 Hz, 1H), 6.25-6.09 (m, 2H), 5.16 (s, 1H), 4.86-4.76 (m, 1H), 3.94-3.65 (m, 3H), 3.63-3.54 (m, 1H), 3.49-3.24 (m, 1H), 3.11-2.83 (m, 2H), 2.69-2.39 (m, 2H), 1.54 (s, 3H), 1.27-1.12 (m, 3H), 1.11-0.98 (m, 12H); LCMS: 716.4 [M+H]$^+$.

Step 4: 2-[3-(tert-Butyl-diphenyl-silanyloxy)-2-fluoro-2-methyl-propyl]-1-{2,6-difluoro-4-[1-(3-fluoro-propyl)-azetidin-3-yloxy]-phenyl}-6-fluoro-3-methyl-2,3,4,9-tetrahydro-1H-beta-carboline

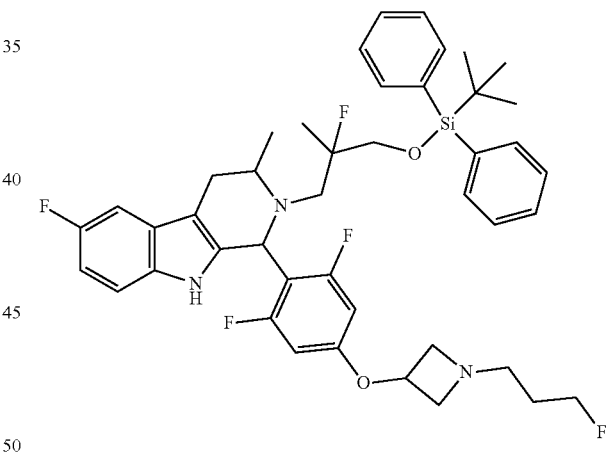

The title compound was prepared from 1-[4-(azetidin-3-yloxy)-2,6-difluoro-phenyl]-2-[3-(tert-butyl-diphenyl-silanyloxy)-2-fluoro-2-methyl-propyl]-6-fluoro-3-methyl-2,3,4,9-tetrahydro-1H-beta-carboline, intermediate 3a (7.05 g, 9.84 mmol) and 1-iodo-3-fluoropropane (2.77 g, 14.7 mmol; CAS No.: 462-40-8) following the procedure outlined for the preparation of example 101. The crude product was purified by silica gel chromatography (mobile phase: dichloromethane/methanol, gradient 0% to 3%) to afford the title compound as a white foam (5.7 g, 75%). LCMS: 776.4 [M+H]$^+$.

Step 5: racemic 3-(1-{2,6-Difluoro-4-[1-(3-fluoro-propyl)-azetidin-3-yloxy]-phenyl}-6-fluoro-3-methyl-1,3,4,9-tetrahydro-beta-carbolin-2-yl)-2-fluoro-2-methyl-propan-1-ol

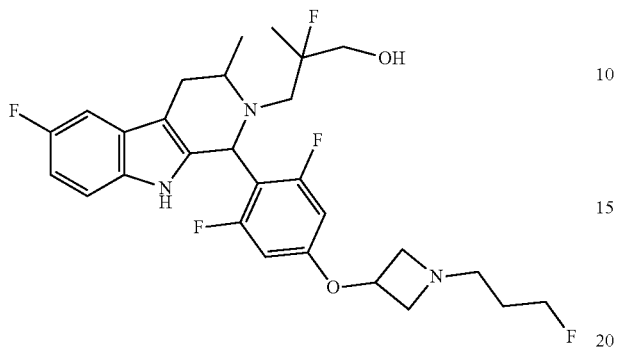

To a mixture of 2-[3-(tert-Butyl-diphenyl-silanyloxy)-2-fluoro-2-methyl-propyl]-1-{2,6-difluoro-4-[1-(3-fluoro-propyl)-azetidin-3-yloxy]-phenyl}-6-fluoro-3-methyl-2,3,4,9-tetrahydro-1H-beta-carboline Intermediate 4a (5.17 g, 6.66 mmol) in THF (80 mL) under argon was added a solution of 1M TBAF in THF (10 mL) and the reaction mixture was stirred for at RT for 24 h. The reaction mixture was poured into a mixture of water and brine and extracted with EtOAc. The aqueous layer was further extracted with EtOAc and the combined organic layers were further washed with water and brine, dried over $Na_2SO_4$, filtered, and concentrated in vacuo. The crude product was purified by silica gel chromatography (mobile phase: dichloromethane/methanol, gradient 0% to 6%) to give two pairs of diastereoisomers (diastereoisomers 1 and diastereoisomers 2). The pair of diastereoisomers 1 was further purified by chiral HPLC (ChiralPak IC, 25% IPA in heptane 0.1% diethylamine). First peak isolated (rt=8.2 mins)=368 isolated as a white solid (467 mg, 13%). $^1$H NMR (400 MHz, $CDCl_3$): 7.32 (br s., 1H), 7.17-7.09 (m, 2H), 6.89-6.83 (m, 1H), 6.38-6.33 (m, 2H), 5.03 (s, 1H), 4.76-4.69 (m, 1H), 4.55 (t, 1H, J=5.9 Hz), 4.47-4.41 (m, 2H), 4.00 (t, 1H, J=4.9 Hz), 3.83-3.76 (m, 2H), 3.60 (q, 1H, J=10.3 Hz), 3.46-3.34 (m, 1H), 3.23-3.09 (m, 4H), 2.67-2.57 (m, 4H), 1.84-1.69 (m, 2H), 1.14-1.08 (m, 6H); LCMS: 538.3 [M+H]$^+$.

Example 369 3-((1S,3S)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2-fluoro-2-methylpropan-1-ol 369

Following the procedures of Example 368, the second peak isolated by chiral HPLC (rt=15.5 mins)=369 isolated as a white solid (480 mg, 13.5%).

Example 370 3-((1R,3R)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2-fluoro-2-methylpropan-1-ol 370

Following the procedures of Example 368, The pair of diastereoisomers 2 was purified by chiral HPLC (ChiralPak IC, 35% IPA in heptane 0.1% diethylamine). The first peak isolated was further purified by chiral HPLC (ChiralPak IA, 25% IPA in heptane 0.1% diethylamine): first peak isolated (rt=8.5 mins)=370 isolated as a white solid (165 mg, 5%).

$^1$H NMR (400 MHz, $CDCl_3$): 7.53 (br. s, 1H), 7.16-7.12 (m, 2H), 6.90-6.84 (m, 1H), 6.33-6.28 (m, 2H), 5.35 (s, 1H), 4.76-4.68 (m, 1H), 4.55 (t, 1H, J=5.9 Hz), 4.45-4.41 (m, 1H), 3.85-3.54 (m, 6H), 3.16-2.92 (m, 4H), 2.79 (t, 1H, J=15.7 Hz), 2.68-2.56 (m, 3H), 1.77 (tdd, J=6.7, 19.3, 19.3 Hz, 2H), 1.23-1.15 (m, 6H); LCMS: 538.3 [M+H]$^+$.

Example 371 3-((1S,3S)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2-fluoro-2-methylpropan-1-ol 371

Following the procedures of Example 368, the pair of diastereoisomers 2 was purified by chiral HPLC (ChiralPak IC, 35% IPA in heptane 0.1% diethylamine). The second peak isolated (rt=14 mins)=371 isolated as a white solid (180 mg, 5%).

Example 431 (R)-3-((1R,3R)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2-fluoro-2-methylpropan-1-ol 431

Step 1: 3-((tert-butyldiphenylsilyl)oxy)-2-fluoro-N-(1-(5-fluoro-1H-indol-3-yl)propan-2-yl)-2-methyl-propan-1-amine

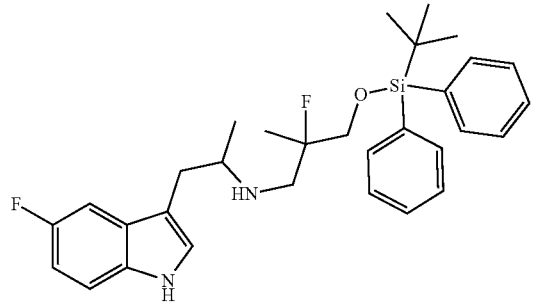 [SMILES: CC(Cc1c[nH]c2ccc(F)cc12)NCC(C)(F)CO[Si](c1ccccc1)(c1ccccc1)C(C)(C)C]

To a solution of 1-(5-fluoro-1H-indol-3-yl)propan-2-amine (5.30 g, 26.2 mmol, 95%, prepared following Yeung, et al, *J. Med. Chem.* 2010, 53, 5155-5164) in 1,4-dioxane (105 mL) cooled with ice bath was added N,N-diisopropylethylamine (6.85 mL), followed by [3-[tert-butyl(diphenyl)silyl]oxy-2-fluoro-2-methyl-propyl]trifluoromethanesulfonate (13.80 g, 28.8 mmol) in dioxane (10 mL), following Example 154, step 5. The mixture was heated at 90° C. (bath) for 18 h. The mixture was concentrated. Diluted $Na_2CO_3$ was added. The contents were extracted with DCM (2×). The combined extracts were dried ($Na_2SO_4$) and concentrated. The crude was purified with flash chromatography (0-50% iPrOAc/heptane with 1% TEA) to give the product (10.38 g, 76%).

Steps 2-5: N-(4-(2-(3-((tert-butyldiphenylsilyl)oxy)-2-fluoro-2-methylpropyl)-6-fluoro-3-methyl-2,3,4,9-tetrahydro-1H-pyrido[3,4-b]indol-1-yl)-3,5-difluorophenyl)-1-(3-fluoropropyl)azetidin-3-amine

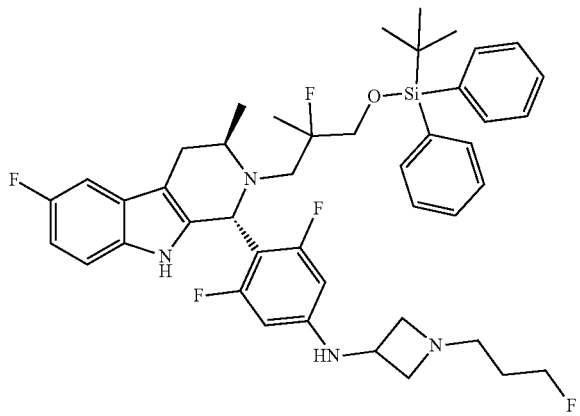 [SMILES: C[C@@H]1Cc2c([nH]c3ccc(F)cc23)[C@@H](c2c(F)cc(NC3CN(CCCF)C3)cc2F)N1CC(C)(F)CO[Si](c1ccccc1)(c1ccccc1)C(C)(C)C]

The compound was prepared in a manner similar to Example 145.

Step 6: racemic 3-(1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2-fluoro-2-methylpropan-1-ol

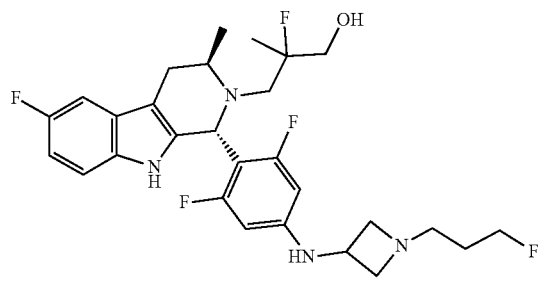 [SMILES: C[C@@H]1Cc2c([nH]c3ccc(F)cc23)[C@@H](c2c(F)cc(NC3CN(CCCF)C3)cc2F)N1CC(C)(F)CO]

To a solution of N-[4-[(1R,3R)-2-[3-[tert-butyl(diphenyl)silyl]oxy-2-fluoro-2-methyl-propyl]-6-fluoro-3-methyl-1,3,4,9-tetrahydropyrido[3,4-b]indol-1-yl]-3,5-difluoro-phenyl]-1-(3-fluoropropyl)azetidin-3-amine (2.231 g, 2.879 mmol) in THF (14.4 mL) was added TBAF in THF (1.0 M, 4.6 mL). The mixture was heated at 50° C. for 24 h. The mixture was concentrated. Diluted with iPrOAc, the contents were washed with dilute $Na_2CO_3$ (2×) and brine, dried ($Na_2SO_4$), and concentrated. The crude was purified with flash chromatography (0-60% B/A, A: DCM, B: 20% 2M $NH_3$ in MeOH/DCM). The collected product was subjected to chiral separation. The stereochemistry assigned to compounds 431-434 in Table 2 are unknown and arbitrary.

Stage 1. Isolation of enantiomers 1 and 4. Enantiomers 2 and 3 remained a mixture. Chiralpak AD (250×30.0, 5 um), 32.5% isocratic 0.1% $NH_4OH$ in Isopropanol at 150 g/min., UV-254 nm, BPR 100 bar, temp 40° C., cycle time 5 min, total time 200 min. Stage 2: Resolution of enantiomers 2 and 3 Chiralpak OX (150×30.0, 5 um), 30% isocratic 0.1% NH4OH in Methanol at 150 g/min, UV-250 nm, BPR 100 bar, temp 40° C., cycle time 3 min, total time 48 min.

Compounds 431-434 were characterized as follows. Enantiomer 1: 324.8 mg. $^1$H NMR (400 MHz, DMSO-d6) δ 10.59 (s, 1H), 7.19-7.08 (m, 2H), 6.85-6.75 (m, 1H), 6.68 (d, J=6.9 Hz, 1H), 6.17-6.06 (m, 2H), 5.01 (s, 1H), 4.81 (t, J=5.8 Hz, 1H), 4.51 (t, J=6.1 Hz, 1H), 4.39 (t, J=6.0 Hz, 1H), 4.33 (d, J=4.2 Hz, 0H), 3.99-3.87 (m, 1H), 3.82-3.72 (m, 0H), 3.67-3.56 (m, 2H), 3.55-3.40 (m, 2H), 3.19-3.05 (m, 1H), 2.95-2.68 (m, 4H), 1.74-1.56 (m, 2H), 1.14-0.99 (m, 6H). LCMS: 537.3 [M+H]$^+$. Enantiomer 2: 251.7 mg. $^1$H NMR (400 MHz, DMSO-d6) δ 10.59 (s, 1H), 7.20-7.07 (m, 2H), 6.86-6.75 (m, 1H), 6.68 (d, J=6.8 Hz, 1H), 6.11 (d, J=12.1 Hz, 2H), 5.01 (s, 1H), 4.81 (t, J=5.8 Hz, 1H), 4.51 (t, J=6.1 Hz, 1H), 4.39 (t, J=6.0 Hz, 1H), 4.00-3.87 (m, 1H), 3.68-3.57 (m, 2H), 3.55-3.41 (m, 2H), 3.20-3.06 (m, 1H), 2.95-2.69 (m, 4H), 1.73-1.56 (m, 2H), 1.17-0.96 (m, 6H). LCMS: 537.3 [M+H]$^+$. Enantiomer 3: 105.5 mg. $^1$H NMR (400 MHz, DMSO-d6) δ 10.55 (s, 1H), 7.17-7.08 (m, 2H), 6.84-6.75 (m, 1H), 6.67 (d, J=6.8 Hz, 1H), 6.14-6.05 (m, 2H), 4.98 (s, 1H), 4.84 (t, J=5.7 Hz, 1H), 4.51 (t, J=6.0 Hz, 1H), 4.39 (t, J=6.0 Hz, 1H), 3.99-3.87 (m, 1H), 3.67-3.57 (m, 2H), 3.57-3.47 (m, 1H), 2.92-2.79 (m, 2H), 2.77-2.69 (m, 2H), 1.73-1.56 (m, 2H), 1.13-0.96 (m, 6H). LCMS: 537.3 [M+H]$^+$. Enantiomer 4: 151.1 mg. $^1$H NMR (400 MHz, DMSO-d6) δ 10.55 (s, 1H), 7.18-7.07 (m, 2H), 6.84-6.75 (m, 1H), 6.67 (d, J=7.0 Hz, 1H), 6.10 (d, J=12.1 Hz, 2H), 4.97 (s, 1H), 4.84 (t, J=5.7 Hz, 1H), 4.51 (t, J=6.1 Hz, 1H), 4.39 (t, J=6.1 Hz, 1H), 3.98-3.89 (m, 1H), 3.66-3.58 (m, 2H), 3.57-3.48 (m, 1H), 2.93-2.79 (m, 2H), 2.79-2.69 (m, 2H), 1.74-1.57 (m, 2H), 1.12-0.96 (m, 6H). LCMS: 537.3 [M+H]$^+$.

Example 432 (S)-3-((1S,3S)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2-fluoro-2-methylpropan-1-ol 432

Following the procedures of Example 431, enantiomer 432 was isolated.

Example 433 (S)-3-((1R,3R)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2-fluoro-2-methylpropan-1-ol 433

Following the procedures of Example 431, enantiomer 433 was isolated.

Example 434 (R)-3-((1R,3S)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2-fluoro-2-methylpropan-1-ol 434

Following the procedures of Example 431, enantiomer 434 was isolated.

Example 901: Breast Cancer Cell ERa High Content Fluorescence Imaging Degradation Assay MCF7 breast cancer cells were seeded on day 1 at a density of 10,000 cells per well in 384 well poly-lysine coated tissue culture plate (Greiner #T-3101-4), in 50 µL/well RPMI (phenol red free), 10% FBS (Charcoal stripped), containing L-glutamine. On day 2, compounds were prepared at 2 compound source concentrations: 100 µM and 1 µM (ultimately to give 2 overlapping titration curves), in a Labcyte low dead volume plate, 10 µL/well, and 10 µL of DMSO in designated wells for backfill, and 5

µM Fulvestrant (control compound) in designated wells. Compounds and controls were dispensed using a Labcyte Echo acoustic dispenser to dispense compounds with a predefined serial dilution (1.8×, 10 point, in duplicate) and appropriate backfill and control compounds (final total volume transferred was 417.5 nL and compound dispense volume ranges from 2.5 nL to 417.5 nL; 0.84% DMSO (v/v) final), ultimately producing a concentration range from 0.05 nM to 835 nM. Cell plates were incubated at 37° C., for 4 hours. Fixation and permeabilization were carried out using a Biotek EL406 plate washer and dispenser as follows. Cells were fixed by addition of 15 µL of 16% paraformaldehyde (Electron Microscopy Sciences #15710-S) directly to the 50 µL cell culture medium in each well using the peristaltic pump 5 µL cassette on a Biotek EL406 (final concentration of formaldehyde was 3.7% w/v). Samples were incubated 30 minutes. Well contents was aspirated and 50 µL/well of Phosphate Buffered Saline (PBS) containing 0.5% w/v bovine serum albumen, 0.5% v/v Triton X-100 (Antibody Dilution Buffer) was added to each well. Samples were incubated for 30 minutes. Well contents were aspirated and washed 3 times with 100 µL/well of PBS. Immunofluorescence staining of estrogen receptor alpha (ESR1) was carried out using a Biotek EL406 plate washer and dispenser as follows. The well supernatant was aspirated from the wells and 25 µL/well of anti-ESR1 mAb (F10) (Santa Cruz sc-8002) diluted 1:1000 in Antibody Dilution Buffer was dispensed. Samples were incubated for 2 hours at room temperature. Samples were washed 4 times with 100 µL/well of PBS. 25 uL/well of secondary antibody solution (Alexafluor 488 conjugate anti-mouse IgG (LifeTechndogies #A21202) diluted 1:1000 and Hoechst 33342 1 µg/ml diluted in Antibody Dilution Buffer) were dispensed into each well. Samples were incubated for 2 hours at room temperature. Samples were washed 3 times with 100 µL/well of PBS using a Biotek EL406. Quantitative fluorescence imaging of ESR1 was carried out using a Cellomics Arrayscan V (Thermo). Fluorescence images of the samples (Channel 1: XF53 Hoechst (DNA stain); Channel 2: XF53 FITC (ESR1 stain)) were acquired using a Cellomics VTI Arrayscan using the Bioapplication "Compartmental Analysis" using the auto-exposure (based on DMSO control wells) setting "peak target percentile" set to 25% target saturation for both channels. Channel 1 (DNA stain) was used to define the nuclear region (Circ). Measurements of "Mean_CircAvgIntCh2", which is the Alexafluor 488 fluorescence intensity (ESR1) within the nuclear region, was measured on a per cell basis and averaged over all the measured cells. Data analysis was carried out using Genedata Screener Software, with DMSO and 5 nM Fulvestrant treated samples being used to define the 0% and 100% changes in ESR1. The "Robust Fit" method was used to define the inflexion point of curve ($EC_{50}$) and the plateau of the maximal effect (Sinf). Degradation data for exemplary Formula I compounds is reported as ER-alpha MCF7 HCS $S_{inf}$(%) values in Table 1.

Example 902 In Vitro Cell Proliferation Assay

Efficacy of estrogen receptor modulator compounds and chemotherapeutic compounds are measured by a cell proliferation assay employing the following protocol (Mendoza et al (2002) Cancer Res. 62:5485-5488).

The CellTiter-Glo® Luminescent Cell Viability Assay is a homogeneous method to determine the number of viable cells in culture based on quantitation of the ATP present, which signals the presence of metabolically active cells. The CellTiter-Glo® Assay is designed for use with multiwell plate formats, making it ideal for automated high-throughput screening (HTS), cell proliferation and cytotoxicity assays. The homogeneous assay procedure involves adding a single reagent (CellTiter-Glo® Reagent) directly to cells cultured in serum-supplemented medium. Cell washing, removal of medium or multiple pipetting steps are not required. The Cell Titer-Glo® Luminescent Cell Viability Assay, including reagents and protocol are commercially available (Promega Corp., Madison, Wis., Technical Bulletin TB288).

The assay assesses the ability of compounds to enter cells and inhibit cell proliferation. The assay principle is based on the determination of the number of viable cells present by quantitating the ATP present in a homogenous assay where addition of the Cell Titer-Glo® reagent results in cell lysis and generation of a luminescent signal through the luciferase reaction. The luminescent signal is proportional to the amount of ATP present.

Procedure: Day 1—Seed Cell Plates (384-well black, clear bottom, microclear, TC plates with lid from Falcon #353962), Harvest cells, Seed cells at 1000 cells per 54 µl per well into 384 well Cell Plates for 3 days assay. Cell Culture Medium: RPMI or DMEM high glucose, 10% Fetal Bovine Serum, 2 mM L-Glutamine, P/S. Incubate O/N (overnight) at 37° C., 5% $CO_2$.

Day 2—Add Drug to Cells, Compound Dilution, DMSO Plates (serial 1:2 for 9 points). Add 20 µl of compound at 10 mM in the 2nd column of 96 well plate. Perform serial 1:2 across the plate (10 µl+20 µl 100% DMSO) for a total of 9 points using Precision Media Plates 96-well conical bottom polypropylene plates from Nunc (cat. #249946) (1:50 dilution). Add 147 µl of Media into all wells. Transfer 3 µl of DMSO+compound from each well in the DMSO Plate to each corresponding well on Media Plate using Rapidplate® (Caliper, a Perkin-Elmer Co.). For 2 drug combination studies, transfer one drug 1.5 µl of DMSO+compound from each well in the DMSO Plate to each corresponding well on Media Plate using Rapidplate. Then, transfer another drug 1.5 µl to the medium plate.

Drug Addition to Cells, Cell Plate (1:10 dilution): Add 6 µl of media+compound directly to cells (54 µl of media on the cells already). Incubate 3 days at 37° C., 5% $CO_2$ in an incubator that will not be opened often.

Day 5—Develop Plates, Thaw Cell Titer Glo Buffer at room temperature: Remove Cell Plates from 37° C. and equilibrate to room temperature for about 30 minutes. Add Cell Titer-Glo® Buffer to Cell Titer-Glo® Substrate (bottle to bottle). Add 30 µl Cell Titer-Glo® Reagent (Promega cat. #G7572) to each well of cells. Place on plate shaker for about 30 minutes. Read luminescence on Analyst HT Plate Reader (half second per well).

Cell viability assays and combination assays: Cells were seeded at 1000-2000 cells/well in 384-well plates for 16 h. On day two, nine serial 1:2 compound dilutions were made in DMSO in a 96 well plate. The compounds were further diluted into growth media using a Rapidplate® robot (Zymark Corp., Hopkinton, Mass.). The diluted compounds were then added to quadruplicate wells in 384-well cell plates and incubated at 37° C. and 5% $CO_2$ After 4 days, relative numbers of viable cells were measured by luminescence using Cell Titer-Glo® (Promega) according to the manufacturer's instructions and read on a Wallac Multilabel Reader® (PerkinElmer, Foster City). EC50 values were calculated using Prism®4.0 software (GraphPad, San Diego). Drugs in combination assays were dosed starting at 4×$EC_{50}$ concentrations. If cases where the EC50 of the drug was >2.5 µM, the highest concentration used was 10 µM. Estrogen receptor modulator compounds and chemotherapeutic agents were added simultaneously or separated by 4 hours (one before the other) in all assays.

An additional exemplary in vitro cell proliferation assay includes the following steps:

1. An aliquot of 100 µl of cell culture containing about $10^4$ cells (see Table 3 for cell lines and tumor type) in medium was deposited in each well of a 384-well, opaque-walled plate.
2. Control wells were prepared containing medium and without cells.
3. The compound was added to the experimental wells and incubated for 3-5 days.
4. The plates were equilibrated to room temperature for approximately 30 minutes.
5. A volume of CellTiter-Glo® Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.
9. Analyze using the Chou and Talalay combination method and Dose-Effect Analysis with CalcuSyn® software (Biosoft, Cambridge, UK) in order to obtain a Combination Index.

Alternatively, cells were seeded at optimal density in a 96 well plate and incubated for 4 days in the presence of test compound. Alamar Blue™ was subsequently added to the assay medium, and cells were incubated for 6 h before reading at 544 nm excitation, 590 nm emission. $EC_{50}$ values were calculated using a sigmoidal dose response curve fit.

Alternatively, Proliferation/Viability was analyzed after 48 hr of drug treatment using Cell Titer-Glo® reagent (Promega Inc., Madison, Wis.). DMSO treatment was used as control in all viability assays. $IC_{50}$ values were calculated using XL fit software (IDBS, Alameda, Calif.)

The cell lines were obtained from either ATCC (American Type Culture Collection, Manassas, Va.) or DSMZ (Deutsche Sammlung von Mikroorganismen und Zellkulturen GmbH, Braunschweig, Del.). Cells were cultured in RPMI 1640 medium supplemented with 10% fetal bovine serum, 100 units/ml penicillin, 2 mM L-glutamine, and 100 mg/ml streptomycin (Life Technology, Grand Island, N.Y.) at 37° C. under 5% $CO_2$.

Example 903 MCF7 In Vitro Cell Proliferation Assay

MCF7 cells were washed with PBS and plated in RPMI 1640 (Gibco 11835-030 [−phenol+glutamine]) and 10% Charcoal Stripped FBS (Gibco 12676-029), in poly-lysine coated 384 well tissue culture plates (Greiner), at 25,000 cells/ml, 40 ul/well, and incubated overnight. Compounds were prepared in serial dilution in DMSO at 500-fold the final desired concentration using a Biomek-FX and diluted 50-fold in RPMI 1640. The control compound fulvestrant and negative control dimethylsulfoxide were also prepared in a similar manner. 5 ul of each individual compound concentration and each control compound was transferred to the cell plate. Fulvestrant was added to control wells at a final concentration of 100 nM). DMSO was added to negative control wells (0.2% v/v). Five microliters (5 µl) of 1 nM Estradiol (in phenol red free RPMI 1640 (Gibco 11835-030) was added to each well of the cell plate (except no estradiol control wells). Cells were incubated for 72 hours then lysed using Cell TiterGlo reagent (Promega #G7572) 40 ul/well and the luminescence was measured on an Envision (Perkin Elmer) plate reader. Data were analyzed using Genedata Screener software, using DMSO and Fulvestrant treated samples to define 0% and 100% inhibition and EC50 values were calculated using curve fitting using Robust method.

Example 904 ERa Co-Activator Peptide Antagonist Assay

Test compounds were prepared at 1 mM in DMSO and serially diluted in a 12 point, 1 to 3-fold titration using a Biomek FX in in 384 well clear V-bottom polypropylene plates (Greiner cat #781280). A 3× compound intermediate dilution was prepared by mixing 1 mL of each concentration of the compound serial dilution with 32.3 mL of TR-FRET Coregulator Buffer E (Life Technologies PV4540). 2 mL of the 3× compound intermediate dilution was transferred to a 1536-well (Aurora Biotechnologies MaKO 1536 Black Plate, #00028905) using a Biomek FX. A Bioraptr Dispenser® (Beckman Coulter) was used to dispense. 2 mL per well of "3× ERa solution": 22 nM ERa (human estrogen receptor alpha, GST-tagged ESR1 ligand binding domain, spanning residues S282-V595, either wild-type sequence or containing the mutations: Y537S or D538G) in TR-FRET Coregulator Buffer E containing 7.5 mM dithiothreitol (DTT); and 2 mL of 3× Assay mix (750 nM Fluorescein-PGC1a peptide sequence; Life Technologies PV4421), 12 nM Estradiol, 15 nM Anti-GST Tb-labeled antibody in TR-FRET Coregulator Buffer E (with 7.5 mM DTT). "No receptor" control wells received buffer without GST-ERa protein. Plates were centrifuged at 1800 rpm for 20 seconds in V-spin centrifuge and incubated for 2 hours at room temperature with the plates covered. Measurements were made using a Perkin Elmer EnVision Fluorescence Reader using TR-FRET setting (Top mirror: Perkin Elmer Lance/ DELFIA Dual emission (PE #2100-4160); Excitation filter: Perkin Elmer UV (TFR) 340 nm (PE #2100-5010); Emission filtes: Chroma 495 nm/10 nm and 520 nm/25 nm (Chroma #PV003 filters for LanthaScreen, 25 mm diameter for EnVision) Excitation light: 100%; Delay: 100 us; Window time: 200; Number of sequential windows. 1, Time between flashes: 2000 us; Number of flashes: 100, Number of flashes ($2^{nd}$ detector): 100. Percentage inhibition values were calculated relative to no compound (DMSO only) controls and a "no ERa controls". Curve fitting and $IC_{50}$ calculations were carried out using Genedata Screener software.

Example 905 In Vivo Mouse Tumor Xenograft Efficacy

Mice: Female severe combined immunodeficiency mice (Fox Chase SCID®, C.B-17/IcrHsd, Harlan) or nude mice (Taconic Farms, Harlan) are 8 to 9 weeks old and had a BW range of 15.1 to 21.4 grams on Day 0 of the study. The animals are fed ad libitum water (reverse osmosis, 1 ppm Cl) and NIH 31 Modified and Irradiated Lab Diet® consisting of 18.0% crude protein, 5.0% crude fat, and 5.0% crude fiber. The mice are housed on irradiated ALPHA-Dri® Bed-o'cobs® Laboratory Animal Bedding in static microisolators on a 12-hour light cycle at 21-22° C. (70-72° F.) and 40-60% humidity. PRC specifically complies with the recommendations of the Guide for Care and Use of Laboratory Animals with respect to restraint, husbandry, surgical procedures, feed and fluid regulation, and veterinary care. The animal care and use program at PRC is accredited by the Association for Assessment and Accreditation of Laboratory Animal Care International (AAALAC), which assures compliance with accepted standards for the care and use of laboratory animals.

Tumor Implantation: Xenografts are initiated with cancer cells. Cells are cultured in RPMI1640 medium supplemented with 10% fetal bovine serum, 2 mM glutamine, 100 units/mL penicillin, 100 µg/mL streptomycin sulfate and 25 µg/mL gentamicin. The cells are harvested during exponential growth and resuspended in phosphate buffered saline (PBS) at a concentration of $5\times10^6$ or $10\times10^6$ cells/mL depending on the doubling time of the cell line.

Tumor cells are implanted subcutaneously in the right flank, and tumor growth is monitored as the average size approached the target range of 100 to 150 mm3. Twenty-one days after tumor implantation, designated as Day 0 of the study, the mice are placed into four groups each consisting of ten mice with individual tumor volumes ranging from 75-172 mm3 and group mean tumor volumes from 120-121 mm3 (see Appendix A). Volume is calculated using the formula:

$$\text{Tumor Volume (mm}^3) = (w^2 \times l)/2,$$

where w=width and l=length in mm of a tumor. Tumor weight may be estimated with the assumption that 1 mg is equivalent to 1 mm3 of tumor volume.

Therapeutic Agents: Estrogen receptor modulator compounds and chemotherapeutic agents are typically prepared from dry powders, stored at room temperature, and protected from light. Drug doses are prepared weekly in 0.5% methylcellulose: 0.2% Tween 80 in deionized water ("Vehicle") and stored at 4° C. Vehicle (+) is solvent/buffer with ethynyl estradiol (ethinyl estradiol, EE2) at 0.1 mg/kg. Vehicle (−) is solvent/buffer without ethynyl estradiol. Doses of compounds are prepared on each day of dosing by diluting an aliquot of the stock with sterile saline (0.9% NaCl). All doses are formulated to deliver the stated mg/kg dosage in a volume of 0.2 mL per 20 grams of body weight (10 mL/kg).

Treatment: All doses are scaled to the body weights of the individual animals and provided by the route indicated.

Endpoint: Tumor volume is measured in 2 dimensions (length and width), using Ultra Cal IV calipers (Model 54 10 111; Fred V. Fowler Company), as follows: tumor volume (mm$^3$)=(length×width$^2$)×0.5 and analyzed using Excel version 11.2 (Microsoft Corporation). A linear mixed effect (LME) modeling approach is used to analyze the repeated measurement of tumor volumes from the same animals over time (Pinheiro J, et al. nlme: linear and nonlinear mixed effects models. R package version 3.1 92. 2009; Tan N, et al. Clin. Cancer Res. 2011; 17(6): 1394-1404). This approach addresses both repeated measurements and modest dropouts due to any non-treatment-related death of animals before study end. Cubic regression splines are used to fit a nonlinear profile to the time courses of log 2 tumor volume at each dose level. These nonlinear profiles are then related to dose within the mixed model. Tumor growth inhibition as a percentage of vehicle control (% TGI) is calculated as the percentage of the area under the fitted curve (AUC) for the respective dose group per day in relation to the vehicle, using the following formula: % TGI=100×(1−AUC$_{dose}$/AUC$_{veh}$) Using this formula, a TGI value of 100% indicates tumor stasis, a TGI value of >1% but <100% indicates tumor growth delay, and a TGI value of >100% indicates tumor regression. Partial response (PR) for an animal is defined as a tumor regression of >50% but <100% of the starting tumor volume. Complete response (CR) was defined as 100% tumor regression (i.e., no measurable tumor) on any day during the study.

Toxicity: Animals are weighed daily for the first five days of the study and twice weekly thereafter. Animal body weights are measured using an Adventurer Pro® AV812 scale (Ohaus Corporation). Percent weight change is calculated as follows: body weight change (%)=[(weight$_{day\ new}$−weight$_{day\ 0}$)/weight$_{day\ 0}$]×100. The mice are observed frequently for overt signs of any adverse, treatment-related side effects, and clinical signs of toxicity recorded when observed. Acceptable toxicity is defined as a group mean body weight (BW) loss of less than 20% during the study and not more than one treatment-related (TR) death among ten treated animals. Any dosing regimen that results in greater toxicity is considered above the maximum tolerated dose (MTD). A death is classified as TR if attributable to treatment side effects as evidenced by clinical signs and/or necropsy, or may also be classified as TR if due to unknown causes during the dosing period or within 10 days of the last dose. A death is classified as NTR if there is no evidence that death was related to treatment side effects.

In-vivo Xenograft Breast Cancer Model; (MCF-7; Tamoxifen-sensitive): Time release pellets containing 0.72 mg 17-f) Estradiol are subcutaneously implanted into nu/nu mice. MCF-7 cells were grown in RPMI containing 10% FBS at 5% $CO_2$, 37° C. Trypsinized cells are pelleted and re-suspended in 50% RPMI (serum free) and 50% Matrigel at $1\times10^7$ cells/mL. MCF-7 cells are subcutaneously injected (100 µL/animal) on the right flank 2-3 days post pellet implantation. Tumor volume (length×width$^2$/2) is monitored bi-weekly. When tumors reach an average volume of ~200 mm$^3$ animals are randomized and treatment is started. Animals are treated with vehicle or compound daily for 4 weeks. Tumor volume and body weight are monitored bi-weekly throughout the study.

In-vivo Xenograft Breast Cancer Model; (Tamoxifen-resistant model): Female nu/nu mice (with supplemental 17-β Estradiol pellets; 0.72 mg; 60 day slow release) bearing MCF-7 tumors (mean tumor volume 200 mm$^3$) are treated with tamoxifen (citrate) by oral gavage. Tumor volume (length×width$^2$/2) and body weight are monitored twice weekly. Following a significant anti-tumor response in which tumor volume remained static, evident tumor growth is first observed at approximately 100 days of treatment. At 120 days of treatment, tamoxifen dose is increased. Rapidly growing tumors are deemed tamoxifen resistant and selected for in vivo passage into new host animals. Tumor Fragments (~100 mm$^3$/animal) from the tamoxifen resistant tumors are subcutaneously implanted into the right flank of female nu/nu mice (with 17-β Estradiol pellets (0.72 mg; 60 day slow release)). Passaged tumors are maintained under constant Tamoxifen selection, and tumor volume (length× width$^2$/2) is monitored weekly. When tumor volume reached ~150-250 mm$^3$, animals are randomized into treatment groups (mean tumor volume 200 mm$^3$) and tamoxifen treatment is terminated. Animals are treated with vehicle or compound daily for 4 weeks. Tumor volume and body weight are monitored twice weekly for the duration of the study.

Example 906 Immature Uterine Wet Weight Assay

Female immature CD-IGS rats (21 days old upon arrival) are treated for three days. Animals are dosed daily for three days. For Antagonist Mode, Vehicle or test compound is administered orally by gavage followed 15 minutes later by an oral dose of 0.1 mg/kg Ethynyl Estradiol. For Agonist Mode, Vehicle or test compound is administered orally by gavage. On the fourth day 24 hours after dose, plasma is collected for pharmacokinetic analysis. Immediately following plasma collection, the animals are euthanized and the uterus removed and weighed.

Uteri and ovaries from 2 animals per group are fixed in 10% neutral buffered formalin and paraffin embedded, sectioned and stained for H&E (SDPath). Stained tissues are analyzed and read by a board certified pathologist. Uteri and ovaries from 4 animals per group are flash frozen in liquid $N_2$ for transcriptional analysis, examining a select set of genes modulated by the estrogen receptor.

Mice were treated with Formula I compounds (1R,3R)-1-(2,6-difluoro-4-((1-(3-fluoropropyl)azetidin-3-yl)oxy)phenyl)-2-(2-fluoro-2-methylpropyl)-3-methyl-2,3,4,9-tetrahydro-1H-pyrido[3,4-b]indole 101 and (1R,3R)-1-(2,6-difluoro-4-(2-(3-(fluoromethyl)azetidin-1-yl)ethoxy)phenyl)-2-(2-fluoro-2-methylpropyl)-3-methyl-2,3,4,9-tetrahydro-1H-pyrido[3,4-b]indole 102, tamoxifen, fulvestrant, AZD9496 (WO 2014/191726, Example 1, page 74; U.S. Pat. No. 9,155,727), and two controls; Vehicle and Vehicle plus ethynyl estradiol (EE). All compounds were dosed PO, QDx3. Uterine Wet Weight (UWW): Body Weight ratios were calculated. The mean Endometrial Height of Uterine cross sections were measured by histology. Endometrial cell height was measured from the basement membrane to the apical (luminal) surface using a slide viewer at 20× magnification. Obliquely cut areas were avoided. In agonist mode UWW assay, Formula I compounds 101 and 102 are antagonists, while AZD9496 is a partial agonist.

Example 907 Adult Uterine Wet Weight-10 Day Assay

Female CD-IGS rats (69 days old, Charles River Laboratories) are purchased and split into groups. Group 1 is ovariectomized at the vendor (Charles River Laboratories) at 60 days of age and the study is started 2 weeks after surgery, while groups 2-8 were intact. Vehicle or test compound is administered orally for 10 days. Two hours after the $10^{th}$ and final dose, cardiac punctures are performed and serum is collected for pharmacokinetic and estradiol analyses. Immediately following serum collection, the animals are euthanized and the uterus and ovaries removed and weighed.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

We claim:
1. A process for preparing a compound of formula (14),

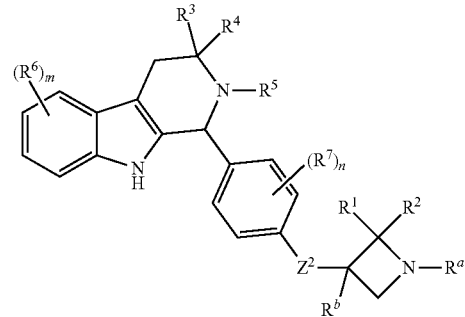

(14)

or a stereoisomer, tautomer, or pharmaceutically acceptable salt thereof,
wherein:
$R^a$ is independently selected from H, $C_1$-$C_6$ alkyl, $C_2$-$C_8$ alkenyl, propargyl, $C_3$-$C_6$ cycloalkyl, and $C_3$-$C_6$ heterocyclyl, optionally substituted with one or more groups independently selected from F, Cl, Br, I, CN, OH, $OCH_3$, and $SO_2CH_3$;
$R^b$ is H;
$Z^2$ is NH;
$R^1$ and $R^2$ are each H;
$R^3$ and $R^4$ are independently selected from H, F, Cl, Br, I, —CN, —$CH_3$, —$CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CH_2NH_2$, —$CH_2NHSO_2CH_3$, —$CH_2NHCH_3$, —$CH_2N(CH_3)_2$, —$CF_3$, —$CH_2CF_3$, —$CH_2CHF_2$, —$CH(CH_3)CN$, —$C(CH_3)_2CN$, —$CH_2CN$, —$CO_2H$, —$COCH_3$, —$CO_2CH_3$, —$CO_2C(CH_3)_3$, —$COCH(OH)CH_3$, —$CONH_2$, —$CONHCH_3$, —$CONHCH_2CH_3$, —$CONHCH(CH_3)_2$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —OP(O)(OH)$_2$, —$S(O)_2N(CH_3)_2$, —$SCH_3$, —$S(O)_2CH_3$, —$S(O)_3H$, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino;
$R^5$ is selected from H, $C_1$-$C_9$ alkyl, $C_3$-$C_9$ cycloalkyl, $C_3$-$C_9$ heterocycle, $C_6$-$C_9$ aryl, $C_6$-$C_9$ heteroaryl, —($C_1$-$C_6$ alkyldiyl)-($C_3$-$C_9$ cycloalkyl), —($C_1$-$C_6$ alkyldiyl)-($C_3$-$C_9$ heterocycle), C(O)$R^b$, C(O)NR$^a$, SO$_2$R$^a$, and SO$_2$NR$^a$, optionally substituted with one or more of halogen, CN, OR$^a$, N(R$^a$)$_2$, $C_1$-$C_9$ alkyl, $C_3$-$C_9$ cycloalkyl, $C_3$-$C_9$ heterocycle, $C_6$-$C_9$ aryl, $C_6$-$C_9$ heteroaryl, C(O)R$^b$, C(O)NR$^a$, SO$_2$R$^a$, and SO$_2$NR$^a$;
each $R^6$ and $R^7$ is independently F or Cl;
m is selected from 0, 1, 2, 3, and 4; and
n is selected from 0, 1, 2, 3, and 4;

the process comprising:
(a) contacting a compound of formula:

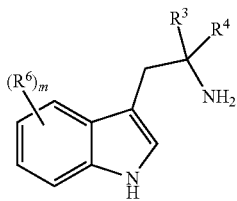
(11)

with a compound of formula X—R⁵, wherein X is I, Br, or —OTf, thereby synthesizing a compound having formula (12):

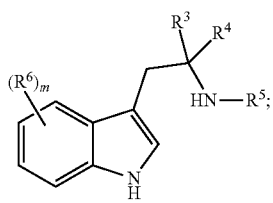
(12)

(b) cyclizing the compound of formula (12) with a compound of formula:

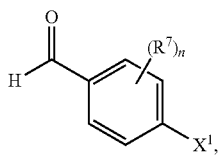
(7)

wherein X¹ is Br or I, thereby synthesizing a compound having formula (13)

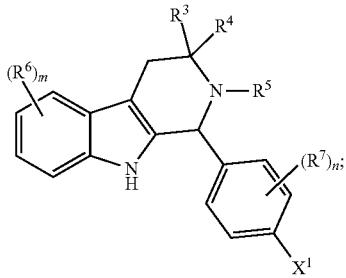
(13)

wherein X¹ is I or Br; and
(c) reacting the compound of formula (13) with a compound having formula

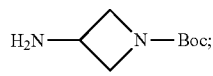

(d) contacting the compound of step (c) with an acid to remove the Boc moiety thereby synthesizing a free amine; and
(e) contacting the compound of step (d) with a compound of formula I—R$^a$;
thereby synthesizing a compound having formula (14).

2. The process of claim 1, wherein the compound of formula I—R$^a$ is 1-iodo-3-fluoropropane.

3. The process of claim 1, wherein R⁵ of compound formula 13 in step (b) is H and wherein the process further comprises step (b1) comprising contacting such compound with
(i) an acyl chloride having formula

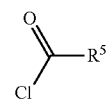

making a compound of formula;

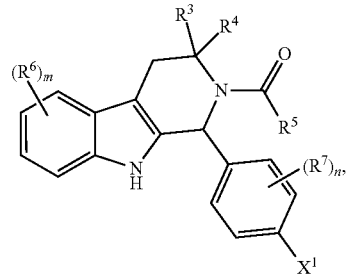
(16)

or a salt thereof, or
(ii) with a sulfonyl chloride having formula

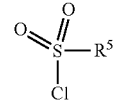

making a compound of formula,

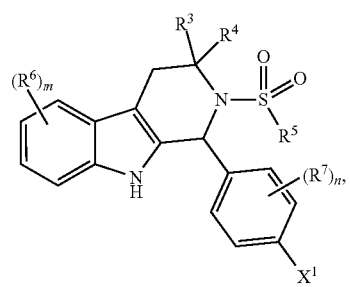
(18)

or a salt thereof.
4. The process of claim 1, wherein X is I or Br.
5. The process of claim 1, wherein X is OTf.
6. The process of claim 1, wherein R³ is H and R⁴ is methyl.
7. The process of claim 1, wherein R⁵ is $C_1$-$C_6$ fluoroalkyl.

8. The process of claim 1, wherein $R^5$ is:

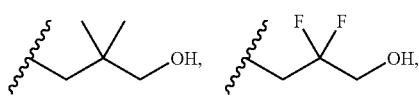

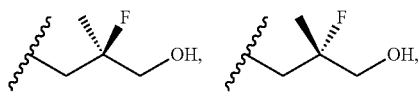

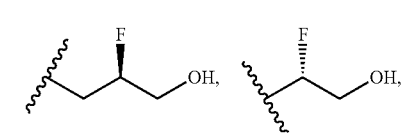

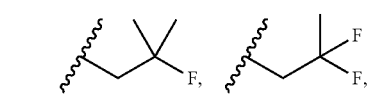

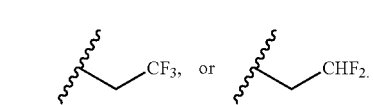

9. The process of claim 1, wherein m is 1.
10. The process of claim 1, wherein m is 0.
11. The process of claim 1, wherein n is 1 or 2.
12. The process of claim 11, wherein $R^7$ is F and n is 1 or 2.
13. The process of claim 12, wherein $R^7$ is F and n is 2.
14. The process of claim 1, wherein $R^a$ is $C_1$-$C_6$ alkyl substituted with one F.
15. The process of claim 1, wherein the compound of formula (14) has Formula (Ik):

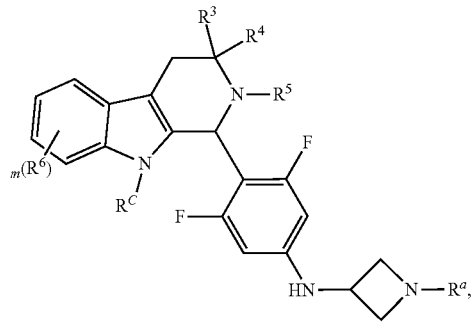

wherein $R^c$ is H, or a stereoisomer, tautomer, or pharmaceutically acceptable salt thereof.

16. The process of claim 1, wherein the compound of formula (14) has formula:

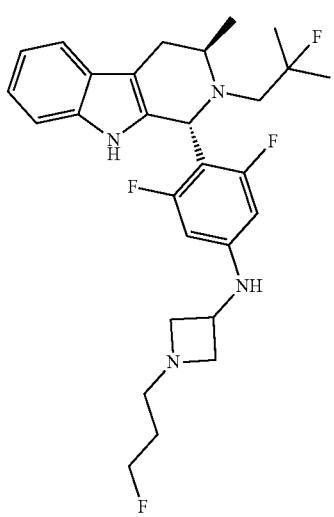

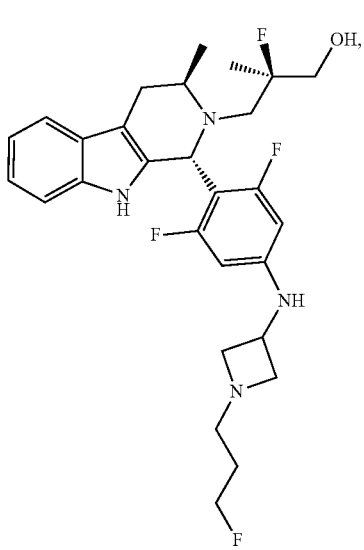

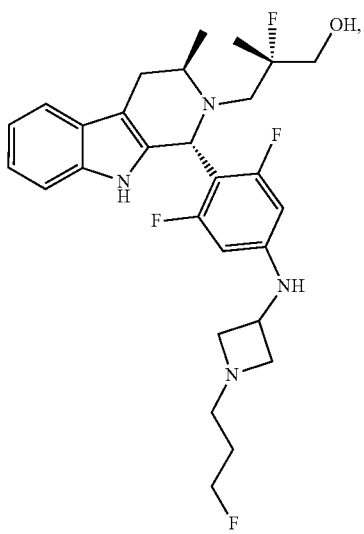

277
-continued
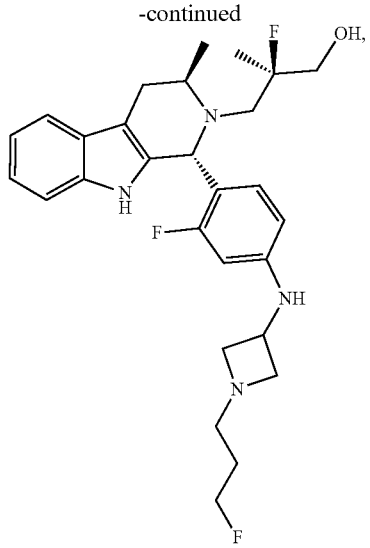
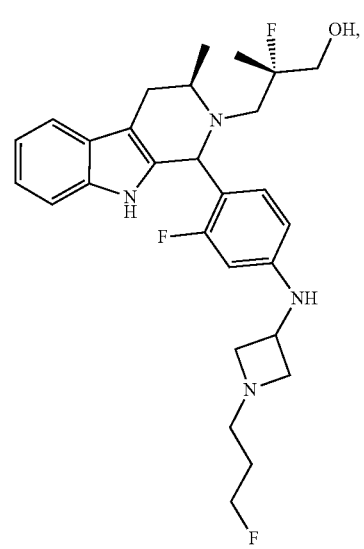
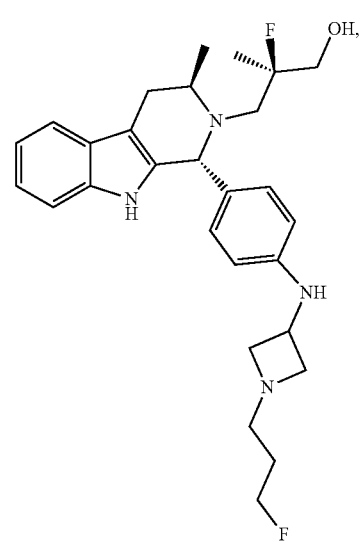
278
-continued
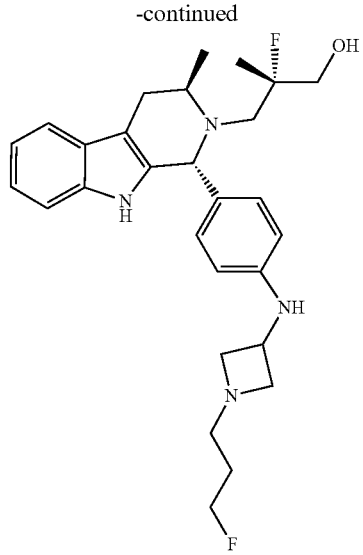
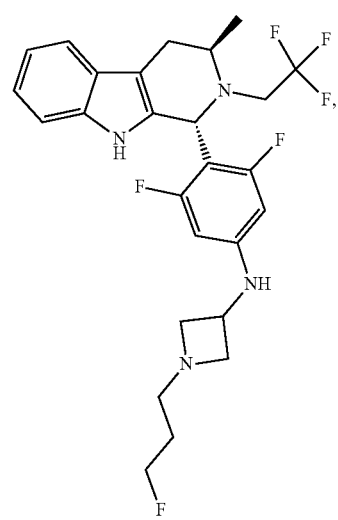
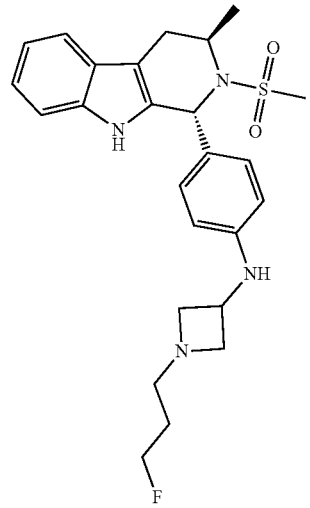

279
-continued
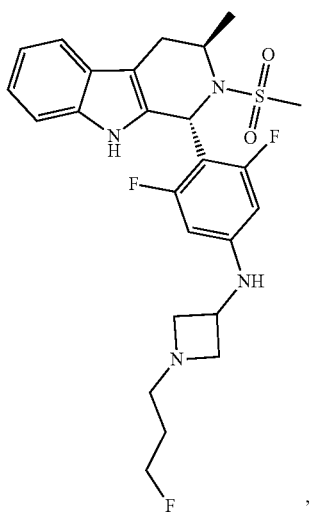
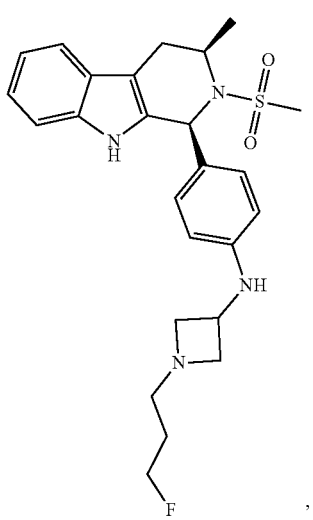
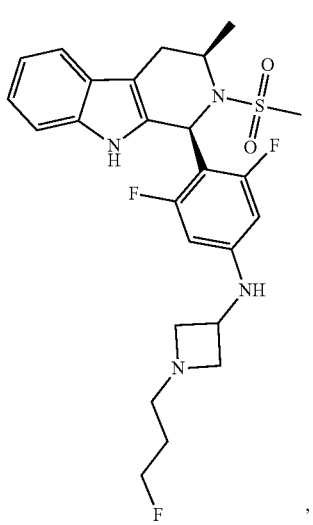
280
-continued
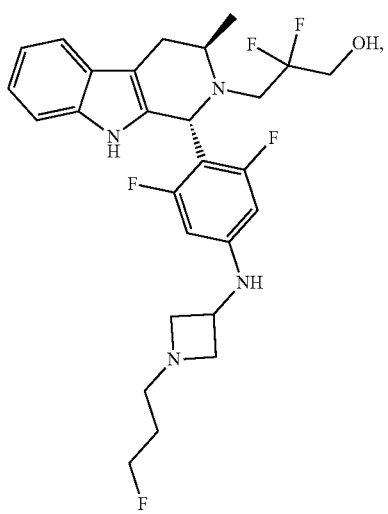

281
-continued
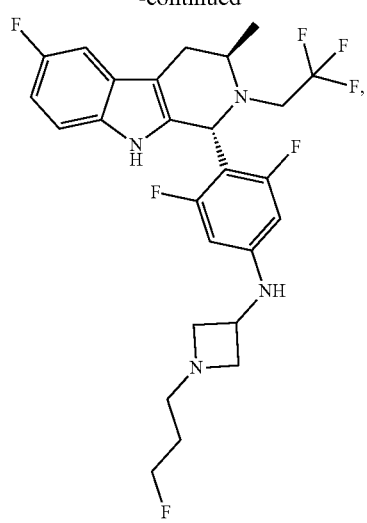
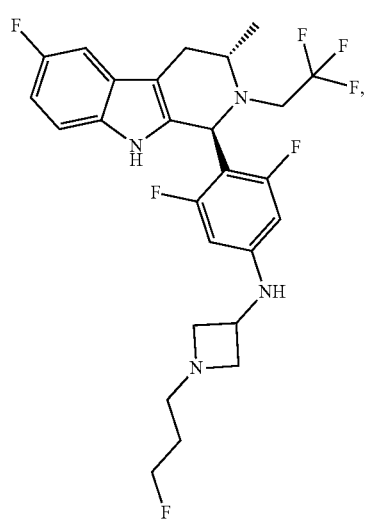
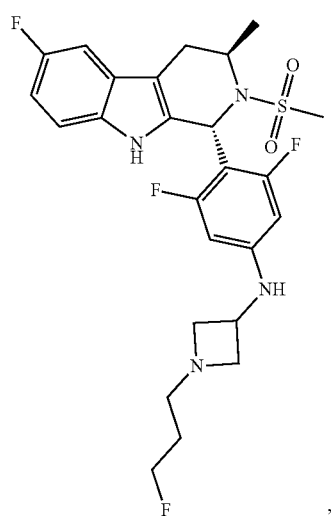
282
-continued
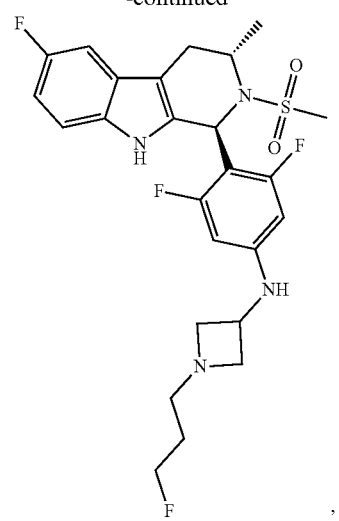
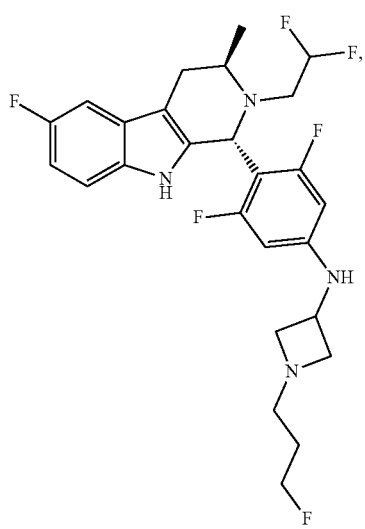
,
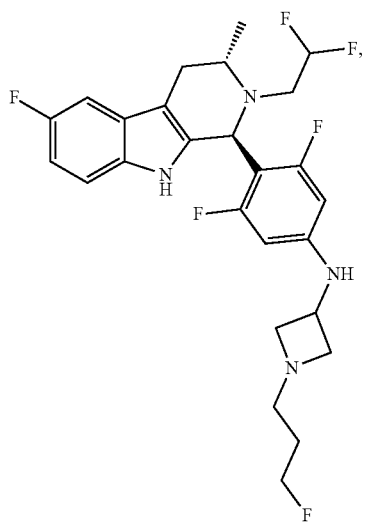

283
-continued
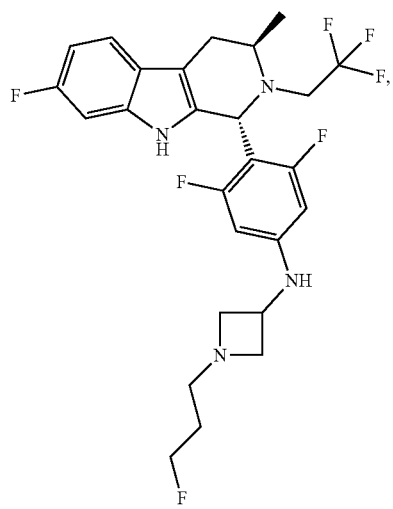
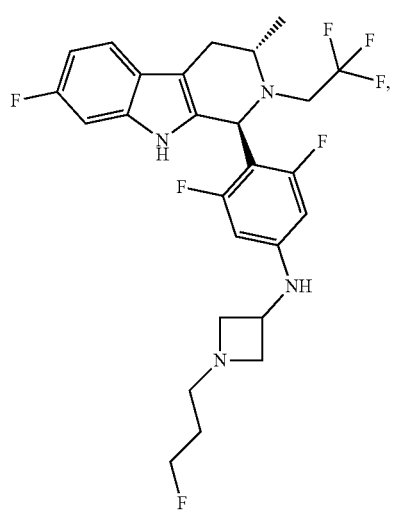
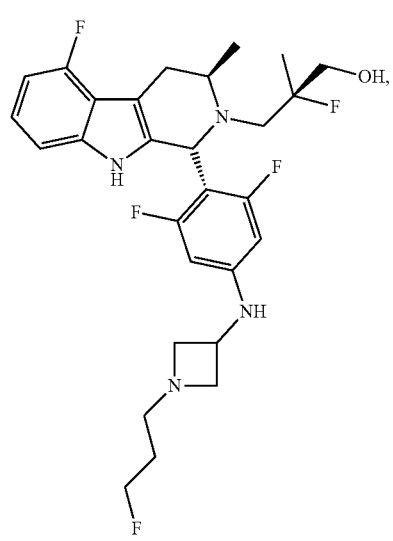
284
-continued
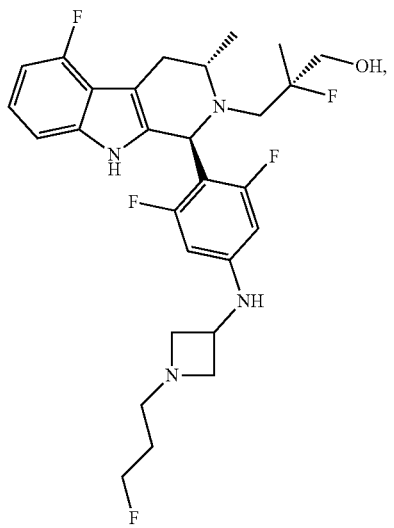
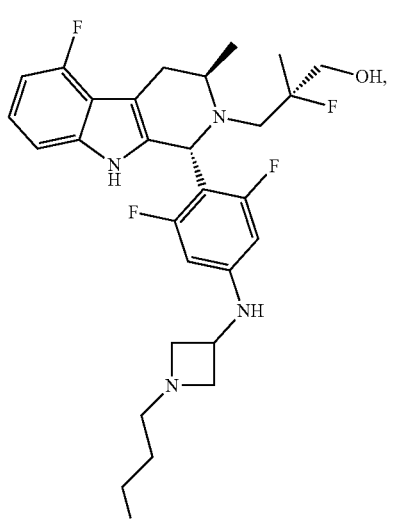
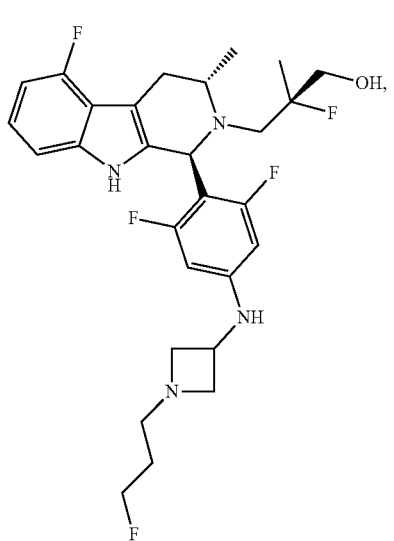

285
-continued
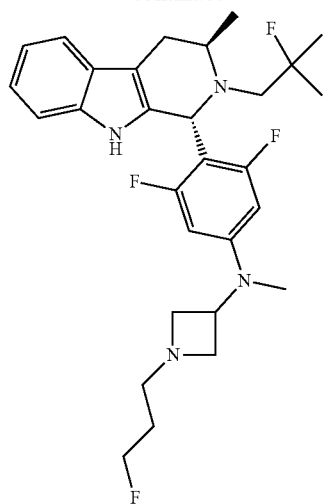
,
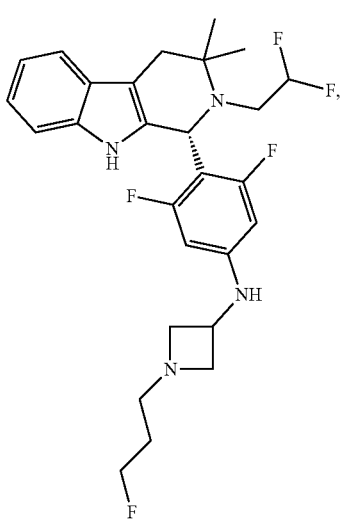
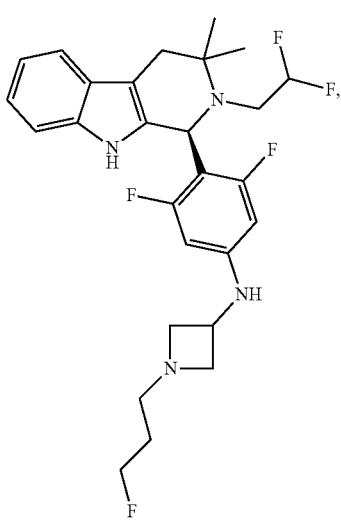
286
-continued
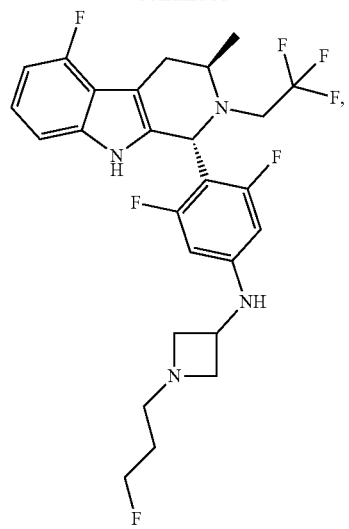
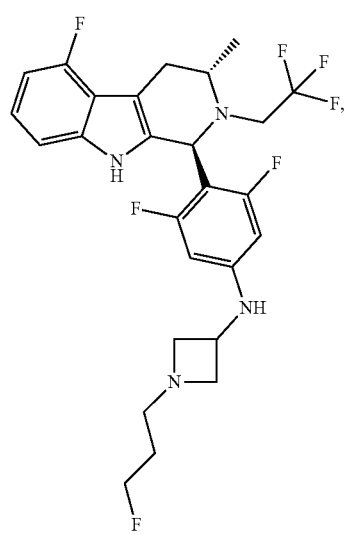
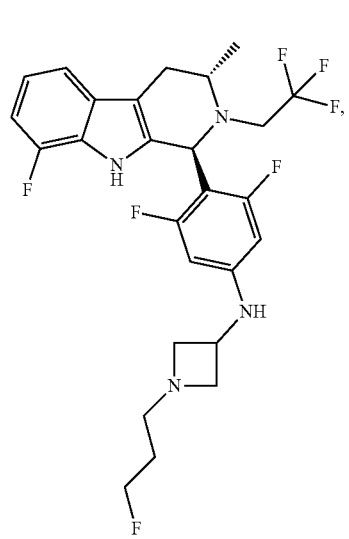

287
-continued
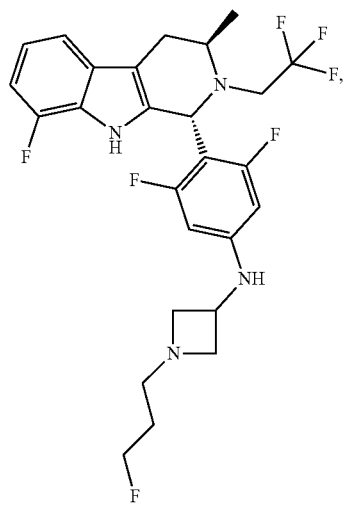
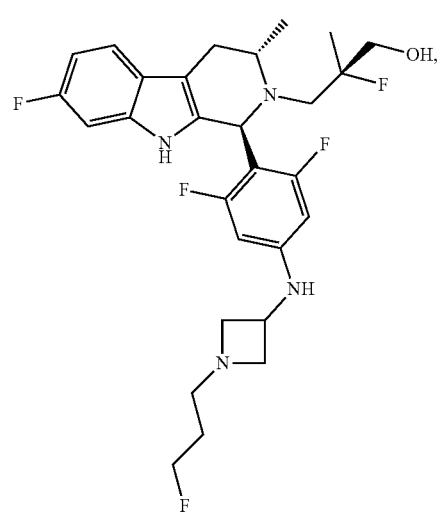
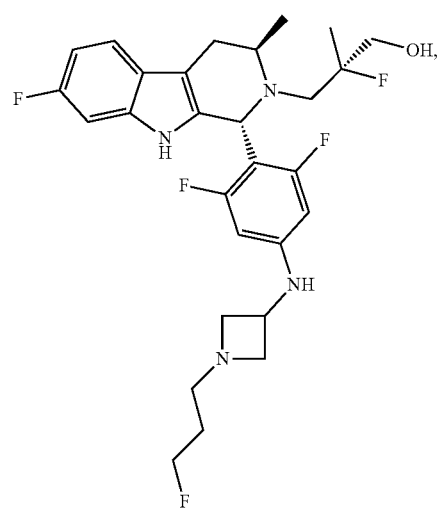
288
-continued
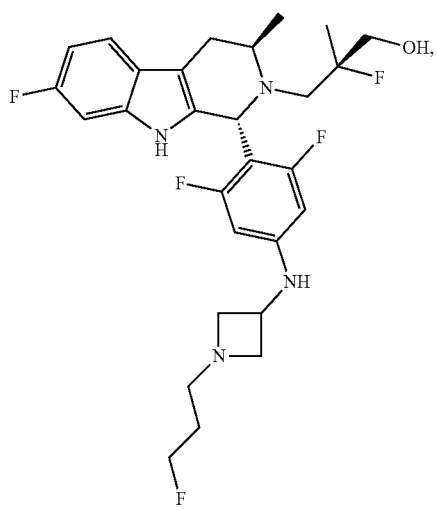
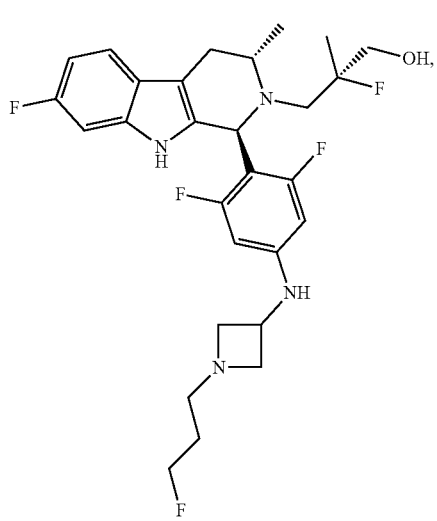
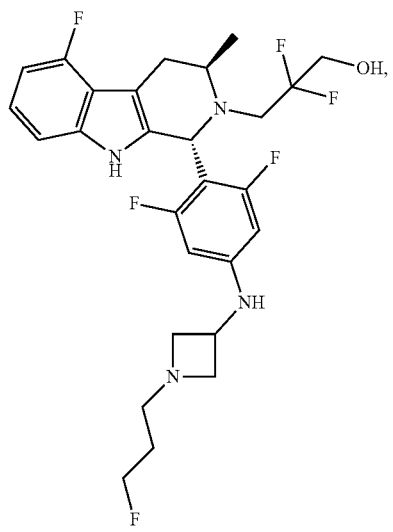

289
-continued
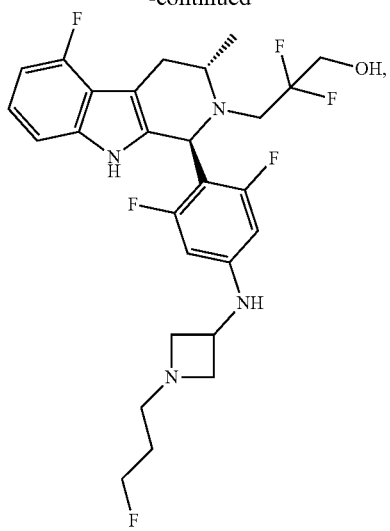
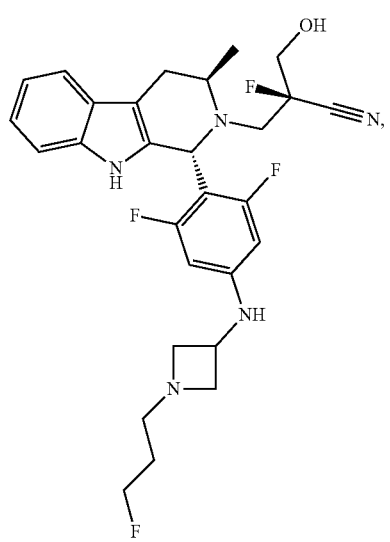
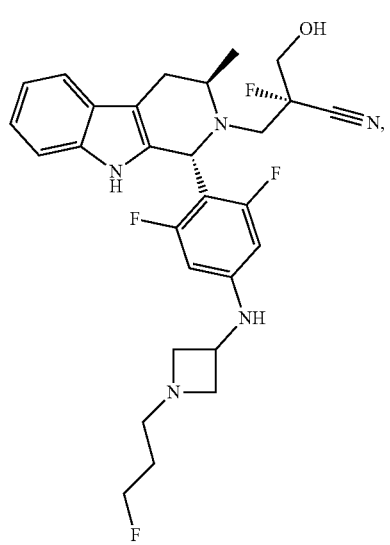
290
-continued
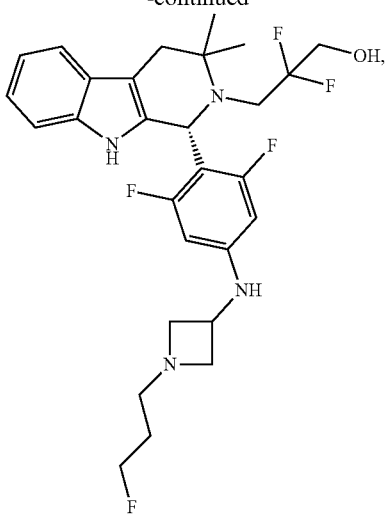
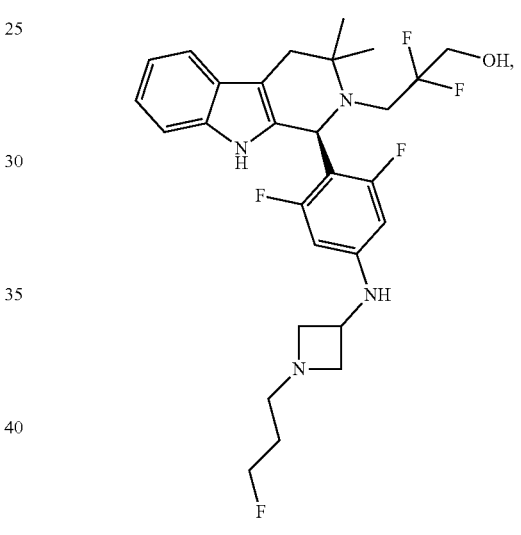
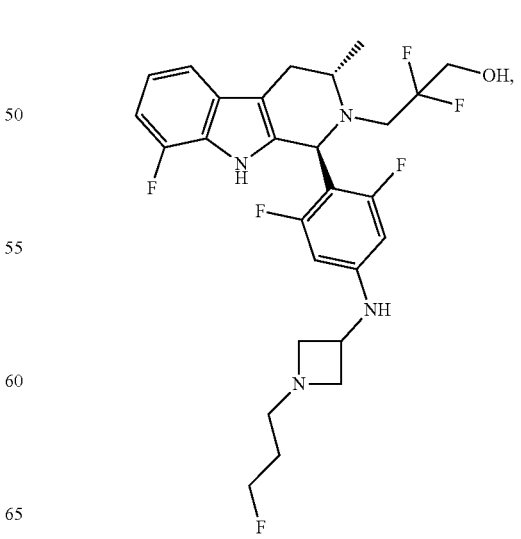

291
-continued
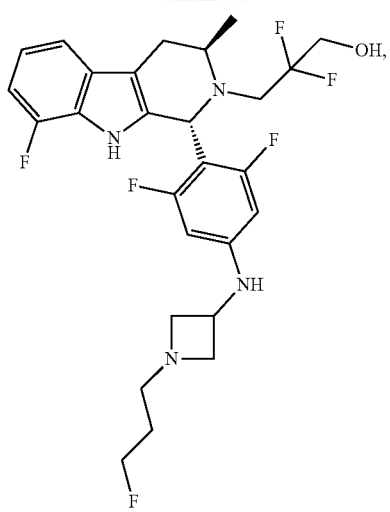
292
-continued
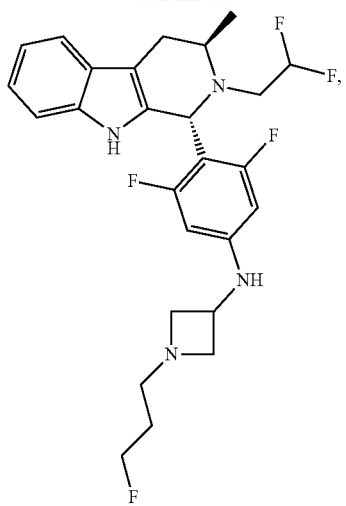
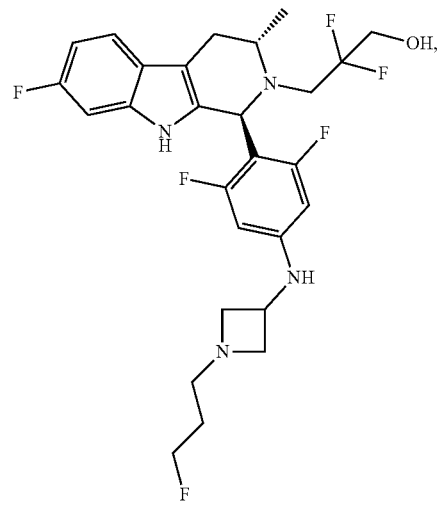
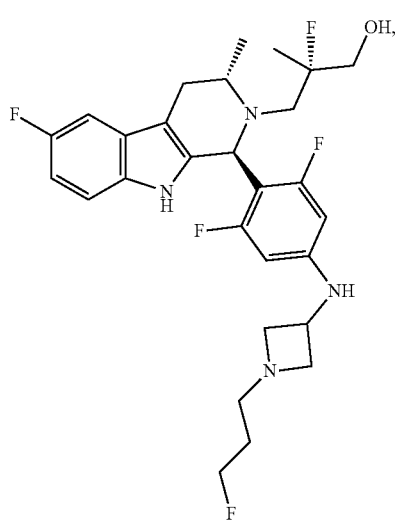

293
-continued

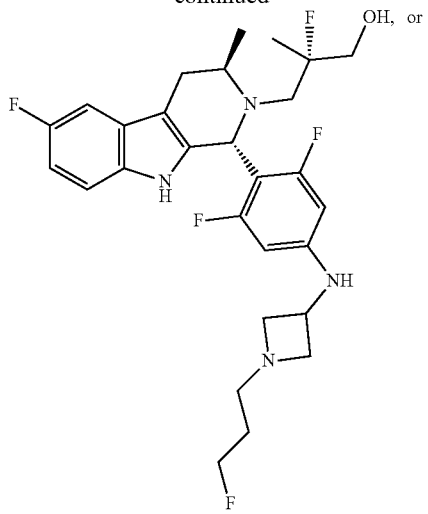

or a pharmaceutically acceptable salt thereof.

17. The process of claim 1, wherein the compound of formula (14) has formula:

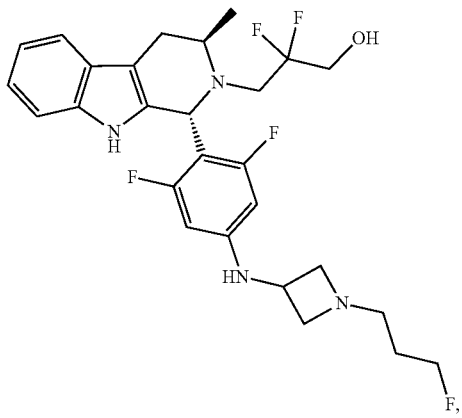 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof.

294

18. A process of making a compound of formula (340):

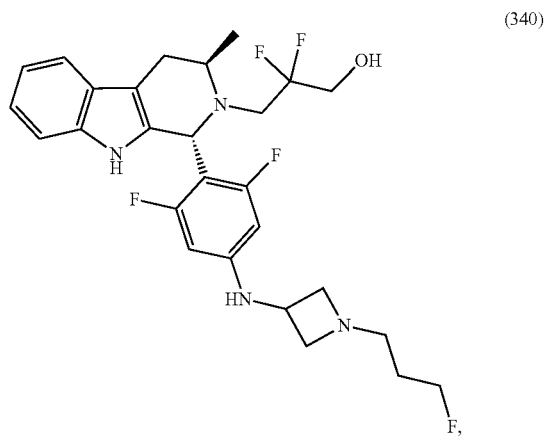 [SMILES: C[C@@H]1Cc2c([nH]c3ccccc23)[C@@H](c2c(F)cc(NC3CN(CCCF)C3)cc2F)N1CC(F)(F)CO]

(340)

or a pharmaceutically acceptable salt thereof, the process comprising:

(a) contacting (2R)-1-(1H-indol-3-yl) propan-2-amine with [3-[tert-butyl(diphenyl)silyl]oxy-2,2-difluoropropyl] trifluoromethanesulfonate in the presence of a base thereby synthesizing a compound of formula (340a);

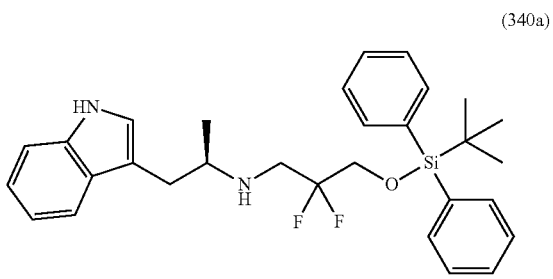 [SMILES: C[C@H](Cc1c[nH]c2ccccc12)NCC(F)(F)CO[Si](c1ccccc1)(c1ccccc1)C(C)(C)C]

(340a)

(b) contacting the compound of formula (340a) with a quaternary ammonium salt thereby synthesizing a compound of formula (340b);

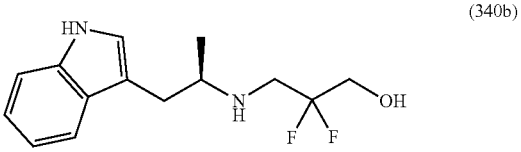 [SMILES: C[C@H](Cc1c[nH]c2ccccc12)NCC(F)(F)CO]

(340b)

(c) contacting the compound of formula (340b) with 4-bromo-2,6-difluorobenzaldehyde in the presence of an acid thereby synthesizing a compound of formula (340c);

(340c)

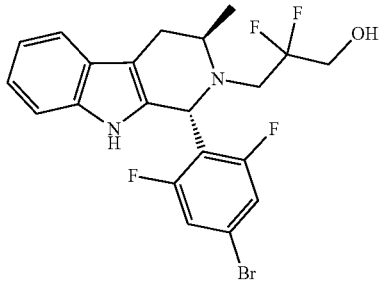

(d) contacting the compound of formula (340c) with tert-butyl 3-aminoazetidine-1-carboxylate in the presence of a palladium catalyst thereby synthesizing a compound of formula (340d);

(340d)

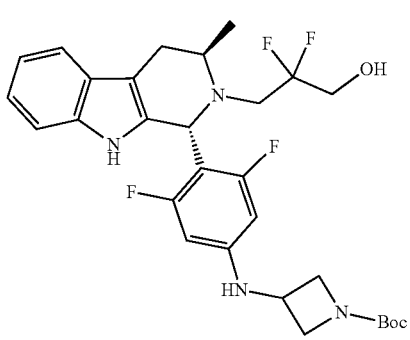

(e) deprotecting the compound of formula (340d) by contacting with an acid thereby synthesizing a compound of formula (340e); and (340e)

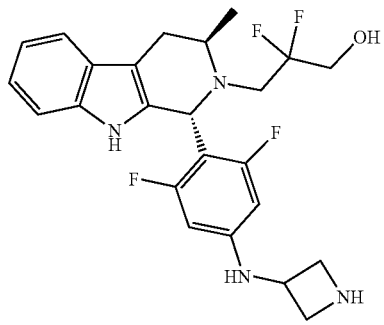

(f) contacting the compound formula (340e) with 1-fluoro-3-iodopropane in the presence of a base, thereby synthesizing the compound of formula (340).

19. The process of claim 18, wherein the base of step (a) is N,N-Diisopropylethylamine (DIPEA).

20. The process of claim 18, wherein the quaternary ammonium salt of step (b) is tetra-n-butylammonium fluoride (TBAF).

21. The process of claim 18, wherein the acid of step (c) is acetic acid.

22. The process of claim 21, wherein the reaction is performed in toluene.

23. The process of claim 18, wherein the palladium catalyst of step (d) is Pd$_2$(dba)$_3$.

24. The process of claim 18, wherein the acid of step (e) is hydrochloric acid or sulfuric acid.

25. The process of claim 24, wherein the acid is sulfuric acid.

26. The process of claim 18, wherein the base in step (f) is N,N-Diisopropylethylamine (DIPEA).

27. A process for making a compound of formula:

(340b)

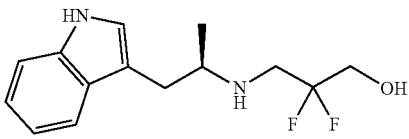

or a salt thereof, the process comprising the steps:

(a) contacting a compound of formula:

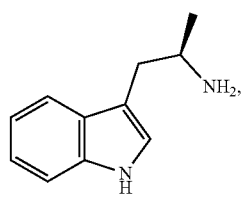

with [3-[tert-butyl(diphenyl)silyl]oxy-2,2-difluoropropyl] trifluoromethanesulfonate in the presence of a base thereby synthesizing a compound of formula (340a);

(340a)

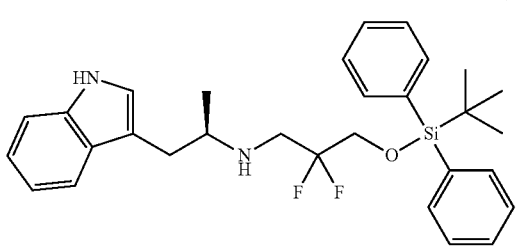

(b) contacting the compound of formula (340a) with a quaternary ammonium salt thereby synthesizing a compound of formula (340b).

28. The process of claim 27, wherein the base of step (a) is N,N-Diisopropylethylamine (DIPEA).

29. The process of claim 27, wherein the quaternary ammonium salt of step (b) is tetra-n-butylammonium fluoride (TBAF).

30. A process of making a compound of formula:
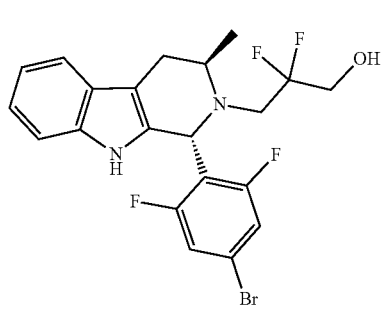
(340c)
the process comprising contacting the compound of formula (340b)
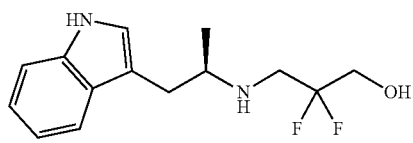
(340b)
with 4-bromo-2,6-difluorobenzaldehyde in the presence of an acid thereby synthesizing a compound of formula (340c).
31. A compound or salt thereof of formula:
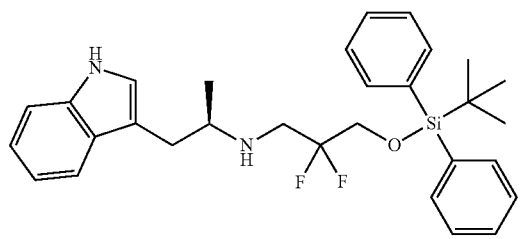
(340a)
or
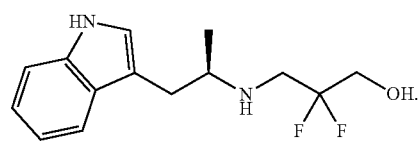
(340b)
32. A compound or salt thereof of formula:
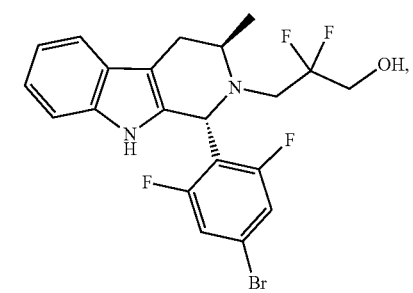
(340c)
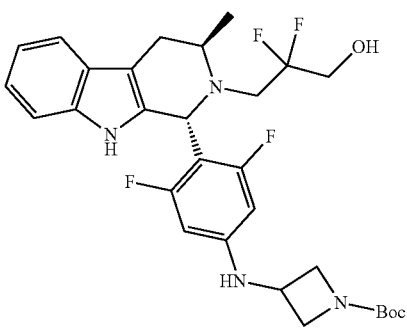
(340d)
or
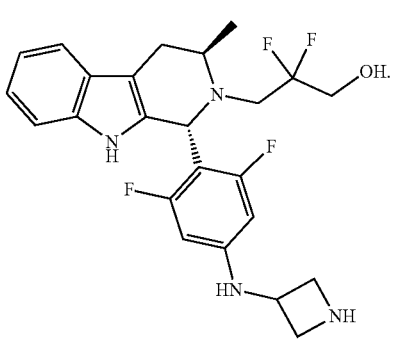
(340e)
* * * * *